United States Patent
Khalifah et al.

(10) Patent No.: US 6,716,858 B1
(45) Date of Patent: Apr. 6, 2004

(54) METHODS FOR INHIBITING DIABETIC COMPLICATIONS

(75) Inventors: Raja Khalifah, Overland Park, KS (US); Billy G. Hudson, Lenexa, KS (US)

(73) Assignee: Kansas University Medical Center, Kansas City, KS (US)

(*) Notice: Subject to any disclaimer, the term of this patent is extended or adjusted under 35 U.S.C. 154(b) by 0 days.

(21) Appl. No.: 09/416,915

(22) Filed: Oct. 13, 1999

Related U.S. Application Data

(63) Continuation-in-part of application No. 08/971,285, filed on Nov. 17, 1997, now Pat. No. 6,228,858, which is a continuation-in-part of application No. 08/711,555, filed on Sep. 10, 1996, now Pat. No. 5,985,857.

(60) Provisional application No. 60/003,268, filed on Aug. 28, 1995, and provisional application No. 60/104,276, filed on Oct. 14, 1998.

(51) Int. Cl.$^7$ .............................................. A61K 31/44
(52) U.S. Cl. ...................... 514/345; 514/349; 514/350; 514/354; 514/356
(58) Field of Search ................................ 514/345, 349, 514/350, 354, 356

(56) References Cited

U.S. PATENT DOCUMENTS

| | | | |
|---|---|---|---|
| 5,288,716 A | 2/1994 | Speck | 514/89 |
| 5,462,946 A | 10/1995 | Mitchell et al. | 514/315 |
| 5,700,654 A | 12/1997 | Roberts et al. | 435/25 |
| 5,985,857 A | 11/1999 | Hudson et al. | 514/89 |
| 6,043,259 A | 3/2000 | Dhalla et al. | |
| 6,051,587 A | 4/2000 | Dakashinamurti et al. | |
| 6,066,659 A | 5/2000 | Speck | |

FOREIGN PATENT DOCUMENTS

| | | |
|---|---|---|
| CA | 2 055 990 | 5/1992 |
| DE | 19 15 497 | 11/1970 |
| DE | 24 61 742 | 7/1976 |
| DE | 37 05 549 | 9/1988 |
| EP | 0 474 874 | 3/1992 |
| FR | 2 349 330 | 11/1997 |
| GB | 1 093 546 | 12/1967 |
| GB | 1 478 560 | 7/1977 |
| JP | 221473 | 8/1997 |
| JP | 158244 | 6/1998 |
| JP | 175954 | 6/1998 |
| WO | WO 92/02216 | 2/1992 |
| WO | WO 97/09981 | 3/1997 |
| WO | WO 99/25690 | 5/1999 |

OTHER PUBLICATIONS

Khalifah, et al., (1999) Biochemical and Biophysical Research Communications, 257:(2) pp. 251–258.
Bucala, et al., (1994) Proceedings of the National Academy of Sciences of the United States of America, 91:(20) pp. 9441–9445.
Booth, et al., (1996) Biochemical and Biophysical Research Communications, US, Academic Press Inc., Orlando, Florida, 220:(1) pp. 113–119.
Baynes, et al., (1998) Journal of the American Society of Nephrology, vol. 9, No. Program and Abstract, Issue pp. 628A.
Akira, I., et al., Chemical Abstracts Service, Columbus Ohio, JP 10 175954, (Kissei Pharmaceutical Co., LTD., Japan) p. 1–7.
Akira, I., et al., Chemical Abstracts Service, Columbus Ohio, JJP 10 158244, (Kissei Pharmaceutical Co., LTD., Japan) p. 1–6.
Williamson, et al., (1993), Diabetes, 42:(6) pp. 801–813, Ref. 139.
Khalifah, et al., (1997) Journal of the American Society of Nephrology, 8: supp. 'S!, pp. A2988–A2988.
"The Merck Manual", (1987), Merck Sharp & Dohme Research Laboratories, Rahway, N.J., "Complications of Diabetes Mellitus", p. 2081.
Booth, et al., (1997) Journal of Biological Chemistry, US, American Society of Biological Chemists, Baltimore, MD, 272:(9) pp. 5430–5437.
Rath, et al., (1996) Journal of Applied Nutrition, 48/3, (68–78), Abstract, p. 68, figures 2–4 and p. 76, paragraph 2.
Jackson, et al., (1993) Biochemical Society Transactions, GB, Colchester, Essex, 21:(3) pp. 650–651.
van den Born, et al., (1992), Kidney Int, 41: pp. 115–123.
van den Heuvel, et al., (1989), Biochem J, 264: pp. 457–465.
Lane et al., (1992), Kidney Int, 41: pp. 1085–1089.
Sampson and O'Connor, (1989), Nutrition Res. 9: pp. 259–272.
Sampson and O'Connor, (1989) J. Nutr., 119: pp. 1940–1948.
Sharma and Dakshinamurti, (1992), J Chromatogr, 578: pp. 45–51.
Vernier et al., (1992), Kidney Int. 41: pp. 1070–1080.
Tamsma, et al., (1994), Diabetologia, 37: pp. 313–320.
van den Born and Berden, (1995), Nephrol Dial Transplant, 10: pp. 1277–1279.
van den Born, et al.(1995), Diabetologia, 38: pp. 161–172.
van den Born, et al. (1995), Diabetologia, 38: pp. 1169–1175.
Kashihara, et al., (1992), Proc Natl Acad Sci U.S.A., 89: pp. 6309–6313.

(List continued on next page.)

*Primary Examiner*—James H. Reamer
(74) *Attorney, Agent, or Firm*—McDonnell Boehnen Hulbert & Berghoff

(57) ABSTRACT

The instant invention provides compositions and methods for modeling post-Amadori AGE formation and the identification and characterization of effective inhibitors of post-Amadori AGE formation, and such identified inhibitor compositions. The instant invention also teaches new methods to treat or prevent diabetic nephropathy, oxidative stress, and protein crosslinking, comprising administering an amount effective of one of the compounds of the invention to treat or prevent the disorder.

18 Claims, 63 Drawing Sheets

OTHER PUBLICATIONS

Raats, et al., (1997), J. Biol. Chem, 272: pp. 26734–26741.
Fu, et al., (1992), Diabetes 41 Suppl, 2: pp. 42–48.
Thorpe and Baynes, (1996), Drugs Aging, 9: pp. 69–77.
Cohen and Ziyadeh, (1996),J. Am Soc. Nephrol, 7: pp. 183–190.
Vlassara, et al., (1994), Proc. Natl. Acad. Sci. U.S.A., 91: pp. 11704–11708.
Sakurai, et al., (1991), J. Nutr. Sci. Vitaminol., 37: pp. 341–348.
Beaven, et al., (1969), J.Pharmacol. Exp. Therapeutics, 165: pp. 14–22.
Fox, et al., (1981), J. Biol. Chem, 256: pp. 9313–9315.
Stegemann and Stalder, (1967), Clin. Chim. Acta, 18: pp. 267–273.
Krisko, et al., (1977), Kidney Internat, 12: pp. 238–243.
Dyer, et al., (1993), J. Clin. Invest, 91: pp. 2463–2469.
Hamlin, et al., (1975), Diabetes, 24: pp. 902–924.
Cameron, et al., (1992), Diabetologia, 35: pp. 946–950.
Ahmed, et al., (1997), Biochem. J, 324: pp. 565–570.
Soulis–Liparota, et al., (1991), Diabetes, 40: pp. 1328–1334.
Soulis–Liparota, et al., (1995), Diabetologia, 38: pp. 387–394.
Odetti, et al., (1990), Diabetes, 39: pp. 796–801.
Degenhardt, et al., (1999), Diab. Res. Clin. Pract, 43: pp. 81–89.
Dyer, et al., (1991), J. Biol. Chem, 266: pp. 11654–11660.
Litchfield, et al., (1999), Int. J. Biochem. & Cell Biol., 31: pp. 1297–1305.
Oxlund and Andreasen, (1992), Diabetologia, 35: pp. 19–25.
Nyengaard, et al., (1997), Daibetes, 46: pp. 94–106.
Kochakian, et al., (1996), Diabetes, 45: pp. 1694–1700.
McCance, et al., (1993), J. Clin. Invest, 91: pp. 2460–2478.
Soulis, et al., (1997), Kidney Int, 50: pp. 627–634.
Rumble, et al., (1997), J. Clin. Invest, 99: pp. 1016–1027.

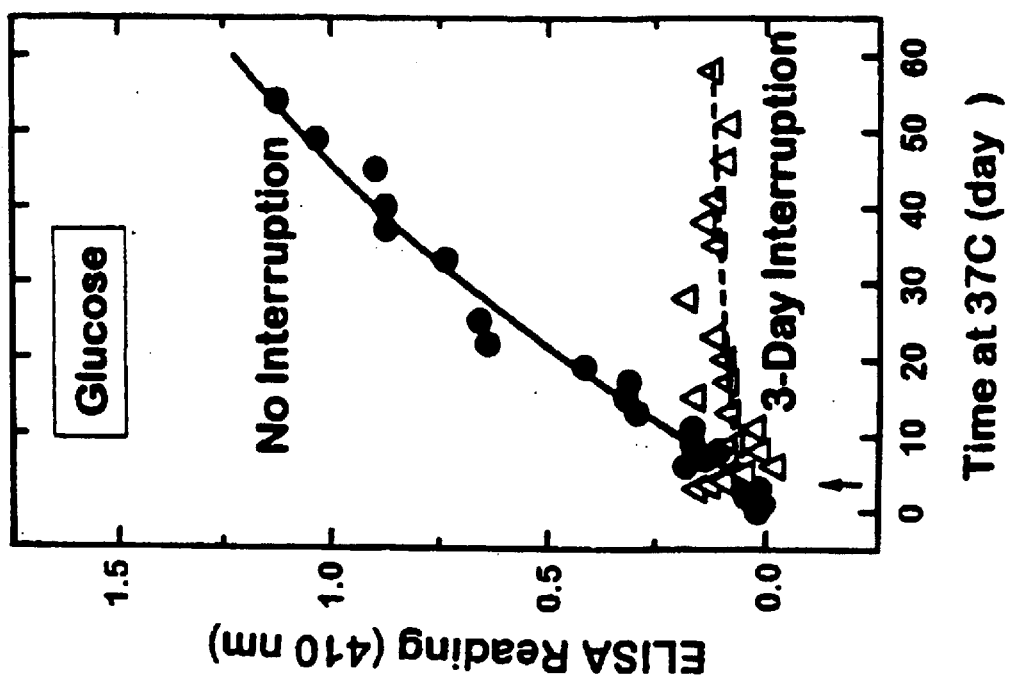
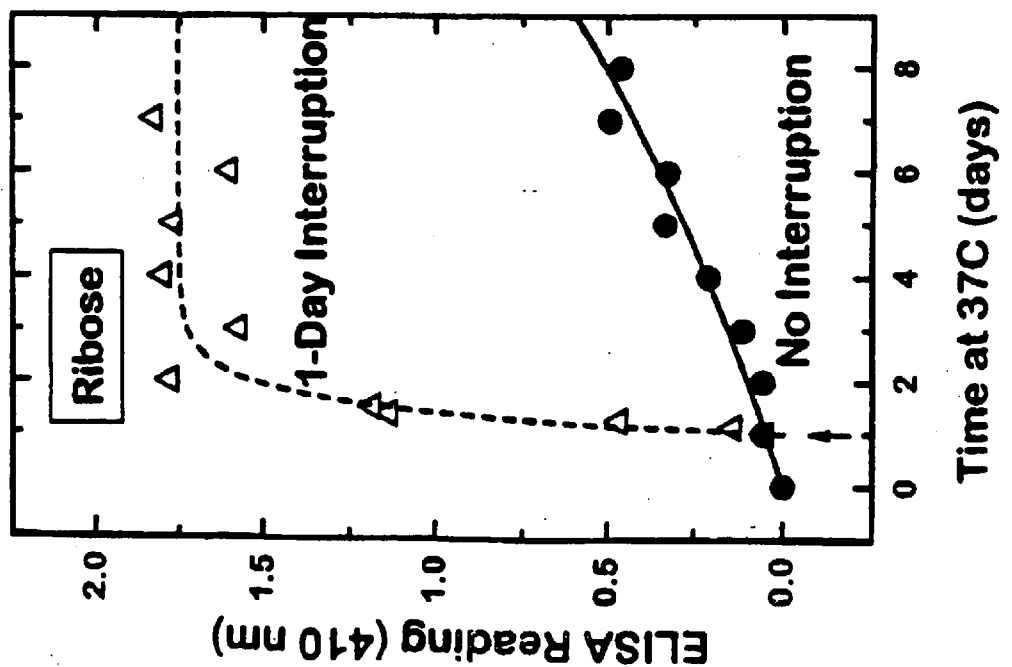
FIG. 7B
FIG. 7A

Scheme 2

Aminoguanidin

Scheme 3

Thiamine

Thiamine-5'-Phosphate

Thiamine Pyrophosphate

Scheme 4

Pyridoxine

Pyridoxamine

Pyridoxal-5'-Phosphate

Pyridoxal

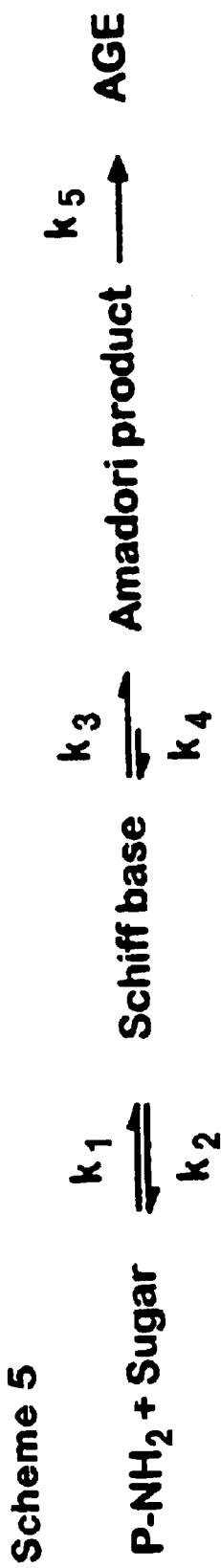
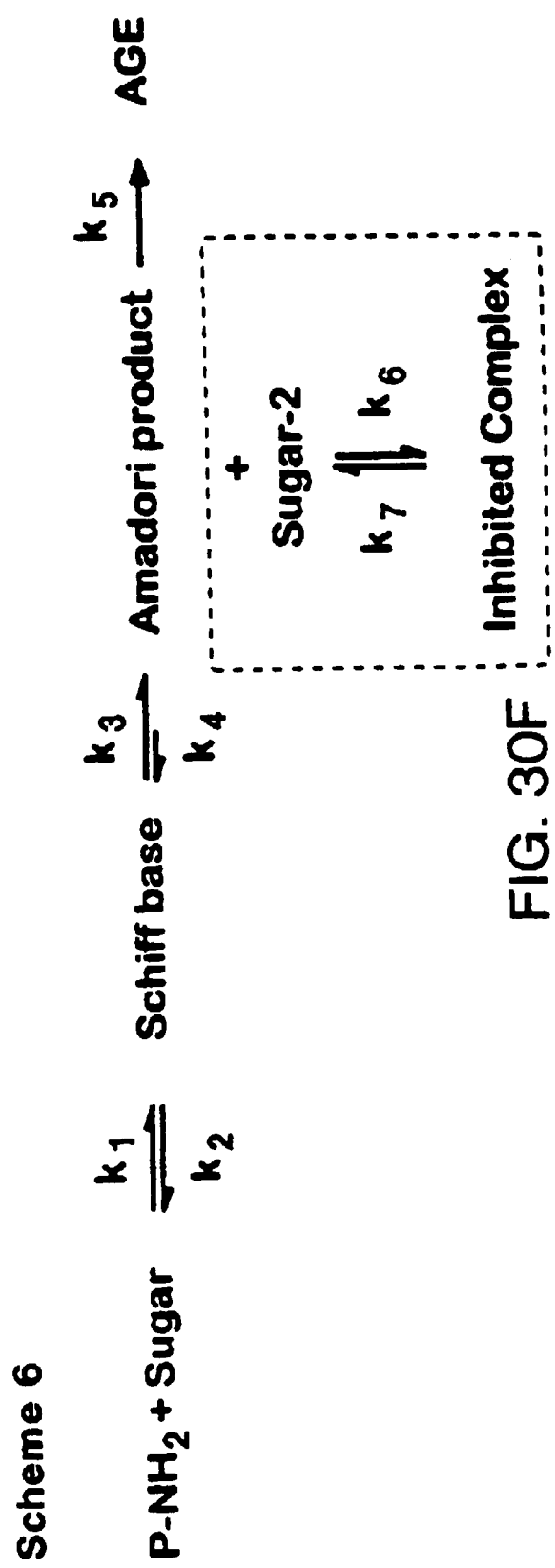
FIG. 30E
FIG. 30F

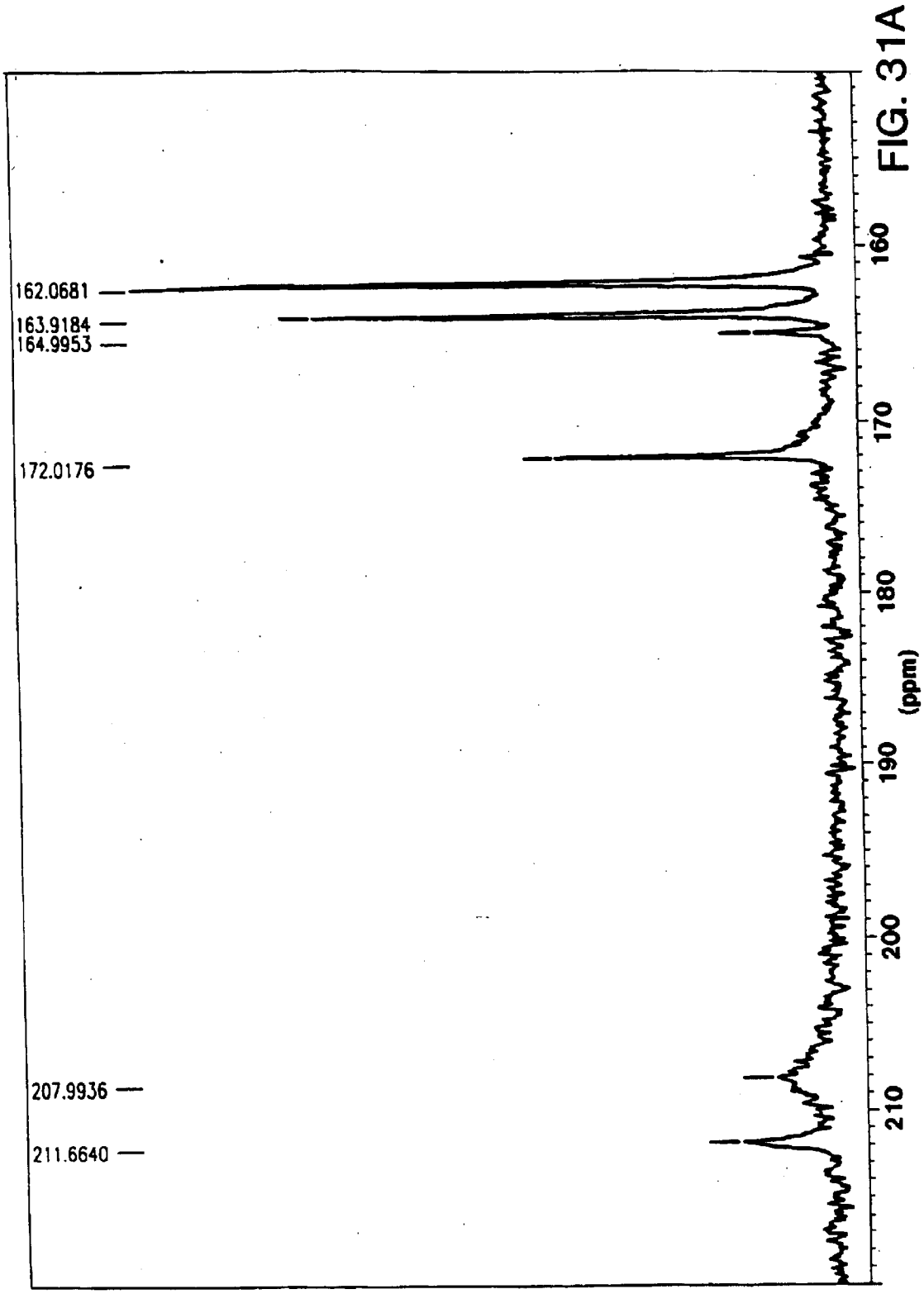

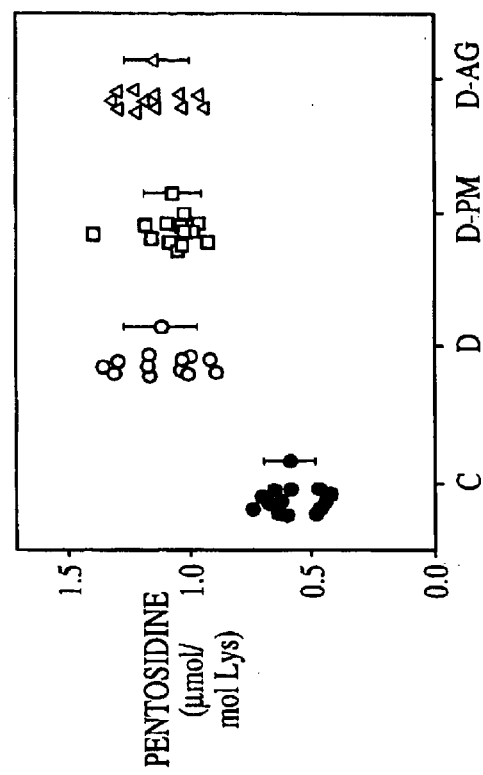
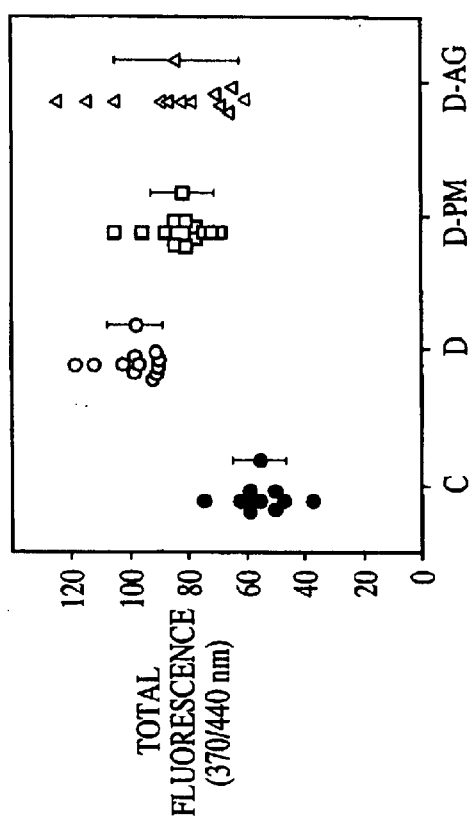
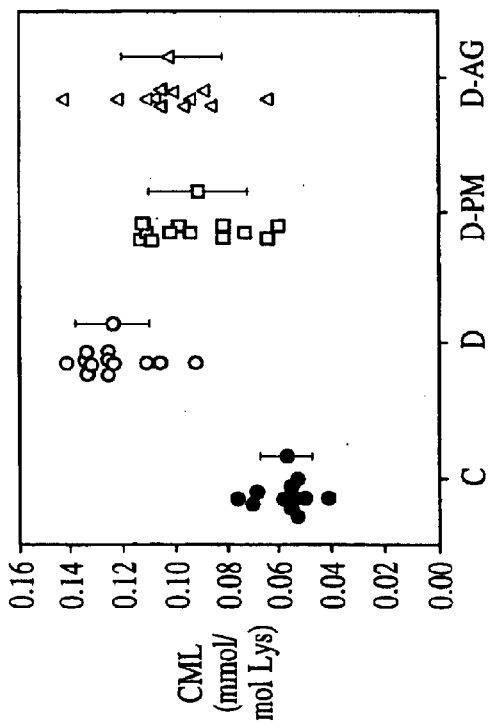
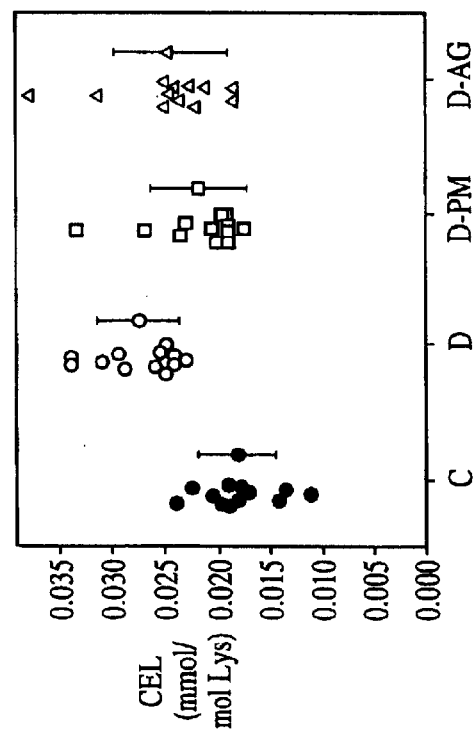
FIG. 45A
FIG. 45B
FIG. 45C
FIG. 45D

METHODS FOR INHIBITING DIABETIC COMPLICATIONS

CROSS REFERENCE

This application is a continuation-in-part of U.S. Patent Applications, Ser. No. 60/104,276 filed Oct. 14, 1998; Ser. No. 08/971,285 filed Nov. 17, 1997 and now U.S. Pat. No. 6,228,858 and Ser. No. 08/711,555, filed Sep. 10, 1996 now U.S. Pat. No. 5,985,857, and claims priority to U.S. Provisional Application for Patent Ser. No. 60/003,268, filed Aug. 28, 1995, the contents of each of which are hereby incorporated by reference in their entirety.

STATEMENT OF GOVERNMENT RIGHTS

Some of the work disclosed has been supported in part by NIH Grant DK 43507 1, therefore, the United States Government may have certain rights in the invention.

BACKGROUND OF THE INVENTION

The instant invention is in the field of Advanced Glycation End-products (AGEs), their formation, detection, identification, inhibition, and inhibitors thereof.

Protein Aging and Advanced Glycosylation End-products

Nonenzymatic glycation by glucose and other reducing sugars is an important post-translational modification of proteins that has been increasingly implicated in diverse pathologies. Irreversible nonenzymatic glycation and crosslinking through a slow, glucose-induced process may mediate many of the complications associated with diabetes. Chronic hyperglycemia associated with diabetes can cause chronic tissue damage which can lead to complications such as retinopathy, nephropathy, and atherosclerotic disease. (Cohen and Ziyadeh, 1996, *J. Amer. Soc. Nephrol.* 7:183–1190). It has been shown that the resulting chronic tissue damage associated with long-term diabetes mellitus arise in part from in situ immune complex formation by accumulated immunoglobulins and/or antigens bound to long-lived structural proteins that have undergone Advanced Glycosylation End-product (AGE) formation, via non-enzymatic glycosylation (Brownlee et al., 1983, *J. Exp. Med.* 158:1739–1744). The primary protein target is thought to be extra-cellular matrix associated collagen. Nonenzymatic glycation of proteins, lipids, and nucleic acids may play an important role in the natural processes of aging. Recently protein advanced glycation has been associated with β-amyloid deposits and formation of neurofibrillary tangles in Alzheimer disease, and possibly other neurodegenerative diseases involving amyloidosis (Colaco and Harrington, 1994, *NeuroReport* 5: 859–861). Glycated proteins have also been shown to be toxic, antigenic, and capable of triggering cellular injury responses after uptake by specific cellular receptors (see for example, Vlassara, Bucala & Striker, 1994, *Lab. Invest.* 70:138–151; Vlassara et al., 1994, *PNAS(USA)* 91:11704–11708; Daniels & Hauser, 1992, *Diabetes* 41:1415–1421; Brownlee, 1994, *Diabetes* 43:836–841; Cohen et al., 1994, *Kidney Int.* 45:1673–1679; Brett et al., 1993, *Am. J. Path.* 143:1699–1712; and Yan et al., 1994, *PNAS(USA)* 91:7787–7791).

The appearance of brown pigments during the cooking of food is a universally recognized phenomenon, the chemistry of which was first described by Maillard in 1912, and which has subsequently led to research into the concept of protein aging. It is known that stored and heat-treated foods undergo nonenzymatic browning that is characterized by crosslinked proteins which decreases their bioavailibility. It was found that this Maillard reaction occurred in vivo as well, when it was found that a glucose was attached via an Amadori rearrangement to the amino-terminal of the α-chain of hemoglobin.

The instant disclosure teaches previously unknown, and unpredicted mechanism of formation of post-Amadori advanced glycation end products (Maillard products; AGEs) and methods for identifying and characterizing effective inhibitors of post-Amadori AGE formation.

The instant disclosure demonstrates the unique isolation and kinetic characterization of a reactive protein intermediate competent in forming post-Amadori AGEs, and for the first time teaching methods which allow for the specific elucidation and rapid quantitative kinetic study of "late" stages of the protein glycation reaction.

In contrast to such "late" AGE formation, the "early" steps of the glycation reaction have been relatively well characterized and identified for several proteins (Harding, 1985, *Adv. Protein Chem.* 37:248–334; Monnier & Baynes eds., 1989, *The Maillard Reaction in Aging, Diabetes, and Nutrition* (Alan R. Liss, New York); Finot et al., 1990, eds. *The Maillard Reaction in Food Processing, Human Nutrition and Physiology* (Birkhauser Verlag, Basel)). Glycation reactions are known to be initiated by reversible Schiff-base (aldimine or ketimine) addition reactions with lysine side-chain ε-amino and terminal α-amino groups, followed by essentially irreversible Amadori rearrangements to yield ketoamine products e.g. 1-amino-1-deoxy-ketoses from the reaction of aldoses (Baynes et al., 1989, in *The Maillard Reaction in Aging, Diabetes, and Nutrition*, ed. Monnier and Baynes, (Alan R. Liss, New York, pp 43–67). Typically, sugars initially react in their open-chain (not the predominant pyranose and furanose structures) aldehydo or keto forms with lysine side chain ε-amino and terminal α-amino groups through reversible Schiff base condensation (Scheme I). The resulting aldimine or ketimine products then undergo Amadori rearrangements to give ketoamine Amadori products, i.e. 1-amino-1-deoxy-ketoses from the reaction of aldoses (Means & Chang, 1982, *Diabetes* 31, Suppl. 3:1–4; Harding, 1985, *Adv. Protein Chem.* 37:248–334). These Amadori products then undergo, over a period of weeks and months, slow and irreversible Maillard "browning" reactions, forming fluorescent and other products via rearrangement, dehydration, oxidative fragmentation, and cross-linking reactions. These post-Amadori reactions, (slow Maillard "browning" reactions), lead to poorly characterized Advanced Glycation End-products (AGEs).

As with Amadori and other glycation intermediaries, free glucose itself can undergo oxidative reactions that lead to the production of peroxide and highly reactive fragments like the dicarbonyls glyoxal and glycoaldehyde. Thus the elucidation of the mechanism of formation of a variety of AGEs has been extremely complex since most in vitro studies have been carried out at extremely high sugar concentrations.

In contrast to the relatively well characterized formation of these "early" products, there has been a clear lack of understanding of the mechanisms of forming the "late" Maillard products produced in post-Amadori reactions, because of their heterogeneity, long reaction times, and complexity. The lack of detailed information about the chemistry of the "late" Maillard reaction stimulated research to identify fluorescent AGE chromophores derived from the reaction of glucose with amino groups of polypeptides. One such chromophore, 2-(2-furoyl)-4(5)-(2-furanyl)-1H-imidazole (FFI) was identified after nonenzymatic browning of bovine serum albumin and polylysine with glucose, and postulated to be representative of the chromophore present in the intact polypeptides. (Pongor et al., 1984, *PNAS(USA)*

81:2684–2688). Later studies established FFI to be an artifact formed during acid hydrolysis for analysis.

A series of U.S. Patents have issued in the area of inhibition of protein glycosylation and cross-linking of protein sugar amines based upon the premise that the mechanism of such glycosylation and cross-linking occurs via saturated glycosylation and subsequent cross-linking of protein sugar amines via a single basic, and repeating reaction. These patents include U.S. Pat. Nos. 4,665,192; 5,017,696; 4,758,853; 4,908,446; 4,983,604; 5,140,048; 5,130,337; 5,262,152; 5,130,324; 5,272,165; 5,221,683; 5,258,381; 5,106,877; 5,128,360; 5,100,919; 5,254,593; 5,137,916; 5,272,176; 5,175,192; 5,218,001; 5,238,963; 5,358,960; 5,318,982; and 5,334,617. (All U.S. Patents cited are hereby incorporated by reference in their entirety).

The focus of these U.S. Patents, are a method for inhibition of AGE formation focused on the carbonyl moiety of the early glycosylation Amadori product, and in particular the most effective inhibition demonstrated teaches the use of exogenously administered aminoguanidine. The effectiveness of aminoguanidine as an inhibitor of AGE formation is currently being tested in clinical trials.

Inhibition of AGE formation has utility in the areas of, for example, food spoilage, animal protein aging, and personal hygiene such as combating the browning of teeth. Some notable, though quantitatively minor, advanced glycation end-products are pentosidine and $N^\epsilon$-carboxymethyllysine (Sell and Monnier, 1989, *J. Biol. Chem.* 264:21597–21602; Ahmed et al., 1986, *J. Biol. Chem.* 261:4889–4894).

The Amadori intermediary product and subsequent post-Amadori AGE formation, as taught by the instant invention, is not fully inhibited by reaction with aminoguanidine. Thus, the formation of post-Amadori AGEs as taught by the instant disclosure occurs via an important and unique reaction pathway that has not been previously shown, or even previously been possible to demonstrate in isolation. It is a highly desirable goal to have an efficient and effective method for identifying and characterizing effective post-Amadori AGE inhibitors of this "late" reaction. By providing efficient screening methods and model systems, combinatorial chemistry can be employed to screen candidate compounds effectively, and thereby greatly reducing time, cost, and effort in the eventual validation of inhibitor compounds. It would be very useful to have in vivo methods for modeling and studying the effects of post-Amadori AGE formation which would then allow for the efficient characterization of effective inhibitors.

Inhibitory compounds that are biodegradeble and/or naturally metabolized are more desirable for use as therapeutics than highly reactive compounds which may have toxic side effects, such as aminoguanidine.

SUMMARY OF THE INVENTION

In accordance with the present invention, a stable post-Amadori advanced glycation end-product (AGE) precursor has been identified which can then be used to rapidly complete the post-Amadori conversion into post-Amadori AGEs. This stable product is a presumed sugar saturated Amadori/Schiff base product produced by the further reaction of the early stage protein/sugar Amadori product with more sugar. In a preferred embodiment, this post-Amadori/Schiff base intermediary has been generated by the reaction of target protein with ribose sugar.

The instant invention provides for a method of generating stable protein-sugar AGE formation intermediary precursors via a novel method of high sugar inhibition. In a preferred embodiment the sugar used is ribose.

The instant invention provides for a method for identifying an effective inhibitor of the formation of late Maillard products comprising: generating stable protein-sugar post-Amadori advanced glycation end-product intermediates by incubating a protein with sugar at a sufficient concentration and for sufficient length of time to generate stable post-Amadori AGE intermediates; contacting said stable protein-sugar post-Amadori advanced glycation end-product intermediates with an inhibitor candidate; identifying effective inhibition by monitoring the formation of post-Amadori AGEs after release of the stable protein-sugar post-Amadori advanced glycation end-product intermediates from sugar induced equilibrium. Appropriate sugars include, and are not limited to ribose, lyxose, xylose, and arabinose. It is believed that certain conditions will also allow for use of glucose and other sugars. In a preferred embodiment the sugar used is ribose.

The instant invention teaches that an effective inhibitor of post-Amadori AGE formation via "late" reactions can be identified and characterized by the ability to inhibit the formation of post-Amadori AGE endproducts in an assay comprising; generating stable protein-sugar post-Amadori advanced glycation end-product intermediates by incubating a protein with sugar at a sufficient concentration and for sufficient length of time to generate stable post-Amadori AGE intermediates; contacting said stable protein-sugar post-Amadori advanced glycation end-product intermediates with an inhibitor candidate; identifying effective inhibition by monitoring the formation of post-Amadori AGEs after release of the stable protein-sugar post-Amadori advanced glycation end-product intermediates from sugar induced equilibrium. In a preferred embodiment the assay uses ribose.

Thus the methods of the instant invention allow for the rapid screening of candidate post-Amadori AGE formation inhibitors for effectiveness, greatly reducing the cost and amount of work required for the development of effective small molecule inhibitors of post-Amadori AGE formation. The instant invention teaches that effective inhibitors of post-Amadori "late" reactions of AGE formation include derivatives of vitamin B6 and vitamin $B_1$, in the preferred embodiment the specific species being pyridoxamine and thiamine pyrophosphate.

The instant invention teaches new methods for rapidly inducing diabetes like pathologies in rats comprising administering ribose to the subject animal. Further provided for is the use of identified inhibitors pyridoxamine and thiamine pyrophosphate in vivo to inhibit post-Amadori AGE induced pathologies.

The present invention encompasses compounds for use in the inhibition of AGE formation and post-Amadori AGE pathologies, and pharmaceutical compositions containing

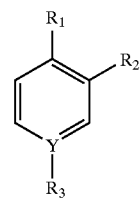

such compounds of the general formula:
Formula I
wherein $R_1$ is $CH_2NH_2$, $CH_2SH$, $COOH$, $CH_2CH_2NH_2$, $CH_2CH_2SH$, or $CH_2COOH$;
$R_2$ is $OH$, $SH$ or $NH_2$;

Y is N or C, such that when Y is N $R_3$ is nothing, and when Y is C, $R_3$ is $NO_2$ or another electron withdrawing group; and salts thereof.

The present invention also encompasses compounds of the general formula

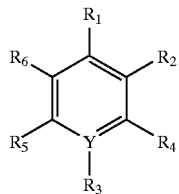

Formula II wherein $R_1$ is $CH_2NH_2$, $CH_2SH$, COOH, $CH_2CH_2NH_2$, $CH_2CH_2SH$, or $CH_2COOH$;

$R_2$ and $R_6$ is H, OH, SH, $NH_2$, C 1–18 alkyl, alkoxy or alkene;

$R_4$ and $R_5$ are H, C 1–18 alkyl, alkoxy or alkene;

Y is N or C, such that when Y is N $R_3$ is nothing, and when Y is C, $R_3$ is $NO_2$ or another electron withdrawing group, and salts thereof In a preferred embodiment at least one of $R_4$, $R_5$ and $R_6$ are H.

In addition, the instant invention also envisions compounds of the formulas

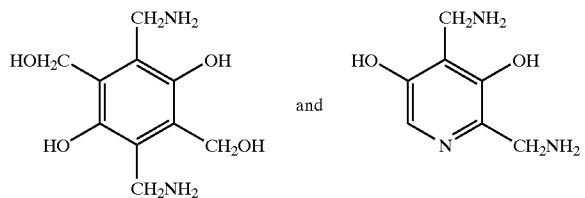

The compounds of the present invention can embody one or more electron withdrawing groups, such as and not limited to —$NH_2$, —NHR, —$NR_2$, —OH, —$OCH_3$, —OCR, and —NH—$COCH_3$ here R is C 1–6 alkyl.

The instant invention encompasses pharmaceutical compositions which comprise one or ore of the compounds of the present invention, or salts thereof, in a suitable carrier. The instant invention encompasses methods for administering pharmaceuticals of the present invention for therapeutic intervention of pathologies which are related to AGE formation in vivo. In one preferred embodiment of the present invention the AGE related pathology to be treated is related to diabetic nephropathy.

The instant invention also teaches methods to treat or prevent diabetic nephropathy, oxidative stress, and protein crosslinking, comprising administering an amount effective of one of the compounds of the invention to treat or prevent the disorder.

BRIEF DESCRIPTION OF THE DRAWINGS

FIG. 2C thiamine (T)

FIG. 7 are two graphs showing a comparison of uninterrupted and interrupted glycation of RNase by glucose (7B) and ribose (7A), as detected by ELISA.

FIG. 8 are two graphs showing kinetics of pentosidine fluorescence (arbitrary units) increase during uninterrupted and interrupted ribose glycation of RNase.

FIG. 10 are graphs of Post-Amadori inhibition of AGE formation by ribose.

FIG. 13 is a series of graphs depicting the effect of vitamin $B_6$ derivatives on AGE formation during uninterrupted glycation of ribonuclease A (RNase A) by ribose.

FIG. 14 is a series of graphs depicting the effect of vitamin $B_1$ derivatives and aminoguanidine (AG) on AGE formation during uninterrupted glycation of ribonuclease A (RNase A) by ribose.

FIG. 15 is a series of graphs depicting the effect of vitamin $B_6$ derivatives on AGE formation during uninterrupted glycation of bovine serum albumin (BSA) by ribose.

FIG. 16 is a series of graphs depicting the effect of vitamin $B_1$ derivatives and aminoguanidine (AG) on AGE formation during uninterrupted glycation of bovine serum albumin (BSA) by ribose.

FIG. 17 is a series of graphs depicting the effect of vitamin B6 derivatives on AGE formation during uninterrupted glycation of human methemoglobin (Hb) by ribose.

FIG. 18 is a series of graphs depicting the effect of vitamin B6 derivatives on post-Amadori AGE formation after interrupted glycation by ribose.

FIG. 30E depicts Scheme 5, kinetics representation of AGE formation. FIG. 30F depicts Scheme 6, kinetics representation of AGE formation and intermediate formation.

FIG. 45: Effect of diabetes and drug treatment on levels of AGEs and fluorescence in skin collagen. Skin collagen was analyzed for concentrations of CML (A), CEL (B) pentosidine (C), and fluorescence (D) in non-diabetic control (●, C), diabetic control (○, D), diabetic PD-treated (□, D-PD), and diabetic AG-treated (△, D-AG). For CML: D vs. C, $p<0.0001$; D-PM vs. D, $p=0.006$; D-AG vs. D, $p=0.025$. For CEL: D vs. C, $p<0.0001$; D-PD vs. D, $p=0.014$; D-AG vs. D, $p=0.022$. For pentosidine: D vs. C and both drug treated groups, $P<0.0001$. For fluorescence: D vs. C, $p<0.0001$; D-PM vs. D, $p=0.0005$; D-AG vs. D, $p=0.026$.

DETAILED DESCRIPTION

Animal Models for Protein Aging

Figure 1A:
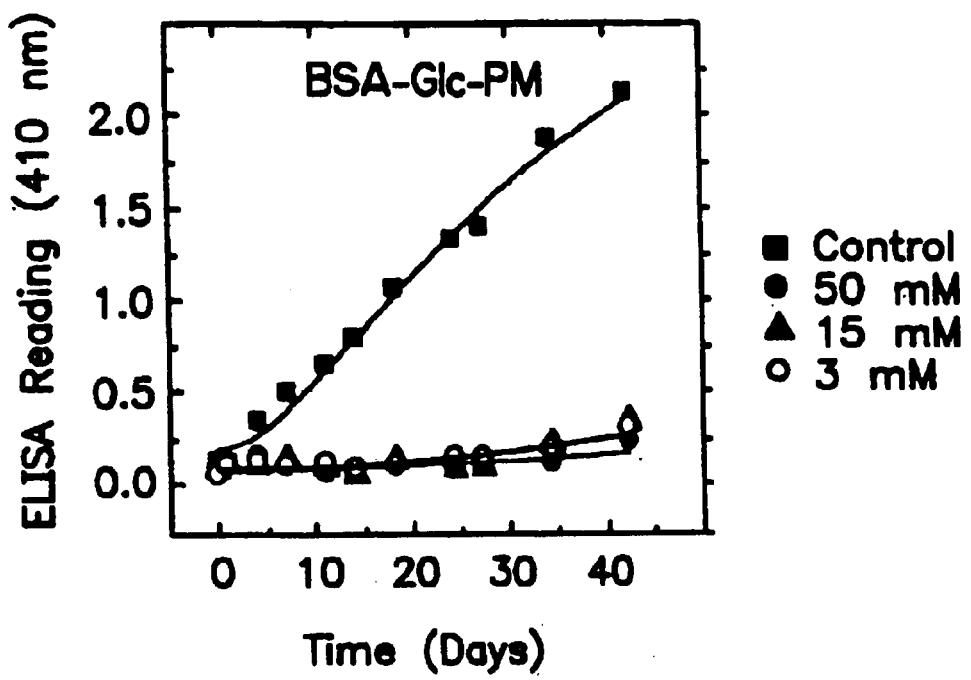
FIG. 1A Pyridoxamine (PM)
Figure 1B:
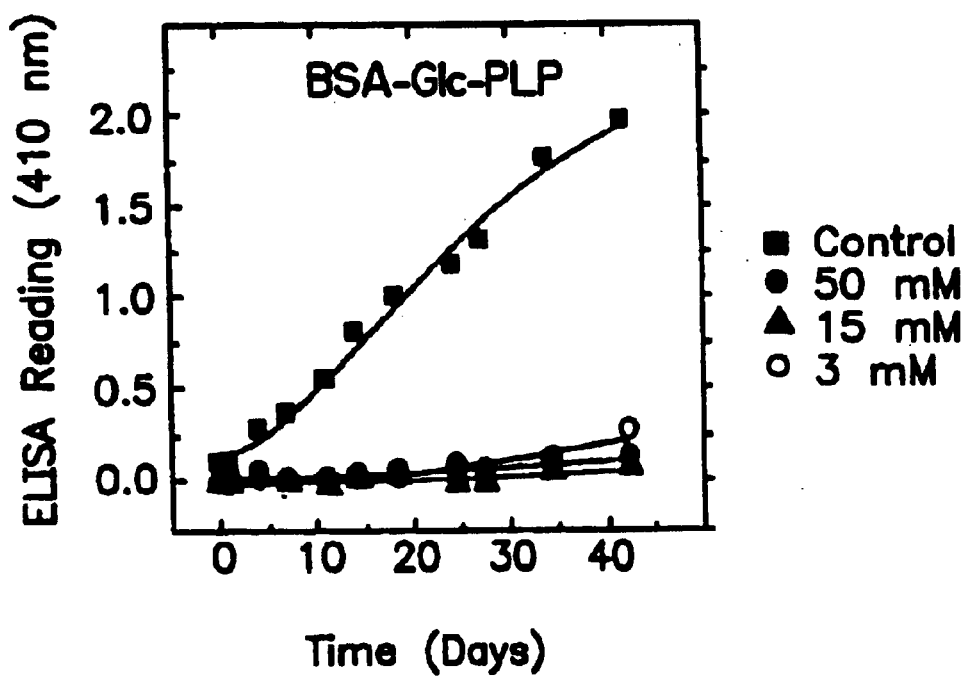
FIG. 1B pyridoxal phosphate (PLP)
Figure 1C:
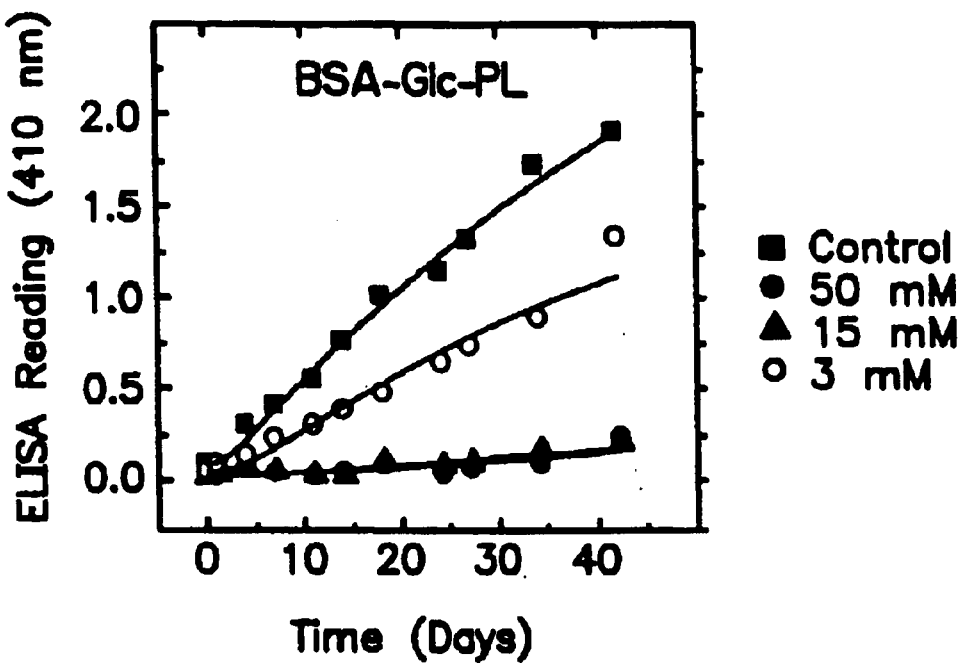
FIG. 1C pyridoxal (PL)
Figure 1D:
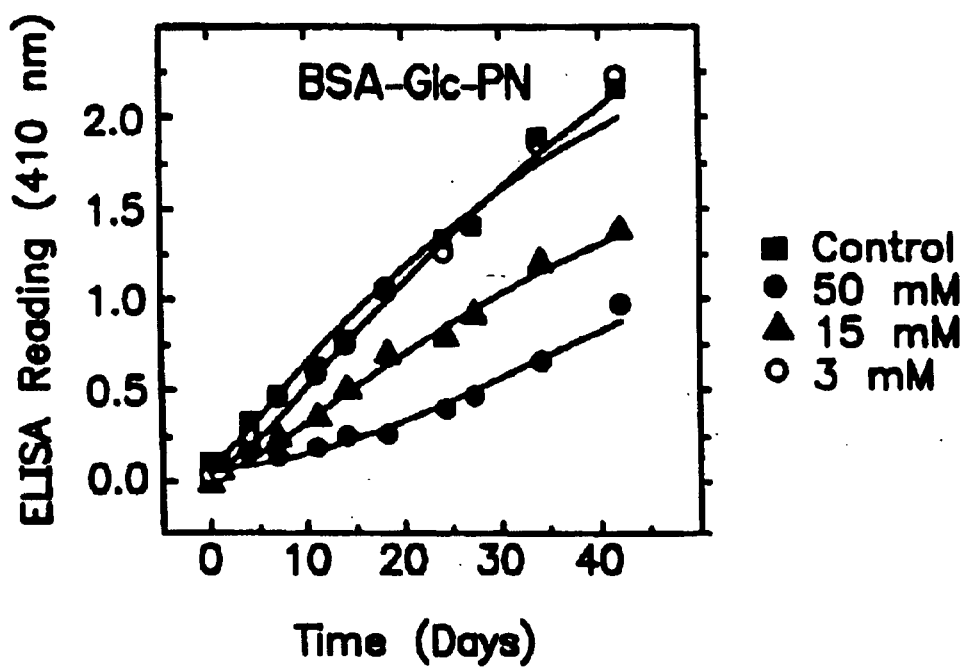
FIG. 1D pyridoxine (PN).
Figure 2A:
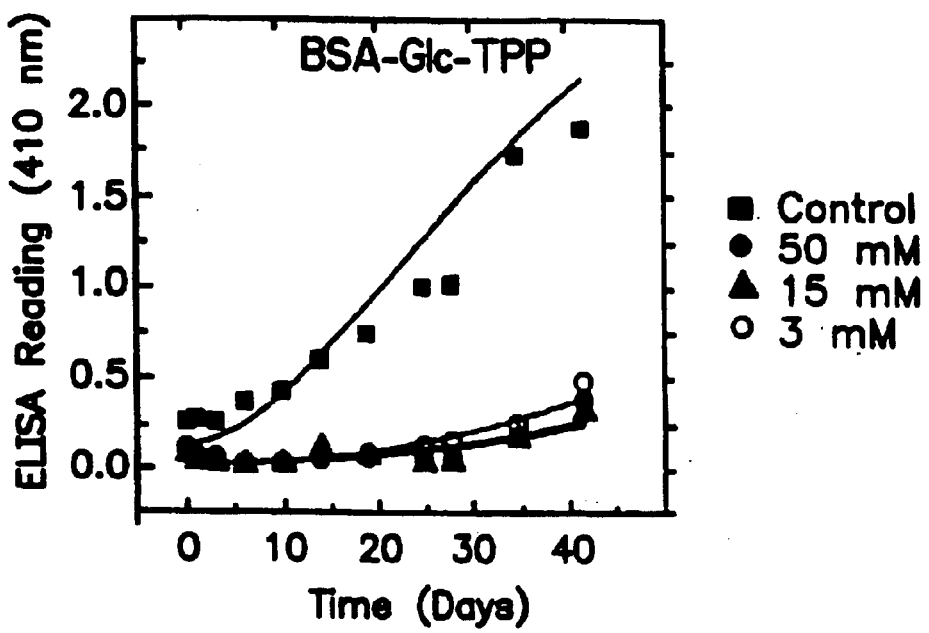
FIG. 2A Thiamine pyrophosphate (TPP)
Figure 2B:
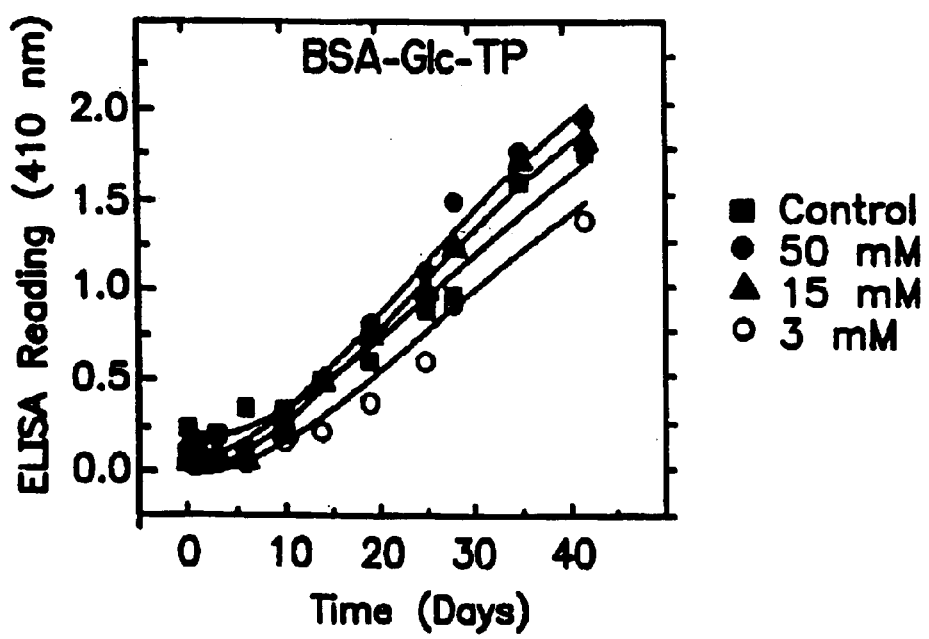
FIG. 2B thiamine monophosphate (TP)
Figure 2C:
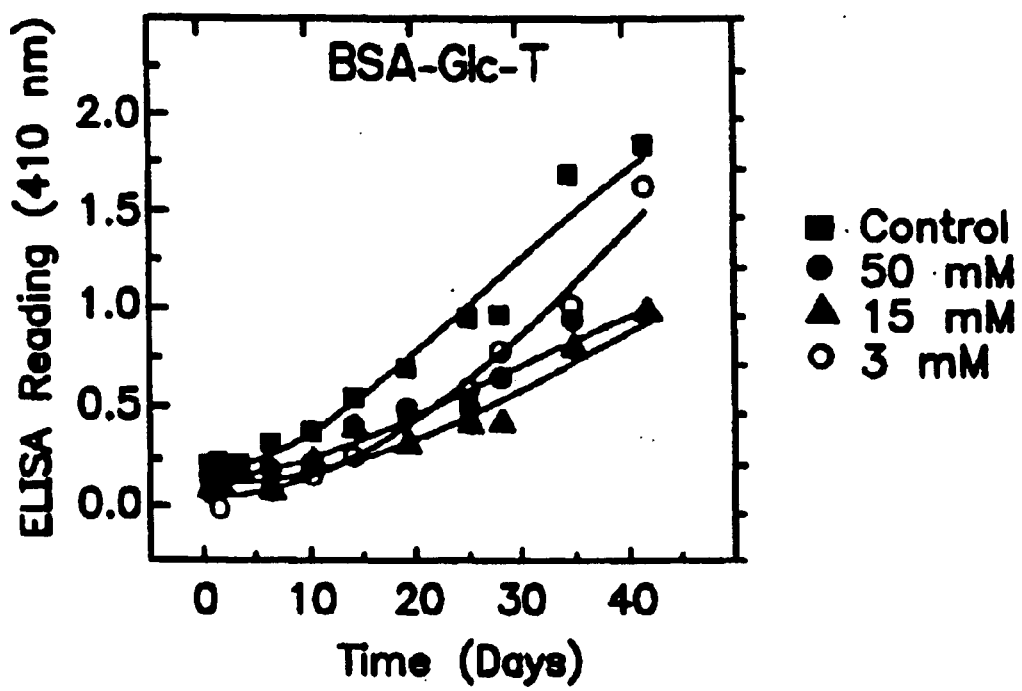
FIG. 2C thiamine (T)
Figure 2D:
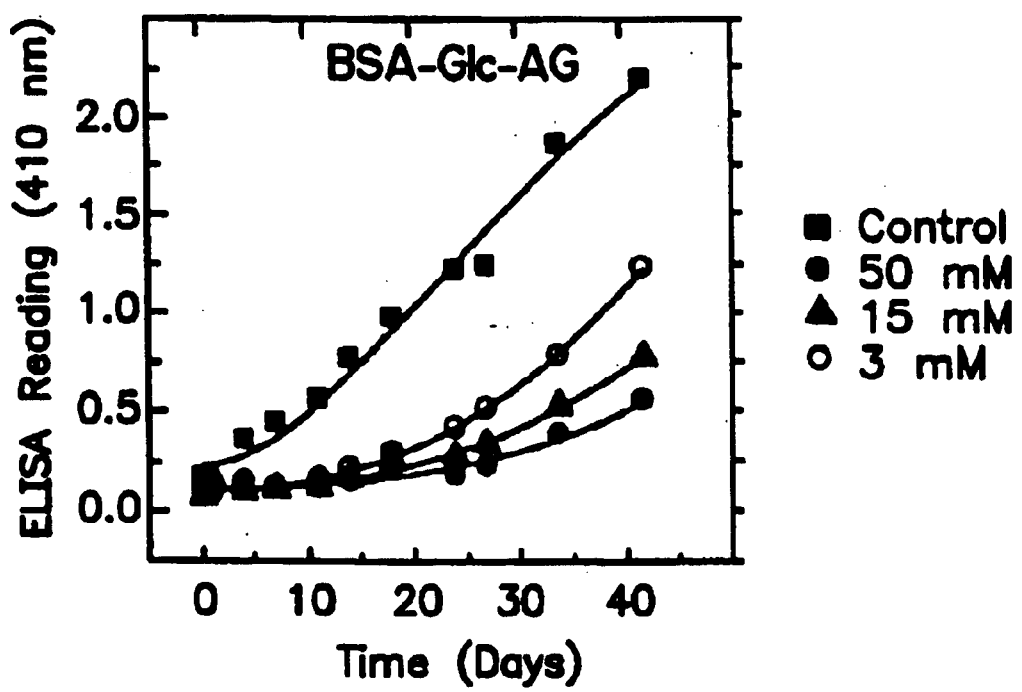
FIG. 2D aminoguanidine (AG).
Figure 3A:
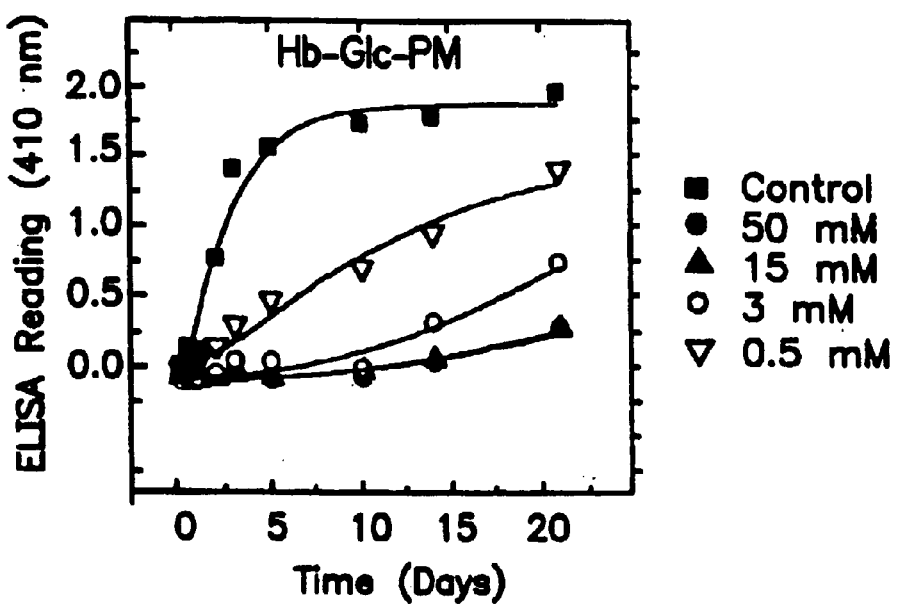
FIG. 3A Pyridoxamine (PM)
Figure 3B:
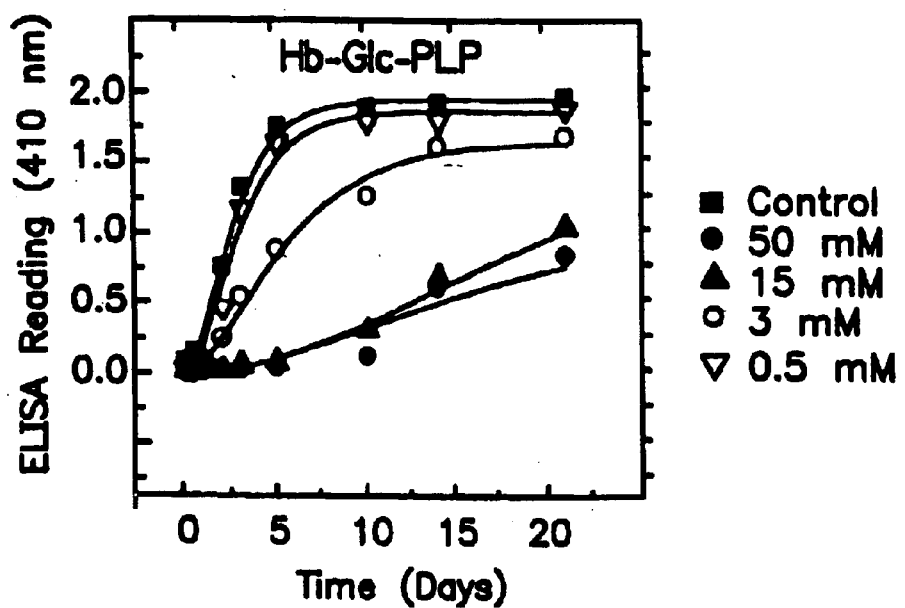
FIG. 3B pyridoxal phosphate (PLP)
Figure 3C:
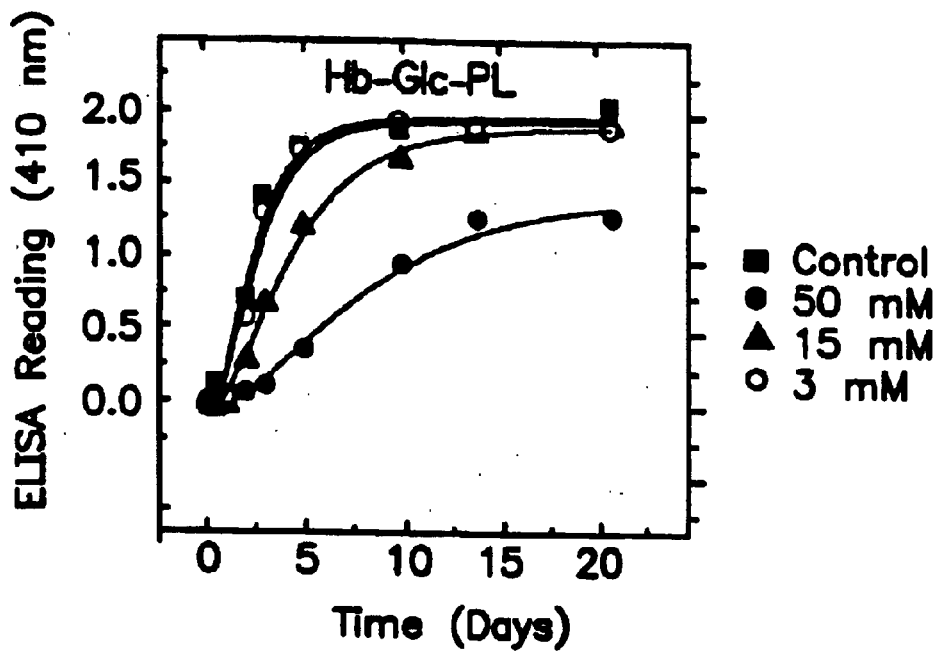
FIG. 3C pyridoxal (PL)
Figure 3D:
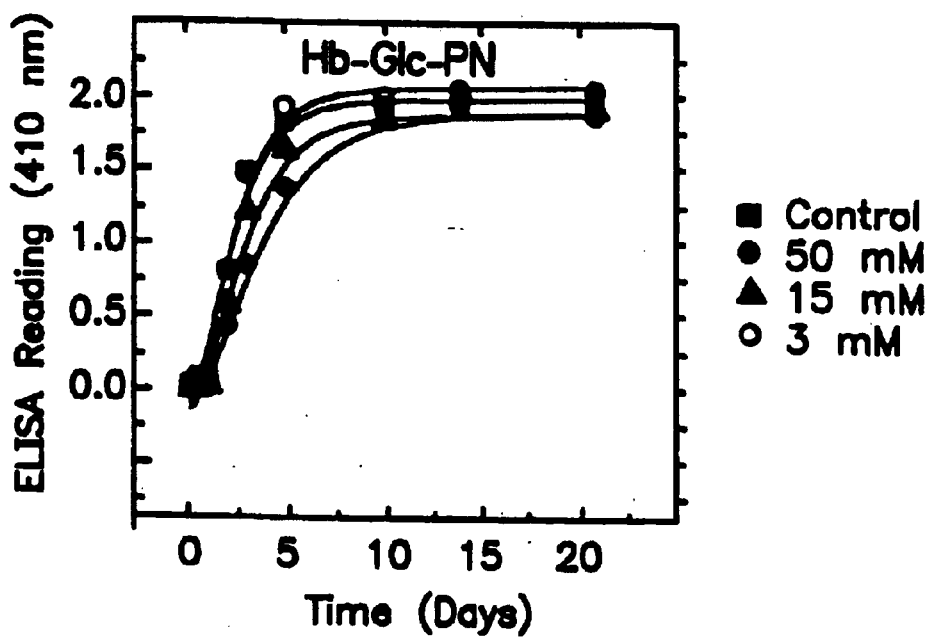
FIG. 3D pyridoxine (PN).

Alloxan induced diabetic Lewis rats have been used as a model for protein aging to demonstrate the in vivo effectiveness of inhibitors of AGE formation. The correlation being demonstrated is between inhibition of late diabetes related pathology and effective inhibition of AGE formation (Brownlee, Cerami, and Vlassara, 1988, *New Eng. J Med.* 318(20):1315–1321). Streptozotocin induction of diabetes in Lewis rats, New Zealand White rabbits with induced diabetes, and genetically diabetic BB/Worcester rats have also been utilized, as described in, for example, U.S. Pat. No. 5,334,617 (incorporated by reference). A major problem with these model systems is the long time period required to demonstrate AGE related injury, and thus to test compounds for AGE inhibition. For example, 16 weeks of treatment was required for the rat studies described in U.S. Pat. No. 5,334,617, and 12 weeks for the rabbit studies. Thus it would be highly desirable and useful to have a model system for AGE related diabetic pathology that will manifest in a shorter time period, allowing for more efficient and expeditious determination of AGE related injury and the effectiveness of inhibitors of post-Amadori AGE formation.

Antibodies to AGEs

An important tool for studying AGE formation is the use of polyclonal and monoclonal antibodies that are specific for AGEs elicited by the reaction of several sugars with a variety of target proteins. The antibodies are screened for resultant specificity for AGEs that is independent of the nature of the protein component of the AGE (Nakayama et al., 1989, *Biochem. Biophys. Res. Comm.* 162: 740–745; Nakayama et al., 1991, *J. Immunol. Methods* 140: 119–125; Horiuchi et al., 1991, *J. Biol. Chem.* 266: 7329–7332; Araki et al., 1992, *J. Biol. Chem.* 267: 10211–10214; Makita et al., 1992, *J. Biol. Chem.* 267: 5133–5138). Such antibodies have been used to monitor AGE formation in vivo and in vitro.

Thiamine—Vitamin $B_1$

The first member of the Vitamin B complex to be identified, thiamine is practically devoid of pharmacodynamic actions when given in usual therapeutic doses; and even large doses were not known to have any effects. Thiamine pyrophosphate is the physiologically active form of thiamine, and it functions mainly in carbohydrate metabolism as a coenzyme in the decarboxylation of α-keto acids. Tablets of thiamine hydrochloride are available in amounts ranging from 5 to 500 mg each. Thiamine hydrochloride injection solutions are available which contain 100 to 200 mg/ml.

For treating thiamine deficiency, intravenous doses of as high as 100 mg/L of parenteral fluid are commonly used, with the typical dose of 50 to 100 mg being administered. GI absorption of thiamine is believed to be limited to 8 to 15 mg per day, but may be exceed by oral administration in divided doses with food.

Repeated administration of glucose may precipitate thiamine deficiency in under nourished patients, and this has been noted during the correction of hyperglycemia.

Surprisingly, the instant invention has found, as shown by in vitro testing, that administration of thiamine pyrophosphate at levels above what is normally found in the human body or administered for dietary therapy, is an effective inhibitor of post-Amadori antigenic AGE formation, and that this inhibition is more complete than that possible by the administration of aminoguanidine.

Pyridoxine—Vitamin $B_6$

Vitamin $B_6$ is typically available in the form of pyridoxine hydrochloride in over-the-counter preparations available from many sources. For example Beach pharmaceuticals Beelith Tablets contain 25 mg of pyridoxine hydrochloride that is equivalent to 20 mg of $B_6$, other preparations include Marlyn Heath Care Marlyn Formula 50 which contain 1 mg of pyridoxine HCl and Marlyn Formula 50 Mega Forte which contains 6 mg of pyridoxine HCl, Wyeth-Ayerst Stuart Prenatal® tablets which contain 2.6 mg pyridoxine HCl, J&J-Merck Corp. Stuart Formula® tablets contain 2 mg of pyridoxine HCl, and the CIBA Consumer Sunkist Children's chewable multivitamins which contain 1.05 mg of pyridoxine HCl, 150% of the U.S. RDA for children 2 to 4 years of age, and 53% of the U.S. RDA for children over 4 years of age and adults. (Physician's Desk Reference for nonprescription drugs, 14th edition (Medical Economics Data Production Co., Montvale, N.J., 1993).

There are three related forms of pyridoxine, which differ in the nature of the substitution on the carbon atom in position 4 of the pyridine nucleus: pyridoxine is a primary alcohol, pyridoxal is the corresponding aldehyde, and pyridoxamine contains an aminomethyl group at this position. Each of these three forms can be utilized by mammals after conversion by the liver into pyridoxal-5'-phosphate, the active form of the vitamin. It has long been believed that these three forms are equivalent in biological properties, and have been treated as equivalent forms of vitamin $B_6$ by the art. The Council on Pharmacy and Chemistry has assigned the name pyridoxine to the vitamin.

The most active antimetabolite to pyridoxine is 4-deoxypyridoxine, for which the antimetabolite activity has been attributed to the formation in vivo of 4-deoxypyridoxine-5-phosphate, a competitive inhibitor of several pyridoxal phosphate-dependent enzymes. The pharmacological actions of pyridoxine are limited, as it elicits no outstanding pharmacodynamic actions after either oral or intravenous administration, and it has low acute toxicity, being water soluble. It has been suggested that neurotoxicity may develop after prolonged ingestion of as little as 200 mg of pyridoxine per day. Physiologically, as a coenzyme, pyridoxine phosphate is involved in several metabolic transformations of amino acids including decarboxylation, transamination, and racemization, as well as in enzymatic steps in the metabolism of sulfur-containing and hydroxyamino acids. In the case of transamination, pyridoxal phosphate is aminated to pyridoxamine phosphate by the donor amino acid, and the bound pyridoxamine phosphate is then deaminated to pyridoxal phosphate by the acceptor α-keto acid. Thus vitamin B complex is known to be a necessary dietary supplement involved in specific breakdown of amino acids. For a general review of the vitamin B complex see *The Pharmacological Basis of Therapeutics*, 8th edition, ed. Gilman, Rall, Nies, and Taylor (Pergamon Press, New York, 1990, pp. 1293–4; pp. 1523–1540).

Surprisingly, the instant invention has discovered that effective dosages of the metabolically transitory pyridoxal amine form of vitamin $B_6$ (pyridoxamine), at levels above what is normally found in the human body, is an effective inhibitor of post-Amadori antigenic AGE formation, and that this inhibition may be more complete than that possible by the administration of aminoguanidine.

Formation of Stable Amadori/Schiff Base Intermediary

The typical study of the reaction of a protein with glucose to form AGEs has been by ELISA using antibodies directed towards antigenic AGEs, and the detection of the production of an acid-stable fluorescent AGE, pentosidine, by HPLC following acid hydrolysis. Glycation of target proteins (i.e. BSA or RNase A) with glucose and ribose were compared by monitoring ELISA reactivity of polyclonal rabbit anti-Glucose-AGE-RNase and anti-Glucose-AGE-BSA antibodies. The antigen was generated by reacting 1 M glucose with RNase for 60 days and BSA for 90 days. The antibodies (R618 and R479) were screened and showed reactivity with only AGEs and not the protein, except for the carrier immunogen BSA.

EXAMPLE 1

Thiamine Pyrophosphate and Pyridoxamine Inhibit the Formation of Antigenic Advanced Glyeation End-Products from Glucose: Comparison with Aminoguanidine Some $B_6$ vitamers, especially pyridoxal phosphate (PLP), have been previously proposed to act as "competitive inhibitors" of early glycation, since as aldehydes they themselves can form Schiff bases adducts with protein amino groups (Khatami et al., 1988, *Life Sciences* 43:1725–1731) and thus limit the amount of amines available for glucose attachment. However, effectiveness in limiting initial sugar attachment is not a predictor of inhibition of the conversion of any Amadori products formed to AGEs. The instant invention describes inhibitors of "late" glycation reactions as indicated by their effects on the is vitro formation of antigenic AGEs (Booth et al., 1996, *Biochem. Biophys. Res. Coin.* 220:113–119).

Chemicals Bovine pancreatic ribonuclease A (RNase) was chromatographically pure, aggregate-free grade from Worthington Biochemicals. Bovine Serum albumin (BSA; fraction V, fatty-acid free), human methemoglobin (Hb), D-glucose, pyridoxine, pyridoxal, pyridoxal 5' phosphate, pyridoxamine, thiamine, thiamine monophosphate, thiamine pyrophosphate, and goat alkaline phosphatase-conjugated anti-rabbit IgG were all from Sigma Chemicals. Aminoguanidine hydrochloride was purchased from Aldrich Chemicals.

Uninterrupted Glycation with Glucose Bovine serum albumin, ribonuclease A, and human hemoglobin were incubated with glucose at 37° C. in 0.4 M sodium phosphate buffer of pH 7.5 containing 0.02% sodium azide. The protein, glucose (at 1.0 M), and prospective inhibitors (at 0.5, 3, 15 and 50 mM) were introduced into the incubation mixture simultaneously. Solutions were kept in the dark in capped tubes. Aliquots were taken and immediately frozen until analyzed by ELISA at the conclusion of the reaction. The incubations were for 3 weeks (Hb) or 6 weeks (RNase, BSA).

Preparation of Polyclonal Antibodies to AGE Proteins

Immunogen preparation followed earlier protocols (Nakayama et al., 1989, *Biochem. Biophys. Res. Comm.* 162:740–745; Horiuchi et al., 1991, *J. Biol. Chem.* 266:7329–7332; Makita et al., 1992, *J. Biol. Chem.* 267:5133–5138). Briefly, immunogen was prepared by glycation of BSA (R479 antibodies) or RNase (R618 antibodies) at 1.6 g protein in 15 ml for 60–90 days using 1.5 M glucose in 0.4 M sodium phosphate buffer of pH 7.5 containing 0.05% sodium azide at pH 7.4 and 37° C. New Zealand white rabbit males of 8–12 weeks were immunized by subcutaneous administration of a 1 ml solution containing 1 mg/ml of glycated protein in Freund's adjuvant. The primary injection used the complete adjuvant and three boosters were made at three week intervals with Freund's incomplete adjuvant. Rabbits were bled three weeks after the last booster. The serum was collected by centrifugation of clotted whole blood. The antibodies are AGE-specific, being unreactive with either native proteins (except for the carrier) or with Amadori intermediates. The polyclonal anti-AGE antibodies have proven to be a sensitive and valuable analytical tool for the study of "late" AGE formation in vitro and in vivo. The nature of the dominant antigenic AGE epitope or hapten remains in doubt, although recently it has been proposed that the protein glycoxidation product carboxymethyl lysine (CML) may be a dominant antigen of some antibodies (Reddy et al., 1995, *Biochem.* 34:10872–10878). Earlier studies have failed to reveal ELISA reactivity with model CmL compounds (Makita et al., 1992, *J. Biol. Chem.* 267:5133–5138).

ELISA detection of AGE products. The general method of Engvall (1981, *Methods Enzymol.* 70:419–439) was used to perform the ELISA. Typically, glycated protein samples were diluted to approximately 1.5 ug/ml in 0.1 M sodium carbonate buffer of pH 9.5 to 9.7. The protein was coated overnight at room temperature onto 96-well polystyrene plates by pippetting 200 ul of the protein solution in each well (0.3 ug/well). After coating, the protein was washed from the wells with a saline solution containing 0.05% Tween-20. The wells were then blocked with 200 ul of 1% casein in carbonate buffer for 2 h at 37° C. followed by washing. Rabbit anti-AGE antibodies were diluted at a titer of about 1:350 in incubation buffer, and incubated for 1 h at 37° C., followed by washing. In order to minimize background readings, antibodies R479 used to detect glycated RNase were raised against glycated BSA, and antibodies R618 used to detect glycated BSA and glycated Hb were raised against glycated RNase. An alkaline phosphatase-conjugated antibody to rabbit IgG was then added as the secondary antibody at a titer of 1:2000 or 1:2500 (depending on lot) and incubated for 1 h at 37° C., followed by washing. The p-nitrophenylphosphate substrate solution was then added (200 ul/well) to the plates, with the absorbance of the released p-nitrophenolate being monitored at 410 nm with a Dynatech MR 4000 microplate reader.

Controls containing unmodified protein were routinely included, and their readings were subtracted, the corrections usually being negligible. The validity of the use of the ELISA method in quantitatively studying the kinetics of AGE formation depends on the linearity of the assay (Kemeny & Challacombe, 1988, *ELISA and Other Solid Phase Immunoassays,* John Wiley & Sons, Chichester, U.K.). Control experiments were carried out, for example, demonstrating that the linear range for RNase is below a coating concentration of about 0.2–0.3 mg/well.

Results

Figures 1, 32A:
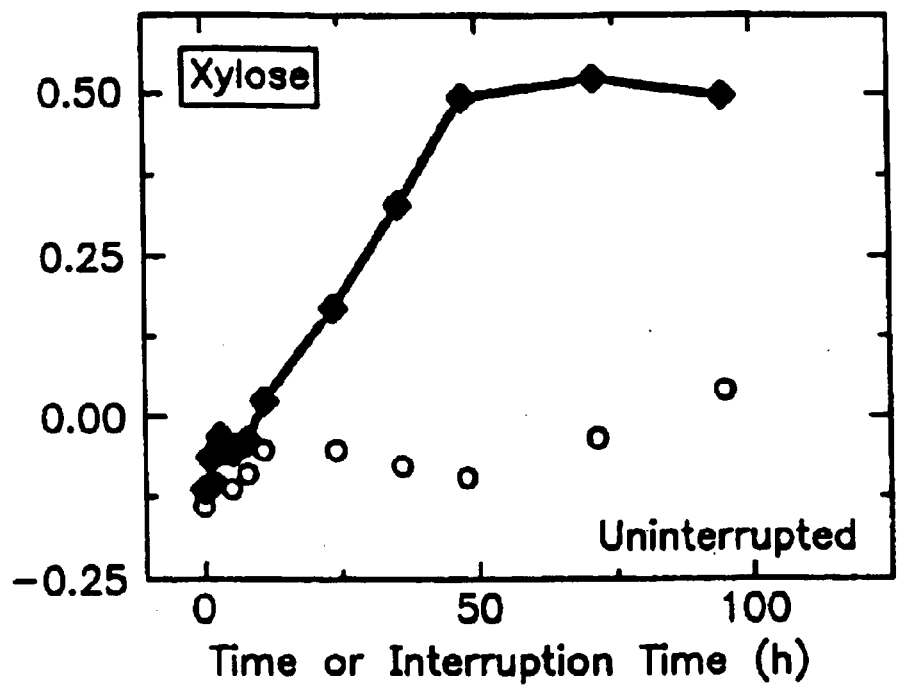
FIG. 1 is a series of graphs depicting the effect of vitamin $B_6$ derivatives on AGE formation in bovine serum albumin (BSA).
Figures 2, 32A:
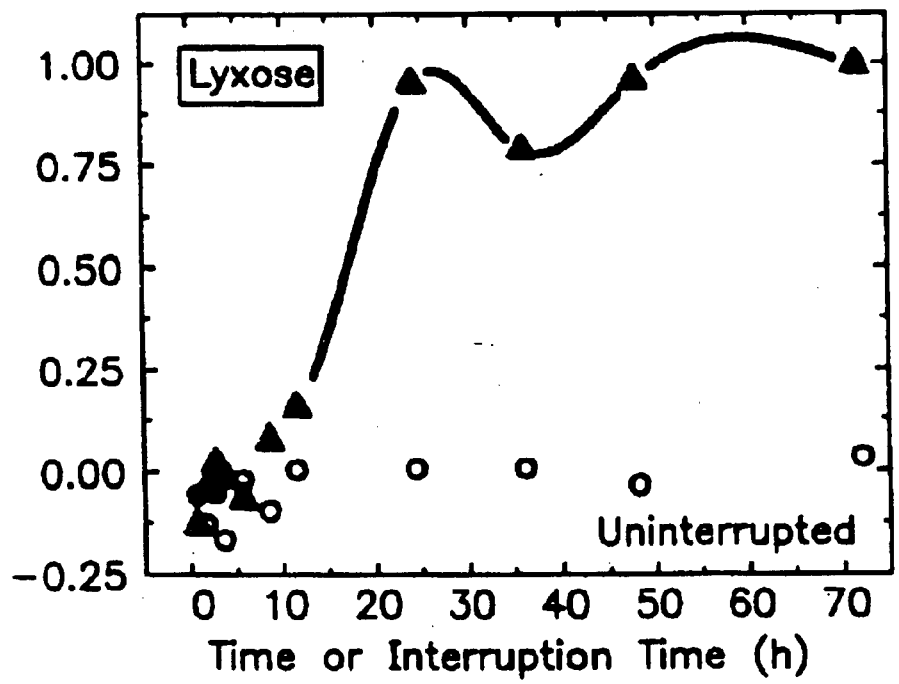
FIG. 2 is a series of graphs depicting the effect of vitamin $B_1$ derivatives and aminoguanidine (AG) on AGE formation in bovine serum albumin.
Figures 3, 32A:
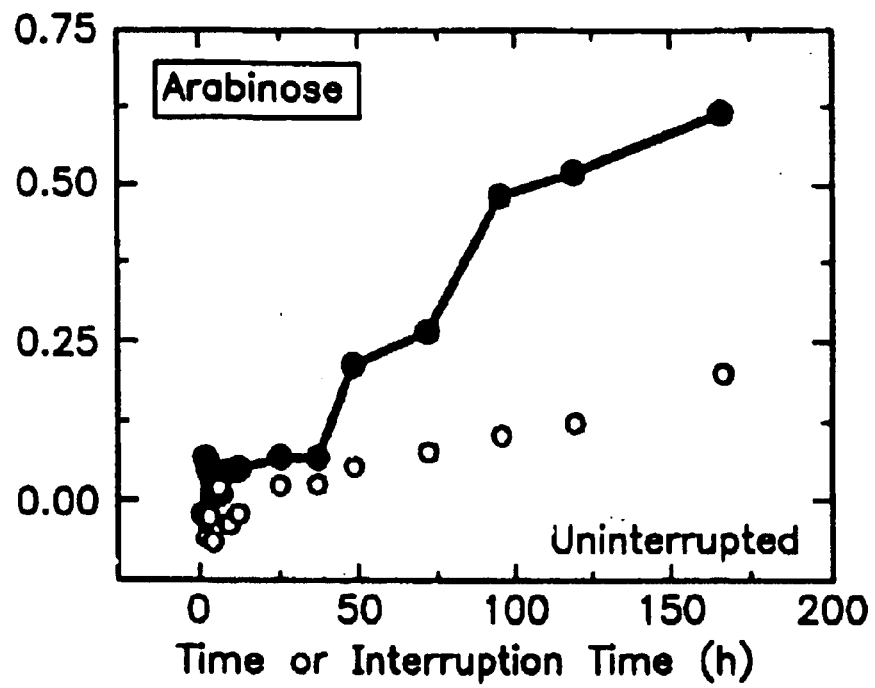
FIG. 3 is a series of graphs depicting the effect of vitamin $B_6$ derivatives on AGE formation in human methemoglobin (Hb).
Figures 4, 32A:
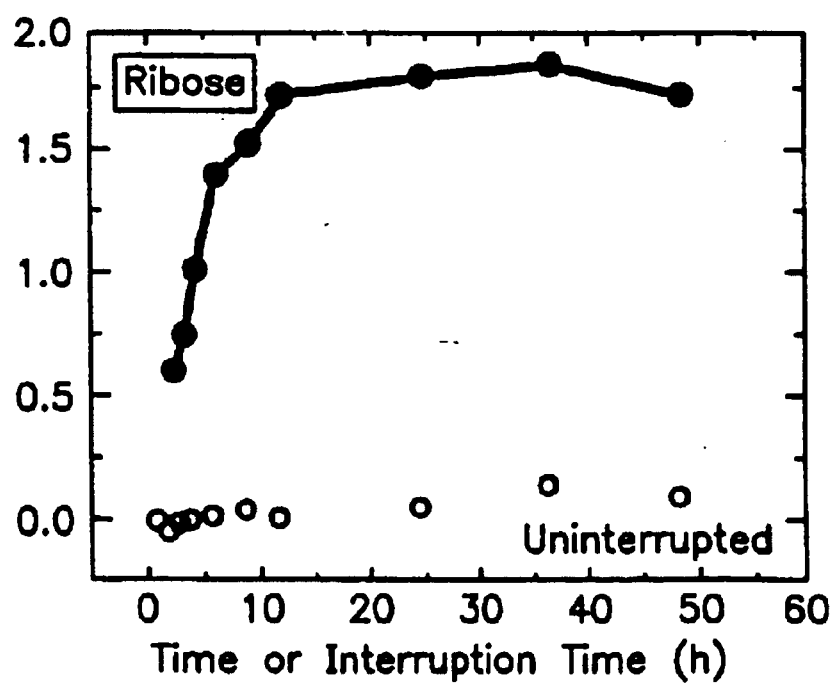
Figure 32B:
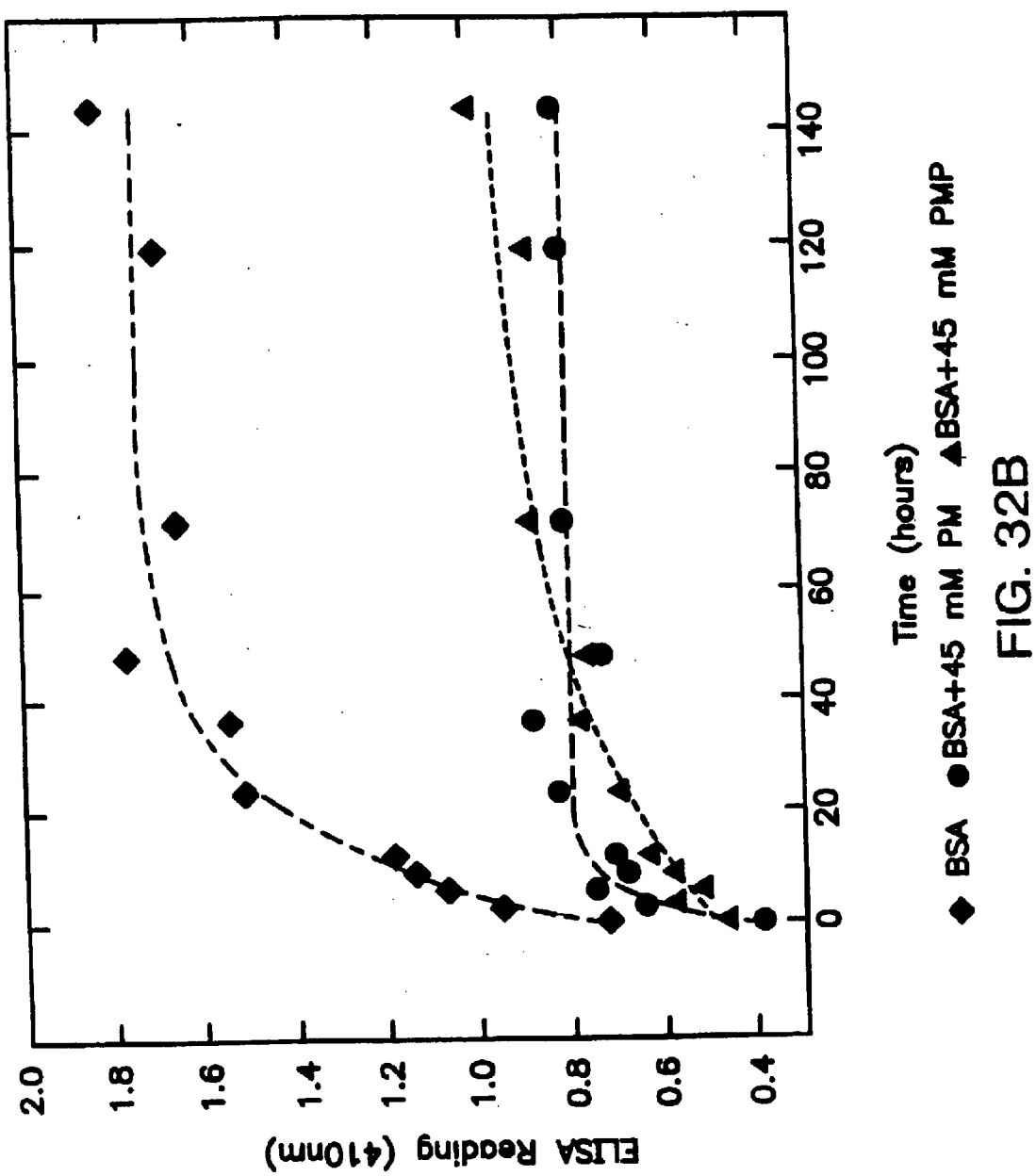
FIG. 32 are graphs which show AGE intermediary formation using the pentoses Xylose, Lyxose, Arabinose and Ribose.

FIGS. 1 A–D are graphs which show the effect of vitamin $B_6$ derivatives on post-Amadori AGE formation in bovine serum albumin glycated with glucose. BSA (10 mg/ml) was incubated with 1.0 M glucose in the presence and absence of the various indicated derivative in 0.4 M sodium phosphate buffer of pH 7.5 at 37° C. for 6 weeks. Aliquots were assayed by ELISA using R618 anti-AGE antibodies. Concentrations of the inhibitors were 3, 15 and 50 mM. Inhibitors used in FIGS. (1A) Pyridoxamine (PM); (1B) pyridoxal phosphate (PLP); (1C) pyridoxal (PL); (1D) pyridoxine (PN).

FIG. 1 (control curves) demonstrates that reaction of BSA with 1.0 M glucose is slow and incomplete after 40 days, even at the high sugar concentration used to accelerate the reaction. The simultaneous inclusion of different concentrations of various $B_6$ vitamers markedly affects the formation of antigenic AGEs. (FIGS. 1A–D) Pyridoxamine and pyridoxal phosphate strongly suppressed antigenic AGE formation at even the lowest concentrations tested, while pyridoxal was effective above 15 mM. Pyridoxine was slightly effective at the highest concentrations tested.

FIGS. 2A–D are graphs which show the effect of vitamin $B_1$ derivatives and aminoguanidine (AG) on AGE formation in bovine serum albumin. BSA (10 mg/ml) was incubated with 1.0 M glucose in the presence and absence of the various indicated derivative in 0.4 M sodium phosphate buffer of pH 7.5 at 37° C. for 6 weeks. Aliquots were assayed by ELISA using R618 anti-AGE antibodies. Concentrations of the inhibitors were 3, 15 and 50 mM. Inhibitors used in FIGS. (2A) Thiamine pyrophosphate (TPP); (2B) thiamine monophosphate (TP); (2C) thiamine (T); (2D) aminoguanidine (AG).

Of the various $B_1$ vitamers similarly tested (FIGS. 2A–D), thiamine pyrophosphate was effective at all concentrations tested (FIG. 2C), whereas thiamine and thiamine monophosphate were not inhibitory. Most significantly it is remarkable to note the decrease in the final levels of AGEs formed observed with thiamine pyrophosphate, pyridoxal phosphate and pyridoxamine. Aminoguanidine (FIG. 2D) produced some inhibition of AGE formation in BSA, but less so than the above compounds. Similar studies were carried out with human methemaglobin and bovine ribonuclease A.

FIGS. 3A–D are graphs which show the effect of vitamin $B_6$ derivatives on AGE formation in human methemoglobin. Hb (1 mg/ml) was incubated with 1.0 M glucose in the presence and absence of the various indicated derivative in 0.4 M sodium phosphate buffer of pH 7.5 at 37° C. for 3 weeks. Aliquots were assayed by ELISA using R618 anti-AGE antibodies. Concentrations of the inhibitors were 0.5, 3, 15 and 50 mM. Inhibitors used in FIGS. (3A) Pyridoxamine (PM); (3B) pyridoxal phosphate (PLP); (3C) pyridoxal (PL); (3D) pyridoxine (PN).

Figure 4A:
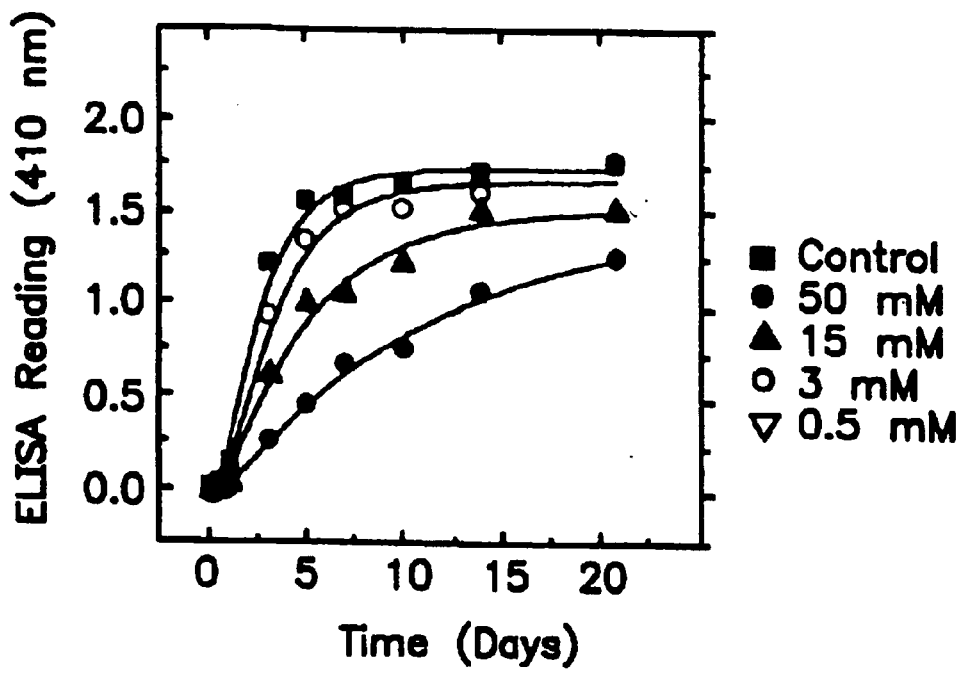
FIG. 4 is a series of graphs depicting the effect of vitamin $B_1$ derivatives and aminoguanidine (AG) on AGE formation in human methemoglobin.
Figure 4B:
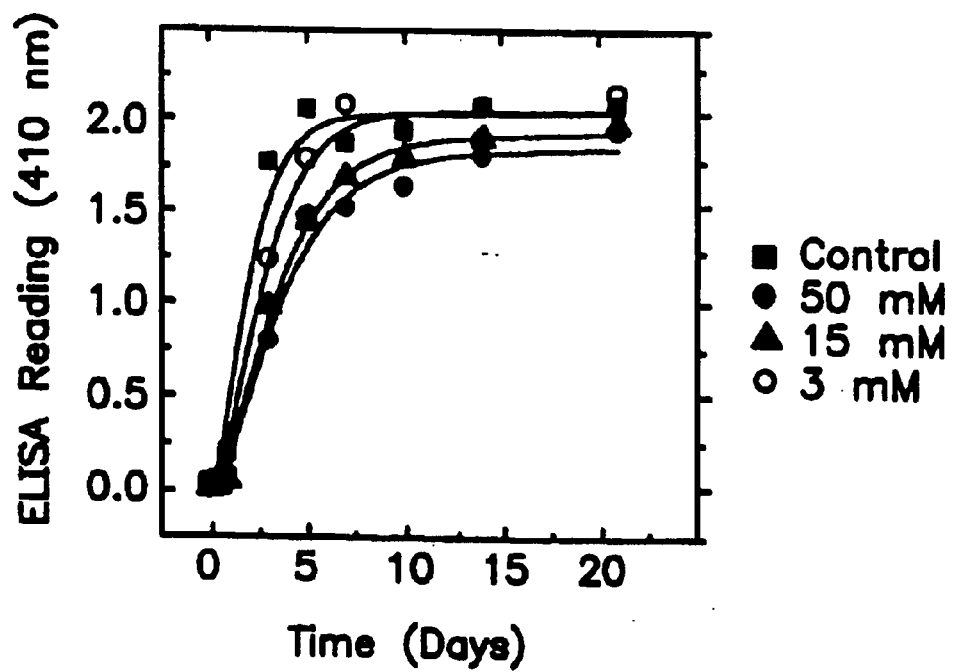
Figure 4C:
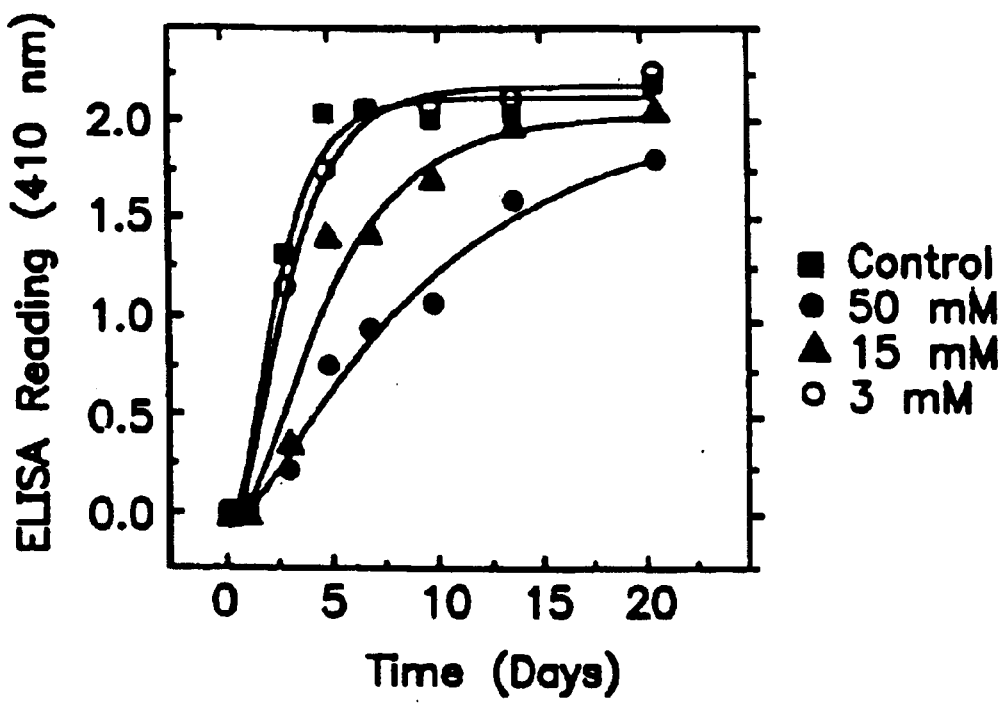
Figure 4D:
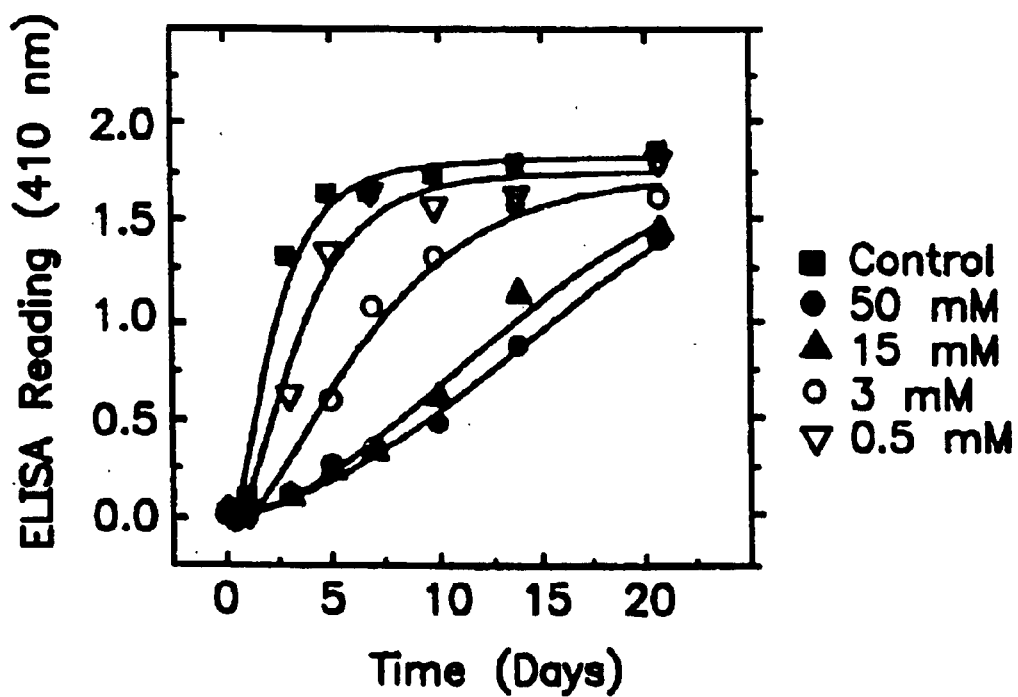

It had been previously reported that Hb of a diabetic patient contains a component that binds to anti-AGE antibodies, and it was proposed that this glycated Hb (termed Hb-AGE, not to be confused with $Hb_{A1c}$) could be useful in measuring long-term exposure to glucose. The in vitro incubation of Hb with glucose produces antigenic AGEs at an apparently faster rate than observed with BSA. Nevertheless, the different $B_6$ (FIGS. 3A–D) and $B_1$ (FIGS. 4A–C) vitamers exhibited the same inhibition trends in Hb, with pyridoxamine and thiamine pyrophosphate being the most effective inhibitors in each of their respective families. Significantly, in Hb, aminoguanidine only inhibited the rate of AGE formation, and not the final levels of AGE formed (FIG. 4D).

With RNase the rate of antigenic AGE formation by glucose was intermediate between that of Hb and BSA, but the extent of inhibition within each vitamer series was maintained. Again pyridoxamine and thiamine pyrophosphate were more effective that aminoguanidine (FIG. 5).

FIGS. 4A–D are graphs which show the effect of vitamin $B_1$ derivatives and aminoguanidine (AG) on AGE formation in human methemoglobin. Hb (1 mg/ml) was incubated with 1.0 M glucose in the presence and absence of the various indicated derivative in 0.4 M sodium phosphate buffer of pH 7.5 at 37° C. for 3 weeks. Aliquots were assayed by ELISA using R618 anti-AGE antibodies. Concentrations of the inhibitors were 0.5, 3, 15 and 50 mM. Inhibitors used in FIGS. (4A) Thiamine pyrophosphate (TPP); (4B) thiamine monophosphate (TP); (4C) thiamine (T); (4D) aminoguanidine (AG).

Figure 5:
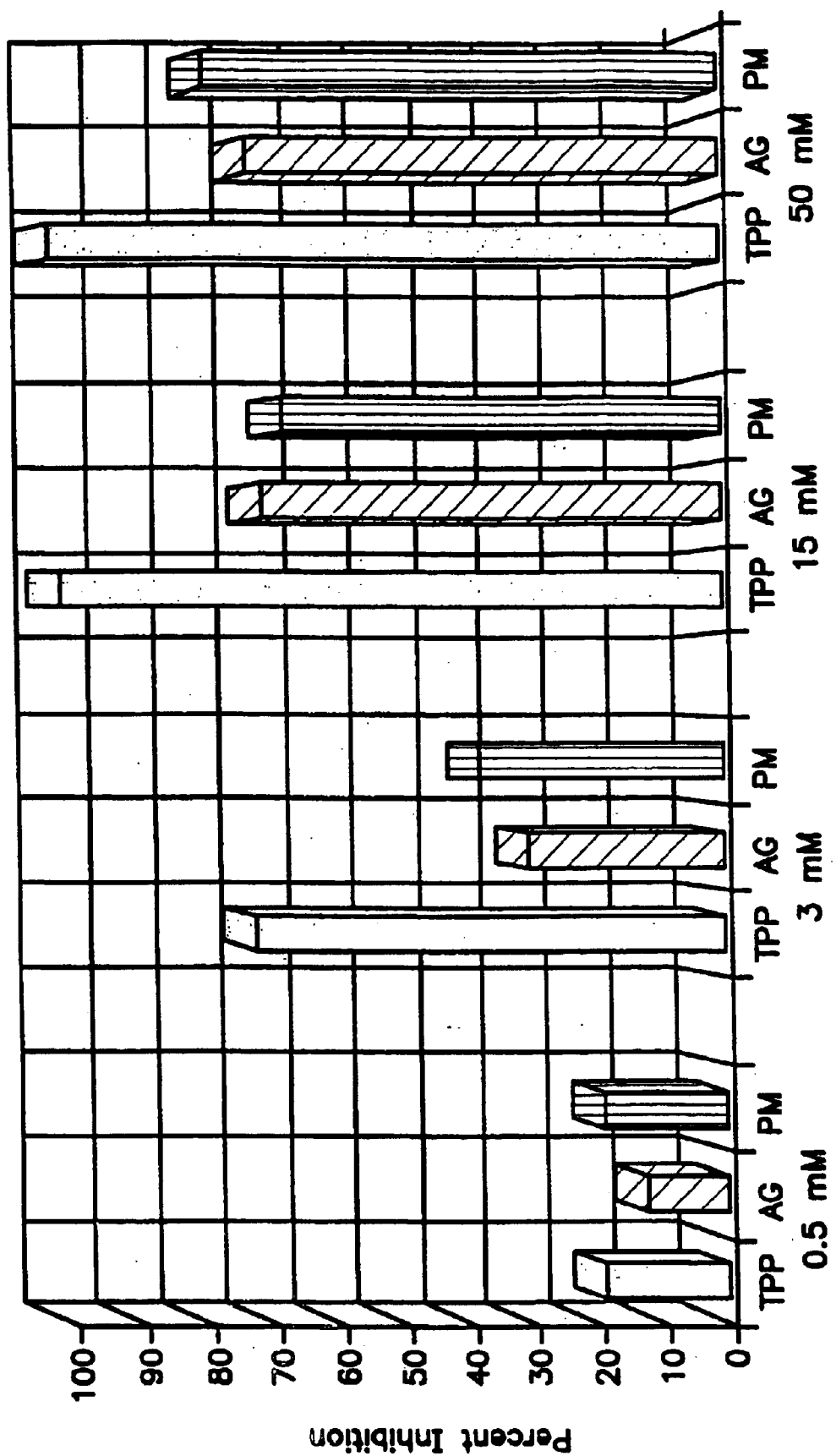
FIG. 5 is a bar graph comparison of the inhibition of the glycation of ribonuclease A by thiamine pyrophosphate (TPP), pyridoxamine (PM) and aminoguanidine (AG).

FIG. 5 is a bar graph which shows a comparison of the inhibition of the glycation of ribonuclease A by thiamine pyrophosphate (TPP), pyridoxamine (PM) and aminoguanidine (AG). RNase (1 mg/ml) was incubated with 1.0 M glucose (glc) in the presence and absence of the various indicated derivative in 0.4 M sodium phosphate buffer of pH 7.5 at 37° C. for 6 weeks. Aliquots were assayed by ELISA using R479 anti-AGE antibodies. The indicated percent inhibition was computed from ELISA readings in the absence and presence of the inhibitors at the 6 week time point. Concentrations of the inhibitors were 0.5, 3, 15 and 50 mM.

Discussion

These results demonstrate that certain derivatives of $B_1$ and $B_6$ vitamins are capable of inhibiting "late" AGE formation. Some of these vitamers successfully inhibited the final levels of AGE produced, in contrast to aminoguanidine, suggesting that they have greater interactions with Amadori or post-Amadori precursors to antigenic AGEs. The Amadori and post-Amadori intermediates represent a crucial juncture where the "classical" pathway of nonenzymatic glycation begins to become essentially irreversible (Scheme I). In earlier inhibition studies "glycation" was usually measured either as Schiff base formed (after reduction with labeled cyanoborohydride) or as Amadori product formed (after acid precipitation using labeled sugar). Such assays do not yield information on inhibition of post-Amadori conversion steps to "late" AGE products, since such steps lead to no change in the amount of labeled sugar that is attached to the proteins. Other "glycation" assays have relied on the sugar-induced increase of non-specific protein fluorescence, but this can also be induced by dicarbonyl oxidative fragments of free sugar, such as glycoaldehyde or glyoxal (Hunt et al., 1988, *Biochem.* 256:205–212), independently of Amadori product formation.

In the case of pyridoxal (PL) and pyridoxal phosphate (PLP), the data support the simple mechanism of inhibition involving competitive Schiff-base condensation of these aldehydes with protein amino groups at glycation sites. Due to internal hemiacetal formation in pyridoxal but not pyridoxal phosphate, stronger inhibition of post-Amadori AGE formation by PLP is expected by this competitive mechanism. This indeed is observed in the data (FIGS. 1B, 1C, FIGS. 3B, 3C). The inhibition by pyridoxamine is necessarily different, as pyridoxamine lacks an aldehyde group. However, pyridoxamine is a candidate amine potentially capable of forming a Schiff-base linkage with the carbonyls of open-chain sugars, with dicarbonyl fragments, with Amadori products, or with post-Amadori intermediates. The mechanism of inhibition of $B_1$ compounds is not obvious. All the forms contain an amino functionality, so that the marked efficiency of only the pyrophosphate form suggests an important requirement for a strong negative charge.

A significant unexpected observation is that the extent of inhibition by aminoguanidine, and some of the other compounds, is considerably less at late stages of the reaction, than during the early initial phase. This suggests a different mechanism of action than that of pyridoxamine and thiamine pyrophosphate, suggesting that the therapeutic potential of these compounds will be enhanced by co-administration with aminoguanidine.

EXAMPLE 2

Kinetics of Non-enzymatic glycation: Paradoxical Inhibition by Ribose and Facile Isolation of Protein Intermediate for Rapid Post-Amadori AGE Formation While high concentrations of glucose are used to cause the non-enzymatic glycation of proteins, paradoxically, it was found that ribose at high concentrations is inhibitory to post-Amadori AGE formation in ribonuclease by acting on the post-Amadori "late" stages of the glycation reaction. This unexpectedly inhibitory effect suggests that the "early" reactive intermediates, presumably Amadori products, can be accumulated with little formation of "late" post-Amadori AGE products (AGEs; Maillard products). Investigation into this phenomenon has demonstrated: (1) ability to define conditions for the kinetic isolation of Amadori (or post-Amadori) glycated intermediate(s); (2) the ability study the fast kinetics of buildup of such an intermediate; (3) the ability to study the surprisingly rapid kinetics of conversion of such intermediates to AGE products in the absence of free or reversibly bound sugar; (4) the ability to use these intermediates to study and characterize inhibition of post-Amadori steps of AGE formation thus providing a novel system to investigate the mechanism of reaction and the efficacy of potential agents that could block AGE formation; and (5) with this knowledge it is also further possible to use $^{13}C$ NMR to study the reactive intermediates and monitor their conversion to various candidate AGEs (Khalifah et al., 1996, *Biochemistry* 35(15):4645–4654).

Chemicals and Materials As in Example 1 above.
Preparation of Polyclonal Antibodies to AGEs
As in Example 1 above.
ELISA Detection of AGE Products As in Example 1 above.

Amino Acid Analysis Amino acid analyses were carried out at the Biotechnology Support Facility of the Kansas University Medical Center. Analyses were performed after hydrolysis of glycated protein (reduced with sodium cyanoborohydride) with 6 N HCl at 110° C. for 18–24 h. Phenyl isothiocyanate was used for derivatization, and PTH derivatives were analyzed by reverse-phase HPLC on an Applied Biosystems amino acid analyzer (420A derivatizer, 130A separation system, 920A data analysis system).

Pentosidine Reverse-Phase HPLC Analysis Pentosidine production in RNase was quantitated by HPLC (Sell & Monnier, 1989, *J. Biol. Chem.* 264:21597–21602; Odetti et al., 1992, *Diabetes* 41:153–159). Ribose-modified protein samples were hydrolyzed in 6 N HCl for 18 h at 100° C. and then dried in a Speed Vac. The samples were then redissolved, and aliquots ere taken into 0.1% trifluoroacetic acid and analyzed by HPLC on a Shimadzu system using a Vydac C-18 column equilibrated with 0.1% TFA. A gradient of 0–6% acetonitrile (0.1% in TFA) was run in 30 min at a flow rate of about 1 ml/min. Pentosidine was detected by 335 nm excitation/385 nm emission fluorescence, and its elution time was determined by running a synthesized standard. Due to the extremely small levels of pentosidine expected (Grandhee & Monnier, 1991, *J. Biol. Chem.* 266:11649–11653; Dyer et al., 1991, *J. Biol. Chem.* 266:11654–11660), no attempt was made to quantitate the absolute concentrations. Only relative concentrations were determined from peak areas.

Glycation Modifications Modification with ribose or glucose was generally done at 37° C. in 0.4 M phosphate buffer of pH 7.5 containing 0.02% sodium azide. The high buffer concentration was always used with 0.5 M ribose modifications. The solutions were kept in capped tubes and opened only to remove timed aliquots that were immediately frozen for later carrying out the various analyses. "Interrupted glycation" experiments were carried out by first incubating protein with the ribose at 37° C. for 8 or 24 h, followed by immediate and extensive dialysis against frequent cold buffer changes at 4° C. The samples were then reincubated by quickly warming to 37° C. in the absence of external ribose. Aliquots were taken and frozen at various intervals for later analysis. Due to the low molecular weight of RNase, protein concentrations were remeasured after dialysis even when low molecular weight cut-off dialysis tubing was used. An alternative procedure was also devised (see below) in which interruption was achieved by simple 100-fold dilution from reaction mixtures containing 0.5 M ribose. Protein concentrations were estimated from UV spectra. The difference in molar extinction between the peak (278 nm) and trough (250 nm) was used for RNase concentration determinations in order to compensate for the general increase in UV absorbance that accompanies glycation. Time-dependent UV-difference spectral studies were carried out to characterize the glycation contributions of the UV spectrum.

Figure 6B:
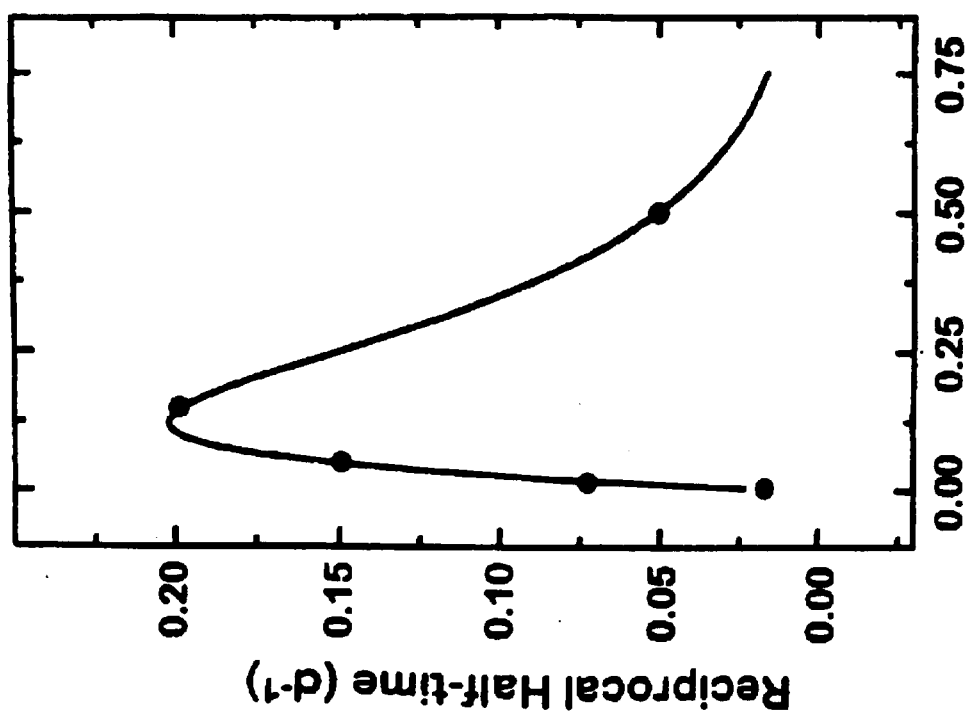
FIG. 6B is a graph showing the dependence of reciprocal half-times on ribose concentration at pH 7.5.

Data Analysis and Numerical Simulations of Kinetics Kinetic data were routinely fit to monoexponential or biexponential functions using nonlinear least-squares methods. The kinetic mechanisms of Schemes 5–6 have been examined by numerical simulations of the differential equations of the reaction. Both simulations and fitting to observed kinetics data were carried out with the SCIENTIST 2.0 software package (Micromath, Inc.). Determination of apparent half-times (FIG. 6B) from kinetic data fit to two-exponential functions (FIG. 6A) was carried out with the "solve" function of MathCAD 4.0 software (MathSoft, Inc.).

Results
Comparison of Glycation by Glucose and Ribose

The reaction of RNase A with ribose and glucose has been followed primarily with ELISA assays, using R479 rabbit AGE-specific antibodies developed against glucose-modified BSA. To a lesser extent, the production of pentosidine, the only known acid-stable fluorescent AGE, was quantitated by HPLC following acid hydrolysis. Preliminary studies using 0.05 M ribose at 37° C. showed that the rate of antigenic AGE formation appears to be modestly increased (roughly 2–3 fold as measured by the apparent half-time) as the pH is increased from 5.0 to 7.5, with an apparent small induction period at the beginning of the kinetics in all cases. The glycation of RNase with 0.05 M ribose at pH 7.5 (half-time near 6.5 days) appears to be almost an order of magnitude faster than that of glycation with 1.0 M glucose (half-time in excess of 30 days; see FIG. 7B, solid line). The latter kinetics also displayed a small induction period but incomplete leveling off even after 60 days, making it difficult to estimate a true half-time.

Figure 6A:
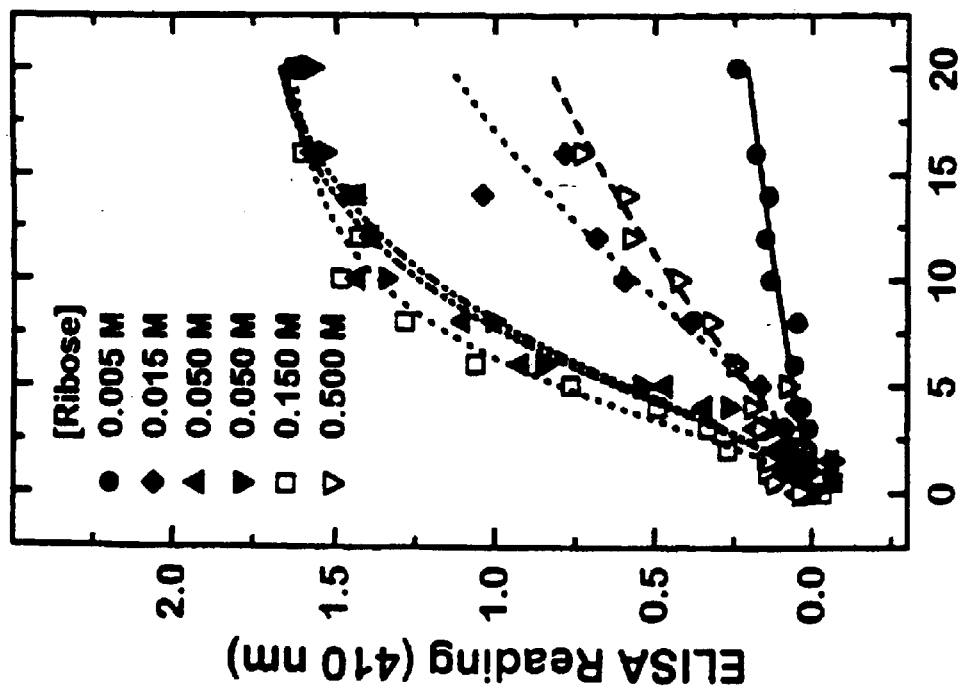
FIG. 6A is a graph of the kinetics of glycation of RNase A (10 mg/mL) by ribose as monitored by ELISA.

When the dependence of the kinetics on ribose concentration was examined at pH 7.5, a most unexpected result was obtained. The rate of reaction initially increased with increasing ribose concentration, but at concentrations above 0.15 M the rate of reaction leveled off and then significantly decreased (FIG. 6A). A plot of the dependence of the reciprocal half-time on the concentration of ribose (FIG. 6B) shows that high ribose concentrations are paradoxically inhibitory to post-Amadori antigenic AGE formation. This unusual but consistent effect was found to be independent of changes in the concentration of either buffer (2-fold) or RNase (10-fold), and it was not changed by affinity purification of the R479 antibody on a column of immobilized AGE-RNase. It is also not due to effects of ribose on the ELISA assay itself. The measured inhibitory effect by ribose on post-Amadori AGE formation is not likely due to ribose interference with antibody recognition of the AGE antigenic sites on protein in the ELISA assay. Prior to the first contact with the primary anti-AGE antibody on the ELISA plates, glycated protein has been diluted over 1000-fold, washed extensively with Tween-20 after adsorption, and blocked with a 1% casein coating followed by further washing with Tween-20.

Kinetics of Formation of post-Amadori Antigenic AGEs by "Interrupted Glycation"

In view of the small induction period seen, an attempt was made to determine whether there was some accumulation during the reaction, of an early precursor such as an Amadori intermediate, capable of producing the ELISA-detectable post-Amadori antigenic AGEs. RNase was glycated at pH 7.5 and 37° C. with a high ribose concentration of 0.5 M, and the reaction was interrupted after 24 h by immediate cooling to 4° C. and dialysis against several changes of cold buffer over a period of 24 h to remove free and reversibly bound (Schiff base) ribose. Such a ribose-free sample was then rapidly warmed to 37° C. without re-adding any ribose, and was sampled for post-Amadori AGE formation over several days. The AGE antigen production of this 24 h "interrupted glycation" sample is shown by the dashed line and open triangles in FIG. 7A, the time spent in the cold dialysis is not included. An uninterrupted control (solid line and filled circles) is also shown for comparison. Dramatically different kinetics of post-Amadori antigenic AGE formation are evident in the two samples. The kinetics of AGE antigen production of the ribose-free interrupted sample now show (1) monoexponential kinetics with no induction period, (2) a greatly enhanced rate of antigenic AGE formation, with remarkable half-times of the order of 10 h, and (3) production of levels of antigen comparable to those seen in long incubations in the continued presence of ribose (see FIG. 6A). Equally significant, the data also demonstrate that negligible AGE antigen was formed during the cold dialysis period, as shown by the small difference between the open triangle and filled circle points at time 1 day in FIG. 7A. Very little, if any, AGE was formed by the "interruption" procedure itself. These observations show that a fully competent isolatable intermediate or precursor to antigenic AGE has been generated during the 24 h contact with ribose prior to the removal of the free and reversibly bound sugar.

Samples interrupted after only 8 h produced a final amount of AGE antigen that was about 72% of the 24 h interrupted sample. Samples of RNase glycated with only 0.05 M ribose and interrupted at 8 h by cold dialysis and reincubation at 37° C. revealed less than 5% production of ELISA-reactive antigen after 9 days. Interruption at 24 h, however, produced a rapid rise of ELISA antigen (similar to FIG. 7A) to a level roughly 50% of that produced in the uninterrupted presence of 0.05 M ribose.

The same general interruption effects were also seen with other proteins (BSA and Hemoglobin). Except for a somewhat different absolute value of the rate constants, and the amount of antigenic AGEs formed during the 24 h 0.5 M ribose incubation, the same dramatic increase in the rate of AGE antigen formation was observed after removal of 0.5 M ribose.

Glycation is much slower with glucose than with ribose (note the difference in time scales between FIG. 7A and FIG. 7B). However, unlike the case with ribose, interruption after 3 days of glycation by 1.0 M glucose produced negligible buildup of precursor to ELISA-reactive AGE antigens (FIG. 7B, dashed curve).

Kinetics of Pentosidine Formation

Figure 8A:
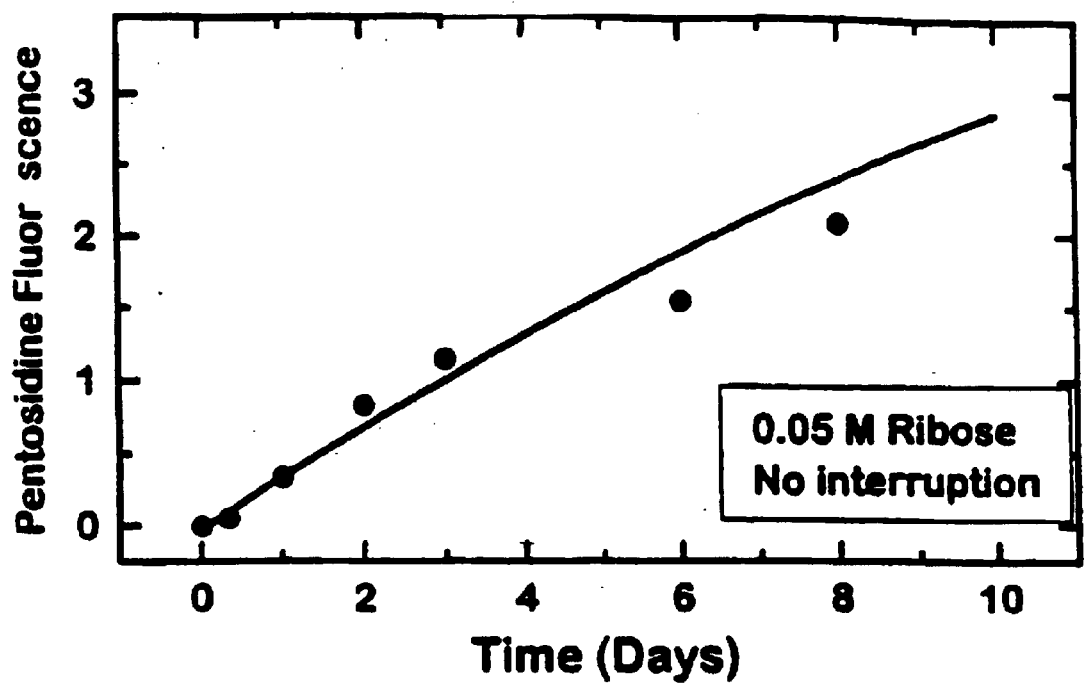
FIG. 8A Uninterrupted glycation in the presence of 0.05 M ribose.
Figure 8B:
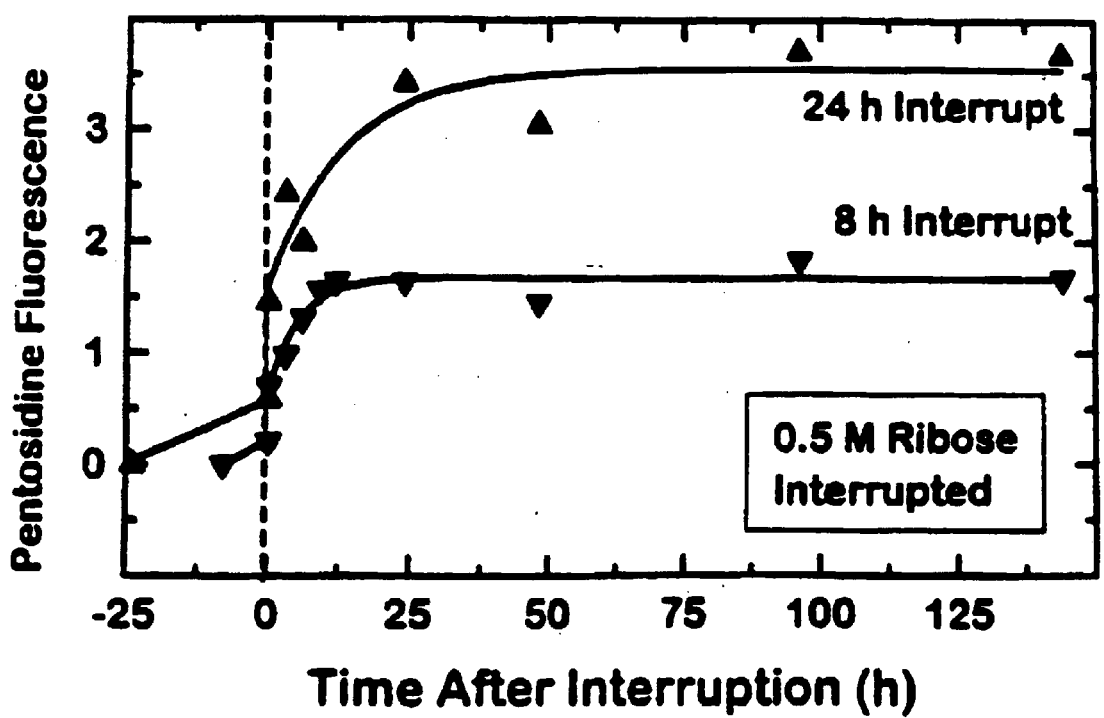
FIG. 8B Interrupted glycation after 8 and 24 hours of incubation.

The samples subjected to ELISA testing were also assayed for the production of pentosidine, an acid-stable AGE. The content of pentosidine was measured for the same RNase samples analyzed for antibody reactivity by ELISA. Glycation by ribose in 0.4 M phosphate buffer at pH 7.5 produced pentosidine in RNase A that was quantitated by fluorescence after acid hydrolysis. FIG. 8A shows that under uninterrupted conditions, 0.05 M ribose produces a progressive increase in pentosidine. However, when glycation is carried out under "interrupted" conditions using 0.5 M ribose, a dramatic increase in the rate of pentosidine formation is seen immediately after removal of excess ribose (FIG. 8B), which is similar to, but slightly more rapid than, the kinetics of the appearance of antigenic AGEs (FIG. 7A). A greater amount of pentosidine was also produced with 24 h interruption as compared with 8 h. Reproducible differences between the kinetics of formation of pentosidine and antigenic AGEs can also be noted. A significant amount of pentosidine is formed during the 24 h incubation and also during the cold dialysis, resulting in a jump of the dashed vertical line in FIG. 8B. Our observations thus demonstrate that a pentosidine precursor accumulates during ribose glycation that can rapidly produce pentosidine after ribose removal (cf. Odetti et al., 1992, Diabetes 41:153–159).

Rate of Buildup of the Reactive Intermediate(s)

The "interrupted glycation" experiments described above demonstrate that a precursor or precursors to both post-Amadori antigenic AGEs and pentosidine can be accumulated during glycation with ribose. The kinetics of formation of this intermediate can be independently followed and quantitated by a variation of the experiments described above. The amount of intermediate generated in RNase at different contact times with ribose can be assayed by the maximal extent to which it can produce antigenic AGE after interruption. At variable times after initiating glycation, the free and reversibly-bound ribose is removed by dialysis in the cold or by rapid dilution (see below). Sufficient time (5 days, which represents several half-lives according to FIG. 7A) is then allowed after warming to 37° C. for maximal development of post-Amadori antigenic AGEs. The ELISA readings 5 days after each interruption point, representing maximal AGE development, would then be proportional to the intermediate concentration present at the time of interruption.

Figure 9:
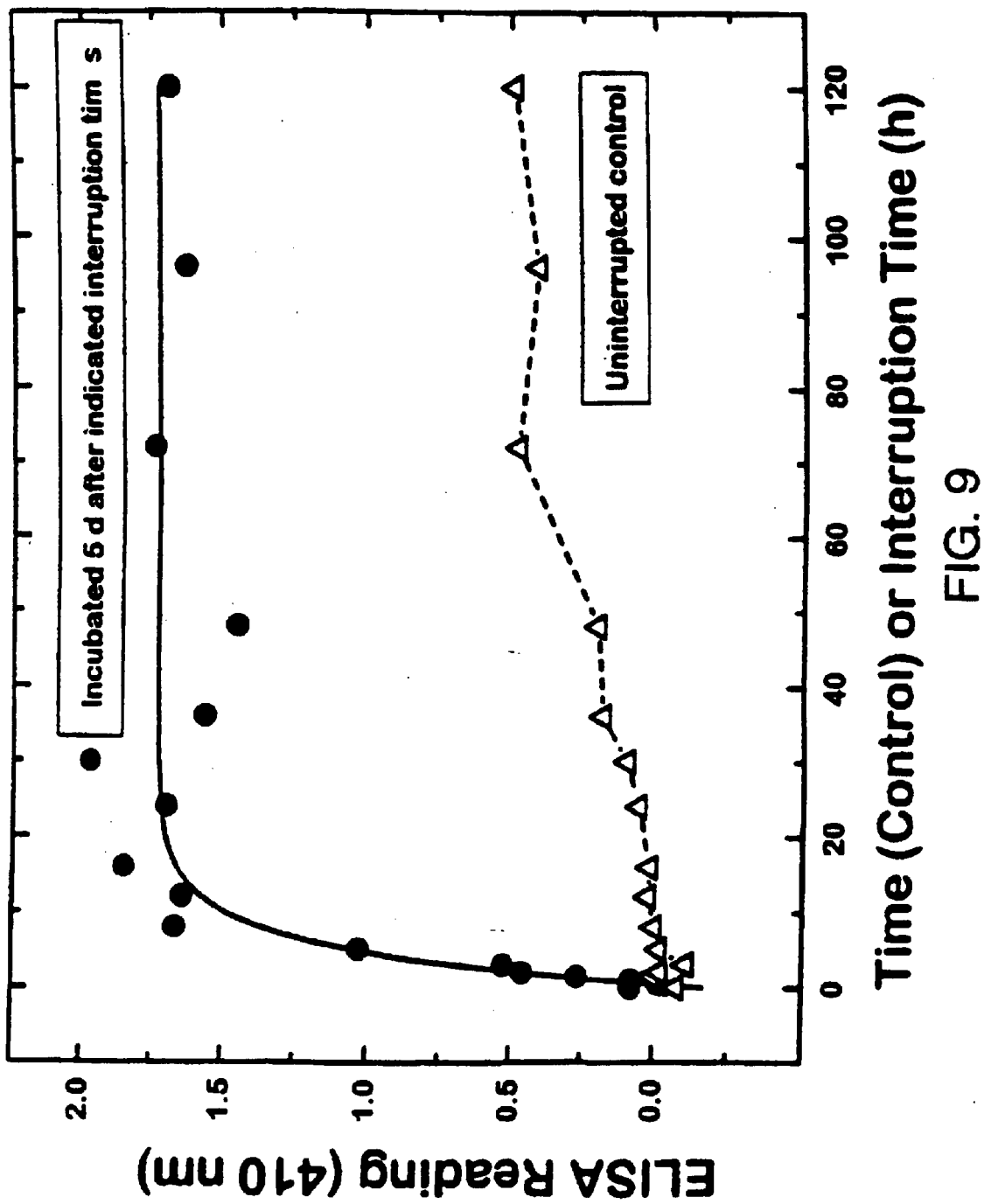
FIG. 9 is a graph which shows the kinetics of reactive intermediate buildup.

FIG. 9 shows such an experiment where the kinetics of intermediate buildup are measured for RNase A in the presence of 0.5 M ribose (solid symbols and curve). For comparison, the amount of AGE present before ribose removal at each interruption point is also shown (open symbols and dashed lines). As expected (cf. FIG. 7A), little AGE is formed prior to removal (or dilution) of ribose, so that ELISA readings after the 5 day secondary incubation periods are mostly a measure of AGE formed after ribose removal. The results in FIG. 9 show that the rate of buildup of intermediate in 0.5 M ribose is exponential and very fast, with a half-time of about 3.3 h. This is about 3-fold more rapid than the observed rate of conversion of the intermediate to antigenic AGEs after interruption (open symbols and dashed curve FIG. 7A).

In these experiments the removal of ribose at each interruption time was achieved by 100-fold dilution, and not by dialysis. Simple dilution reduced the concentration of ribose from 0.05 M to 0.005 M. It was independently determined (FIG. 6A) that little AGE is produced in this time scale with the residual 5 mM ribose. This dilution approach was primarily dictated by the need for quantitative point-to-point accuracy. Such accuracy would not have been achieved by the dialysis procedure that would be carried out independently for each sample at each interruption point. Our results show that dilution was equivalent to dialysis.

A separate control experiment (see FIG. 10 below) demonstrated that the instantaneous 100-fold dilution gave nearly identical results to the dialysis procedure. These control experiments demonstrate that the reversible ribose-protein binding (Schiff base) equilibrium is quite rapid on this time scale. This is consistent with data of Bunn and Higgins (1981, *Science* 213: 222–224) that indicated that the half-time of Schiff base formation with 0.5 M ribose should be on the order of a few minutes. The 100-fold rapid dilution method to reduce ribose is a valid method where quantitative accuracy is essential and cannot be achieved by multiple dialysis of many samples.

Figure 10A:
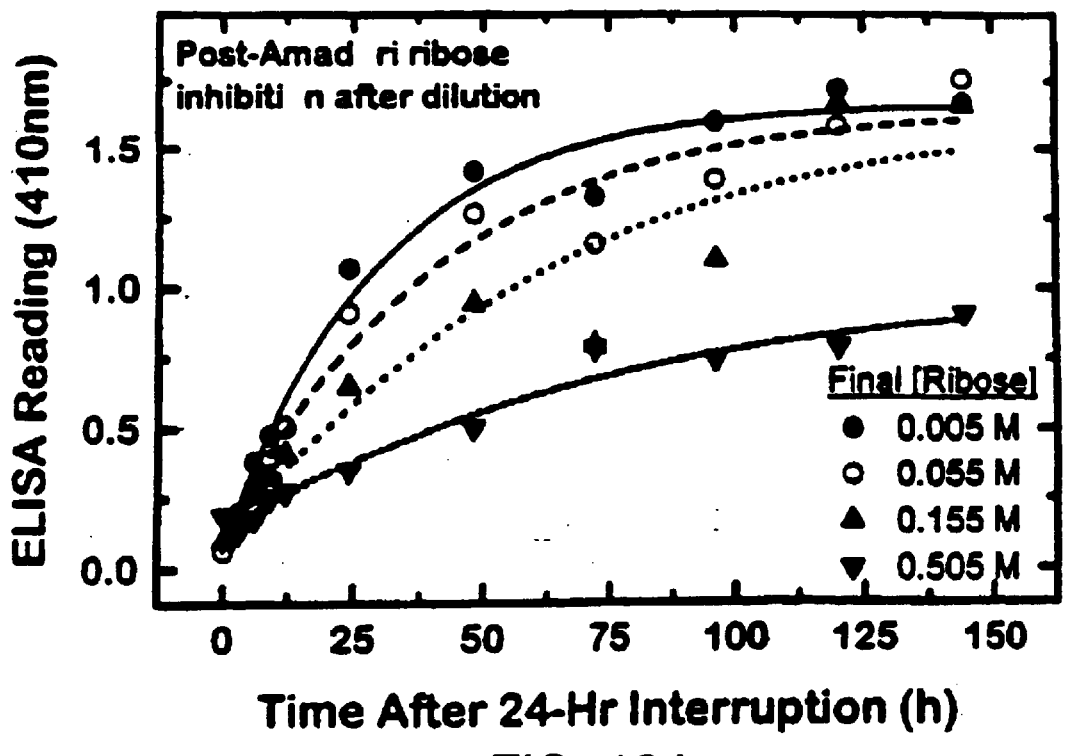
FIG. 10A graphs data where aliquots were diluted into inhibitor containing buffers at time 0.
Figure 10B:
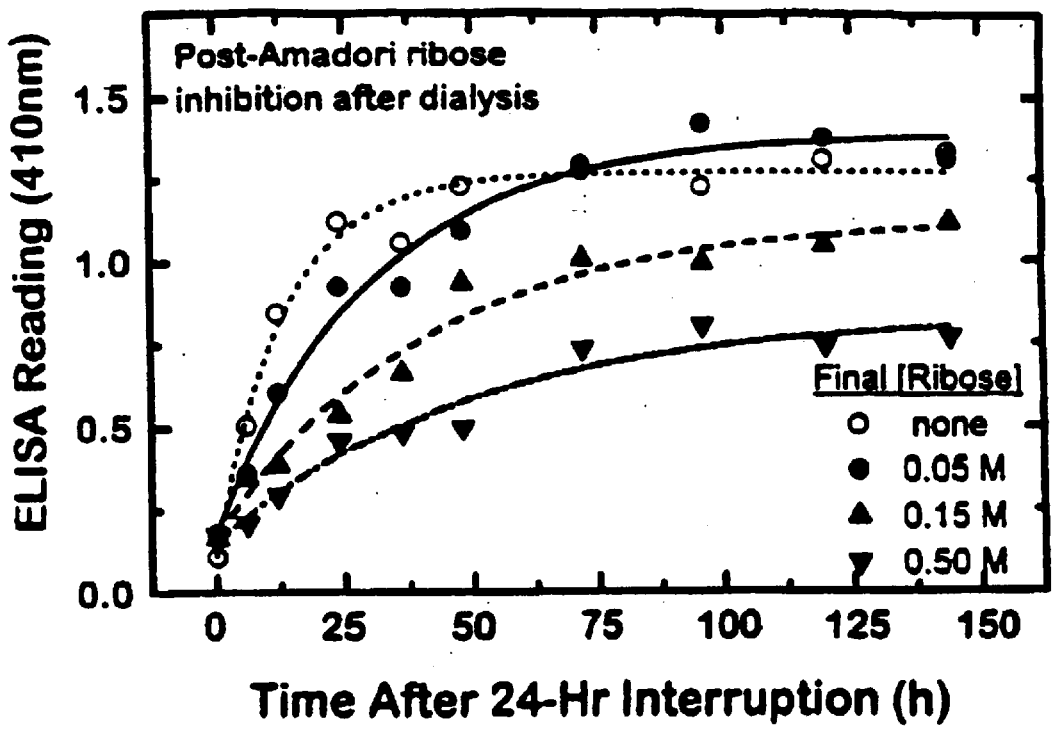
FIG. 10B graphs data where samples were interrupted at 24 h, and then diluted into inhibitor containing buffers.

Direct Inhibition of Post-Amadori AGE Formation from the Intermediate by Ribose and Glucose The increase in the rate of AGE formation after interruption and sugar dilution suggests, but does not prove, that high concentrations of ribose are inhibiting the reaction at or beyond the first "stable" intermediate, presumably the Amadori derivative (boxed in Scheme I). A test of this was then carried out by studying the effect of directly adding ribose, on the post-Amadori reaction. RNase was first incubated for 24 h in 0.5 M ribose in order to prepare the intermediate. Two protocols were then carried out to measure possible inhibition of the post-Amadori formation of antigenic AGEs by different concentrations of ribose. In the first experiment, the 24 h ribated sample was simply diluted 100-fold into solutions containing varying final concentrations of ribose ranging from 0.005 M to 0.505 M (FIG. 10A). The rate and extent of AGE formation are clearly seen to be diminished by increasing ribose concentrations. Significantly, up to the highest concentration of 0.5 M ribose, the kinetics appear exponential and do not show the induction period that occurs with uninterrupted glycation (FIGS. 6A and 7A) in high ribose concentrations.

A second experiment (FIG. 10B) was also conducted in which the 24 h interrupted sample was extensively dialyzed in the cold to release free and reversibly bound ribose as well as any inhibitory products that may have formed during the 24 h incubation with ribose. Following this, aliquots were diluted 100-fold into varying concentrations of freshly made ribose, and the formation of antigenic AGE products was monitored as above. There results were nearly identical to the experiment of FIG. 10A where the dialysis step was omitted. In both cases, the rate and extent of AGE formation were diminished by increasing concentrations of ribose, and the kinetics appeared exponential with no induction period.

The question of whether glucose or other sugars can also inhibit the formation of AGEs from the reactive intermediate obtained by interrupted glycation in 0.5 M ribose was also investigated. The effects of glucose at concentrations of 1.0–2.0 M were tested (data not shown). Glucose was clearly not as inhibitory as ribose. When the 24 h ribose interrupted sample was diluted 100-fold into these glucose solutions, the amount of antigenic AGE formed was diminished by about 30%, but there was little decrease in the apparent rate constant. Again, the kinetics appeared exponential.

Effect of pH on Post-Amadori Kinetics of AGE Formation

Figure 11:
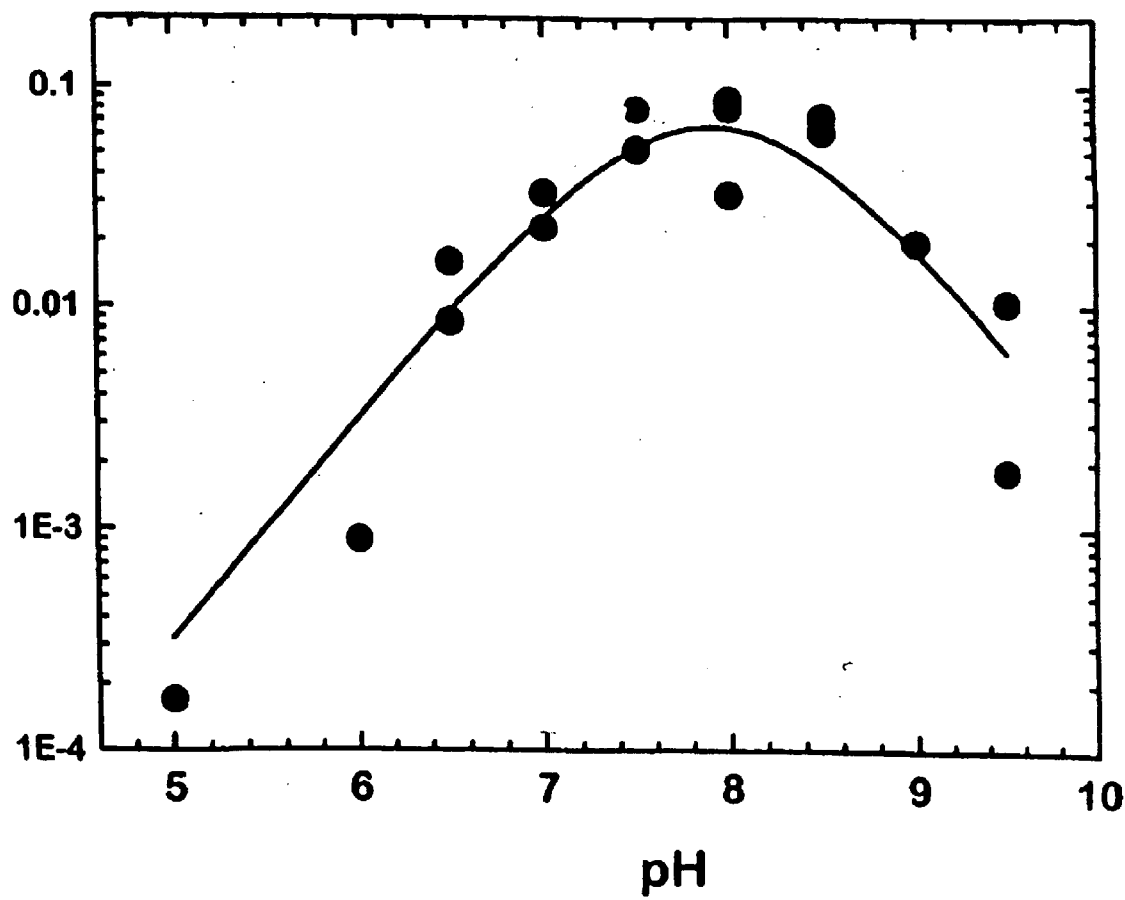
FIG. 11 is a graph showing dependence of the initial rate of formation of antigenic AGE on pH following interruption of glycation.

The interrupted glycation method was used to investigate the pH dependence of the post-Amadori kinetics of AGE formation from the reactive intermediate. In these experiments, RNase A was first reacted for 24 h with 0.5 M ribose at pH 7.5 to generate the reactive intermediate. The kinetics of the decay of the intermediate to AGEs were then measured by ELISA. FIG. 11 shows that an extremely wide pH range of 5.0–9.5 was achievable when the kinetics were measured by initial rates. A remarkable bell-shaped dependence was observed, showing that the kinetics of antigenic AGEs formation are decreased at both acidic and alkaline pH ranges, with an optimum near pH 8.

Figure 12A:
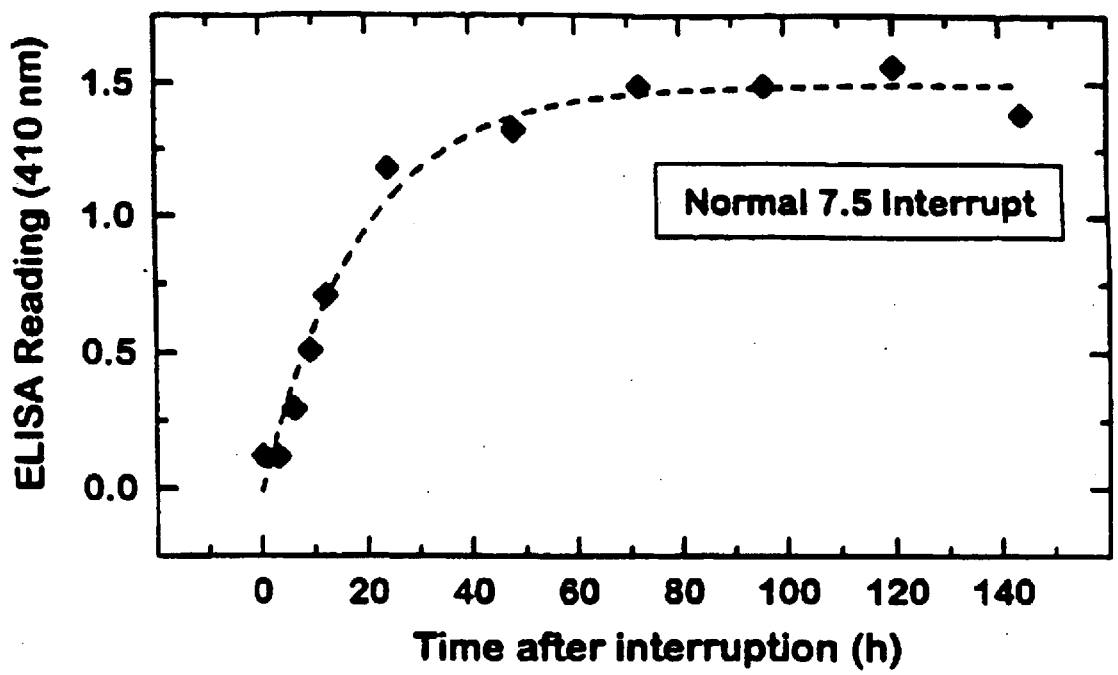
FIG. 12 are two graphs showing the effect of pH jump on ELISA detected AGE formation after interrupted glycation. Interrupted samples left 12 days at 37° C. in pH 5.0 buffer produced substantial AGEs (33%.
FIG. 12B) when pH was changed to 7.5, as compared to the normal control sample not exposed to low pH (FIG. 12A).
Figure 12B:
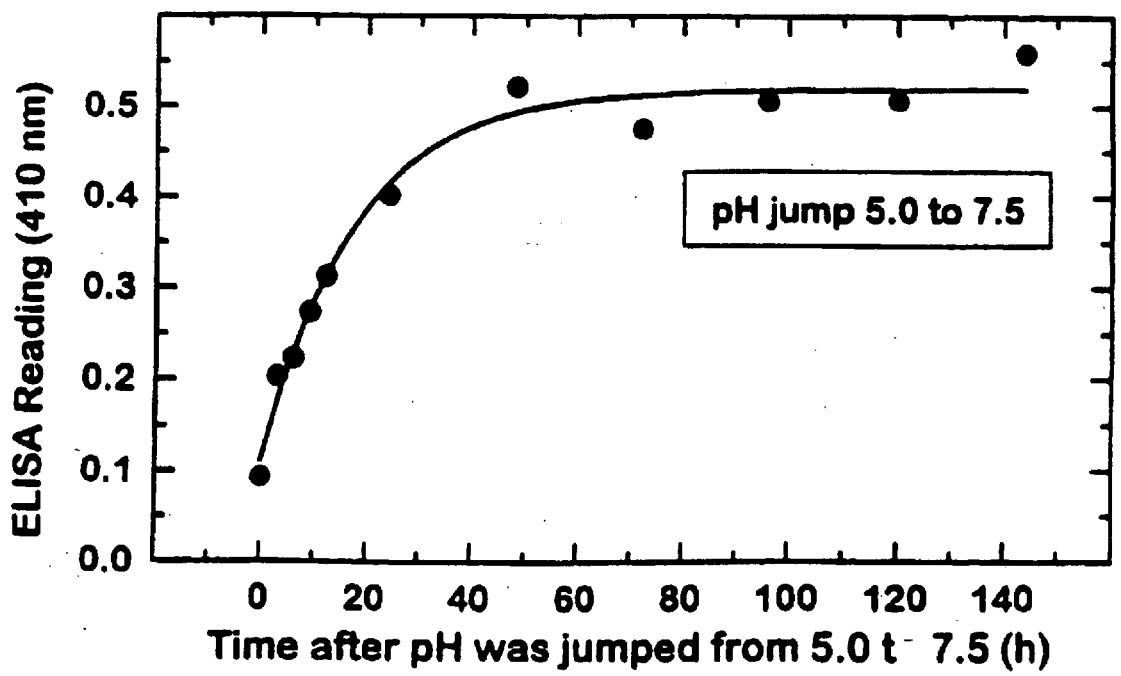

A single "pH jump" experiment was also carried out on the pH 5.0 sample studied above which had the slowest rate of antigenic AGE formation. After 12 days at 37° C. in pH 5.0 buffer, the pH was adjusted quickly to 7.5, and antigenic AGE formation was monitored by ELISA. Within experimental error, the sample showed identical kinetics (same first order rate constant) of AGE formation to interrupted glycation samples that had been studied directly at pH 7.5 (FIG. 12). In this experiment, the relative amounts of antigenic AGE could not be directly compared on the same ELISA plate, but the pH-jumped sample appeared to have formed substantial though somehow diminished levels of antigenic AGEs. These results demonstrate that intermediate can be prepared free of AGE and stored at pH 5 for later studies of conversion to AGEs.

Inhibition of Post-Amadori AGE Formation by Aminoguanidine

Figure 20A:
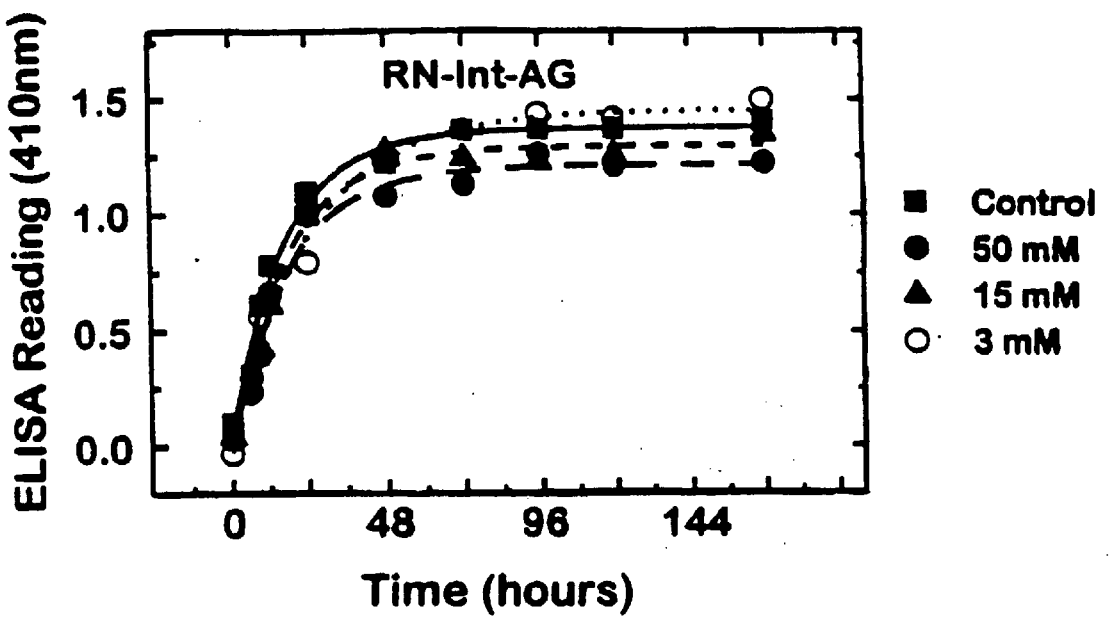
FIG. 20A RNase, FIG. 20B BSA.
Figure 20B:
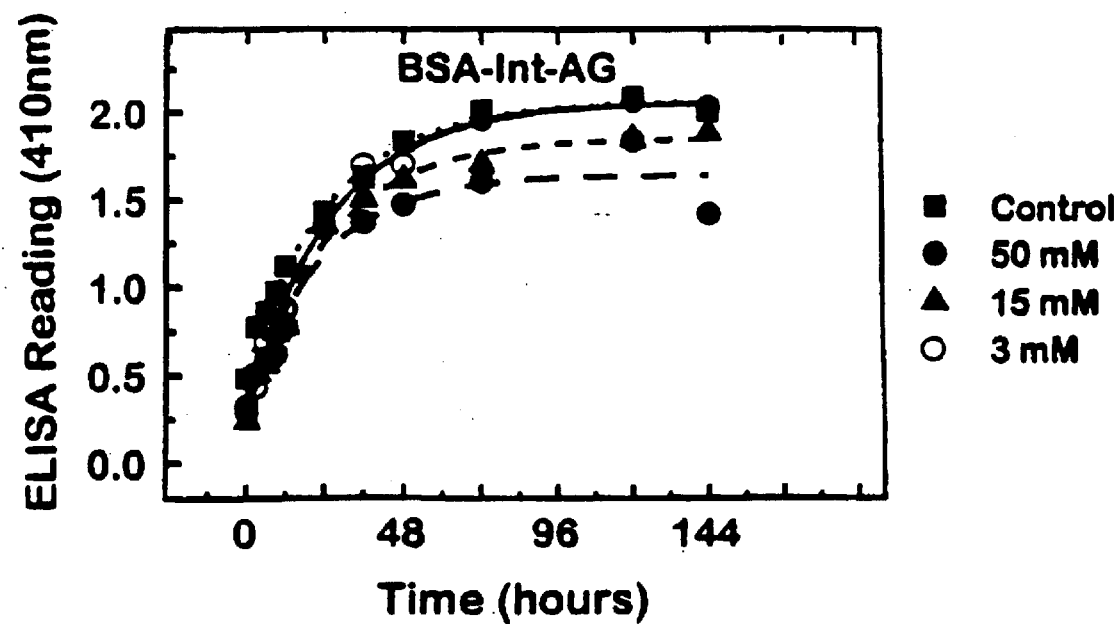
FIG. 20 are graphs depicting the effect of aminoguanidine on post-Amadori AGE formation after interrupted glycation by ribose.

The efficacy of aminoguanidine was tested by this interrupted glycation method, i.e., by testing its effect on post-Amadori formation of antigenic AGEs after removal of excess and reversibly bound ribose. FIG. 20A demonstrates that aminoguanidine has modest effects on blocking the formation of antigenic AGEs in RNase under these conditions, with little inhibition below 50 mM. Approximately 50% inhibition is achieved only at or above 100–250 mM. Note again that in these experiments, the protein was exposed to aminoguanidine only after interruption and removal of free and reversibly bound ribose. Comparable results were also obtained with the interrupted glycation of BSA (FIG. 20B).

Amino Acid Analysis of Interrupted Glycation Samples

Amino acid analysis was carried out on RNase after 24 h contact with 0.5 M ribose (undialyzed), after extensive dialysis of the 24 h glycated sample, and after 5 days of incubation of the latter sample at 37° C. These determinations were made after sodium cyanoborohydride reduction, which reduces Schiff base present on lysines or the terminal amino group. All three samples, normalized to alanine (12 residues), showed the same residual lysine content (4.0±0.5 out of the original 10 in RNase). This indicates that after 24 h contact with 0.5 M ribose, most of the formed Schiff base adducts had been converted to Amadori or subsequent products. No arginine or histidine residues were lost by modification.

Discussion

The use of rapidly reacting ribose and the discovery of its reversible inhibition of post-Amadori steps have permitted the dissection and determination of the kinetics of different steps of protein glycation in RNase. Most previous kinetic studies of protein "glycation" have actually been restricted to the "early" steps of Schiff base formation and subsequent Amadori rearrangement. Some kinetic studies have been carried out starting with synthesized fructosylamines, i.e. small model Amadori compounds of glucose (Smith and Thornalley, 1992, Eur. J. Biochem. 210:729–739, and references cited therein), but such studies, with few exceptions, have hitherto not been possible with proteins. One notable exception is the demonstration by Monnier (Odetti et al., 1992, supra) that BSA partially glycated with ribose can rapidly produce pentosidine after ribose removal. The greater reactivity of ribose has also proven a distinct advantage in quantitatively defining the time course of AGE formation. It is noted that glucose and ribose are both capable of producing similar AGE products, such as pentosidine (Grandhee & Monnier, 1991, supra; Dyer et al. 1991, supra), and some $^{13}C$ NMR model compound work has been done with ADP-ribose (Cervantes-Laurean et al., 1993, Biochemistry 32:1528–1534). The present work shows that antigenic AGE products of ribose fully cross-react with anti-AGE antibodies directed against glucose-modified proteins, suggesting that ribose and glucose produce similar antigenic AGEs. The primary kinetic differences observed between these two sugars are probably due to relative differences in the rate constants of steps leading to post-Amadori AGE formation, rather than in the mechanism.

The results presented reveal a marked and paradoxical inhibition of overall AGE formation by high concentrations of ribose (FIG. 6) that has not been anticipated by earlier studies. This inhibition is rapidly reversible in the sense that it is removed by dialysis of initially modified protein (FIG. 7A) or by simple 100-fold dilution (as used in FIG. 11). The experiments of FIG. 10 demonstrate that it is not due to the accumulation of dialyzable inhibitory intermediates during the initial glycation, since dialysis of 24 h modified protein followed by addition of different concentrations of fresh ribose induces the same inhibition. The data of FIG. 10A,B show that the inhibition occurs by reversible and rapid interaction of ribose with protein intermediate containing reactive Amadori products. The inhibition is unlikely to apply to the early step of formation of Amadori product due to the rapid rate of formation of the presumed Amadori intermediate that was determined in the experiment of FIG. 9. The identification of the reactive intermediate as an Amadori product is well supported by the amino acid analysis carried out (after sodium cyanoborohydrate reduction) before and after dialysis at the 24 h interruption point. The unchanged residual lysine content indicates that any dischageable Schiff bases have already been irreversibly converted (presumably by Amadori rearrangement) by the 24 h time.

The secondary ribose suppression of "late" but not "early" glycation steps significantly enhances the accumulation of a fully-competent reactive Amadori intermediate containing little AGE. Its isolation by the interruption procedure is of importance for kinetic and structural studies, since it allows one to make studies in the absence of free or Schiff base bound sugar and their attendant reactions and complications. For example, the post-Amadori conversion rates to antigenic AGE and pentosidine AGE products have been measured (FIG. 7A, open symbols, and FIG. 8B), and demonstrated to be much faster (t ½~10 h) than reflected in the overall kinetics under uninterrupted conditions (FIG. 6A and FIG. 8A). The rapid formation of pentosidine that was measured appears consistent with an earlier interrupted ribose experiment on BSA by Odetti et al. (1992, supra). Since ribose and derivatives such as ADP-ribose are normal metabolites, the very high rates of AGE formation seen here suggest that they should be considered more seriously as sources of potential glycation in various cellular compartments (Cervantes-Laurean et al., 1993, supra), even though their concentrations are well below those of the less reactive glucose.

Another new application of the isolation of intermediate is in studying the pH dependence of this complex reaction. The unusual bell-shaped pH profile seen for the post-Amadori AGE formation (FIG. 11) is in striking contrast to the mild pH dependence of the overall reaction. The latter kinetics reflect a composite effect of pH on all steps in the reaction, including Schiff base and Amadori product formation, each of which may have a unique pH dependence. This complexity is especially well illustrated by studies of hemoglobin glycation (Lowery et al., 1985, J. Biol. Chem. 260:11611–11618). The bell-shaped pH profile suggests, but does not prove, the involvement of two ionizing groups. If true, the data may imply the participation of a second amino group, such as from a neighboring lysine, in the formation of dominant antigenic AGEs. The observed pH profile and the pH-jump observations described suggest that a useful route to isolating and maintaining the reactive intermediate would be by the rapid lowering of the pH to near 5.0 after 24 h interruption.

The kinetic studies provide new insights into the mechanisms of action of aminoguanidine (guanylhydrazine), an AGE inhibitor proposed by Cerami and co-workers to combine with Amadori intermediates (Brownlee et al., 1986, supra). This proposed pharmacological agent is now in Phase III clinical trials for possible therapeutic effects in treating diabetes (Vlassara et al., 1994, supra). However, its mechanism of AGE inhibition is likely to be quite complex, since it is multifunctional. As a nucelophilic hydrazine, it can reversibly add to active carbonyls, including aldehydo carbonyls of open-chain glucose and ribose (Khatami et al., 1988, Life Sci. 43:1725–1731; Hirsch et al., 1995, Carbohyd. Res. 267:17–25), as well as keto carbonyls of Amadori compounds. It is also a guanidinium compound that can scavange highly reactive dicarbonyl glycation intermediates such as glyoxal and glucosones (Chen & Cerami, 1993, J. Carbohyd. Chem. 12:731–742; Hirsch et al., 1992, Carbohyd. Res. 232:125–130; Ou & Wolff, 1993, Biochem. Pharmacol. 46:1139–1144). The interrupted glycation method allowed examination of aminoguanidine efficacy on only post-Amadori steps of AGE formation. Equally important, it allowed studies in the absence of free sugar or dicarbonyl-reactive fragments from free sugar (Wolff & Dean, 1987, *Biochem. J.* 245:243–250; Wells-Knecht et al., 1995, *Biochemistry* 34:3702–3709) that can combine with aminoguanidine. The results of FIG. 20 demonstrate that aminoguanidine has, at best, only a modest effect on post-Amadori AGE formation reactions, achieving 50% inhibition at concentrations above 100–250 mM. The efficacy of aminoguanidine thus predominantly arises either from inhibiting early steps of glycation (Schiff base formation) or from scavenging highly reactive dicarbonyls generated during glycation. Contrary to the original claims, it does not appear to inhibit AGE formation by complexing the Amadori intermediate.

The use of interrupted glycation is not limited for kinetic studies. Interrupted glycation can simplify structural studies of glycated proteins and identifying unknown AGEs using techniques such as $^{13}$C NMR that has been used to detect Amadori adducts of RNase (Neglia et al., 1983, *J. Biol. Chem.* 258:14279–14283; 1985, *J. Biol. Chem.* 260:5406–5410). The combined use of structural and kinetic approaches should also be of special interest. For example, although the identity of the dominant antigenic AGEs reacting with the polyclonal antibodies remains uncertain, candidate AGEs, such as the recently proposed (carboxymethyl) lysine (Reddy et al., 1995, *Biochemistry* 34:10872–10878; cf. Makita et al., 1992, *J. Biol. Chem.* 267:5133–5138) should display the same kinetics of formation from the reactive intermediate that we have observed. The availability of the interrupted kinetics approach will also help to determine the importance of the Amadori pathway to the formation of this AGE. Similarly, monitoring of the interrupted glycation reaction by techniques such as $^{13}$C NMR should identify resonances of other candidate antigenic AGEs as being those displaying similar kinetics of appearance. Table I lists the $^{13}$C NMR peaks of the Amadori intermediate of RNase prepared by reaction with C-2 enriched ribose. The downfield peak near 205 ppm is probably due to the carbonyl of the Amadori product. In all cases, the ability to remove excess free and Schiff base sugars through interrupted glycation will considerably simplify isolation, identification, and structural characterization.

Table I lists the peaks that were assigned to the Post-Amadori Intermediate due to their invariant or decreasing intensity with time. Peak positions are listed in ppm downfield from TMS.

TABLE I

125MHz C-13 NMR Resonances of Ribonuclease Amadori Intermediate Prepared by 24 HR Reaction with 99% [2-C13]Ribose

| 216.5 ppm | 108.5 ppm |
|---|---|
| 211.7 | 105.9 |
| 208 | 103.9 |
|  | 103 |
| 172 | 95.8 |
| 165 |  |
| 163.9 | 73.65 |
| 162.1 | 70.2 |
|  | 69.7 |

Figure 31B:
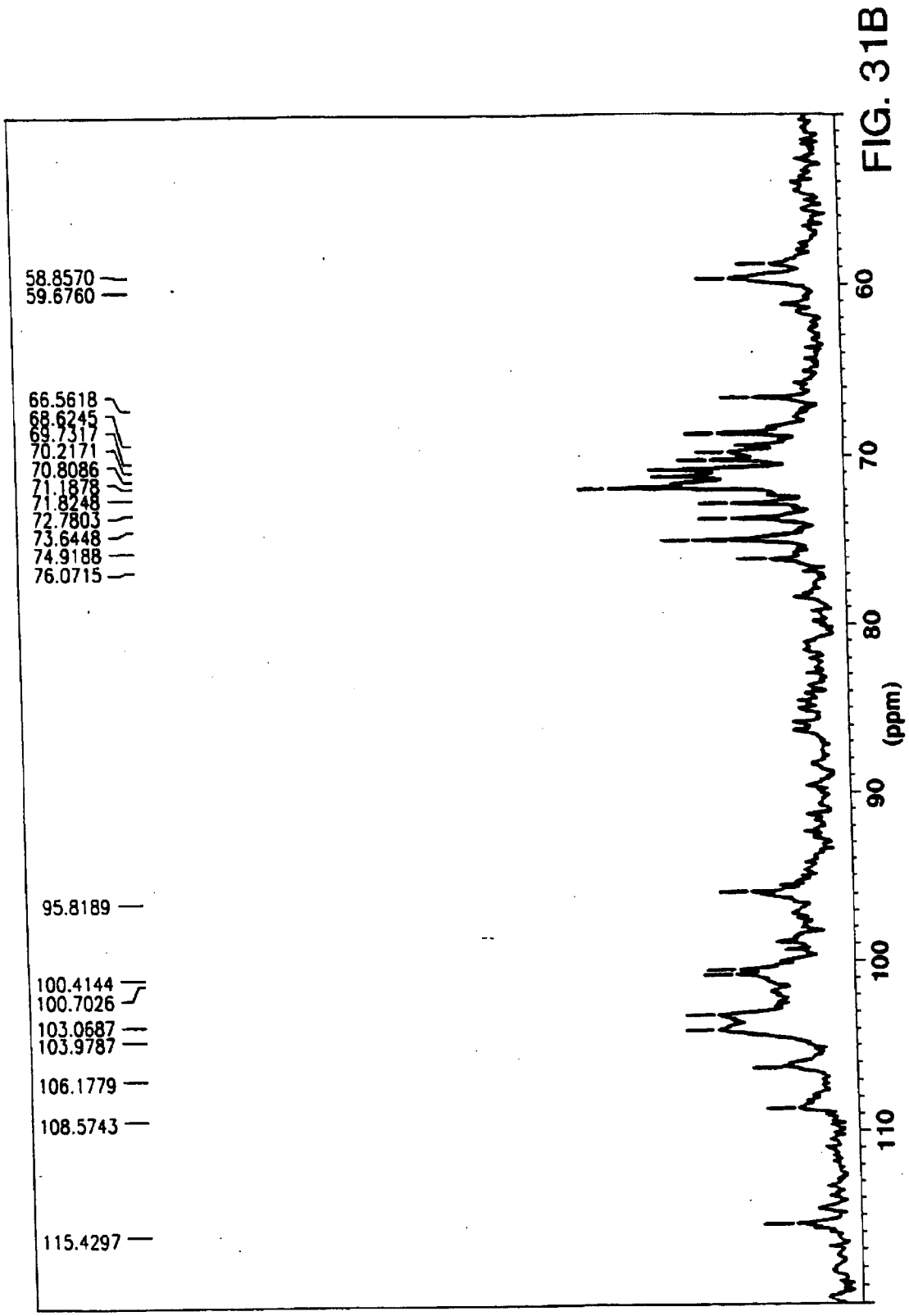
FIG. 31 shows a 125 MHz C-13 NMR Resonance spectrum of Riobonuclease Amadori Intermediate prepared by 24 HR reaction with 99% [2-C13]Ribose.

Ribonuclease A was reacted for 24 hr with 0.5 M ribose 99% enriched at C-2, following which excess and Schiff base bound ribose was removed by extensive dialysis in the cold. The sample was then warmed back to 37° C. immediately before taking a 2 hr NMR scan. The signals from RNase reacted with natural abundance ribose under identical conditions were then subtracted from the NMR spectrum. Thus all peaks shown are due to enriched C-13 that originated at the C-2 position. Some of the peaks arise from degradation products of the intermediate, and these can be identified by the increase in the peak intensity over time. FIG. 31 shows the NMR spectrum obtained.

EXAMPLE 3

Vitro Inhibition of the Formation of Antigenic Advanced Glycation End-Products (AGEs) by Derivatives of Vitamins $B_1$ and $B_6$ and Aminoguanidine. Inhibition of Post-Amadori Kinetics Differs from that of Overall Glycation The interrupted glycation method for following post-Amadori kinetics of AGE formation allows for the rapid quantitative study of "late" stages of the glycation reaction. Importantly, this method allows for inhibition studies that are free of pathways of AGE formation which arise from glycoxidative products of free sugar or Schiff base (Namiki pathway) as illustrated in scheme I. Thus the interrupted glycation method allows for the rapid and unique identification nd characterization of inhibitors of "late" stages of glycation which lead to antigenic AGE formation.

Among the vitamin $B_1$ and $B_6$ derivatives examined, pyridoxamine and thiamine pyrophosphate are unique inhibitors of the post-Amadori pathway of AGE formation. Importantly, it was found that efficacy of inhibition of overall glycation of protein, in the presence of high concentrations of sugar, is not predictive of the ability to inhibit the post-Amadori steps of AGE formation where free sugar is removed. Thus while pyridoxamine, thiamine pyrophosphate and aminoguanidine are potent inhibitors of AGE formation in the overall glycation of protein by glucose, aminoguanidine differs from the other two in that it is not an effective inhibitor of post-Amadori AGE formation. Aminoguanidine markedly slows the initial rate of AGE formation by ribose under uninterrupted conditions, but has no effect on the final levels of antigenic AGEs produced. Examination of different proteins (RNase, BSA and hemoglobin), confirmed that the inhibition results are generally non-specific as to the protein used, even though there are individual variations in the rates of AGE formation and inhibition.

Chemicals and Materials As in Example 1 Above.
Preparation of Polyclonal antibodies to AGEs
  As in Example 1 above.
ELISA detection of AGE Products As in Example 1 above.
  Uninterrupted ribose glycation assays Bovine serum albumin, ribonuclease A, and human hemoglobin were incubated with ribose at 37° C. in 0.4 M sodium phosphate buffer of pH 7.5 containing 0.02% sodium azide. The protein (10 mg/ml or 1 mg/ml), 0.05 M ribose, and prospective inhibitors (at 0.5, 3, 15 and 50 mM) were introduced into the incubation mixture simultaneously. Solutions were kept in the dark in capped tubes. Aliquots were taken and immediately frozen until analyzed by ELISA at the conclusion of the reaction. The incubations were for 3 weeks (Hb) or 6 weeks (RNase, BSA). Glycation reactions were monitored for constant pH throughout the duration of the experiments.
Interrupted (post-Amadori) Ribose Glycation Assays
  Glycation was first carried out by incubating protein (10 mg/ml) with 0.5 M ribose at 37° C. in 0.4 M phosphate buffer at pH 7.5 containing 0.2% sodium azide for 24 h in the absence of inhibitors. Glycation was then interrupted to remove excess and reversibly bound (Schiff base) sugar by extensive dialysis against frequent cold buffer changes at 4°

C. The glycated intermediate samples containing maximal amount of Amadori product and little AGE (depending on protein) were then quickly warmed to 37° C. without re-addition of ribose. This initiated conversion of Amadori intermediates to AGE products in the absence or presence of various concentrations (typically 3, 15 and 50 mM) of prospective inhibitors. Aliquots were taken and frozen at various intervals for later analysis. The solutions were kept in capped tubes and opened only to remove timed aliquots that were immediately frozen for later carrying out the various analyses.

Numerical Analysis of kinetics data Kinetics data (time progress curves) was routinely fit to mono- or bi-exponential functions using non-linear least squares methods utilizing either SCIENTIST 2.0 (MicroMath, Inc.) or ORIGIN (Microcal, Inc.) software that permit user-defined functions and control of parameters to iterate on. Standard deviations of the parameters of the fitted functions (initial and final ordinate values and rate constants) were returned as measures of the precision of the fits. Apparent half-times for bi-exponential kinetics fits were determined with the "solve" function of MathCad software (MathSoft, Inc.).

Results

Inhibition by Vitamin $B_6$ Derivatives of the Overall Kinetics of AGE Formation from Ribose.

Figure 13A:
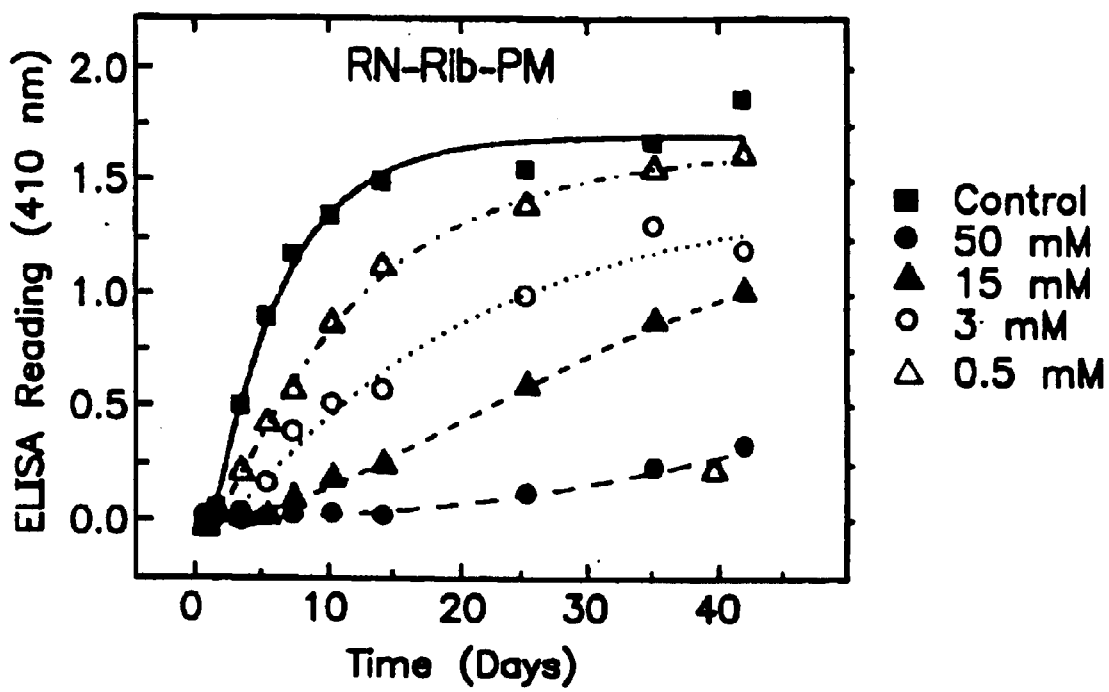
FIG. 13A Pyridoxamine (PM)
Figure 13B:
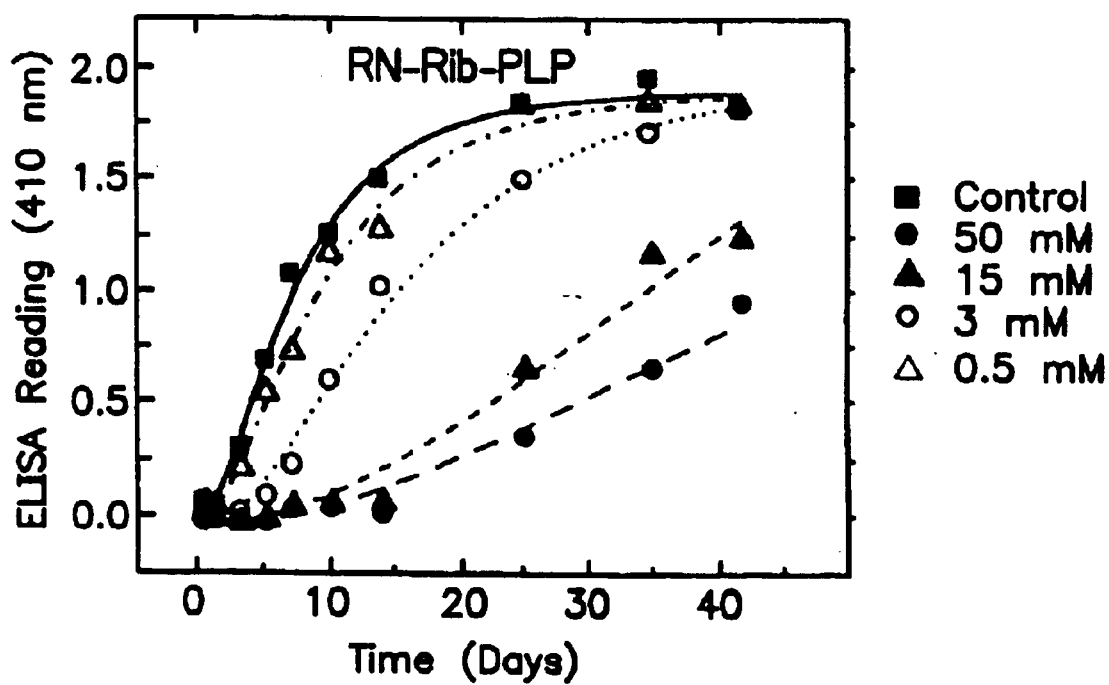
FIG. 13B pyridoxal-5'-phosphate (PLP)
Figure 13C:
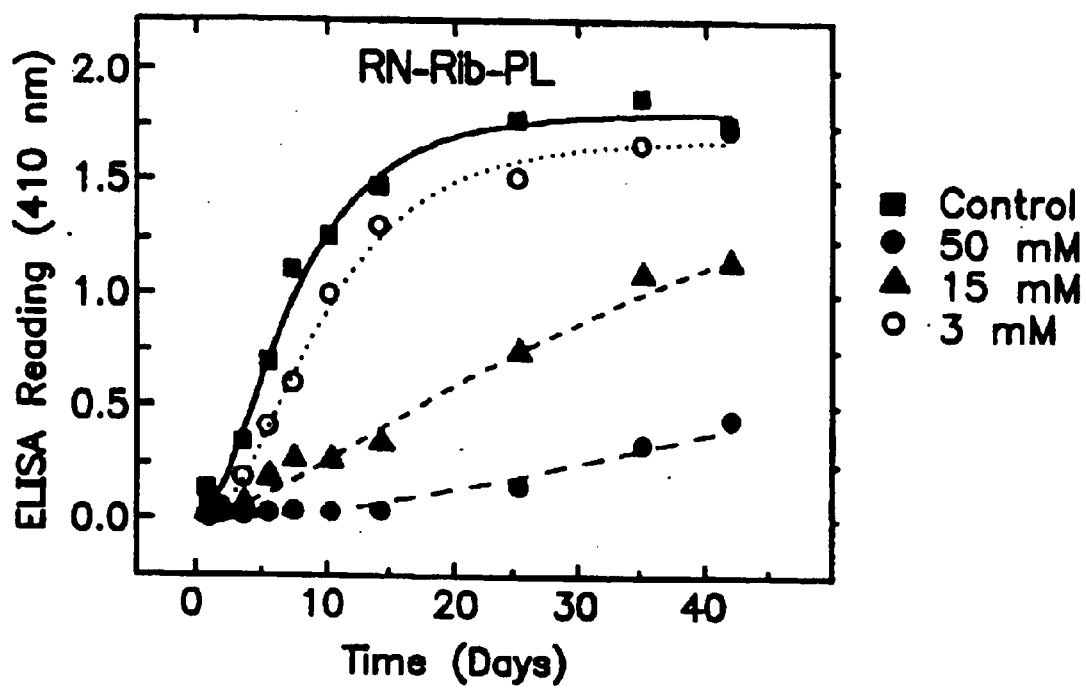
FIG. 13C pyridoxal (PL)
Figure 13D:
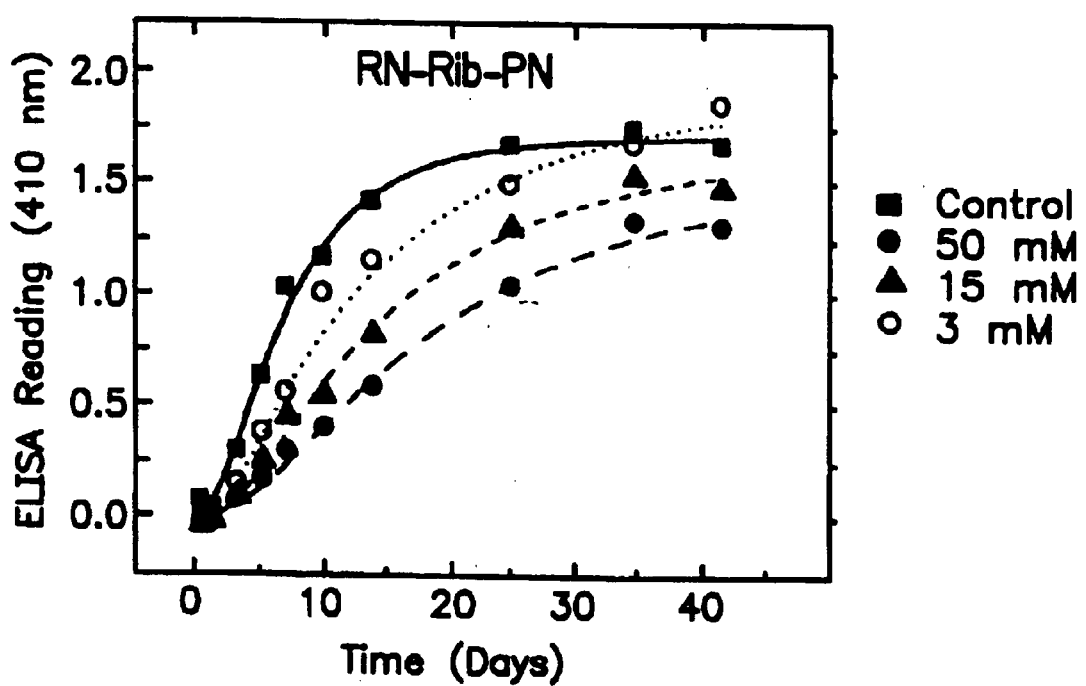
FIG. 13D pyridoxine (PN).

The inhibitory effects of vitamin $B_1$ and $B_6$ derivatives on the kinetics of antigenic AGE formation were evaluated by polyclonal antibodies specific for AGEs. Initial inhibition studies were carried out on the glycation of bovine ribonuclease A (RNase) in the continuous presence of 0.05 M ribose, which is the concentration of ribose where the rate of AGE formation is near maximal. FIG. 13 (control curves, filled rectangles) demonstrates that the formation of antigenic AGEs on RNase when incubated with 0.05 M ribose is relatively rapid, with a half-time of approximately 6 days under these conditions. Pyridoxal-5'-phosphate (FIG. 13B) and pyridoxal (FIG. 13C) significantly inhibited the rate of AGE formation on RNase at concentrations of 50 mM and 15 mM. Surprisingly, pyridoxine, the alcohol form of vitamin $B_6$, also moderately inhibited AGE formation on RNase (FIG. 13D). Of the $B_6$ derivatives examined, pyridoxamine at 50 mM was the best inhibitor of the "final" levels of AGE formed on RNase over the 6-week time period monitored (FIG. 13A).

Inhibition by Vitamin $B_1$ Derivatives of the Overall Kinetics of AGE Formation from Ribose.

Figure 14A:
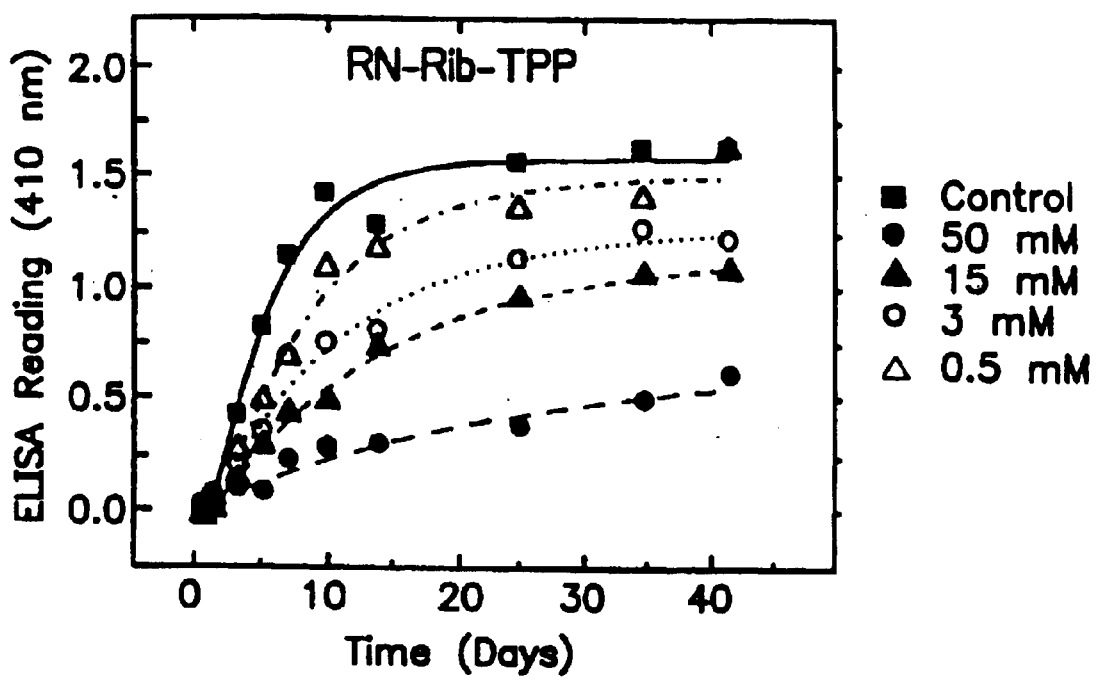
FIG. 14A Thiamine pyrophosphate (TPP)
Figure 14B:
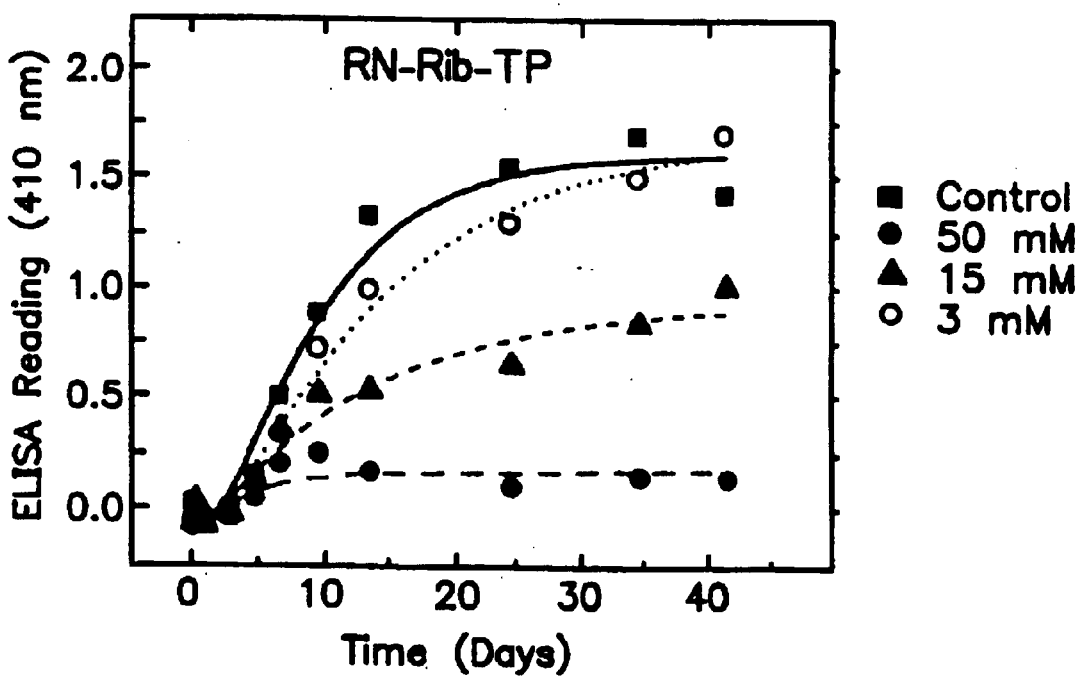
FIG. 14B thiamine monophosphate (TP)
Figure 14C:
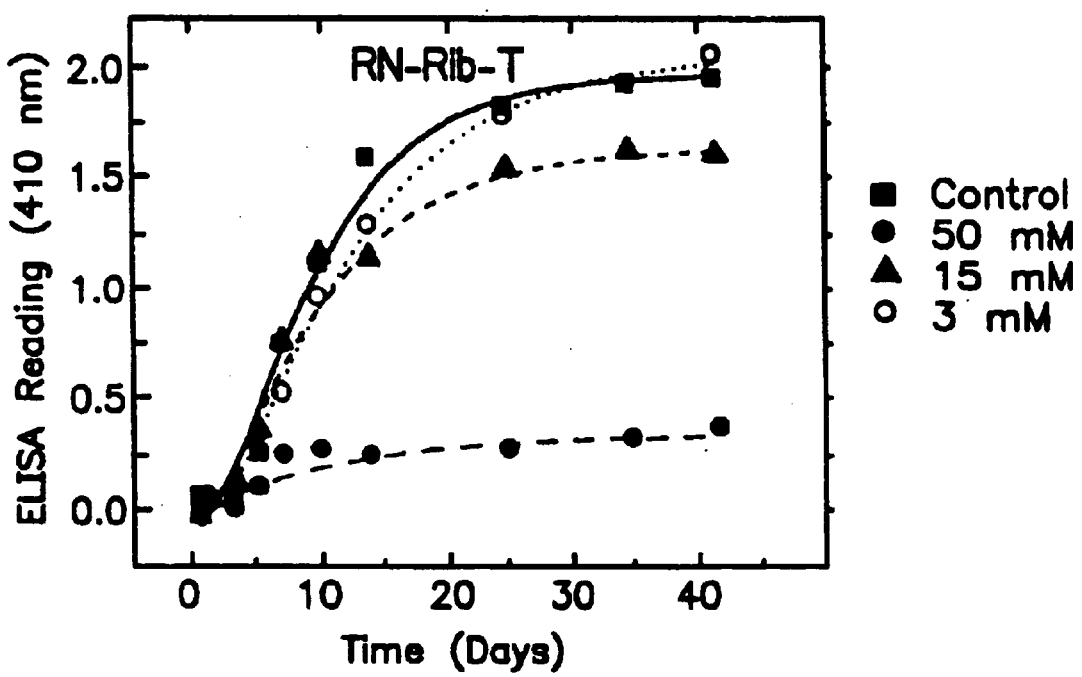
FIG. 14C thiamine (T)

All of the $B_1$ vitamers inhibited antigenic AGE formation on RNase at high concentrations, but the inhibition appeared more complex than for the $B_6$ derivatives (FIGS. 14A–C). In the case of thiamine pyrophosphate as the inhibitor (FIG. 14A), both the rate of AGE formation and the final levels of AGE produced at the plateau appeared diminished. In the case of thiamine phosphate as the inhibitor (FIG. 14B), and thiamine (FIG. 14C), there appeared to be little effect on the rate of AGE formation, but a substantial decrease in the final level of AGE formed in the presence of the highest concentration of inhibitor. In general, thiamine pyrophosphate demonstrated greater inhibition than the other two compounds, at the lower concentrations examined.

Figure 14D:
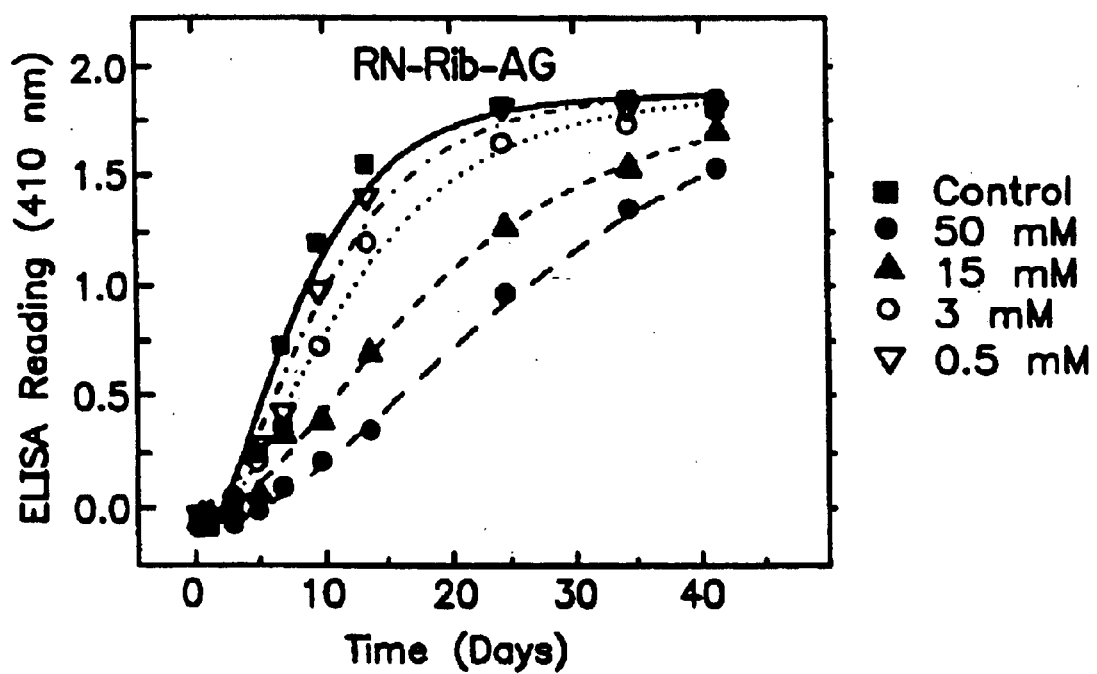
FIG. 14D aminoguanidine (AG).

Inhibition by Aminoguanidine of the Overall Kinetics of AGE Formation from Ribose Inhibition of AGE formation by aminoguanidine (FIG. 14D) was distinctly different from that seen in the $B_1$ and $B_6$ experiments. Increasing concentration of aminoguanidine decreased the rate of AGE formation on RNase, but did not reduce the final level of AGE formed. The final level of AGE formed after the 6-weeks was nearly identical to that of the control for all tested concentrations of aminoguanidine.

Figure 15A:
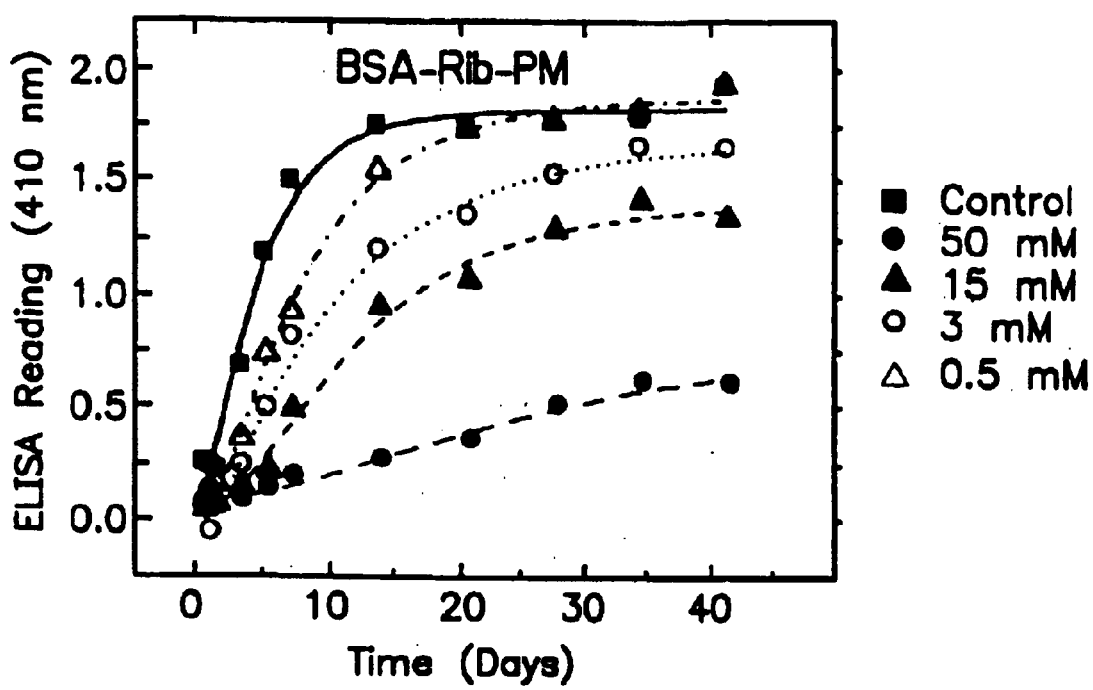
FIG. 15A Pyridoxamine (PM)
Figure 15B:
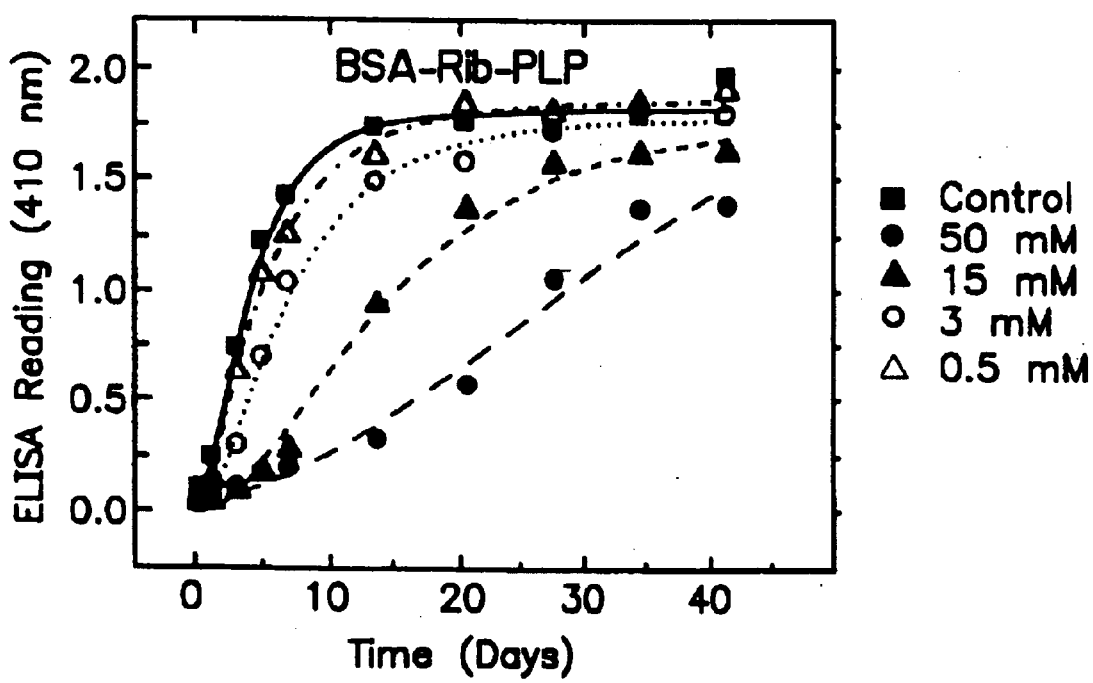
FIG. 15B pyridoxal-5'-phosphate (PLP)
Figure 15C:
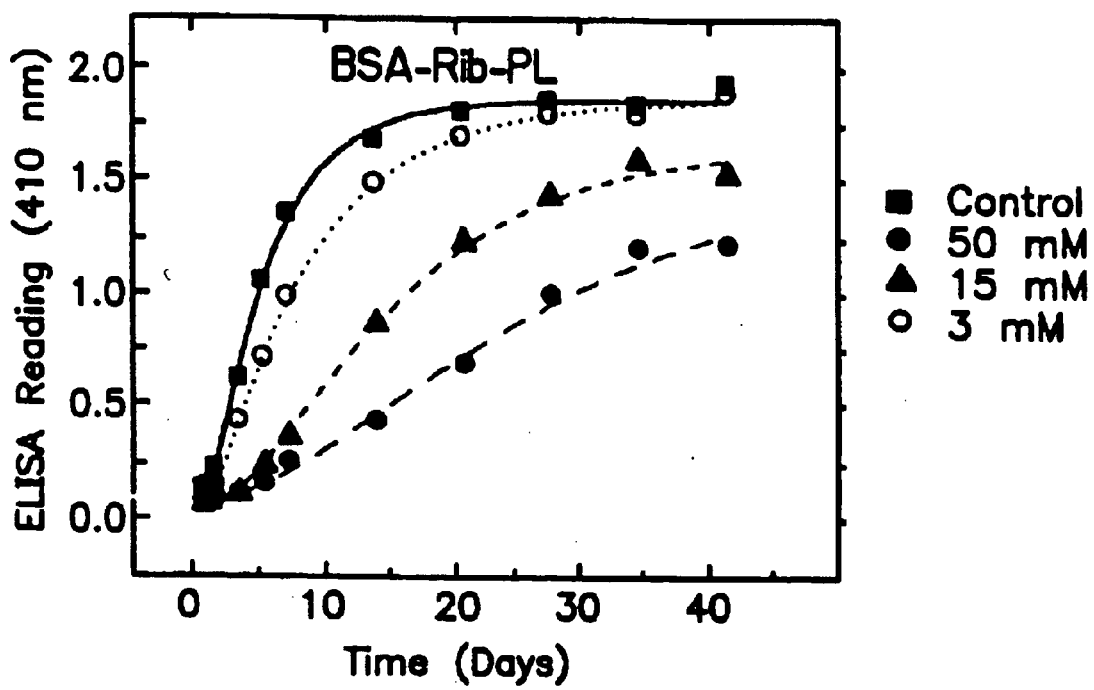
FIG. 15C pyridoxal (PL)
Figure 15D:
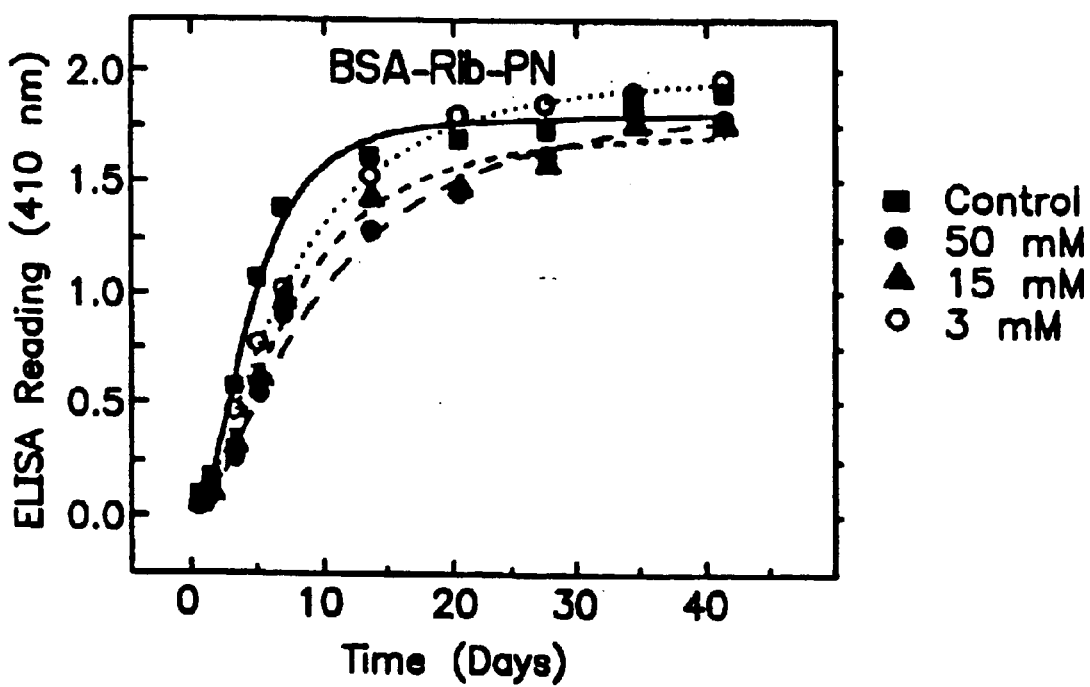
FIG. 15D pyridoxine (PN).
Figure 16A:
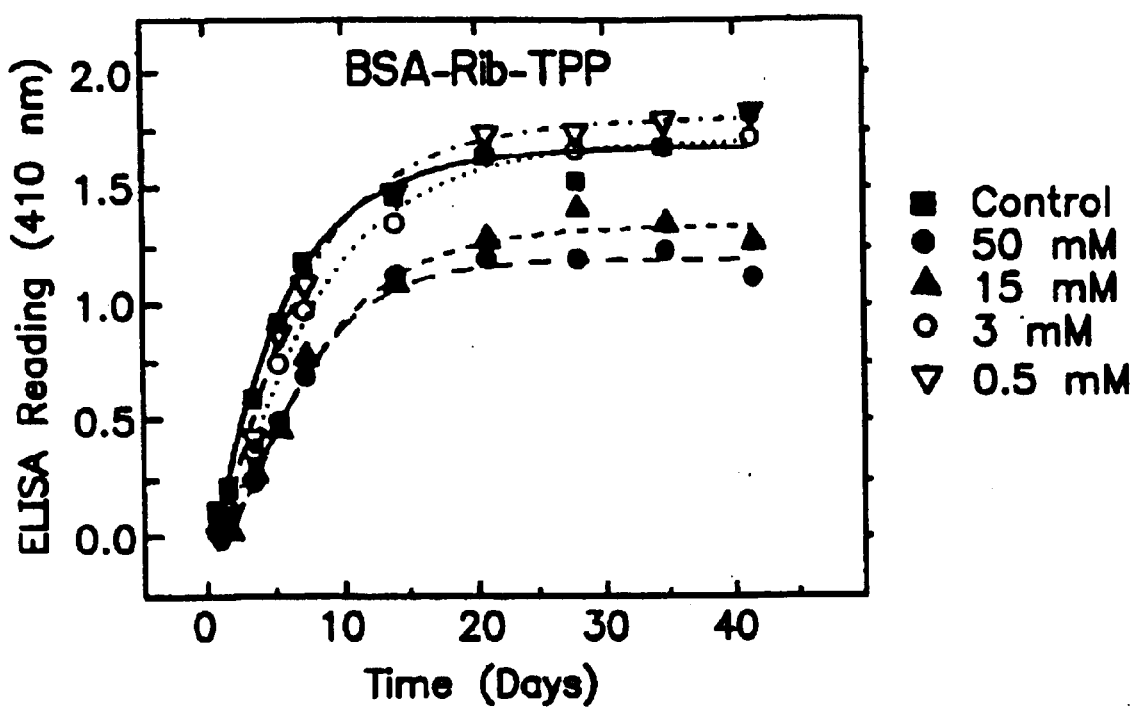
FIG. 16A Thiamine pyrophosphate (TPP)
Figure 16B:
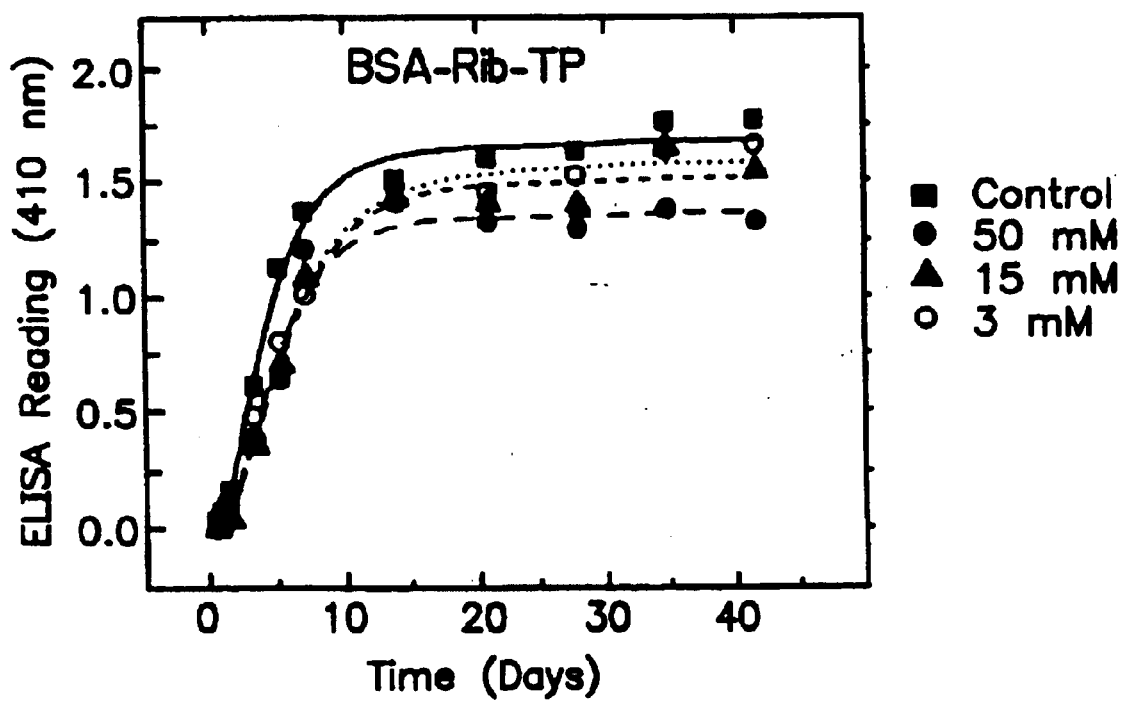
FIG. 16B thiamine monophosphate (TP)
Figure 16C:
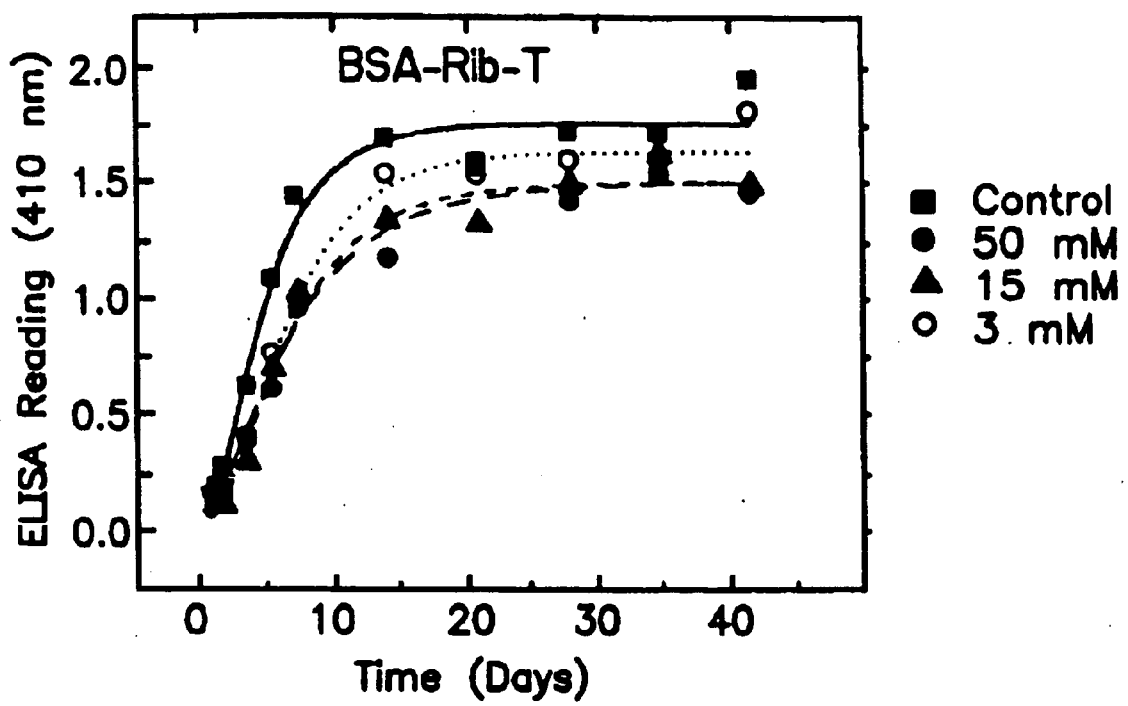
FIG. 16C thiamine (T)
Figure 16D:
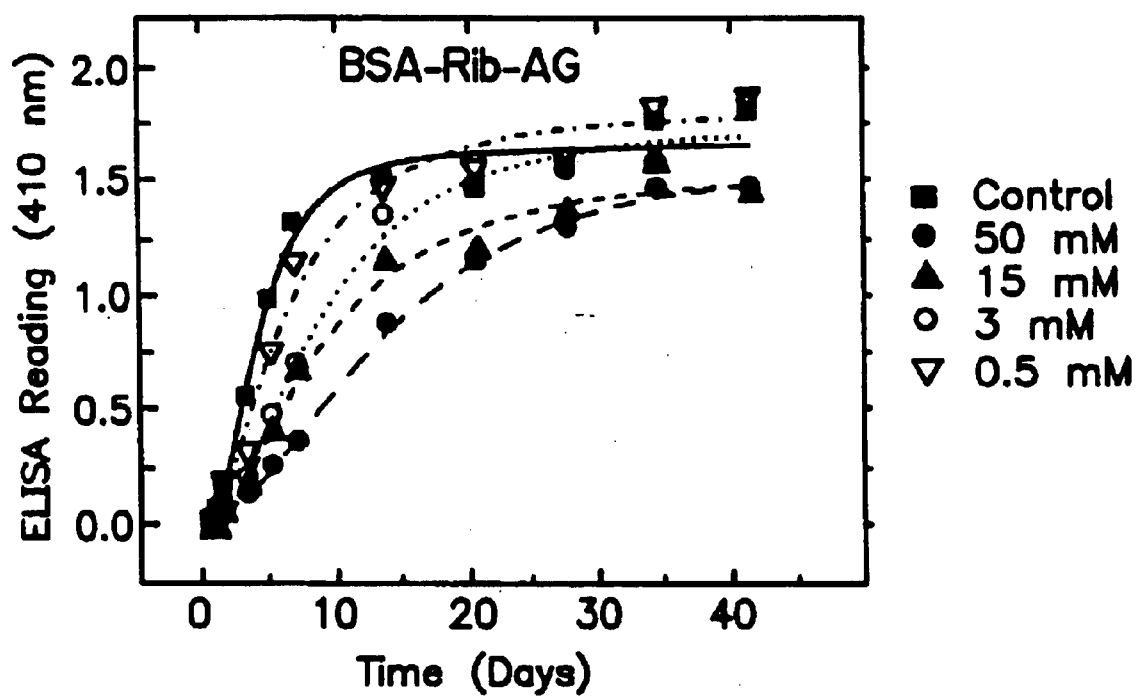
FIG. 16D aminoguanidine (AG).

Inhibition of the Overall Kinetics of AGE Formation in Serum Albumin and Hemoglobin from Ribose Comparative studies were carried out with BSA and human methemoglobin (Hb) to determine whether the observed inhibition was protein-specific. The different derivatives of vitamin $B_6$ (FIGS. 15A–D) and vitamin $B_1$ (FIGS. 16A–C) exhibited similar inhibition trends when incubated with BSA as with RNase, pyridoxamine and thiamine pyrophosphate being the most effective inhibitors or each family. Pyridoxine failed to inhibit AGE formation on BSA FIG. 15D). Pyridoxal phosphate and pyridoxal (FIGS. 15B–C) mostly inhibited the rate of AGE formation, but not the final levels of AGE formed. Pyridoxamine (FIG. 15A) exhibited some inhibition at lower concentrations, and at the highest concentration tested appeared to inhibit the final levels of AGE formed more effectively than any of the other $B_6$ derivatives. In the case of $B_1$ derivatives, the overall extent of inhibition of AGE formation with BSA (FIGS. 16A–C), was less than that observed with RNase (FIGS. 14A–C). Higher concentrations of thiamine and thiamine pyrophosphate inhibited the final levels of AGEs formed, without greatly affecting the rate of AGE formation (FIG. 16C). Aminoguanidine again displayed the same inhibition effects with BSA as seen with RNase (FIG. 16D), appearing to slow the rate of AGE formation without significantly affecting the final levels of AGE formed.

Figure 17A:
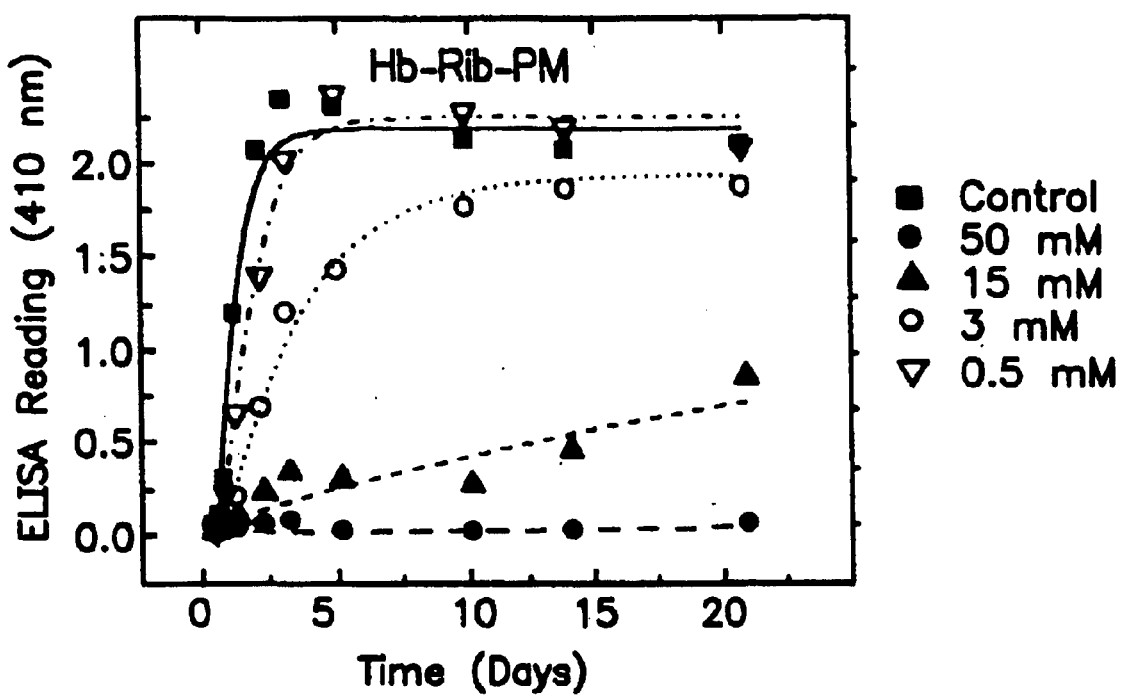
FIG. 17A Pyridoxamine (PM)
Figure 17B:
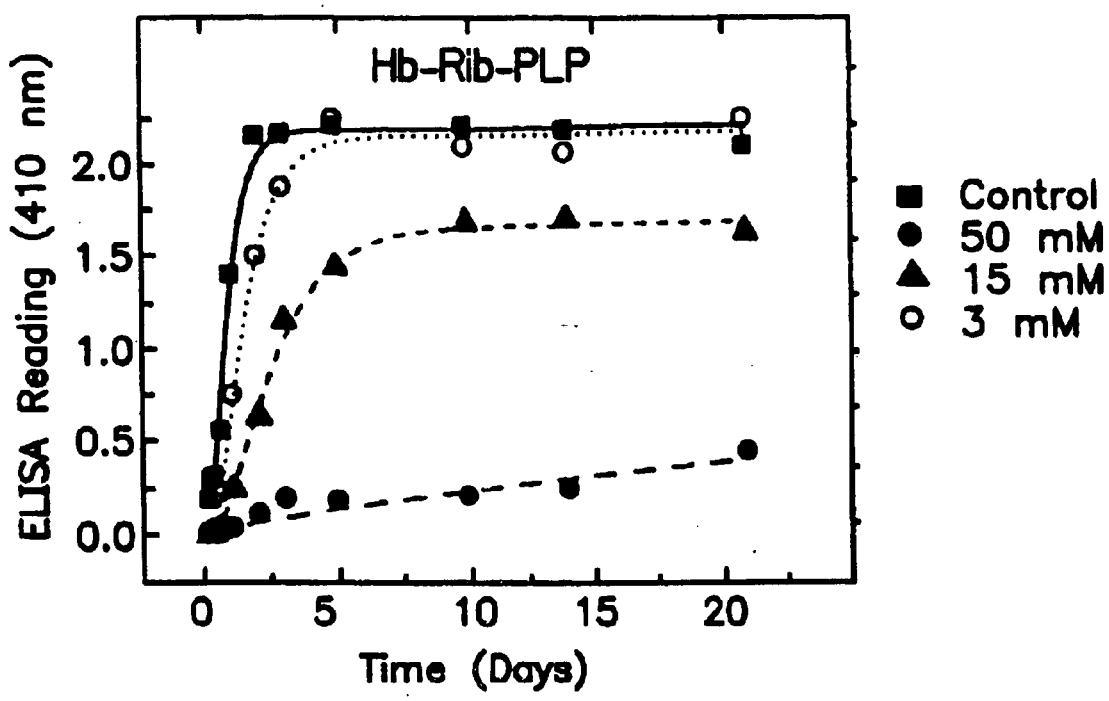
FIG. 17B pyridoxal-5'-phosphate (PLP)
Figure 17C:
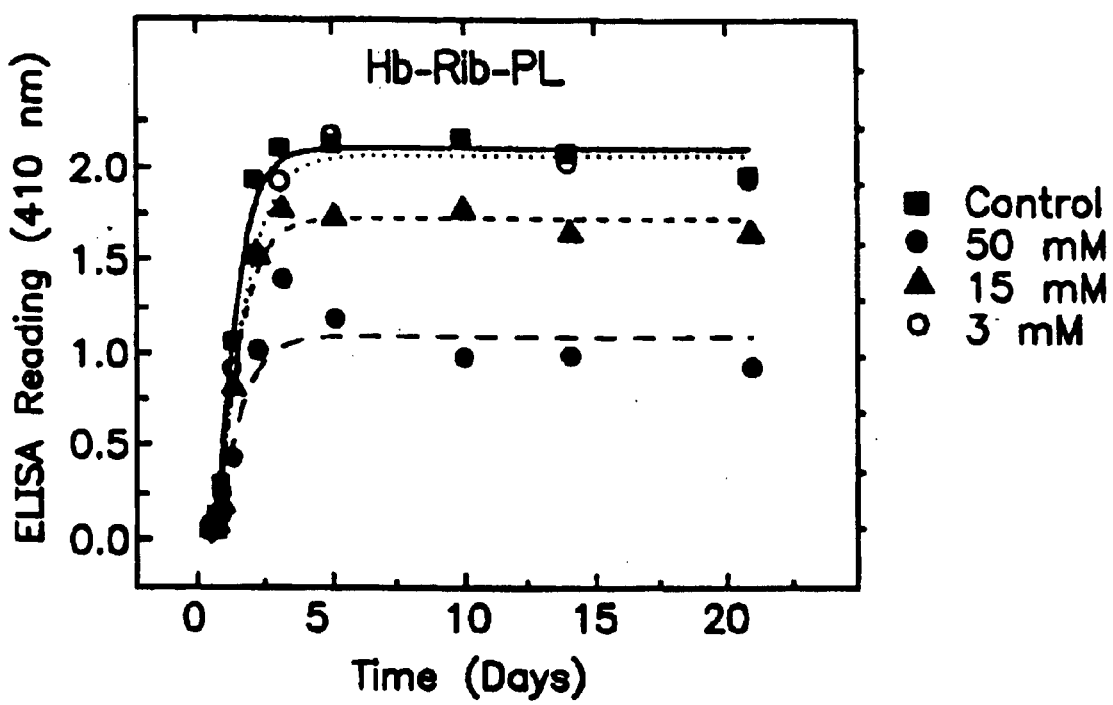
FIG. 17C pyridoxal (PL)
Figure 17D:
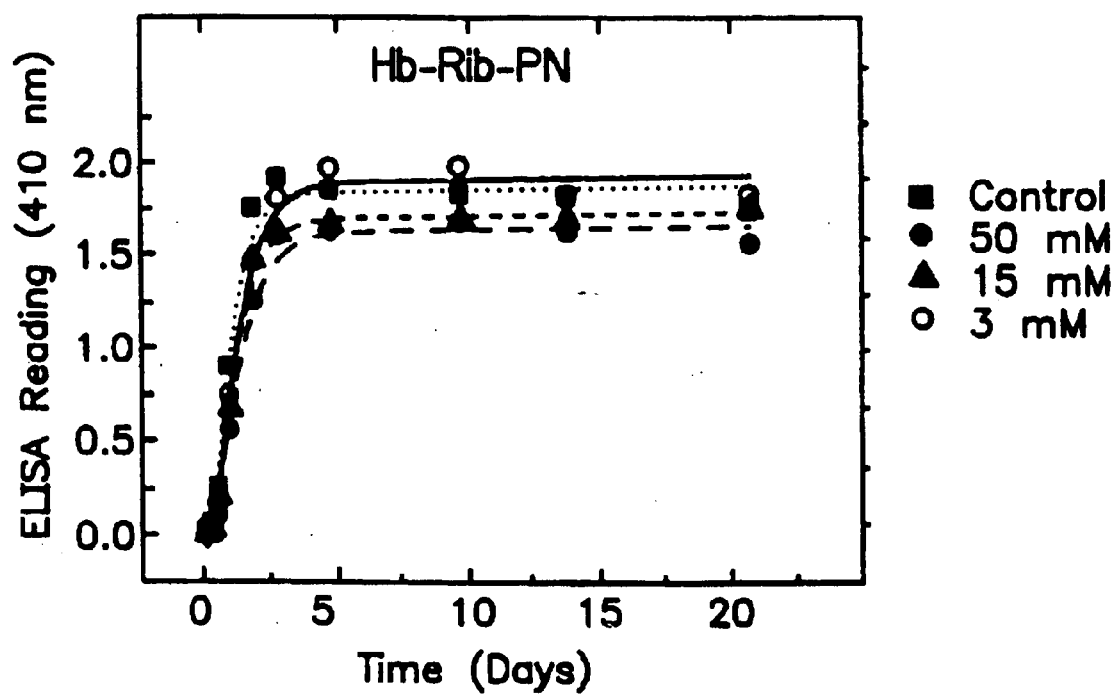
FIG. 17D pyridoxine (PN).

The kinetics of AGE formation was also examined using Hb in the presence of the $B_6$ and $B_1$ vitamin derivatives, and aminoguanidine. The apparent absolute rates of AGE formation were significantly higher with Hb than with either RNase or BSA. However, the tested inhibitors showed essentially similar behavior. The effects of the vitamin $B_6$ derivatives are shown in FIG. 17. Pyridoxamine showed the greatest inhibition at concentrations of 3 mM and above (FIG. 17A), and was most effective when compared to pyridoxal phosphate (FIG. 17B), pyridoxal (FIG. 17C), and pyridoxine (FIG. 17D). In the case of the $B_1$ vitamin derivatives (data not shown), the inhibitory effects were more similar to the BSA inhibition trends than to RNase. The inhibition was only modest at the highest concentrations tested (50 mM), being nearly 30–50% for all three $B_1$ derivatives. The primary manifestation of inhibition was in the reduction of the final levels of AGE formed.

Inhibition by Vitamin $B_6$ Derivatives of the Kinetics of Post-Amadori Ribose AGE Formation Using the interrupted glycation model to assay for inhibition of the "late" post-Amadori AGE formation, kinetics were examined by incubating isolated Amadori intermediates of either RNase or BSA at 37° C. in the absence of free or reversibly bound ribose. Ribose sugar that was initially used to prepare the intermediates was removed by cold dialysis after an initial glycation reaction period of 24 h. After AGE formation is allowed to resume, formation of AGE is quite rapid (half-times of about 10 h) in the absence of any inhibitors. FIG. 18 shows the effects of pyridoxamine (FIG. 18A), pyridoxal phosphate (FIG. 18B), and pyridoxal (FIG. 18C) on the post-Amadori kinetics of BSA. Pyridoxine did not produce any inhibition (data not shown). Similar experiments were carried out on RNase. Pyridoxamine caused nearly complete inhibition of AGE formation with RNase at 15 mM and 50 mM (FIG. 18D). Pyridoxal did not show any significant inhibition at 15 mM (the highest tested), but pyridoxal phosphate showed significant inhibition at 15 mM. Pyridoxal phosphate is known to be able to affinity label the active site of RNase (Raetz and Auld, 1972, *Biochemistry* 11:2229–2236).

Figure 18A:
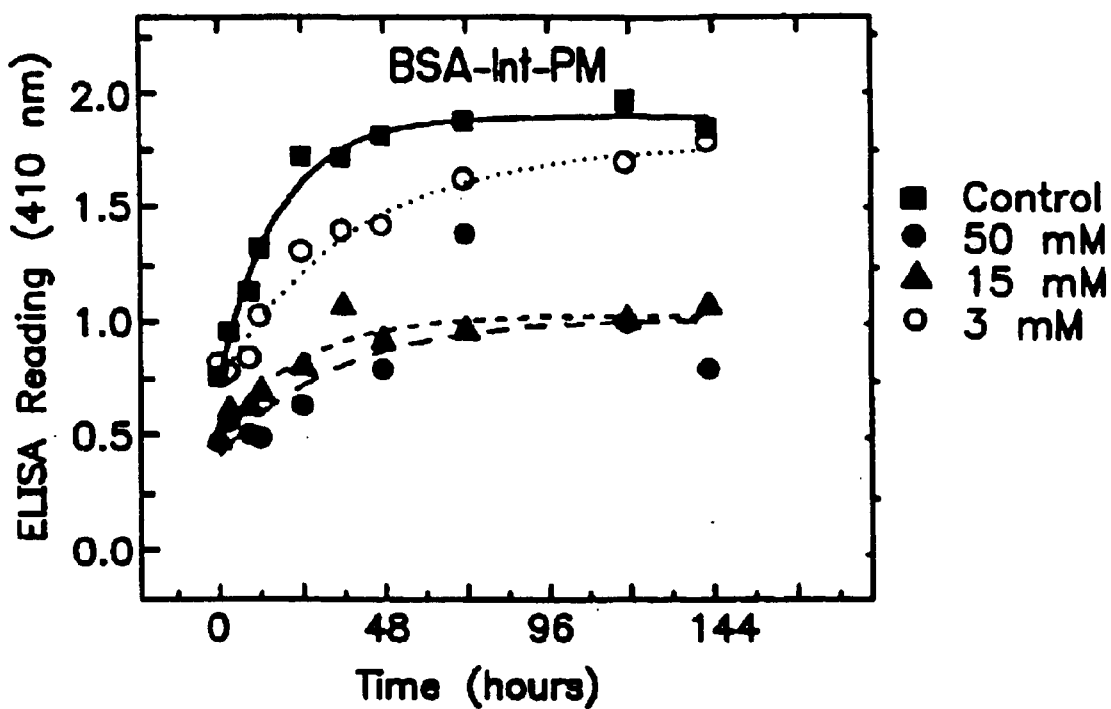
FIG. 18A BSA and Pyridoxamine (PM)
Figure 18B:
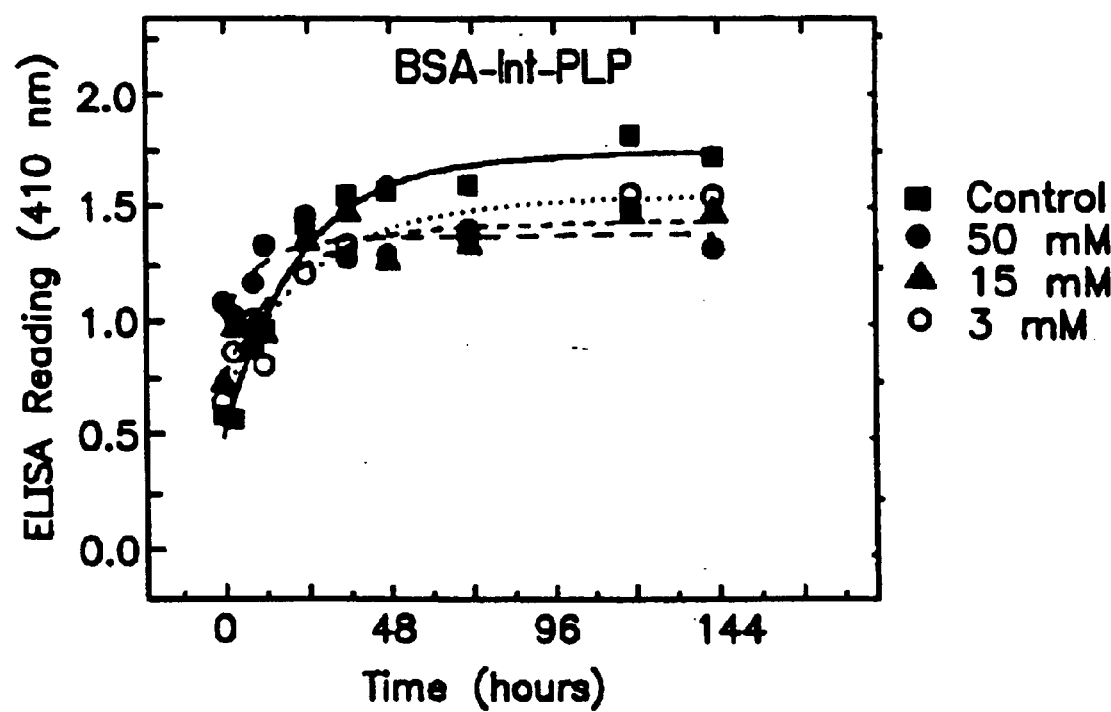
FIG. 18B BSA and pyridoxal-5'-phosphate (PLP)
Figure 18C:
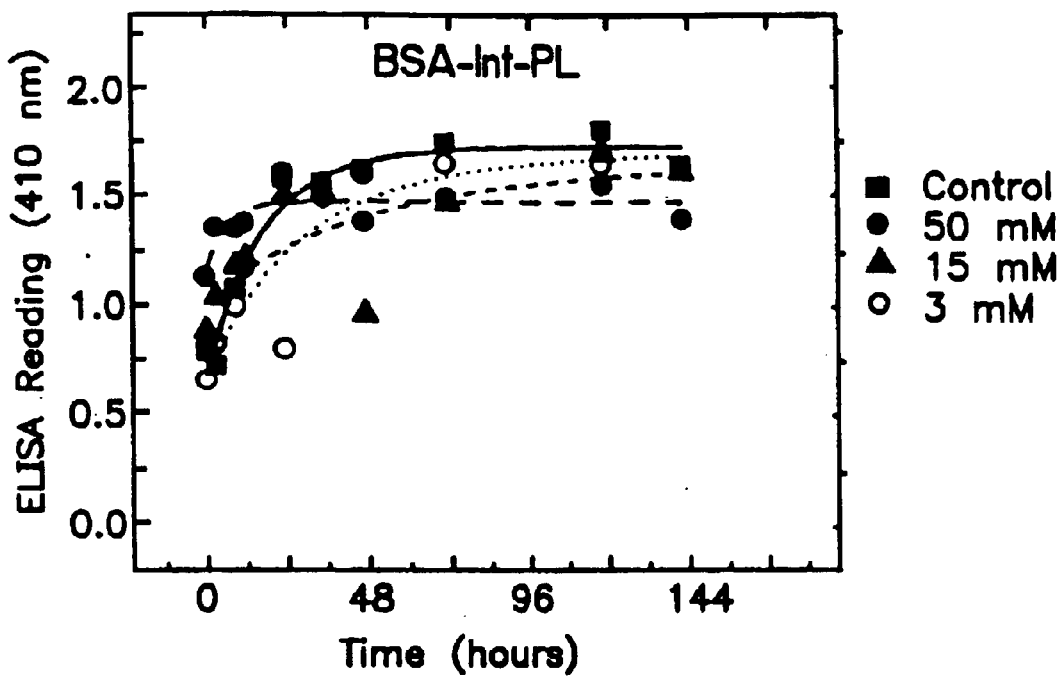
FIG. 18C BSA and pyridoxal (PL)
Figure 18D:
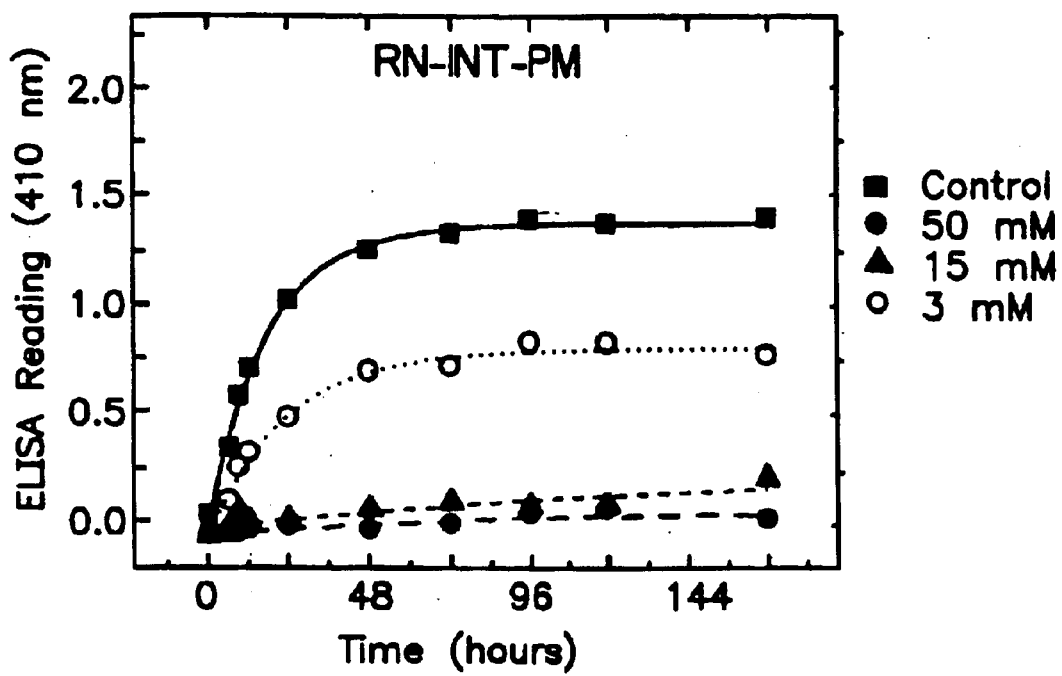
FIG. 18D RNase and pyridoxamine (PM).

With BSA, unlike RNase, a significant amount of antigenic AGE formed during the 24 h initial incubation with RNase (25–30%), as evidenced by the higher ELISA readings after removal of ribose at time zero for FIGS. 18A–C. For both BSA and RNase, the inhibition, when seen, appears to manifest as a decrease in the final levels of AGE formed rather than as a decrease in the rate of formation of AGE.

Figure 19A:
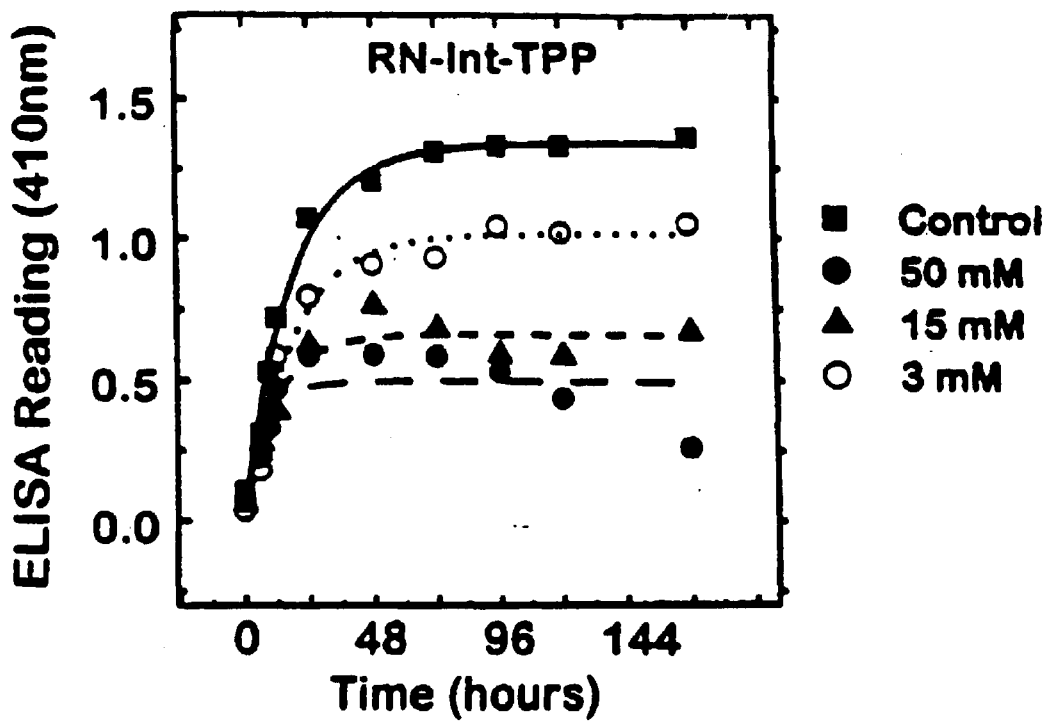
FIG. 19A RNase, FIG. 19B BSA.
Figure 19B:
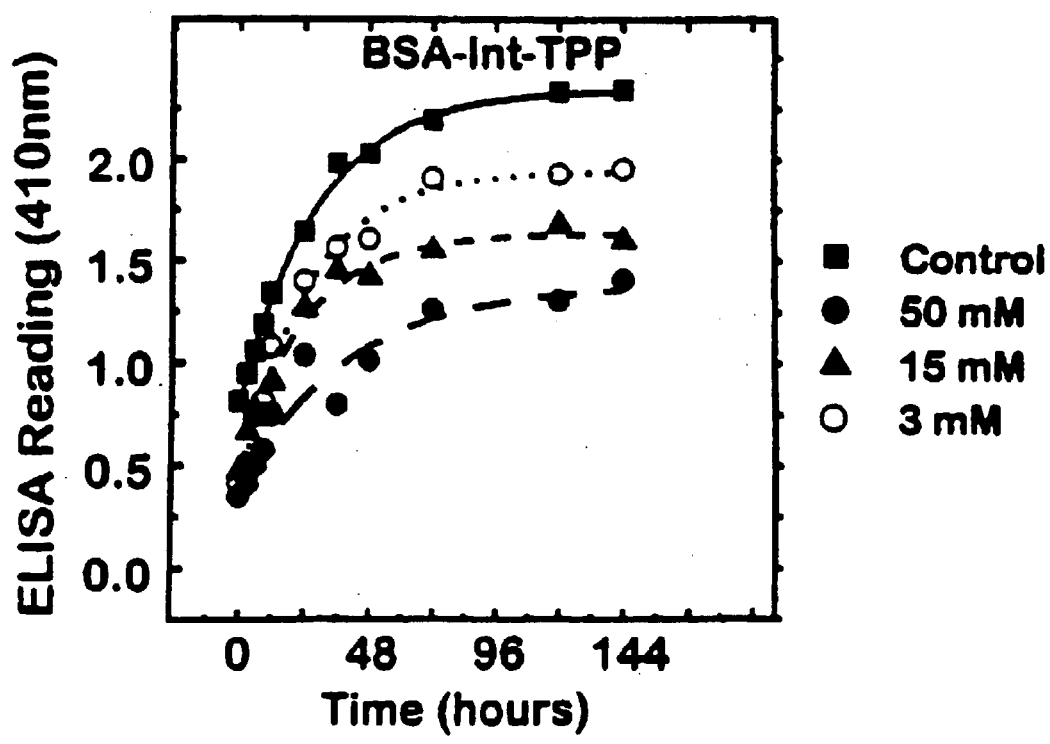
FIG. 19 are graphs depicting the effect of thiamine pyrophosphate on post-Amadori AGE formation after interrupted glycation by ribose.

Inhibition by Vitamin $B_1$ Derivatives of the Kinetics of Post-Amadori Ribose AGE Formation Thiamine pyrophosphate inhibited AGE formation more effectively than the other $B_1$ derivatives with both RNase and BSA (FIG. 19). Thiamine showed no effect, while thiamine phosphate showed some intermediate effect. As with the $B_6$ assays, the post-Amadori inhibition was most apparently manifested as a decrease in the final levels of AGE formed.

Figure 21:
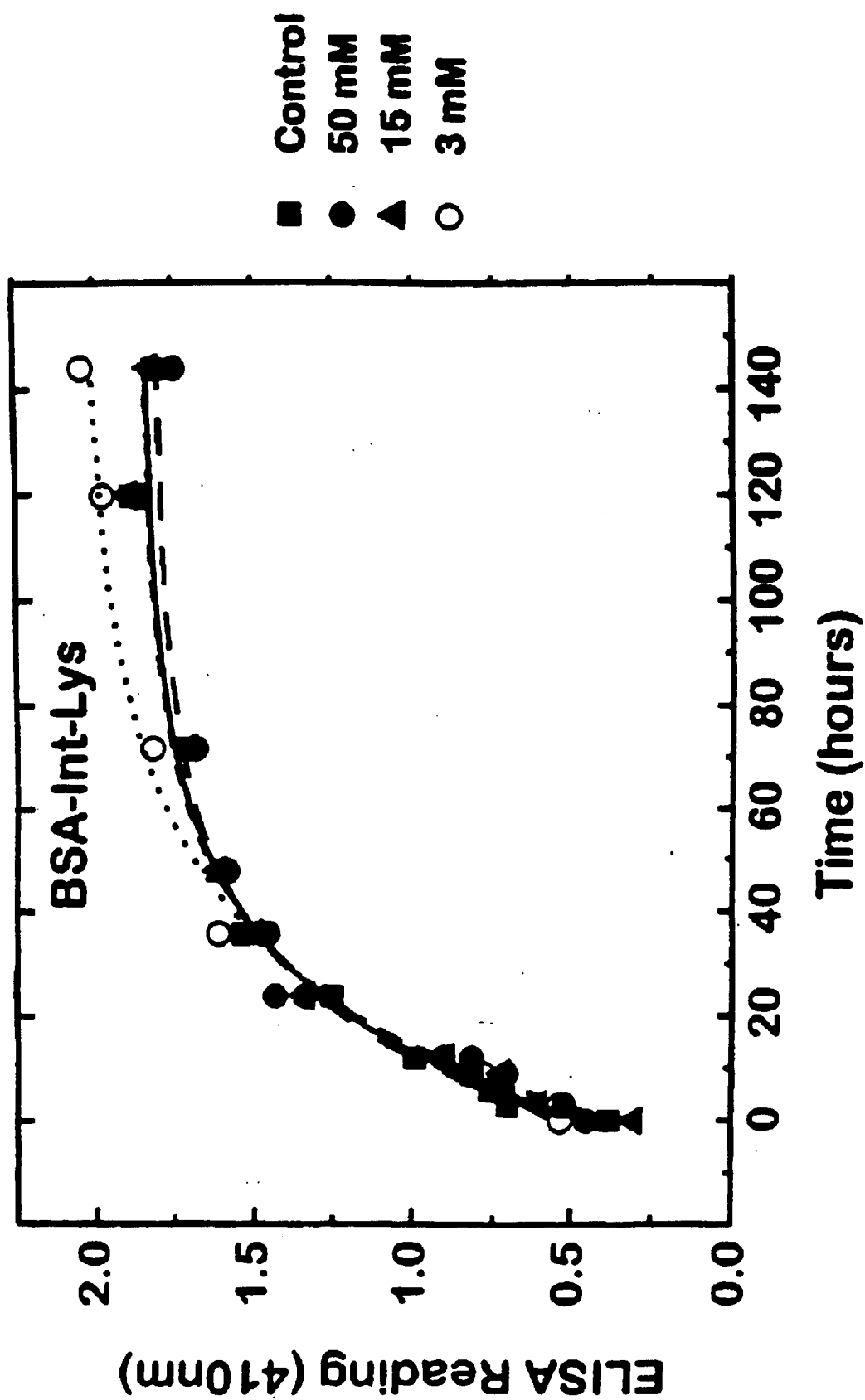
FIG. 21 is a graph depicting the effect of N-acetyl-L-lysine on post-Amadori AGE formation after interrupted glycation by ribose.

Effects of Aminoguanidine and $N^\alpha$-acetyl-L-lysine on the Kinetics of Post-Amadori Ribose AGE Formation FIG. 20 shows the results of testing aminoguanidine for inhibition of post-Amadori AGE formation kinetics with both BSA and RNase. At 50 mM, inhibition was about 20% in the case of BSA (FIG. 20B), and less than 15% with RNase (FIG. 20A). The possibility of inhibition by simple amino-containing functionalities was also tested using Na-acetyl-L-lysine (FIG. 21), which contains only a free $N^{68}$-amino group. $N^{60}$-acetyl-L-lysine at up to 50 mM failed to exhibit any significant inhibition of AGE formation.

Discussion

Numerous studies have demonstrated that aminoguanidine is an apparently potent inhibitor of many manifestations of nonenzymatic glycation (Brownlee et al., 1986; Brownlee, 1992,1994, 1995). The inhibitory effects of aminoguanidine on various phenomena that are induced by reducing sugars are widely considered as proof of the involvement of glycation in many such phenomena. Aminoguanidine has recently entered into a second round of Phase III clinical trials for ameliorating the complications of diabetes thought to be caused by glycation of connective tissue proteins due to high levels of sugar.

Data from the kinetic study of uninterrupted "slow" AGE formation with RNase induced by glucose (Example 1) confirmed that aminoguanidine is an effective inhibitor, and further identified a number of derivatives of vitamins $B_1$ and $B_6$ as equally or slightly more effective inhibitors. However, the inhibition by aminoguanidine unexpectedly appeared to diminish in effect at the later stages of the AGE formation reaction. Due to the slowness of the glycation of protein with glucose, this surprising observation could not be fully examined. Furthermore, it has been suggested that there may be questions about the long-term stability of aminoguanidine (Ou and Wolff, 1993, supra).

Figure 22A:
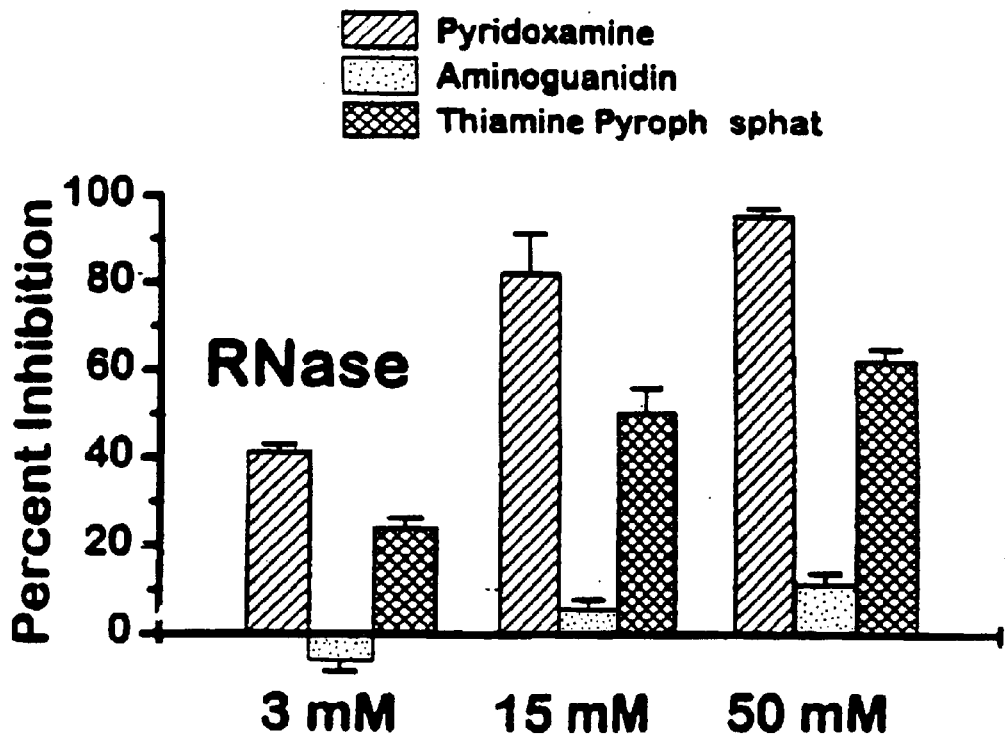
FIG. 22 are bar graphs showing a comparison of post-Amadori inhibition of AGE formation by thiamine pyrophosphate (TPP), pyridoxamine (PM) and aminoguanidine (AG) after interrupted glycation of RNase (FIG. 22A) and BSA (FIG. 22B) by ribose.
Figure 22B:
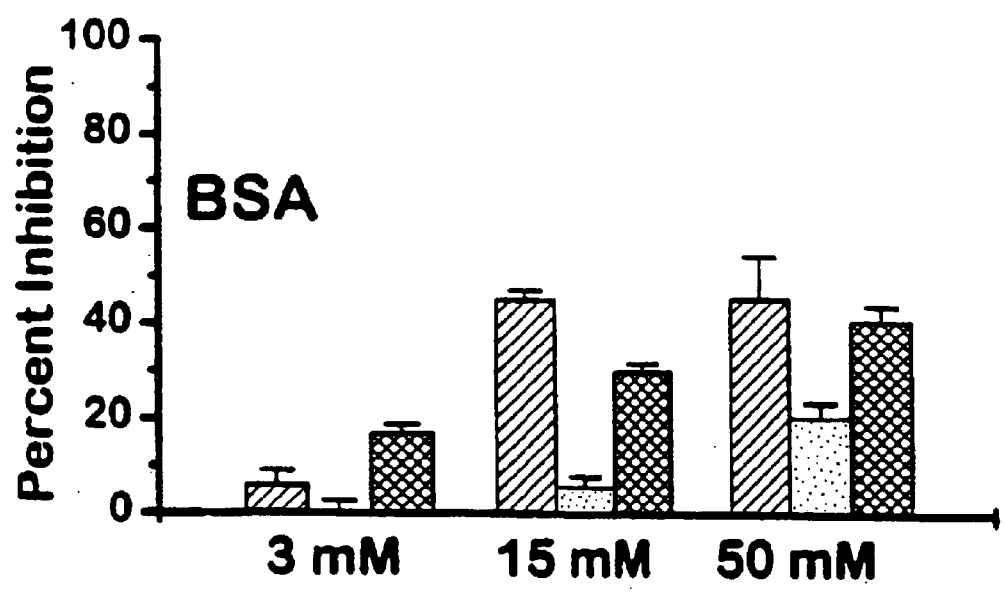

Analysis using the much more rapid glycation by ribose allowed for the entire time-course of AGE formation to be completely observed and quantitated during uninterrupted glycation of protein. The use of interrupted glycation uniquely allowed further isolation and examination of only post-Amadori antigenic AGE formation in the absence of free and reversibly bound (Schiff base) ribose. Comparison of the data from these two approaches with the earlier glucose glycation kinetics has provided novel insights into the mechanisms and effectiveness of various inhibitors. FIG. 22 are bar graphs which depict summarized comparative data of percent inhibition at defined time points using various concentrations of inhibitor. FIG. 22A graphs the data for inhibition after interrupted glycation of RNase AGE formation in ribose. FIG. 22B graphs the data for inhibition after interrupted glycation of BSA AGE formation by ribose.

The overall results unambiguously demonstrate that aminoguanidine slows the rate of antigenic AGE formation in the presence of sugar but has little effect on the final amount of post-Amadori AGE formed. Thus observations limited to only the initial "early" stages of AGE formation which indicate efficacy as an inhibitor may in fact be misleading as to the true efficacy of inhibition of post-Amadori AGE formation. Thus the ability to observe a full-course of reaction using ribose and interrupted glycation gives a more complete picture of the efficacy of inhibition of post-Amadori AGE formation.

EXAMPLE 4

Animal Model & Testing of In Vivo Effects of AGE Formation/Inhibitors

Hyperglycemia can be rapidly induced (within one or two days) in rats by administration of streptozocin (aka. streptozotocin, STZ) or alloxan. This has become a common model for diabetes melitus. However, these rats manifest nephropathy only after many months of hyperglycemia, and usually just prior to death from end-stage renal disease (ESRD). It is believed that this pathology is caused by the irreversible glucose chemical modification of long-lived proteins such as collagen of the basement membrane. STZ-diabetic rats show albuminuria very late after induction of hyperglycemia, at about 40 weeks usually only just prior to death.

Because of the dramatic rapid effects of ribose demonstrated in vitro in the examples above, it was undertaken to examine the effects of ribose administration to rats, and the possible induction of AGEs by the rapid ribose glycation. From this study, a rat model for accelerated ribose induced pathology has been developed.

Effects of Very Short-term Ribose Administration In Vivo

Phase I Protocol

Two groups of six rats each were given in one day either:
  a. 300 mM ribose (two intraperitoneal infusions 6–8 hours apart, each 5% of body weight as ml); or
  b. 50 mM ribose (one infusion)

Rats were then kept for 4 days with no further ribose administration, at which time they were sacrificed and the following physiological measurements were determined: (i) initial and final body weight; (ii) final stage kidney weight; (iii) initial and final tail-cuff blood pressure; (iv) creatinine clearance per 100 g body weight.

Albumin filtration rates were not measured, since no rapid changes were initially anticipated. Past experience with STZ-diabetic rats shows that albuminuria develops very late (perhaps 40 weeks) after the induction of hyperglycemia and just before animals expire.

Renal Physiology Results a. Final body weight and final single kidney weight was same for low and high ribose treatment groups.

b. Tail-cuff blood pressure increased from 66±4 to 83±3 to rats treated with low ribose (1×50 mM), and from 66±4 to 106±5 for rats treated with high ribose (2×300 mM). These results are shown in the bar graph of FIG. 23.

c. Creatinine clearance, as cc per 100 g body weight, was decreased (normal range expected about 1.0–1.2) in a dose-dependent fashion to 0.87±0.15 for the low ribose group, and decreased still further 30% to 0.62±0.13 for the high ribose group. These results are shown in the bar graph of FIG. 24.

Phase I Conclusion

A single day's ribose treatment caused a dose-dependent hypertension and a dose-dependent decrease in glomerular clearance function manifest 4 days later. These are significant metabolic changes of diabetes seen only much later in STZ-diabetic rats. These phenomenon can be hypothesized to be due to ribose irreversible chemical modification (glycation) of protein in vivo.

Effect of Exposure to Higher Ribose Concentrations for Longer Time

Phase II Protocol

Groups of rats (3–6) were intraperitoneally given 0.3 M "low ribose dose" (LR) or 1.0 M "high ribose dose" (HR) by twice-daily injections for either (i) 1 day, (ii) a "short-term" (S) of 4 days, or (iii) a "long-term" (L) of 8 days. Additionally, these concentrations of ribose were included in drinking water.

Figure 23:
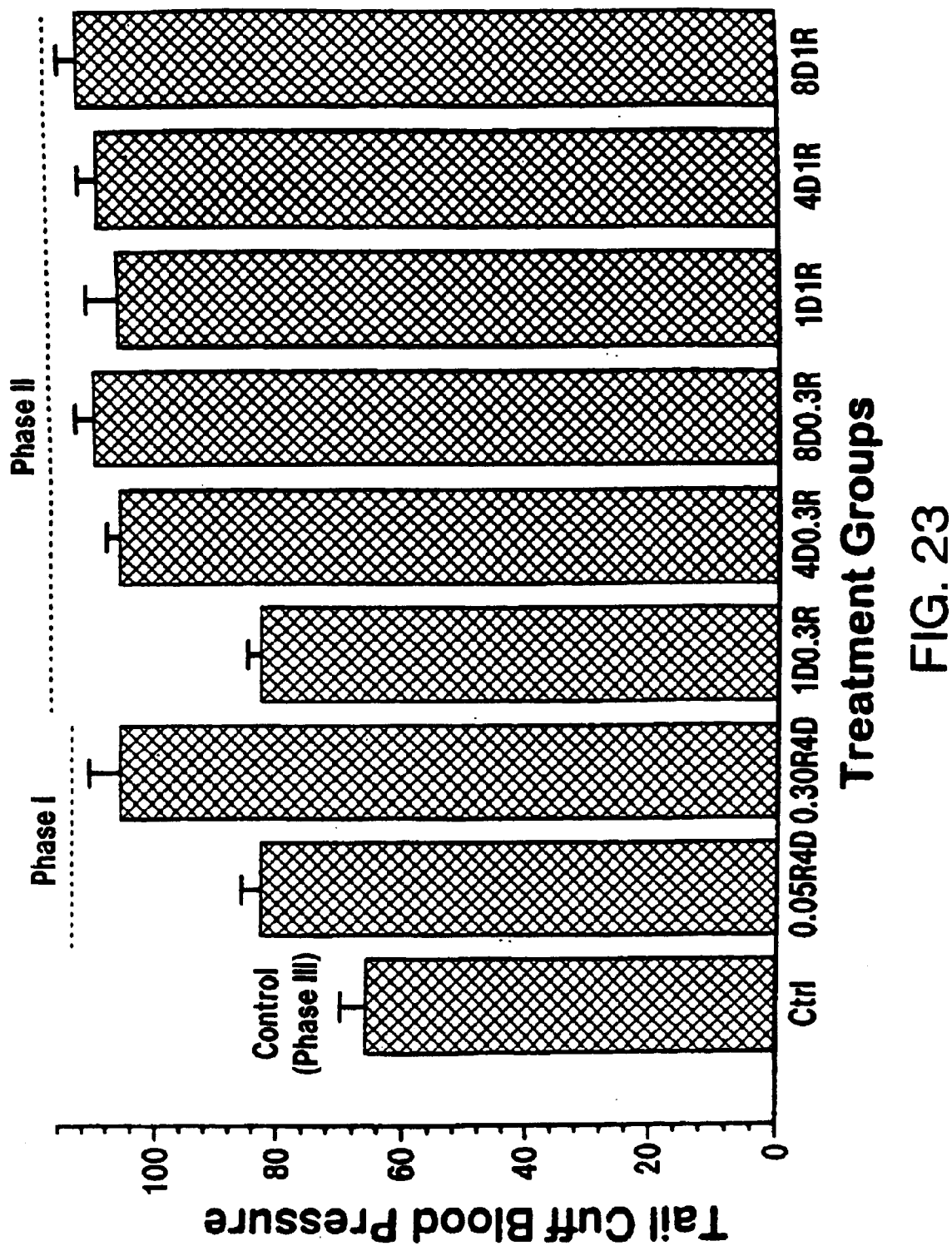
FIG. 23 is a bar graph showing the effects of Ribose treatment in vivo alone on rat tail-cuff blood pressure. Treatment was with 0.05 M, 0.30 M, and 1 M Ribose (R) injected for 1, 2 or 8 Days (D).
Figure 24:
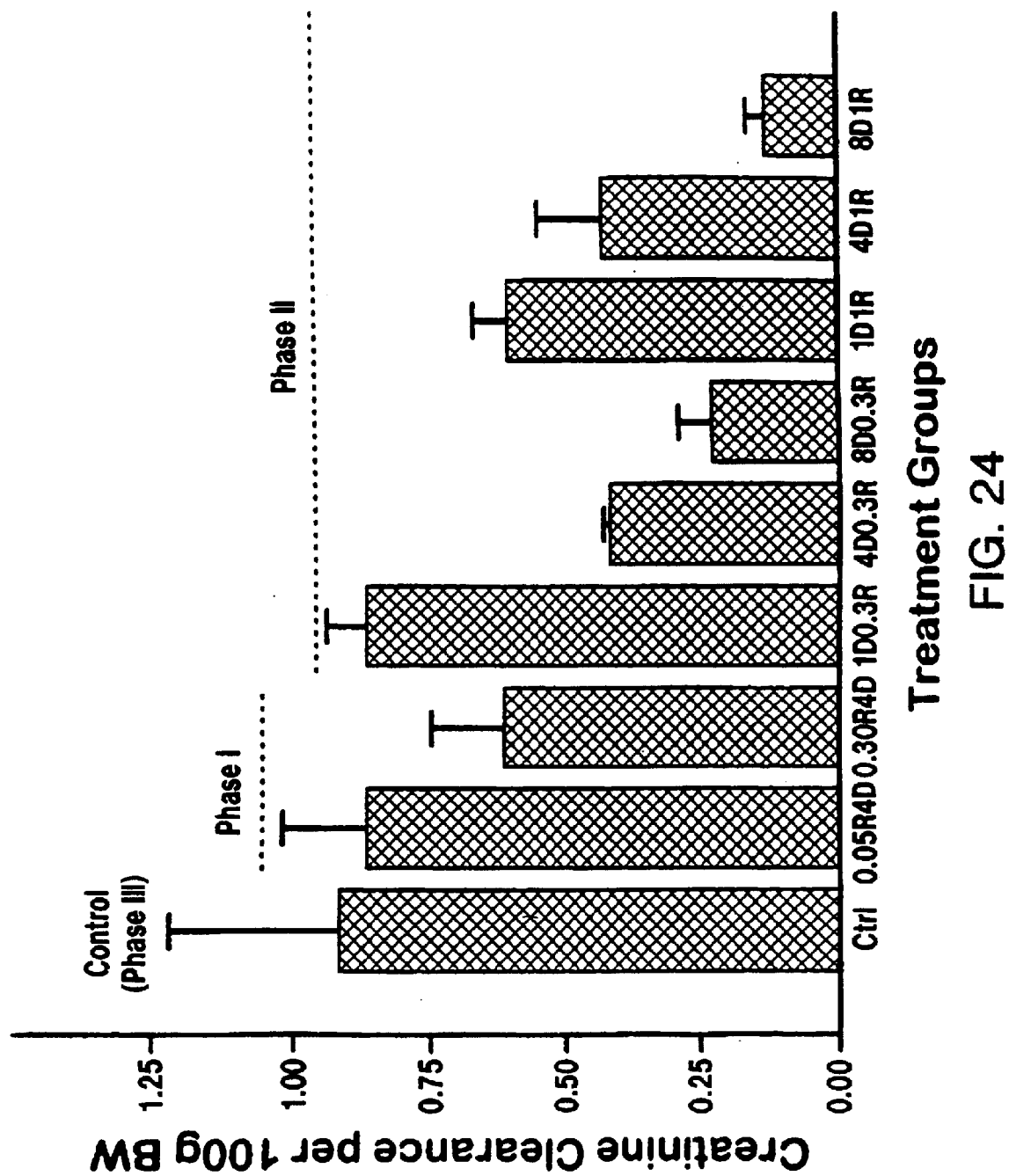
FIG. 24 is a bar graph showing the effects of Ribose treatment in vivo alone on rat creatinine clearance (Clearance per 100 g Body Weight). Treatment was with 0.05 M, 0.30 M, and 1 M Ribose (R) injected for 1, 2 or 8 Days (D).
Figure 25:
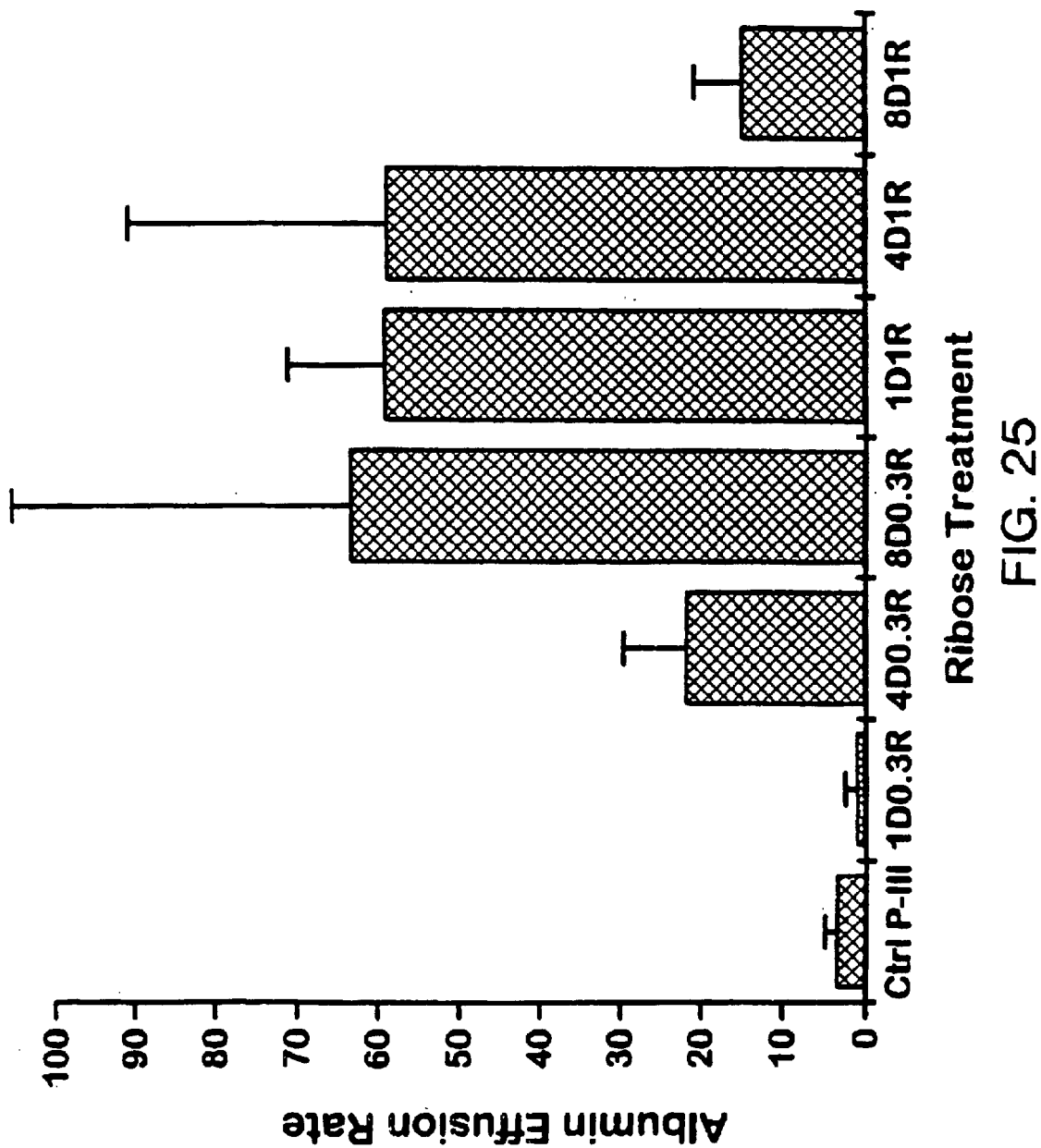
FIG. 25 is a bar graph showing the effects of Ribose treatment in vivo alone on rat Albuminuria (Albumin effusion rate). Treatment was with 0.30 M, and 1 M Ribose (R) injected for 1, 2 or 8 Days (D).

Renal Physiology Results a. Tail-cuff blood pressure increased in all groups of ribose-treated rats, confirming Phase I results. (FIG. 23).

b. Creatinine clearance decreased in all groups in a ribose dose-dependent and time-dependent manner (FIG. 24).

c. Albumin Effusion Rate (AER) increased significantly in a ribose-dependent manner at 1-day and 4-day exposures. However, it showed some recovery at 8 day relative to 4 day in the high-dose group but not in the low-dose group. These results are shown in the bar graph of FIG. 25.

d. Creatinine clearance per 100 g body weight decreased for both low- and high-ribose groups to about the same extent in a time-dependent manner (FIG. 24).

Phase 11 Conclusion

Exposure to ribose for as little as 4 days leads to hypertension and renal dysfunction, as manifest by both decreased creatinine clearance and increased albumin filtration. These changes are typical of diabetes and are seen at much later times in STZ-diabetic rats.

Intervention by Two New Therapeutic Compounds and Aminoguanidine

Phase III Protocol

Sixty rats were randomized into 9 different groups, including those exposed to 1 M ribose for 8 days in the presence and absence of aminoguanidine, pyridoxamine, and thiamine pyrophosphate as follows:

Control Groups:
(i) no treatment;
(ii) high dose (250 mg/kg body weight) of pyridoxamine ("compound-P");
(iii) high dose (250 mg/kg body weight of thiamine pyrophosphate ("compound-T" or "TPP"); and
(iv) low dose (25 mg/kg body weight) of aminoguanidine ("AG").

Test Groups:
(i) only 1 M ribose-saline (2×9 cc daily IP for 8 days);
(ii) ribose plus low dose ("LP") of pyridoxamine (25 mg/kg body weight injected as 0.5 ml with 9 cc ribose);
(iii) ribose plus high dose ("HP") of pyridoxamine (250 mg/kg body weight injected as 0.5 ml with 9 cc ribose);
(iv) ribose plus high dose ("HT") of thiamine pyrophosphate (250 mg/kg body weight injected as 0.5 ml with 9 cc ribose); and
(v) ribose plus low dose of amino guanidine (25 mg/kg body weight injected as 0.5 ml with 9 cc ribose).

Unlike Phase II, no ribose was administered in drinking water. Intervention compounds were pre-administered for one day prior to introducing them with ribose.

Figure 26:
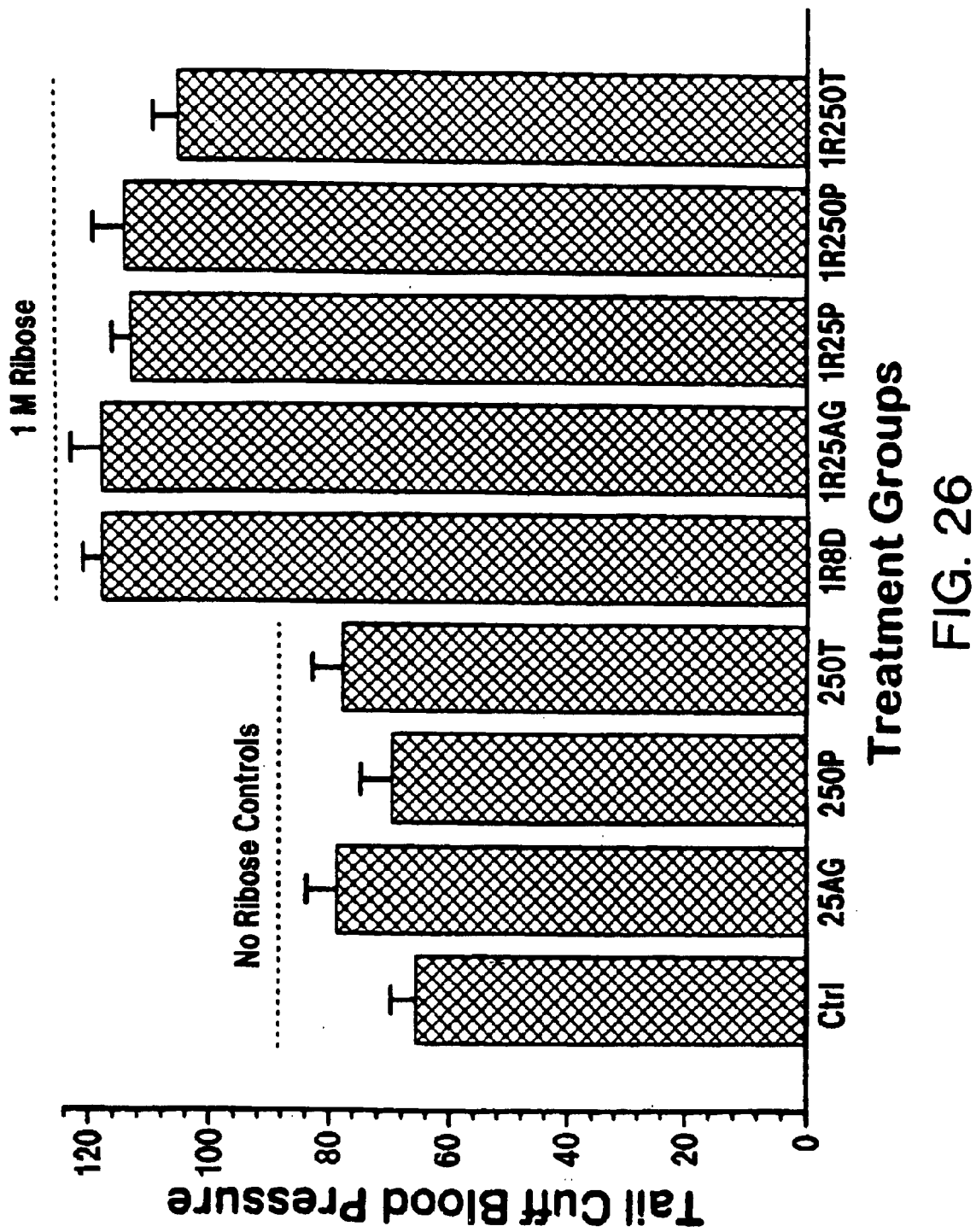
FIG. 26 is a bar graph showing the effects of inhibitor treatment in vivo, with or without ribose, on rat tail-cuff blood pressure. Treatment groups were: 25 mg/kg body weight aminoguanidine (AG); 25 or 250 mg/kg body weight Pyridoxamine (P); 250 mg/kg body weight Thiamine pyrophosphate (T), or with 1 M Ribose (R).
Figure 27:
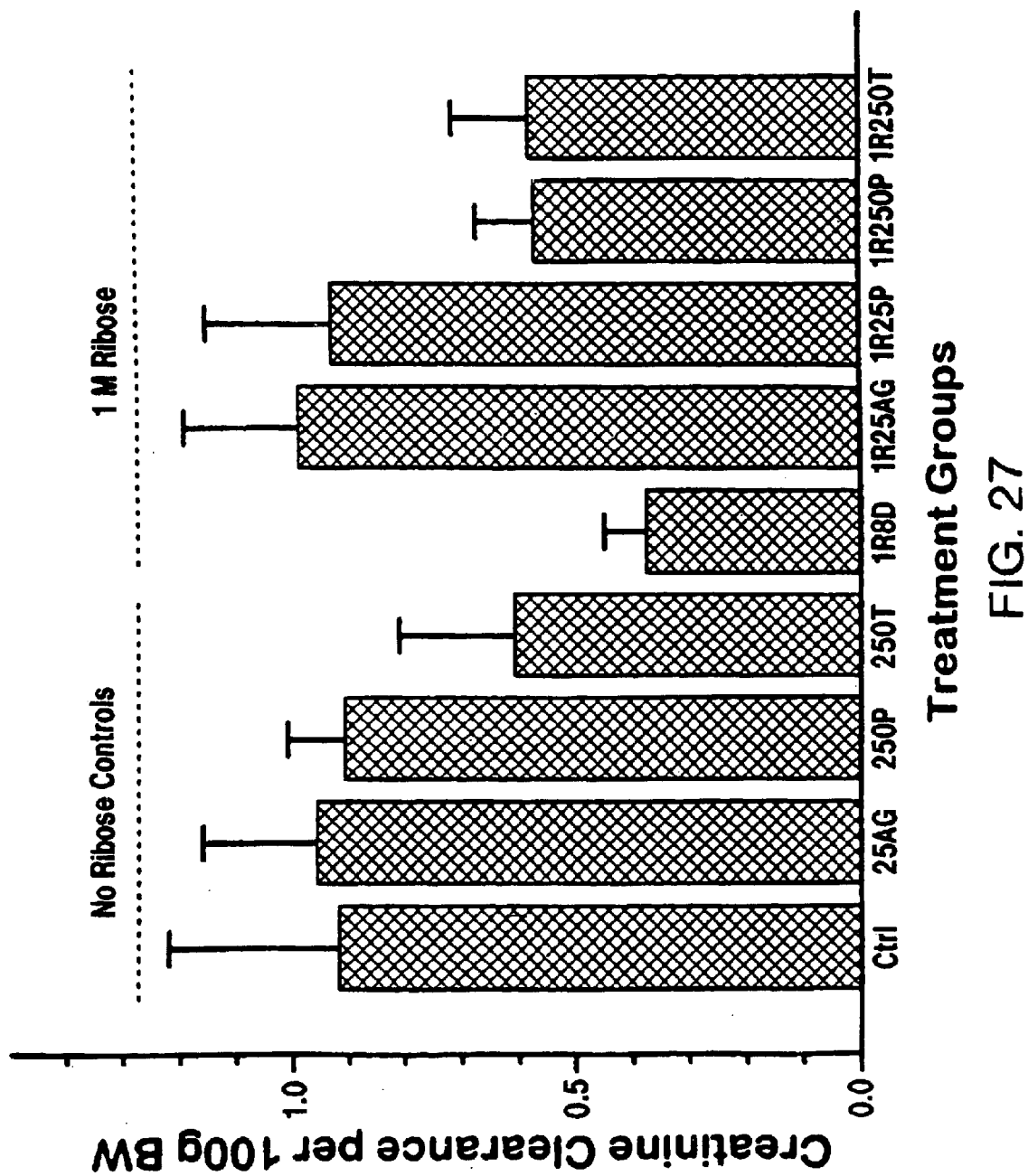
FIG. 27 is a bar graph showing the effects of inhibitor treatment in vivo, with or without ribose, on rat creatinine clearance (Clearance per 100 g body weight). Treatment groups were: 25 mg/kg body weight aminoguanidine (AG); 25 or 250 mg/kg body weight Pyridoxamine (P); 250 mg/kg body weight Thiamine pyrophosphate (T), or with 1 M Ribose (R).
Figure 28:
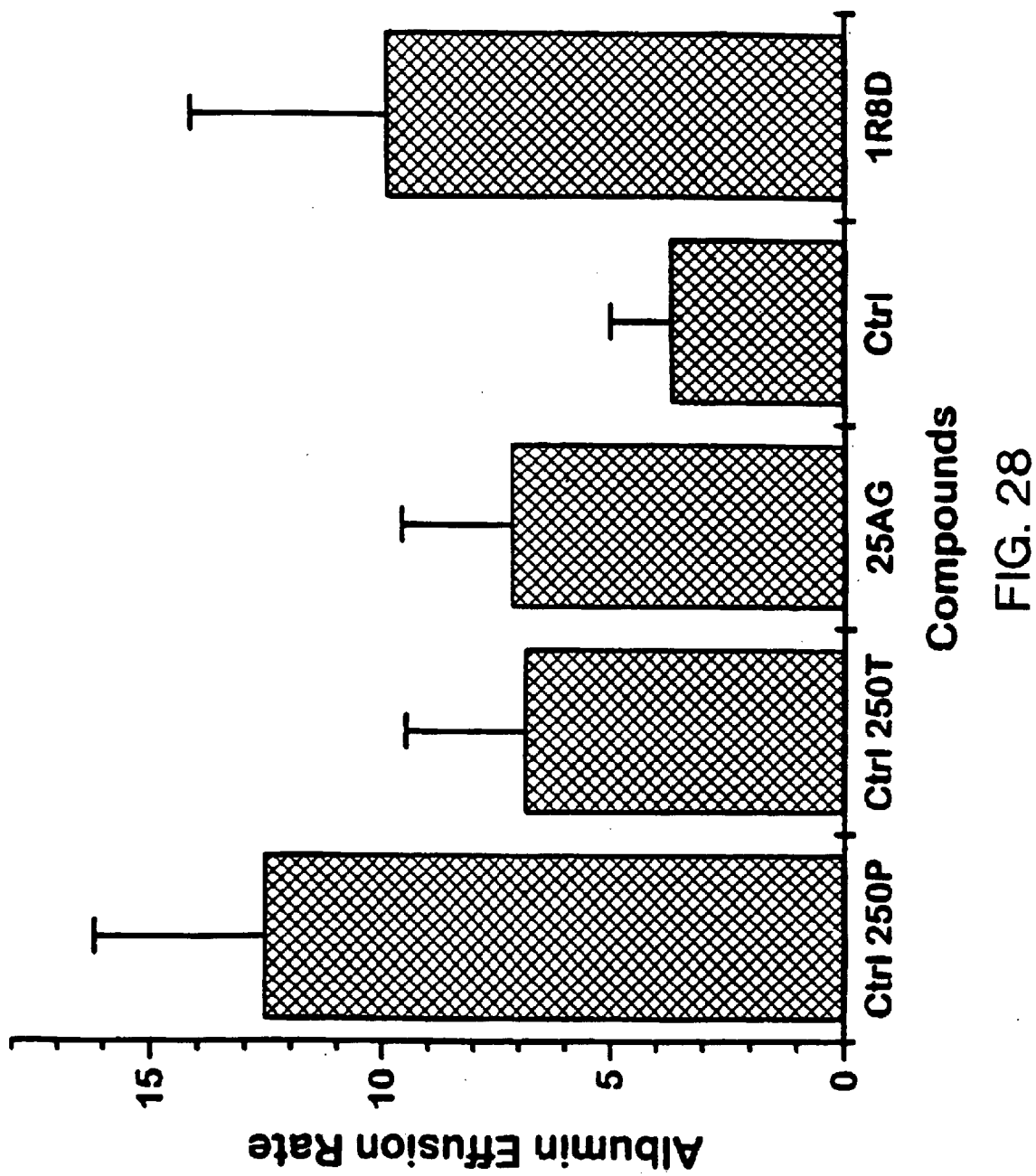
FIG. 28 is a bar graph showing the effects of inhibitor treatment in vivo without ribose, and ribose alone on rat Albuminuria (Albumin effusion rate). Treatment groups were: 25 mg/kg body weight aminoguanidine (AG); 250 mg/kg body weight Pyridoxamine (P); 250 mg/kg body weight Thiamine pyrophosphate (T), or treatment with 1 M Ribose (R) for 8 days (D). Control group had no treatment.
Figure 29:
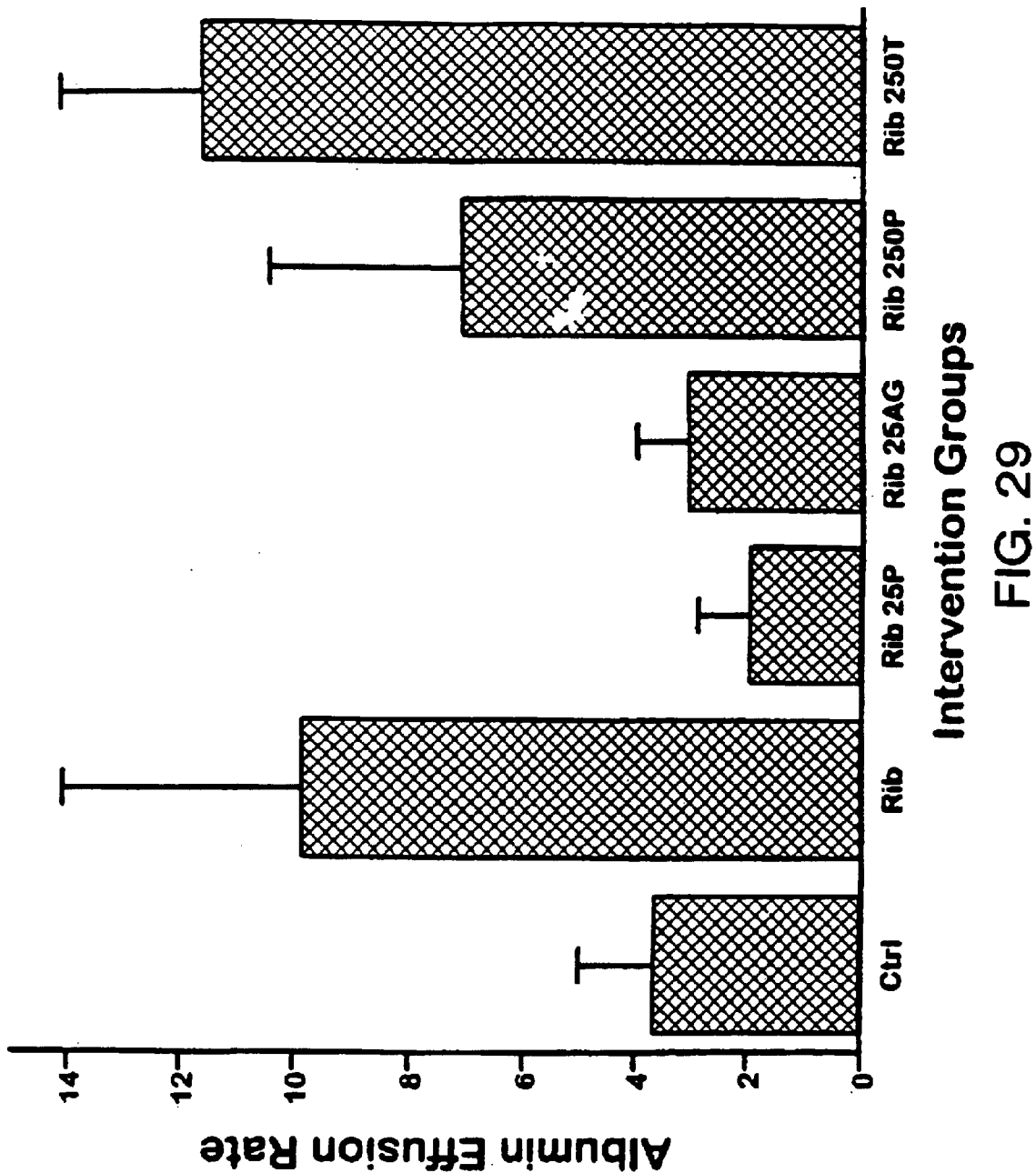
FIG. 29 is a bar graph showing the effects of inhibitor treatment in vivo, with 1 M ribose, on rat Albuminuria (Albumin effusion rate). Treatment groups were: 25 mg/kg body weight aminoguanidine (AG); 25 and 250 mg/kg body weight Pyridoxamine (P); 250 mg/kg body weight Thiamine pyrophosphate (T), or treatment with 1 M Ribose (R) for 8 days (D) alone. Control group had no treatment.
Figure 30A:
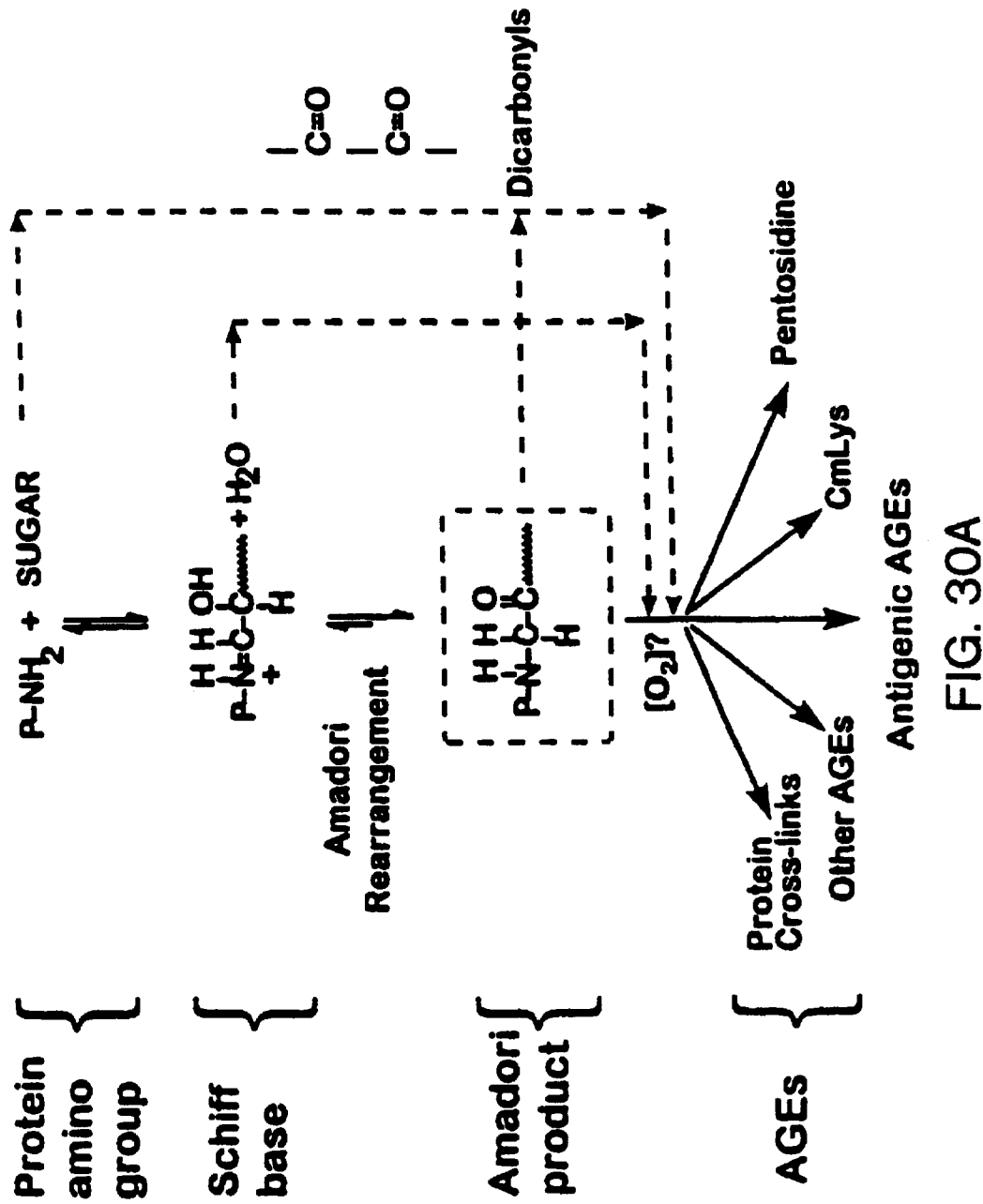
FIG. 30A depicts Scheme 1 showing a diagram of AGE formation from protein.
Figure 30B:
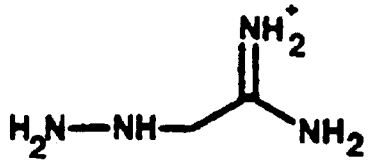
FIG. 30B depicts Scheme 2, a chemical structure of aminoguanidine.
Figure 30C:
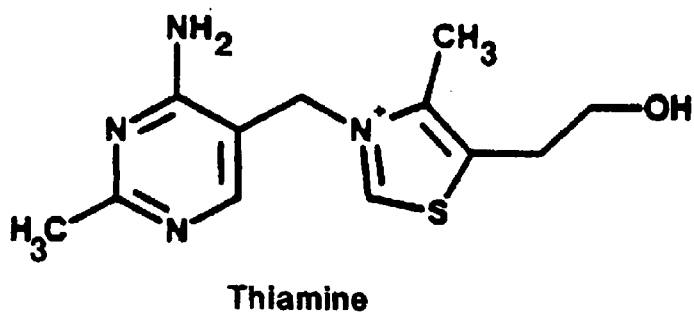
FIG. 30C depicts Scheme 3, chemical structures for thiamine, thiamine-5'-phosphate, and thiamine pyrophosphate.
Figure 30C:
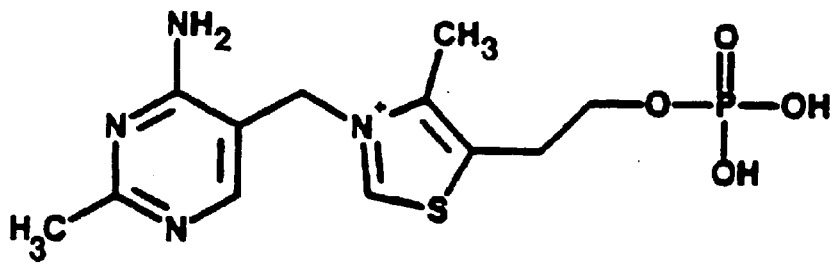
Figure 30C:
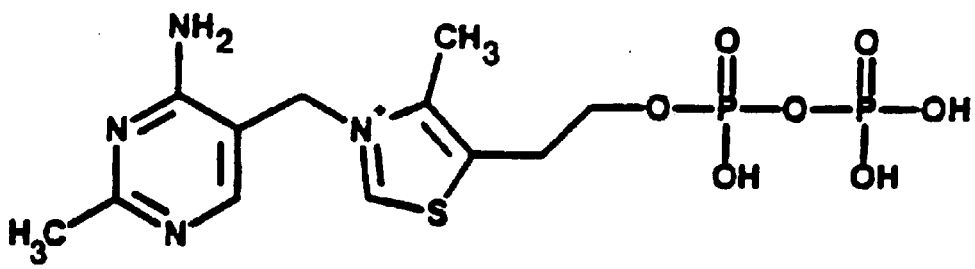
Figure 30D:
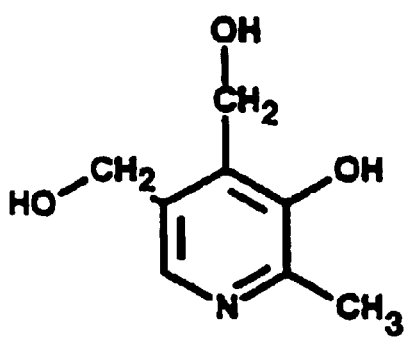
FIG. 30D depicts Scheme 4, chemical structures of pyridoxine, pyridoxamine, pyridoxal-5'-phosphate, and pyridoxal.
Figure 30D:
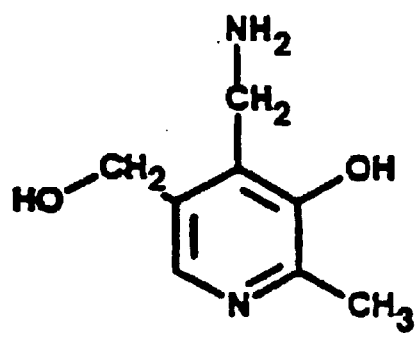
Figure 30D:
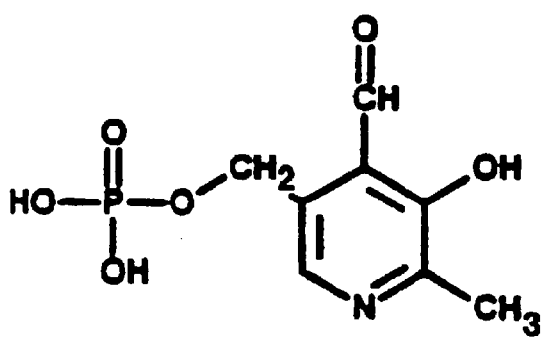
Figure 30D:
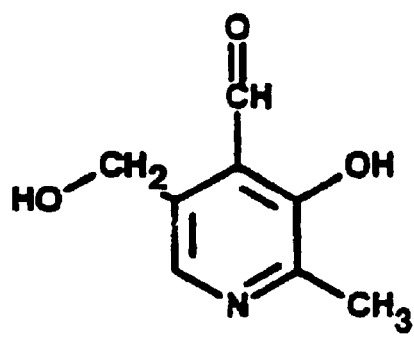

Renal Physiology Results a. Blood pressure was very slightly increased by the three compounds alone (control group); ribose-elevated BP was not ameliorated by the co-administration of compounds. These results are shown in the bar graph of FIG. 26.

b. Creatinine clearance in controls was unchanged, except for TPP which diminished it.

c. Creatinine clearance was normalized when ribose was co-administerd with low dose (25 mg/kg) of either aminoguanidine or pyridoxamine. These results are shown in the bar graph of FIG. 27.

d. High concentrations (250 mg/kg) or pyridoxamine and TPP showed only partial protection against the ribose-induced decrease in creatinine clearance (FIG. 27).

e. Albumin effusion rate (AER) was elevated by ribose, as well as by high dose of pyridoxamine and TPP, and low dose of aminoguanidine in the absence of ribose. These results are shown in the bar graph of FIG. 28.

f. Albumin effusion rate was restored to normal by the co-administration of low dose of 25 both aminoguanidine and pyridoxamine. These results are shown in the bar graph of FIG. 29.

Phase III Conclusions

As measured by two indicies of renal function, pyridoxamine and aminoguanidine, both at 25 mg/kg, were apparently effective, and equally so, in preventing the ribose-induced decrease in creatinine clearance and ribose-induced mild increase in albuminuria.

(i) Thiamine pyrophosphate was not tested at 25 mg/kg; (ii) thiamine pyrophosphate and pyridoxamine at 250 mg/kg were partially effective in preventing creatinine clearance decreases but possibly not in preventing mild proteinuria; (iii) at these very high concentrations and in the absence of ribose, thiamine pyrophosphate alone produced a decrease in creatinine clearance, and both produced mild increases in albuminuria.

SUMMARY

Renal Function and Diabetes

Persistent hyperglycemia in diabetes mellitus leads to diabetic nephropathy in perhaps one third of human patients. Clinically, diabetic nephropathy is defined by the presence of:

1. decrease in renal function (impaired glomerular clearance)
2. an increase in urinary protein (impaired filtration)
3. the simultaneous presence of hypertension Renal function depends on blood flow (not measured) and the glomerular clearance, which can be measured by either inulin clearance (not measured) or creatinine clearance. Glomerular permeability is measured by albumin filtration rate, but this parameter is quite variable. It is also a log-distribution function: a hundred-fold increase in albumin excretion represents only a two-fold decrease in filtration capacity.

Ribose Diabetic Rat Model

By the above criteria, ribose appears to very rapidly induce manifestations of diabetic nephropathy, as reflected in hypertension, creatinine clearance and albuminuria, even though the latter is not large. In the established STZ diabetic rat, hyperglycemia is rapidly established in 1–2 days, but clinical manifestations of diabetic nephropathy arise very late, perhaps as much as 40 weeks for albuminuria. In general, albuminuria is highly variable from day to day and from animal to animal, although unlike humans, most STZ rats do eventually develop nephropathy.

Intervention by Compounds

Using the ribose-treated animals, pyridoxamine at 25 mg/kg body weight appears to effectively prevent two of the three manifestations usually attributed to diabetes, namely the impairment of creatinine clearance and albumin filtration. It did so as effectively as aminoguanidine. The effectiveness of thiamine pyrophosphate was not manifest, but it should be emphasized that this may be due to its use at elevated concentrations of 250 mg/kg body weight. Pyridoxamine would have appeared much less effective if only the results at 250 mg/kg body weight are considered.

Effect of Compounds Alone

Overall, the rats appeared to tolerate the compounds well. Kidney weights were not remarkable and little hypertension developed. The physiological effects of the compounds were only tested at 250 mg/kg. Thiamine pyrophosphate, but not pyridoxamine, appeared to decrease creatinine clearance at this concentration. Both appeared to slightly increase albuminuria, but these measurements were perhaps the least reliable.

Human Administration

A typical adult human being of average size weighs between 66–77 Kg. Typically, diabetic patients may tend to be overweight and can be over 112 Kg. The Recommended dietary allowances for an adult male of between 66–77 Kg, as revised in 1989, called for 1.5 mg per day of thiamine, and 2.0 mg per day of Vitamin $B_6$ (Merck Manual of Diagnosis and Therapy, 16th edition (Merck & Co., Rathaway, N.J., 1992) pp 938–939).

Based upon the rat model approach, a range of doses for administration of pyridoxamine or thiamine pyrophosphate that is predicted to be effective for inhibiting post-Amadori AGE formation and thus inhibiting related pathologies would fall in the range of 1 mg/100 g body weight to 200 mg/100 g body weight. The appropriate range when co-administered with aminoguanidine will be similar. Calculated for an average adult of 75 Kg, the range (at 10 mg/l Kg body weight) can be approximately 750 mg to upwards of 150 g (at 2 g/l Kg body weight). This will naturally vary according to the particular patient.

EXAMPLE 5

In Vivo Inhibition of the Formation of Advanced Glyeation End-Products (AGEs) by Derivatives of Vitamins $B_1$ and $B_6$ and Aminoguanidine. Inhibition of Diabetic Nephropathy.

The interrupted glycation method, as described in the examples above, allows for the rapid generation of stable well-defined protein Amadori intermediates from ribose and other pentose sugars for use in in vivo studies.

The effects of 25 mg/kg/day pyridoxamine (PM) and aminoguanidine (AG) on renal pathology induced by injecting Sprague-Dawley rats daily with 50 mg/kg/day of ribose-glycated Amadori-rat serum albumin (RSA), AGE-RSA, and unmodified RSA for 6 weeks. Hyperfiltration (increased creatinine clearance) was transiently seen with rats receiving Amadori-RSA and AGE-RSA, regardless of the presence of PM and AG.

Individuals from each group receiving Amadori-RSA and AGE-RSA exhibited microalbuminuria, but none was seen if PM was co-administered. Immnunostaining with anti-RSA revealed glomerular staining in rats treated with AGE-RSA and with Amadori-RSA; and this staining was decreased by treatment with PM but not by AG treatment. A decrease in glomerular sulfated glycosaminoglycans (Alcian blue pH 1.0 stain) was also found in rats treated with glycated (Amadori and AGE) RSA. This appears to be due to reduced heparan sulfate proteoglycans (HSPG), as evidenced by diminished staining with mAb JM-403 that is specific for HSPG side-chain. These HSPG changes were ameliorated by treatment with PM, but not by AG treatment.

Thus we conclude that pyridoxamine can prevent both diabetic-like glomerular loss of heparan sulfate and glomerular deposition of glycated albumin in SD rats chronically treated 25 with ribose-glycated albumin.

Materials and Methods

Chemicals

Rat serum albumin (RSA) (fraction V, essentially fatty acid-free 0.005%; A2018), D-ribose, pyridoxamine, and goat alkaline phosphatase-conjugated anti-rabbit IgG were all from Sigma Chemicals. Aminoguanidine hydrochloride was purchased from Aldrich Chemicals.

Preparation of Ribated RSA

Rat serum albumin was passed down an Affi-Gel Blue column (Bio-Rad), a heparin-Sepharose CL-6B column (Pharmacia) and an endotoxin-binding affinity column (Detoxigel, Pierce Scientific) to remove any possible contaminants. The purified rat serum albumin (RSA) was then dialyzed in 0.2 M phosphate buffer (pH 7.5). A portion of the RSA (20 mg/ml) was then incubated with 0.5 M ribose for 12 hours at 37° C. in the dark. After the 12 hour incubation the reaction mixture was dialyzed in cold 0.2 M sodium phosphate buffer over a 36 hour period at 4° C. (this dialysis removes not only the free ribose, but also the Schiff-base intermediaries). At this stage of the glycation process, the ribated protein is classified as Amadori-RSA and is negative for antigenic AGEs, as determined by antibodies reactive with AGE protein (as described previously; R618, antigen:glucose modified AGE-Rnase). The ribated protein is then divided into portions that will be injected either as: a)Amadori-RSA, b)$NaBH_4$-reduced Amadori-RSA, c)AGE-RSA.

The ribated protein to be injected as Amadori-RSA is simply dialyzed against cold PBS at 4° C. for 24 hours. A portion of the Amadori-RSA in 0.2 M sodium phosphate is reduced with $NaBH_4$ to form $NaBH_4$-reduced Amadori-RSA. Briefly, aliquots were reduced by adding 5 uL of $NaBH_4$ stock solution (100 mg/ml in 0.1 M NaOH) per mg of protein, incubated for 1 hour at 37° C., treated with HCl to discharge excess $NaBH_4$, and then dialyzed extensively in cold PBS at 4° C. for 36 hours. The AGE-RSA was formed by reincubating the Amadori-RSA in the absence of sugar for 3 days. The mixture was then dialyzed against cold PBS at 4° C. for 24 hours. All solutions were filtered (22 um filter) sterilized and monitored for endotoxins by a limulus amoebocyte lysate assay (E-Toxate, Sigma Chemical) and contained <0.2 ng/ml before being frozen (−70° C.) down into individual aliquots until it was time for injection.

Animal Studies

Male Sprague-Dawley rats (Sasco, 100 g) were used. After a 1 week adaptation period, rats were placed in metabolic cages to obtain a 24 hour urine specimen for 2 days before administration of injections. Rats were then divided into experimental and control groups and given tail vein injections with either saline, unmodified RSA (50 mg/kg), Amadori-RSA (50 mg/kg), $NaBH_4$-reduced Amadori-RSA (50 mg/kg), or AGE-RSA (50 mg/kg).

Rats injected with Amadori-RSA and AGE-RSA were then either left untreated, or further treated by the administration of either aminoguanidine (AG; 25 mg/kg), pyridoxamine (PM; 25 mg/kg), or a combination of AG and PM (10 mg/kg each) through the drinking water. Body weight and water intake of the rats were monitored weekly in order to adjust dosages. At the conclusion of the experimental study the rats were placed in metabolic cages to obtain 24 hour urine specimen for 2 days prior to sacrificing the animals.

Total protein in the urine samples was determined by Bio-Rad assay. Albumin in urine was determined by competitive ELISA using rabbit anti-rat serum albumin (Cappell) as primary antibody (1/2000) and goat anti-rabbit IgG (Sigma Chemical) as a secondary antibody (1/2000). Urine was tested with Multistix 8 SG (Miles Laboratories) for glucose, ketone, specific gravity, blook, pH, protein, nitrite, and leukocytes. Nothing remarkable was detected other than some protein.

Creatinine measurements were preformed with a Beckman creatinine analyzer II. Blood samples were collected by heart puncture before termination and were used in the determination of creatinine clearance, blood glucose (glucose oxidase, Sigma chemical), fructosamine (nitroblue tetrazolium, Sigma chemical), and glycated Hb (columns, Pierce chemicals). Aorta, heart, both kidneys and the rat tail were visually inspected and then quickly removed after perfusing with saline through the right ventricle of the heart. One kidney, aorta, rat tail, and the lower $2/3$ of the heart were snap-frozen and then permanently stored at $-70°$ C. The other kidney was sectioned by removing both ends (cortex) to be snap-frozen, with the remaining portions of the kidney being sectioned into thirds with two portions being placed into neutral buffered formalin and the remaining third minced and placed in 2.5% glutaraldehyde/2% paraformaldehyde.

Light Microscopy

After perfusion with saline, kidney sections were fixed in ice-cold 10% neutral buffered formalin. Paraffin-embedded tissue sections from all rat groups (n=4 per group) were processed for staining with Harris' alum hematoxylin and eosin (H&E), perodic acid/Schiff reagent (PAS), and alcian blue (pH 1.0 and pH 2.5) stains for histological examination. The alcian blue sections were scored by two investigators in a blinded fashion.

Electron Microscopy

Tissues were fixed in 2.5% glutaraldehyde/2% paraformaldehyde (0.1 M sodium cacodylate, pH 7.4), post-fixed for 1 hour in buffered osmium tetroxide (1.0%), prestained in 0.5% uranyl acetate for 1 hour and embedded in Effapoxy resin. Ultrathin sections were examined by electron microscopy.

Immunofluorescence

Parrafin-embedded sections were deparaffinized and then blocked with 10% goat serum in PBS for 30 min at room temperature. The sections were then incubated for 2 hour at 37° C. with primary antibody, either affinity purified polyclonal rabbit anti-AGE antibody, or a polyclonal sheep anti-rat serum albumin antibody (Cappell). The sections were then rinsed for 30 min with PBS and incubated with secondary antibody, either affinity purified FITC-goat anti-rabbit IgG (H+L) double stain grade (Zymed) or a Rhodamine-rabbit anti-sheep IgG (whole) (Cappell) for 1 hour at 37° C. The sections were then rinsed for 30 min with PBS in the dark, mounted in aqueous mounting media for immunocytochemistry (Biomeda), and cover slipped. Sections were scored in a blinded fashion. Kidney sections were evaluated by the number and intensity of glomerular staining in 5 regions around the periphery of the kidney. Scores were normalized for the immunofluorescent score per 100 glomeruli with a scoring system of 0–3.

Preparation of Polyclonal Antibodies to AGE-Proteins

Immunogen was prepared by glycation of BSA (R479 antibodies) or Rnase (R618 antibodies) at 1.6 g protein in 15 ml for 60–90 days using 1.5 M glucose in 0.4 M phosphate containing 0.05% sodium azide at pH 7.4 and 37° C. New Zealand white rabbit males of 8–12 weeks were immunized by subcutaneous administration of a 1 ml solution containing 1 mg/ml of glycated protein in Freund's adjuvant. The primary injection used the complete adjuvant and three boosters were made at three week intervals with Freund's incomplete adjuvant. The rabbits were bled three weeks after the last booster. The serum was collected by centrifugation of clotted whole blood. The antibodies are AGE-specific, being unreactive with either native proteins or with Amadori intermediates.

ELISA Detection of AGE Products

The general method of Engvall (21) was used to perform the ELISA. Glycated protein samples were diluted to approximately 1.5 ug/ml in 0.1 M sodium carbonate buffer of pH 9.5 to 9.7. The protein was coated overnight at room temperature onto a 96-well polystyrene plate by pippetting 200 ul of protein solution into each well (about 0.3 ug/well). After coating, the excess protein was washed from the wells with a saline solution containing 0.05% Tween-20. The wells were then blocked with 200 ul of 1% casein in carbonate buffer for 2 hours at 37° C. followed by washing. Rabbit anti-AGE antibodies were diluted at a titer of 1:350 in incubation buffer and incubated for 1 hour at 37° C., followed by washing. In order to minimize background readings, antibody R618 used to detect glycated RSA was generated by immunization against glycated Rnase. An alkaline phosphatase-conjugated antibody to rabbit IgG was then added as the secondary antibody at a titer of 1:2000 and incubated for 1 hour at 37° C., followed by washing. The p-nitrophenolate being monitored at 410 nm with a Dynatech MR4000 microplate reader.

Results

The rats in this study survived the treatments and showed no outward signs of any gross pathology. Some of the rats showed some small weight changes and tail scabbing.

Initial screening of kidney sections with PAS and H&E stains did not reveal any obvious changes, and some EM sections did not reveal any gross changes in the glomerular basement membrane (GBM). However, upon Alcian Blue staining, striking differences were discovered. Alcian blue staining is directed towards negatively charged groups in tissues and can be made selective via changes in the pH of staining. At pH 1.0 Alcian blue is selective for mucopolysaccharides, and at pH 2.5 detects glucoronic groups. Thus negative charges are detected depending upon the pH of the stain.

Figure 33:
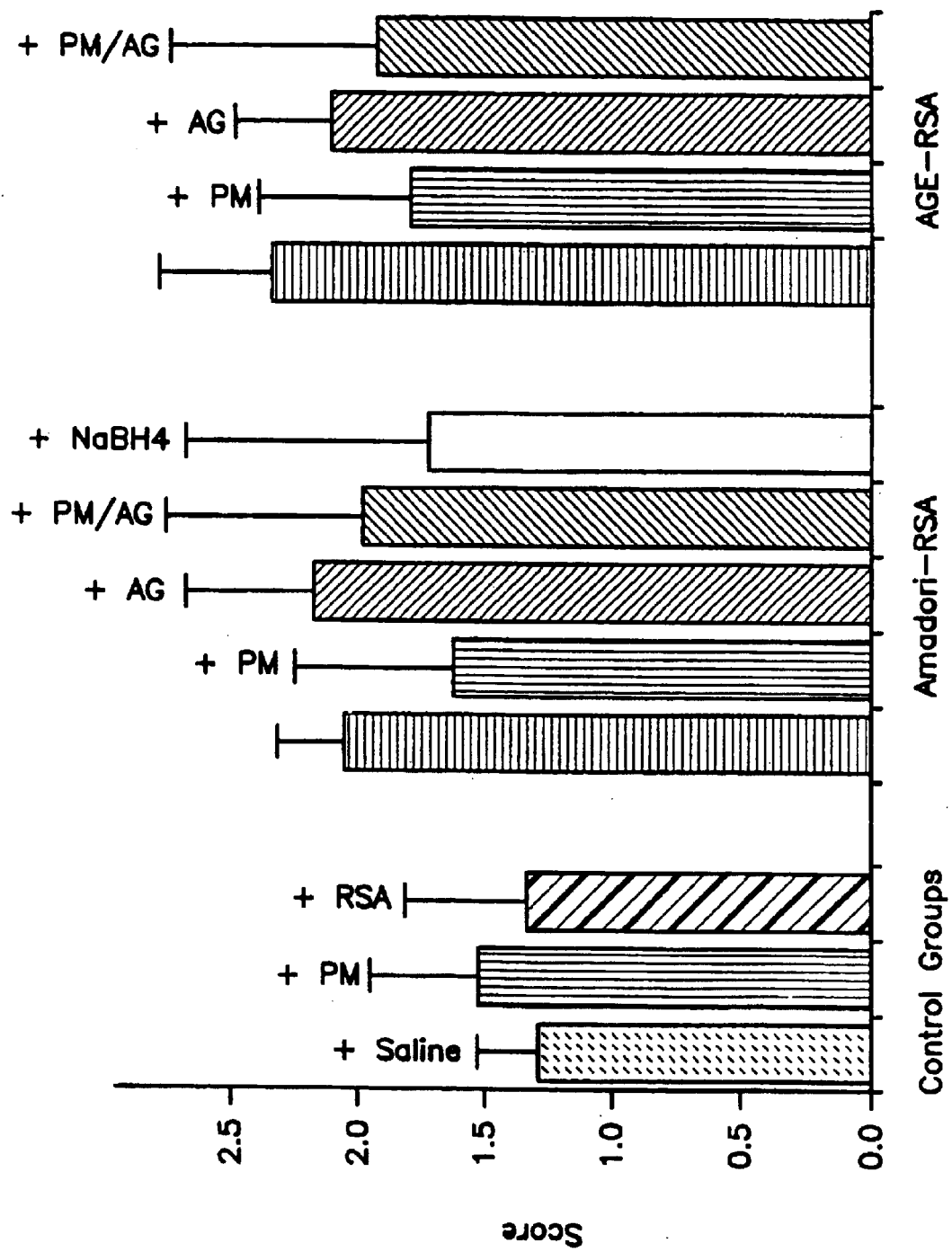
FIG. 33 is a graph showing the results of glomeruli staining at pH 2.5 with Alcian blue.

At pH 2.5 Alcian blue staining showed that Amadori-RSA ($p<0.05$) and AGE-RSA ($p<0.01$) induced increased staining for acidic glycosaminoglycans (GAG) over control levels (FIG. 33). For both AGE-RSA and Amadori-RSA, treatment with pyridoxamine (PM) prevented the increase in staining ($p<0.05$ as compared with controls). In contrast, treatment with aminoguanidine (AG) or combined PM and AG at 10 mg/kg each, did not prevent the increase.

Figure 34:
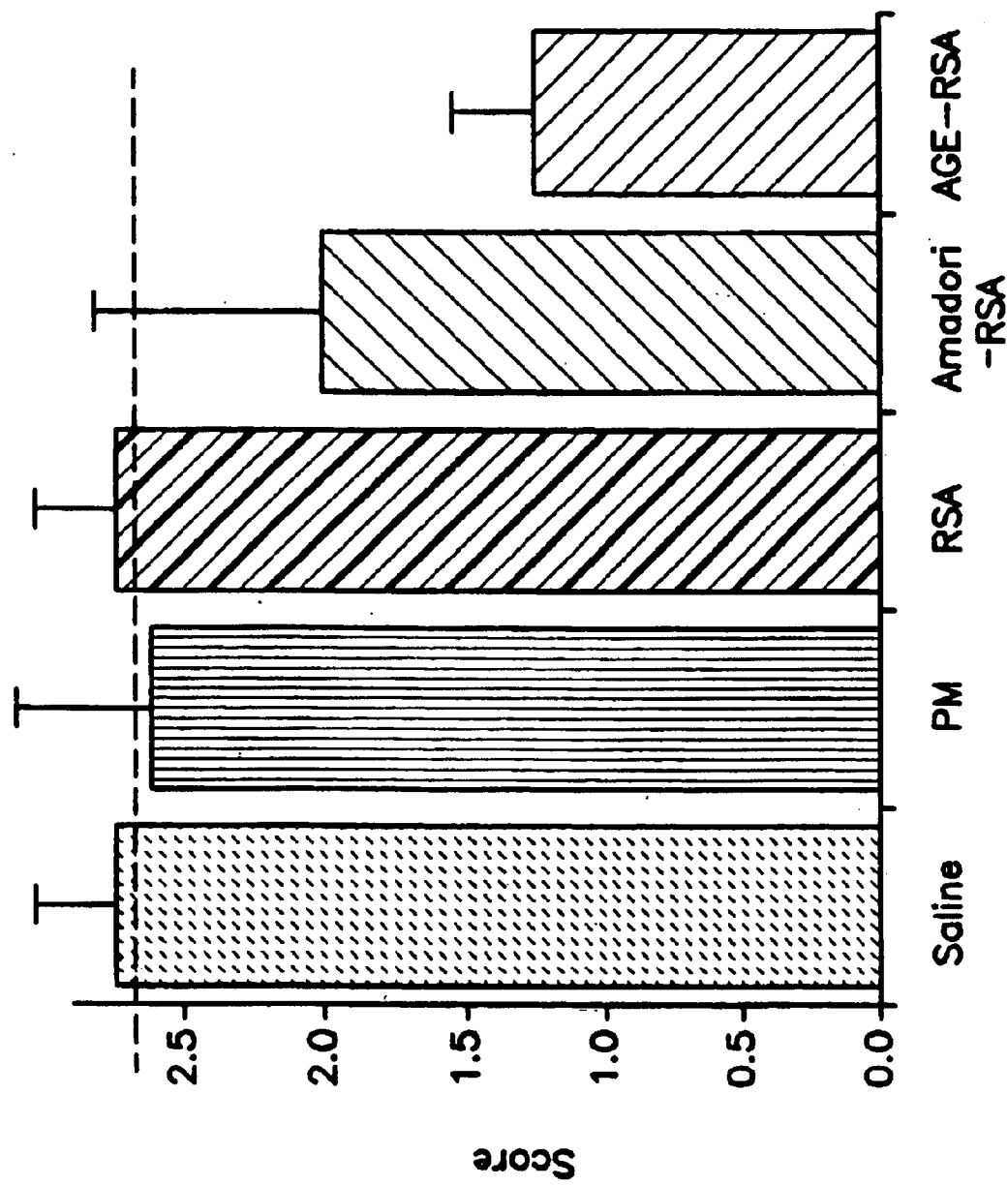
FIG. 34 is a graph showing the results of glomeruli staining at pH 1.0 with Alcian blue.

At pH 1.0 Alcian blue staining was significantly decreased by AGE-RSA ($p<0.001$) (FIG. 34). However, no significant difference was seen with Amadori-RSA. Due to faint staining, treatment with PM, AG and combined could not be quantitated.

Figure 35:
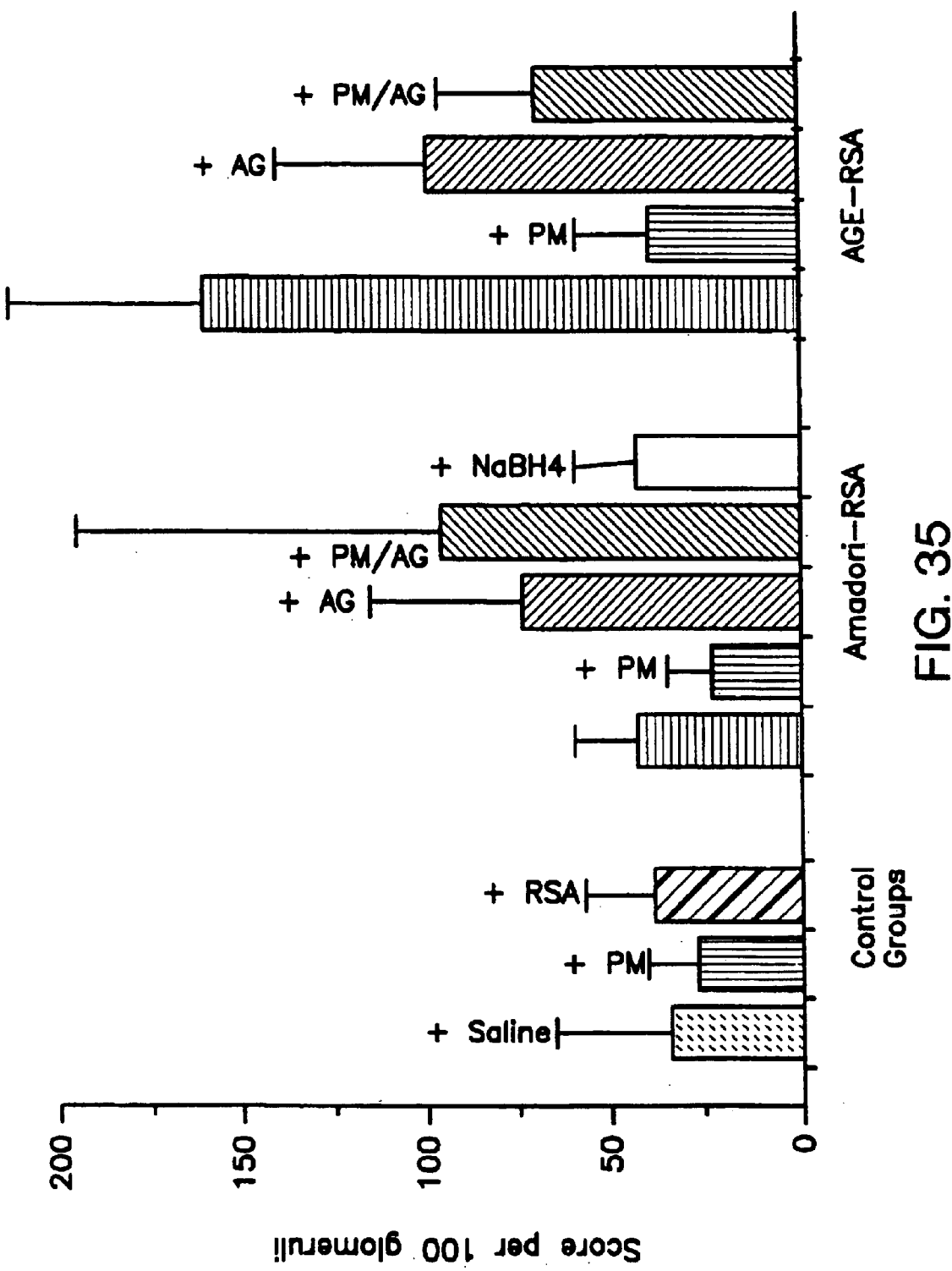
FIG. 35 is a graph showing the results of immunofluroescent glomeruli staining for RSA.

Immunofluorescent glomerular staining for RSA showed elevated staining with Amadori-RSA and AGE-RSA injected animals (FIG. 35). Significant reduction of this effect was seen in the rats treated with PM, and not with AG or combined AG & PM.

Figure 36:
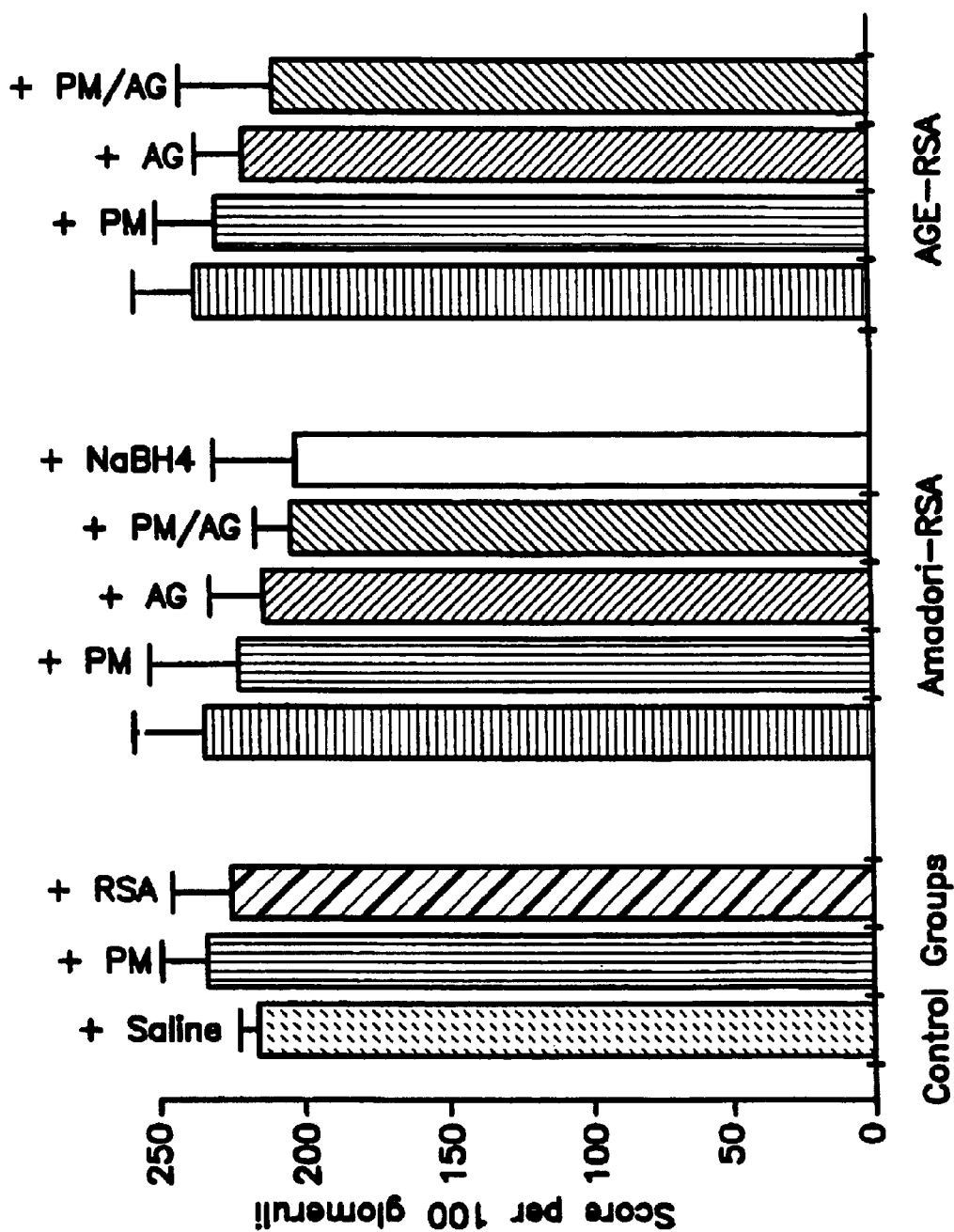
FIG. 36 is a graph showing the results of immunofluroescent glomeruli staining for Heparan Sulfate Proteoglycan Core protein.
Figure 37:
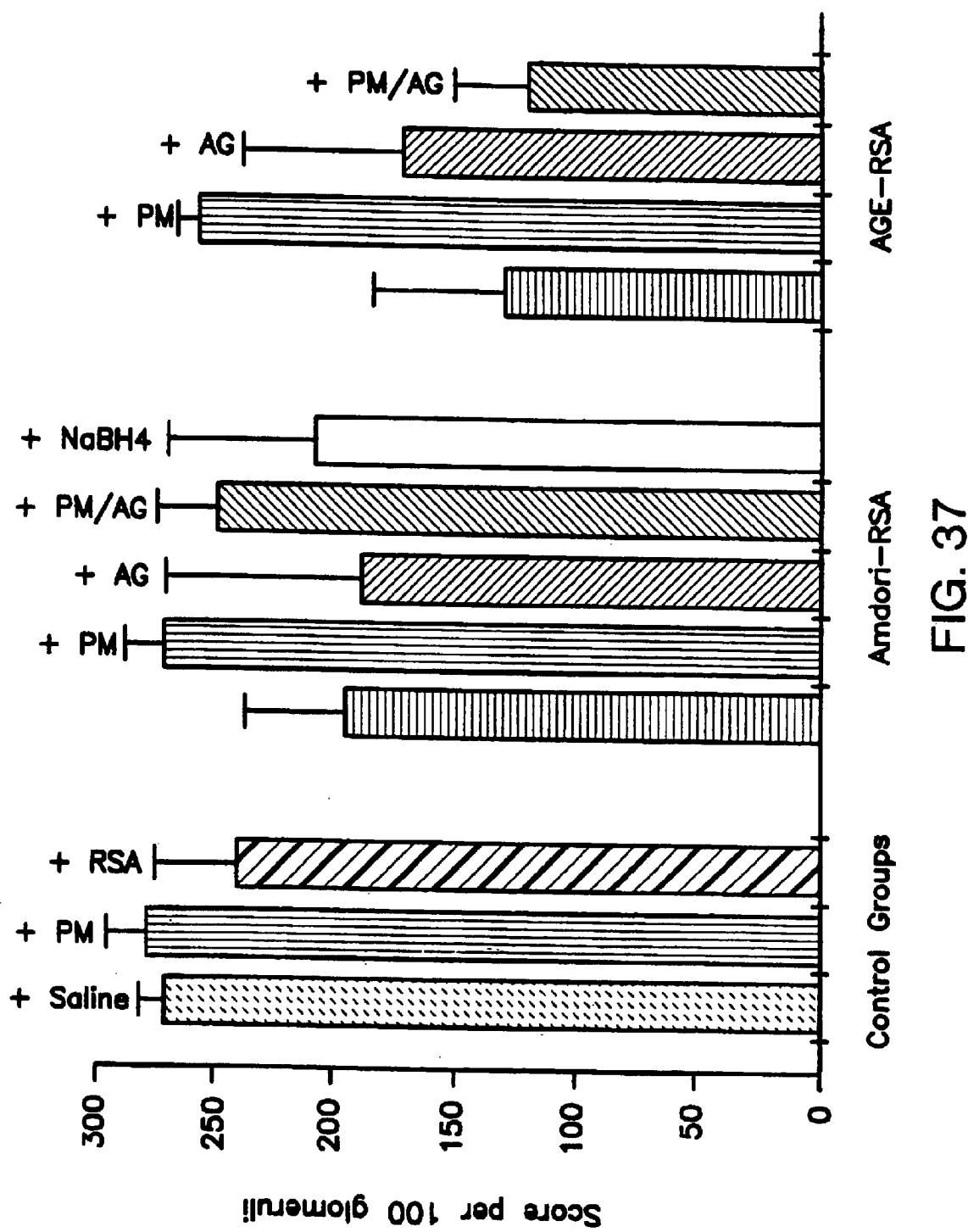
FIG. 37 is a graph showing the results of immunofluroescent glomeruli staining for Heparan Sulfate Proteoglycan side-chain.

Immunofluorescent glomerular staining for Heparan Sulfate Proteoglycan Core protein showed slightly reduced staining with Amadori-RSA and AGE-RSA injected animals but were not statistically significant(FIG. 36). A reduction of this effect was seen in the rats treated with PM, and not with AG or combined AG & PM. However, immunofluorescent glomerular staining for Heparan Sulfate Proteoglycan side-chain showed highly reduced staining with Amadori-RSA and AGE-RSA injected animals (FIG. 37) A significant reduction of this effect was seen in the rats treated with PM, and not with AG or combined AG & PM.

Figure 38:
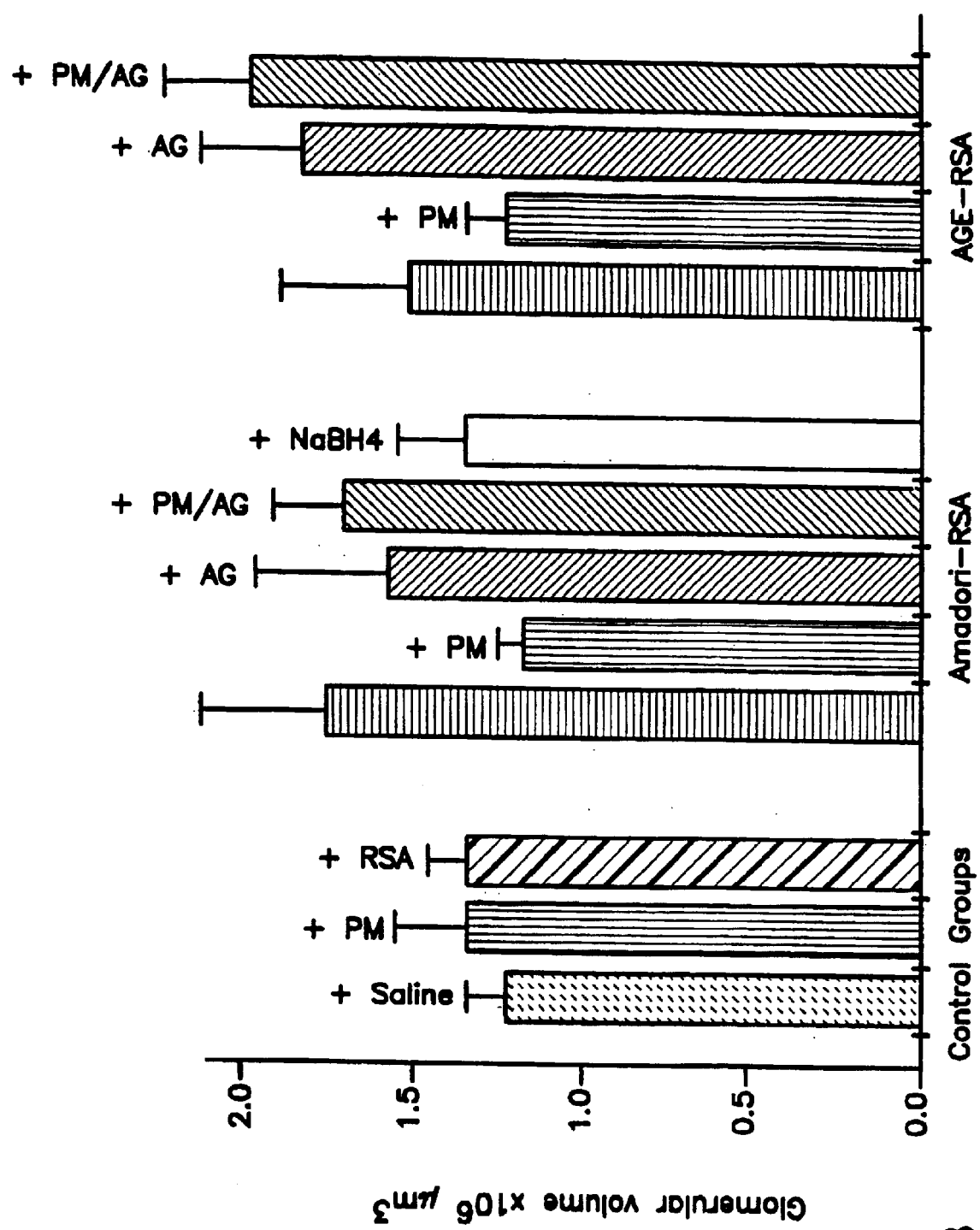
FIG. 38 is a graph showing the results of analysis of glomeruli sections for average glomerular volume.

Analysis of average glomerular volume by blinded scoring showed that Amadori-RSA and AGE-RSA caused significant increase in average glomeruli volume (FIG. 38). A significant reduction of this effect was seen with treatment of the rats with PM. No effect was seen with treatment with AG or combined AG and PM at 10 mg/kg each.

EXAMPLE 6

Prevention of Nephropathy, Including Increased Glomerular Volume, Loss of Heparan Sulfate, and Protein Deposition We report here the 6-week effects of ribose glycated albumins (Amadori-rich or early AGE-modified) on rat kidney structure and function in the presence and absence of pyridoxamine (PM). For comparison, we also studied the effects of aminoguanidine (AG) (Pimagedine), a non-Amadorin AGE inhibitor, and the combination of the two.

Results. Creatinine hyperfiltration was seen at 3–6 weeks with rats receiving glycated RSA independently of the presence of PM or AG. A glomerular volume increase was produced by both Amadori-rich and earlyAGE-RSA that was prevented by PM but not AG. No significant microalbuminuria developed by 6 weeks, but glomerular histochemical staining revealed albumin deposition in rats treated with early AGE-RSA and with Amadori-rich RSA that was prevented by PM. Alcian Blue glomerular staining at pH 1.0 revealed loss of sulfated groups in rats treated with both Amadori-rich and early AGE-albumin. This was identified, using monoclonal Ab JM-403 (van den Born et al., Kidney Int 41:115–23, 1992), as loss of heparan sulfate proteoglycan side-chains. PM prevented this loss, whereas AG did not. However, heparan sulfate core protein, as measured by polyclonal antibody BL-31 (van den Heuvelet al., Biochem J 264:457–65, 1989), was unchanged. No changes in chondroitin sulfate were detected. Across all samples, significant linear correlations were found between heparan sulfate loss and glomerular albumin deposition (p=0.001), glomerular volume increase (p=0.02) and urinary albumin excretion (p=0.001).

Conclusions. Glycated albumin produces an early diabetic-like nephropathy as reflected in a loss of heparan sulfate, an increase in glomerular volume and an increase in albumin deposition. As used herein, "diabetic mammal" encompasses both those mammals that are currently diabetic, and those that are glucose intolerant and/or have a pancreatic insufficiency, regardless of their blood sugar level. Pyridoxamine, in contrast to aminoguanidine, consistently prevented most of these changes. Results suggest that pyridoxamine may have promising therapeutic potential for inhibiting diabetic complications arising from nonenzymatic advanced glycation reactions.

Materials

Rat serum albumin (essentially fatty acid free, fraction V) was purchased from Sigma Chemicals and was further purified before use as follows. It was passed down an Affi-Gel Blue column (Bio-Rad), a heparin-Sepharose CL-6B column (Pharmnacia) and an endotoxin-binding affinity column (Detoxigel, Pierce) to remove any possible contaminants. Antibodies to heparan sulfate side-chain (monoclonal JM-403) and to heparan sulfate proteoglycan core protein (BL-31) were those described earlier. Antibodies to chondroitin sulfate were purchased from Chemicon. Antibodies to determine advanced glycation end products (AGE) in glycated albumin were obtained from sera of rabbits that had been immunized against either glucose-modified (R618) or ribose-modified (R619) ribonuclease A. Antibodies to unmodified rat serum albumin were purchased from Cappell. Secondary goat anti-rabbit IgG conjugates were obtained from Zymed, Cappell, Nordic and Dako. Pyridoxamine (pyridoxamine) was purchased from Sigma Chemicals as the dihydrochloride. Aminoguanidine hydrochloride was purchased from Aldrich Chemicals.

Preparation of Glycated Rat Serum Albumin (Amadori-albumin and "Early" AGE-albumin The purified rat serum albumin (RSA) was dialyzed in 0.2 M phosphate buffer (pH 7.5). A portion of the RSA (20 mg/ml) was then incubated with 0.5 M ribose for 12 hours at 37° C. in the dark, conditions determined to give optimal amounts of Amadori-albumin while producing minimal amounts of ELISA-detectable AGEs. After the 12 hour incubation, the reaction mixture was dialyzed against several changes of 0.2 M sodium phosphate buffer over a 36 hour period at 4° C. in order to remove excess free ribose as well as any ribose condensed in (reversible) Schiff base form with primary amino groups of the protein. This ribated protein is defined as "Amadori-RSA" and was simply dialyzed against cold PBS at 4° C. for 24 hours prior to injection into rats, and it was verified to be negative for antigenic AGEs as determined by R618 anti-AGE antibodies. One portion of the Arnadori-RSA was then used to prepare $NaBH_4$-reduced Amadori-RSA that was expected to not be very toxic due to deactivation. This was prepared in 0.2 M sodium phosphate by adding 5 μl of $NaBH_4$ stock solution (100 mg/ml in 0.1 M NaOH) per mg of protein. It was incubated for 1 hour at 37° C., treated with HCl to discharge excess $NaBH_4$, and then dialyzed extensively against cold PBS at 4° C. for 36 hours. The major portion of Amadori-RSA went into preparing albumin modified to a limited extent with advanced glycation end product ("early" AGE-RSA). This "AGE-RSA" was prepared by re-incubating Amadori-RSA (in the absence of sugar) for only 2–3 days at 37° C., conditions known to lead to near maximal formation of the AGEs CML and pentosidine, although this "early" AGE-RSA is still capable of degradation to form fluorescent and other "late" AGEs. The AGE-modified protein was then dialyzed against cold PBS at 4° C. for 24 hours to remove any reactive small products or intermediates that may have been formed, such as glucosones or glyoxal. All solutions were filtered (22 μm) sterilized and monitored for endotoxins by a limulus amoebocyte lysate assay (E-Toxate, Sigma Chemicals). After verifying that the endotoxin levels were <0.2 ng/ml, they were frozen (−70° C.) down into individual aliquots until injected into animals. The lysine and carboxymethyl lysine contents of the Amadori-RSA and AGE-RSA were determined by amino acid analysis.

Animal Studies

All animals studies were carried out in conformance with institutional guidelines for animal research protocols. Male Sprague-Dawley 100 g rats (Sasco Co., Omaha Nebr.) were used in these studies. After a 1 week adaptation period, rats were placed in metabolic cages for 2 days to get two 24 hour urine specimens before starting treatment. Rats were then given daily single tail vein injections for 6 weeks according to the following treatment groups: saline, unmodified RSA (50 mg/kg), Amadori-RSA (50 mg/kg), $NaBH_4$-reduced Amadori-RSA (50 mg/kg), and AGE-RSA (50 mg/kg). Groups of rats injected with Amadori-RSA or AGE-RSA were also administered aminoguanidine (25 mg/kg/day), pyridoxamine (25 mg/kg/day), a combination of the two (10 mg/kg/day each), or with nothing added to the drinking water. Body weight and water intake of the rat were monitored weekly in order to adjust dosages. At the conclusion of the study, the rats were placed in metabolic cages for two days to get two 24 hour urine specimens before sacrificing the animals.

Metabolic Conversions and Bioavailability of Pyridoxamine

In addition to the glycated albumin studies, we carried out an investigation of the bioavailability of pyridoxamine when introduced through drinking water, and its possible redistribution into the vitamin B6 pool. Determination of the common B6 vitamers in plasma was carried out by HPLC methods as described below. Rats (n=4) were kept in standard cages as in the other experiments and were given pyridoxamine at 25 mg/kg/day for 48 hours, following which blood samples were withdrawn intra-cardially for serum analysis of the B6 vitamers. The concentrations were compared to endogenous $B_6$ vitamer levels of control rats.

Clinical Chemistry Measurements

Total protein in urine was determined by Bio-Rad assay. Albumin in urine was determined by competitive ELISA using rabbit anti-rat serum albumin (Cappell) as primary antibody (1:2000) and goat anti-rabbit IgG (Sigma) as a secondary antibody (1:2000). Urine was tested with Multistix 8 SG (Miles) for glucose, ketone, specific gravity, blood, pH, protein, nitrite and leukocytes. Creatinine measurements were performed with a Beckman creatinine analyzer II. Intracardiac blood samples were collected before termination and were used in the determination of creatinine clearance, blood glucose (glucose oxidase, Sigma), fructosamine (nitroblue tetrazolium, Sigma), and glycated Hb (Glycotest II analytical boronate columns, Pierce).

Tissue Analysis

Aorta, heart, both kidneys and the rat tail were visually inspected and then quickly removed after perfusing with saline through the right ventricle of the heart. One kidney, aorta, rat tail, and the lower two thirds of the heart were snap-frozen and then permanently stored at −70° C. The other kidney was sectioned by removing both ends (cortex) to be snap-frozen, with the remaining portion being sectioned into thirds with two portions being placed into neutral buffered formalin and the other third minced and placed in 2.5% glutaraldehyde/ 2% paraformaldehyde.

Light Microscopy

After perfusion with saline, kidney sections were fixed in ice-cold 10% neutral buffered formalin. Paraffin-embedded tissue sections from all rat groups were processed for staining with Harris' alum hematoxylin and eosin (H&E), periodic acid/Schiff reagent (PAS), and Alcian Blue (pH 1.0 and pH 2.5) stains for histological examination in a blinded fashion.

Electron Microscopy

Tissues were fixed in 2.5% glutaraldehyde/2% paraformaldehyde (0.1 M sodium cacodylate, pH 7.4), post-fixed for 1 hour in buffered osmium tetroxide (1.0%), prestained in 0.5% uranyl acetate for 1 hour, and embedded in Effapoxy resin. Ultra-thin sections were examined by a JEOL 100S transmission electron microscope.

Immunofluorescence with Anti-rat Serum Albumin and Anti-AGE-RNase

Paraffin-embedded sections were deparaffinized and then blocked with 10% goat serum in PBS for 30 minutes at room temperature. The sections were then incubated for 2 hours at 37° C. with either an affinity purified polyclonal rabbit anti-AGE antibody or with a polyclonal sheep anti-rat serum albumin antibody (Cappell). The sections were then rinsed for 30 minutes with PBS and then incubated with either an affinity purified FITC-goat anti-rabbit IgG (H+L) double stain grade (Zymed) or a Rhodamine-rabbit anti-sheep IgG (whole) (Cappell) for 1 hour at 37° C. The sections were then rinsed for 30 minutes with PBS in the dark, mounted in aqueous mounting media for immunocytochemistry (Biomeda), and cover slipped. Sections were scored in a blinded fashion. Kidney sections were evaluated by the number and intensity of glomerular staining in 5 regions around the periphery of the kidney. Scores were normalized for the immunofluorescent score per 100 glomeruli with a scoring system of 0–3, with 0=none while 3=intense staining.

Immunofluorescence for Chondroitin and Heparan Sulfate Proteoglycans

Heparan sulfate side-chain: Monoclonal JM-403 was used that is specific for basement membrane heparan sulfate, and frozen sections were equilibrated with PBS for 20 minutes at room temperature. Sections were incubated with primary antibody (1:250) for 1 hour at room temperature. Antibody dilutions were carried out in PBS containing 1% bovine serum albumin, 5% rat sera, and 0.05% sodium azide. Sections were then rinsed for 20 minutes with PBS and then incubated with secondary antibody (1:50), goat anti-mouse IgM (Fc) FITC (Nordic) for 1 hour.

Basement membrane heparan sulfate core protein: Determination was carried out with polyclonal BL-31. Frozen sections were incubated with primary antibody (1:50) for 1.5 hours at room temperature. Sections were then rinsed for 20 minutes and then incubated with secondary antibody (1:50), goat anti-rabbit IgG FITC (Cappell) for 1 hour. Sections were then rinsed for 20 minutes with PBS in dark, mounted in aqueous mounting media for immunocytochemistry (Biomeda), and cover slipped.

Chondroitin sulfate proteoglycan: Determination was with rabbit antibodies. Paraffin-embedded sections were deparaffinized and digested for 90 minutes with chondroitinase ABC (proteus vulgaris, Sigma Chemicals) at 0.5 U/ml in 0.05 M Tris-HCl, pH 8.0 containing 0.05 M NaCl. Tissues were blocked with 10% BSA in PBS for 30 minutes at room temperature. Sections were then incubated for 2 hours at 37° C. with rabbit anti-chondroitin sulfate proteoglycan IgG (Chemicon) purified from bovine nasal cartilage and diluted 1:100. Sections were rinsed for 30 minutes with PBS and incubated for 1 hour with 1:50 diluted secondary antibody (Zymed), an affinity purified FITC-goat anti-rabbit IgG (H+L) double stain grade. Sections were then rinsed for 30 minutes with PBS in the dark, mounted in aqueous mounting media (Biomeda) and cover slipped.

Quantitation: All immunostained sections were scored in a blinded fashion. Scores were normalized for the immunofluorescent score per 100 glomeruli with a scoring system of 0–3.

Morphometry/Glomerular Volume

Periodic acid-Schiff stained paraffin embedded sections were used to determine glomerular volumes. The mean glomerular area in each rat were calculated using a computer-assisted morphometric program (NIH Image software). The mean volume (Vg) was then calculated from the respective mean glomerular area (Ag) as $Vg=(B/k)*Ag^{3/2}$ where $B=1.38$ is the size distribution coefficient and $k=1.1$ is the shape coefficient for glomeruli idealized as a sphere. (Lane et al. Kidney Int 41:1085–9, 1992)

Determination of Plasma Vitamin B6 forms by HPLC

The procedures of Sampson and O° Connor (Nutrition Res. 9:259–272 (1989)) and Sharma and Dakshinamurti (Sampson and O° Connor J Nutr 119:1940–8, (1989) Sharma and Dakshinamurti, J Chromatogr 578:45–51, (1992)) were followed, using a Shimadzu HPLC with RF-551 fluorescence monitor. Excitation was at 328 nm and emission was followed at 393 nm. An Ultremex C18 guard column (30×4.6 mm, 5 micron particle size) (Phenomenex) preceded an Ultremex C18 ion-pair column (octadecylsilane, 150×4.6 mm, 3 micron particle size) (Phenomenex). Solvent A contained 0.033 M phosphoric acid and 0.008 M 1-octanesulfonic acid, adjusted to pH 2.2 with 6 N KOH. Solvent B contained 0.033 M phsophoric acid and 10% (v/v) 2-propanol, adjusted to pH 7.5 with 6 N KOH. The post-column reagent contained 1 mg/ml sodium bisulfite in 1.0 M potassium phosphate buffer adjusted to pH 7.5 with 6 N KOH. Elution following injection was with a linear gradient to 100% B in 10 minutes; 100% B for 15 minutes; linear gradient to 100% A in 4.5 minutes. Samples were plasma aliquots (250 $\mu$l ) mixed with 10% (w/v) metaphosphoric acid (225 $\mu$l ) and 25 $\mu$l deoxypyridoxine as internal standard (30 nm/ml in 5% metaphosphoric acid). They were vortexed and centrifuged at 8500×G for 5 minutes at room temperature to precipitate protein, then loaded on the column immediately after extracting with 1 volume of methylene chloride to remove lipids, and filtered through a 0.2 micron Nylon-66 filter (Rainin).

Results

General Observations and Creatinine Clearance Hyperfiltration

The rats in this study were generally healthy and all gained weight during the 6 weeks of experiment, as summarized in Table 2. Blood glucose levels remained normal and there was not significant elevation of fructosamine, as expected from the small amount of glycated albumin (comprising $\leq 2\%$ of total plasma albumin) being administered daily. Subjective observations mainly revealed tail scabbing and sensitivity in the animals receiving AGE-RSA injections without drug treatments, precluding the study of rat tail collagen for alterations. Although some observations were made on rats exposed to two weeks of treatments, almost all the results reported in this study are for the 6 week duration. The one exception is the creatinine clearance where interesting and significant differences were observed between 2 and 6 week treatments (Table 1). A transient hyperfiltration effect independent of presence of PM or AG was noted at 2 weeks for rats injected with Amadori-RSA, and a similar but smaller hyperfiltration was also observed for rats injected with AGE- RSA at 6 weeks. There were no statistically significant differences among groups with the other parameters such as body weight, except for some elevation ($p<0.05$) in fructosamine in three of the groups (Amadori-RSA+PM, Amadori-RSA+AG, AGE-RSA+PM+ AG).

TABLE 2

Sprague-Dawley rats body weight, blood glucose, fructosamine and creatinine clearance at 6 weeks[a]

| Groups (n = 4) | Body Wt (g) | Fructosamine (mmole/L) | Blood Glc (g/dL) | Creat C-2wk (ml/(min*100g)) | Creat C-6wk |
|---|---|---|---|---|---|
| Controls | | | | | |
| Saline | 328 ± 31 | 1.04 ± 0.15 | 102 ± 5 | 0.54 ± 0.07 | 0.50 ± 0.07 |
| PM (25 mg/kg/day) | 340 ± 30 | 1.06 ± 0.07 | 107 ± 8 | 0.66 ± 0.07 | 0.66 ± 0.17 |
| RSA (unmodified) | 358 ± 35 | 1.16 ± 0.12 | 104 ± 15 | 0.86 ± 0.16 | 0.70 ± 0.02 |
| Amadori-RSA treated | | | | | |
| Untreated | 362 ± 15 | 1.40 ± 0.31 | 96 ± 10 | 1.02 ± 0.10[#] | 0.60 ± 0.10 |
| Amadori-RSA +PM | 310 ± 20 | 1.76 ± 0.29 | 90 ± 9 | 1.05 ± 0.20[#] | 0.57 ± 0.15 |
| Amadori-RSA +AG | 294 ± 23 | 1.64 ± 0.16 | 105 ± 7 | 0.75 ± 0.10 | 0.64 ± 0.12 |
| Amadori +PM/AG | 319 ± 27 | 1.98 ± 0.46 | 95 ± 13 | 1.00 ± 0.20 | 0.66 ± 0.14 |
| NaBH$_4$-reduced | 363 ± 35 | 1.47 ± 0.18 | 108 ± 13 | n.a. | 0.86 ± 0.07 |
| AGE-RSA treated | | | | | |
| AGE-RSA | 323 ± 38 | 1.28 ± 0.18 | 112 ± 7 | 0.56 ± 0.04 | 0.86 ± 0.11[#] |
| AGE-RSA + PM | 313 ± 21 | 1.40 ± 0.05 | 100 ± 11 | 0.64 ± 0.02 | 0.91 ± 0.06[##] |

TABLE 2-continued

Sprague-Dawley rats body weight, blood glucose, fructosamine and creatinine clearance at 6 weeks[a]

| Groups (n = 4) | Body Wt (g) | Fructosamine (mmole/L) | Blood Glc (g/dL) | Creat C-2wk | Creat C-6wk |
|---|---|---|---|---|---|
| | | | | (ml/(min*100g)) | |
| AGE-RSA + AG | 323 ± 36 | 1.49 ± 0.14 | 107 ± 12 | 0.68 ± 0.08 | 0.88 ± 0.04 |
| AGE-RSA + PM/AG | 360 ± 37 | 1.73 ± 0.19 | 118 ± 6 | 0.64 ± 0.08 | 0.94 ± 0.03[##] |

[a]RSA and glycated RSA (Amadori-RSA or AGE-RSA) were given at 50 mg/kg/day by tail vein injection. Pyridoxamine (PM) and aminoguanidine (AG) were given by drinking water separately at 25 mg/kg/day or combined (PM ± AG) at 10 mg/kg/day each. Values given are averages (n = 4) with standard errors. ANOVA comparison of creatinine clearance between rats at 2 weeks and 6 weeks is given at p < 0.05 ([#]) or at p < 0.01 ([##]).

Microalbuminuria

Over the limited 6 week course of experiments, there was no statistically significant increase in albuminuria among the different groups. For most groups, there was individual variation, and some animals did approach microalbuminuria range. It may also be noteworthy that the inclusion of pyridoxamine for groups receiving Amadori-RSA and AGE-RSA led to very low intra-group scatter and to the lowest means.

Glomerular volume changes

Figure 39:
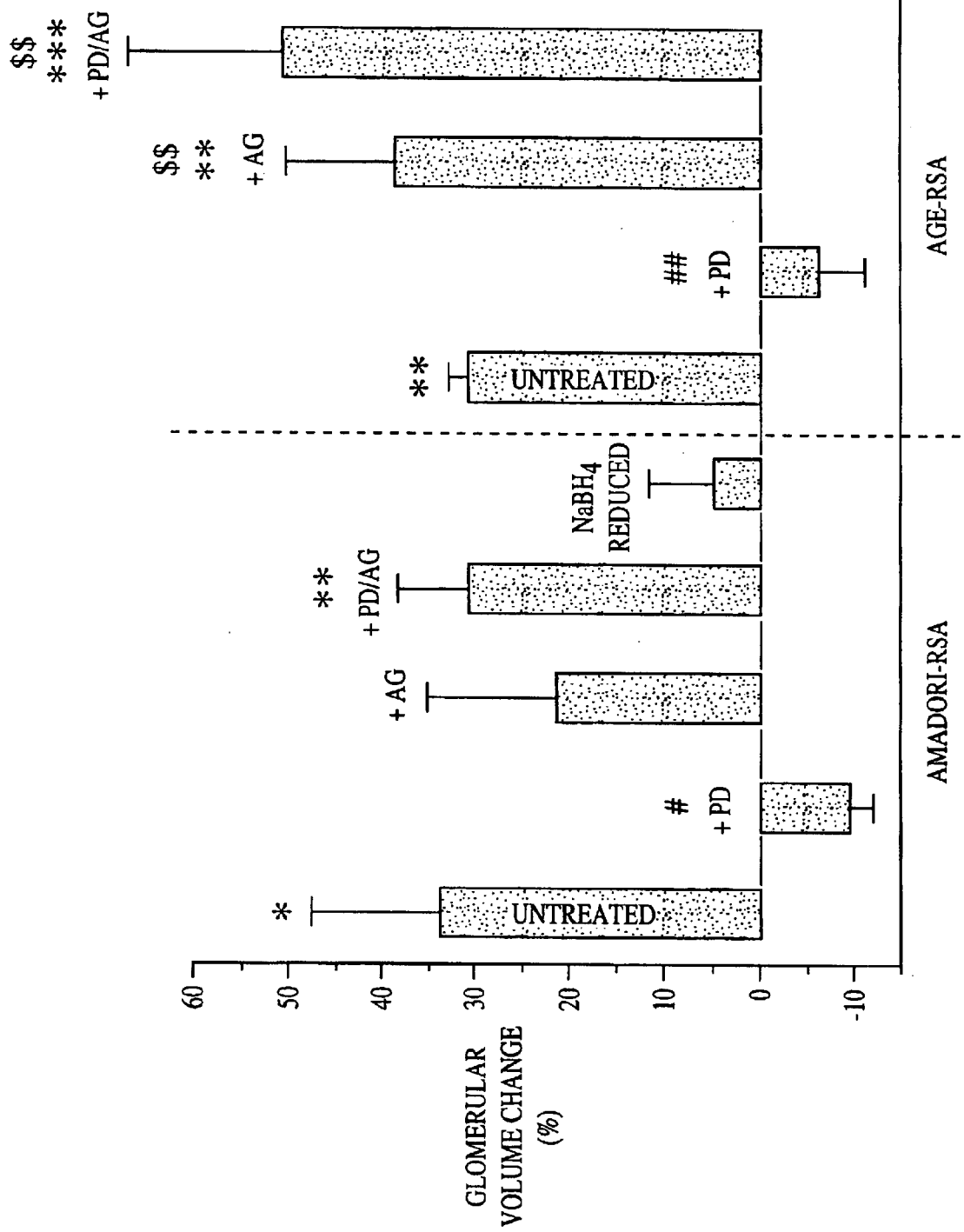
FIG. 39 Relative change in glomerular volume (GV) at 6 weeks for the study groups. GV was computed from PAS stained sections as described in Methods. Values and standard errors for each group (n=4) are given as the percent change relative to controls. ANOVA analysis of statistical significance is reported for comparison with controls ($p<0.05$ *, $<0.01$ , $<0.001$ *), with untreated subgroups ($p<0.05$ #), and with pyridoxamine (PM) treated subgroups ($p<0.05$ $, $<0.01$ $$)

PAS stained glomerular sections were examined and revealed no marked pathology. However, they were also used to estimate the glomerular volume (GV), as described in Methods. The average glomerular volumes of the treatment groups are presented in FIG. 39 as percent change relative to control groups at 6 weeks. GV was computed from PAS stained sections as described in Methods. Values and standard errors for each group (n=4) are given as the percent change relative to controls. ANOVA analysis of statistical significance is reported for comparison with controls (p<0.05 *, <0.01 , <0.001 *), with untreated subgroups (p<0.05 #), and with pyridoxamine (PM) treated subgroups (p<0.05 $, <0.01 $$).

It can be seen that Amadori-RSA injection did lead to a significant 35% increase (p<0.05) in GV, whereas inclusion of pyridoxamine (25 mg/kg/day) led to no significant changes from controls (p>0.05). The combination of PM+AG (10 mg/kg/day each) did not prevent the change in GV, as it differed from the controls (p<0.05). No statistically significant differences were found for the other two treatment subgroups (AG or NaBH$_4$ reduction).

Very similar changes were seen in the case of AGE-RSA injected groups. The untreated subgroup showed a significant (p<0.01) 30% increase in glomerular volume when compared to controls. A significant elevation in GV persisted in the two subgroups receiving simultaneous aminoguanidine (p<0.01) or the combination of PM+AG (p<0.001). However, this increase was completely prevented when pyridoxamine was administered, and this subgroup differed significantly from the two other treatment subgroups that received AG alone (p<0.01) or the combination at lower dose of AG+PM (p<0.001).

Glomerular staining with Alcian Blue

Since PAS as well as H&E staining did not reveal gross pathological abnormalities, glomerular sections were examined for other changes that may be related to filtration barrier alterations. In particular, staining was carried out with Alcian Blue at both pH 2.5 (specific for acidic glycosaminoglycans) and pH 1.0 (specific for sulfated glycosaminoglycans). Under the latter conditions, changes were observed that were difficult to score quantitatively due to the lightness of the staining. In the case of pH 2.5 staining, there was a 50–60% increase in acidic glycosaminoglycans in the groups receiving Amadori-RSA (p<0.05) or AGE-RSA (p<0.01) (Table 3). In both cases, the animals receiving pyridoxamine at 25 mg/kg/day in addition to glycated RSA did not show a significant increase in staining (p>0.05) when compared to the controls. This is in contrast to administration of the same amount of aminoguanidine, as those subgroups showed a significant elevation (p<0.05) compared to the controls.

The most interesting changes that could be quantitated occurred at pH 1.0, as shown in Table 3. Amadori-RSA and AGE-RSA administered groups showed a decrease in staining as compared to the controls. The latter difference was statistically significant (p<0.001) and indicated that a loss of sulfated groups was being produced by this glycated albumin. The most likely candidates were sulfated proteoglycans. Consequently, we attempted to identify the nature of the proteoglycans that appeared to be affected. Immunohistochemical staining for chondroitin sulfate did not reveal measurable changes (data not shown). The results with heparan sulfate are described below.

TABLE 3

Scoring of histochemical glomerular staining for sulfated (Alcian Blue pH 1.0) or acidic (Alcian Blue and 2.5) glycosaminoglycans and for heparan sulfate core protein[a]

| Groups (n = 4) | Alcian Blue pH 1.0 | Alcian Blue pH 2.5 | HS core protein (Ab BL-31) |
|---|---|---|---|
| Controls | | | |
| Saline | 2.75 ± 0.14 | 1.31 ± 0.12 | 215 ± 4 |
| PM (25 mg/kg/day) | 2.62 ± 0.24 | 1.56 ± 0.21 | 234 ± 8 |
| RSA (unmodified) | 2.75 ± 0.14 | 1.38 ± 0.24 | 226 ± 10 |
| Amadori-RSA treated | | | |
| Untreated | 2.00 ± 0.41 | 2.12 ± 0.12[#] | 235 ± 12 |
| Amadori-RSA ± PM | nd | 1.69 ± 0.31 | 222 ± 16 |
| Amadori-RSA ± AG | nd | 2.25 ± 0.25[#] | 213 ± 10 |
| Amadori ± PM/AG | nd | 2.06 ± 0.39 | 204 ± 6 |
| NaBH$_4$-reduced AGE-RSA treated | nd | 1.81 ± 0.47 | 203 ± 14 |
| AGE-RSA | 1.25 ± 0.14[###] | 2.44 ± 0.21[##] | 238 ± 10 |
| AGE-RSA + PM | nd | 1.88 ± 0.30 | 228 ± 1 |

TABLE 3-continued

Scoring of histochemical glomerular staining for sulfated
(Alcian Blue pH 1.0) or acidic (Alcian Blue and 2.5) glycosaminoglycans
and for heparan sulfate core protein[a]

| Groups (n = 4) | Alcian Blue pH 1.0 | Alcian Blue pH 2.5 | HS core protein (Ab BL-31) |
|---|---|---|---|
| AGE-RSA + AG | nd | 2.19 ± 0.19[#] | 219 ± 8 |
| AGE-RSA + PM/AG | nd | 2.00 ± 0.41 | 208 ± 16 |

[a]RSA and glycated RSA (Amadori-RSA or AGE-RSA) were given at 50 mg/kg/day by tail vein injection. Pyridoxamine (PM) and aminoguanidine (AG) were given by drinking water separately at 25 mg/kg/day or combined (PM ± AG) at 10 mg/kg/day each. Values given are averages (n = 4) with standard errors. ANOVA analysis is given at $p < 0.05$([#]), $p < 0.01$([##]) or at $p < 0.001$([###]) significance relative to control groups.

Immunohistochemical Staining for Glomerular Heparan Sulfate Proteoglycan

Immunohistochemical staining was carried out for all groups of the study using antibodies specific for either heparan sulfate (HS) side-chains (mAb JM-403) or core protein (Ab BL-31). In the case of HS core protein, use of BL-31 antibody revealed no difference in staining (p>0.05) from any of the groups of this study, regardless of administration of glycated albumin or treatment with the AGE inhibitors (Table 3). In contrast to HS core protein staining with Ab BL-31, staining for the heparan sulfate with monoclonal JM-403 revealed interesting and significant changes. Quantitative scoring changes are reported in FIG. 40 as values relative to controls at 6 weeks. Fluorescein-conjugated JM-403 monoclonal antibody was used. Values and standard errors for each group (n=4) are given as the percent change relative to controls. ANOVA analysis of statistical significance is reported for comparison with controls (p<0.05 *, <0.01 , <0.001 *), with untreated subgroups (p<0.05 #, <0.01 ##), and with pyridoxamine (PM) treated subgroups (p<0.05 $, <0.01 $$).

It can be seen that a loss in HS was produced by both Amadori-RSA (25% decrease, p<0.01) and AGE-RSA (50% decrease, p<0.001). In both cases, the presence of pyridoxamine completely prevented this loss (p<0.05 and p<0.01, respectively when compared to corresponding untreated subgroups). In the case of Amadori-RSA, AG appeared to not prevent this loss (p=0.07), but the combination of PM+AG apparently did lead to a difference from the untreated group (p=0.07). In the case of AGE-RSA injection, the presence of AG alone (p<0.01) or at lower dose in combination with PM (p<0.001) still led to a significant 30–50% HS decrease as compared to controls. Furthermore the normal HS level seen with pyridoxamine was significantly different (p<0.001) from the loss of heparan sulfate observed with aminoguanidine at an equivalent dose of 25 mg/kg/day.

Immunohistochemical Staining for Glomerular Albumin Cross-linking

Figure 41:
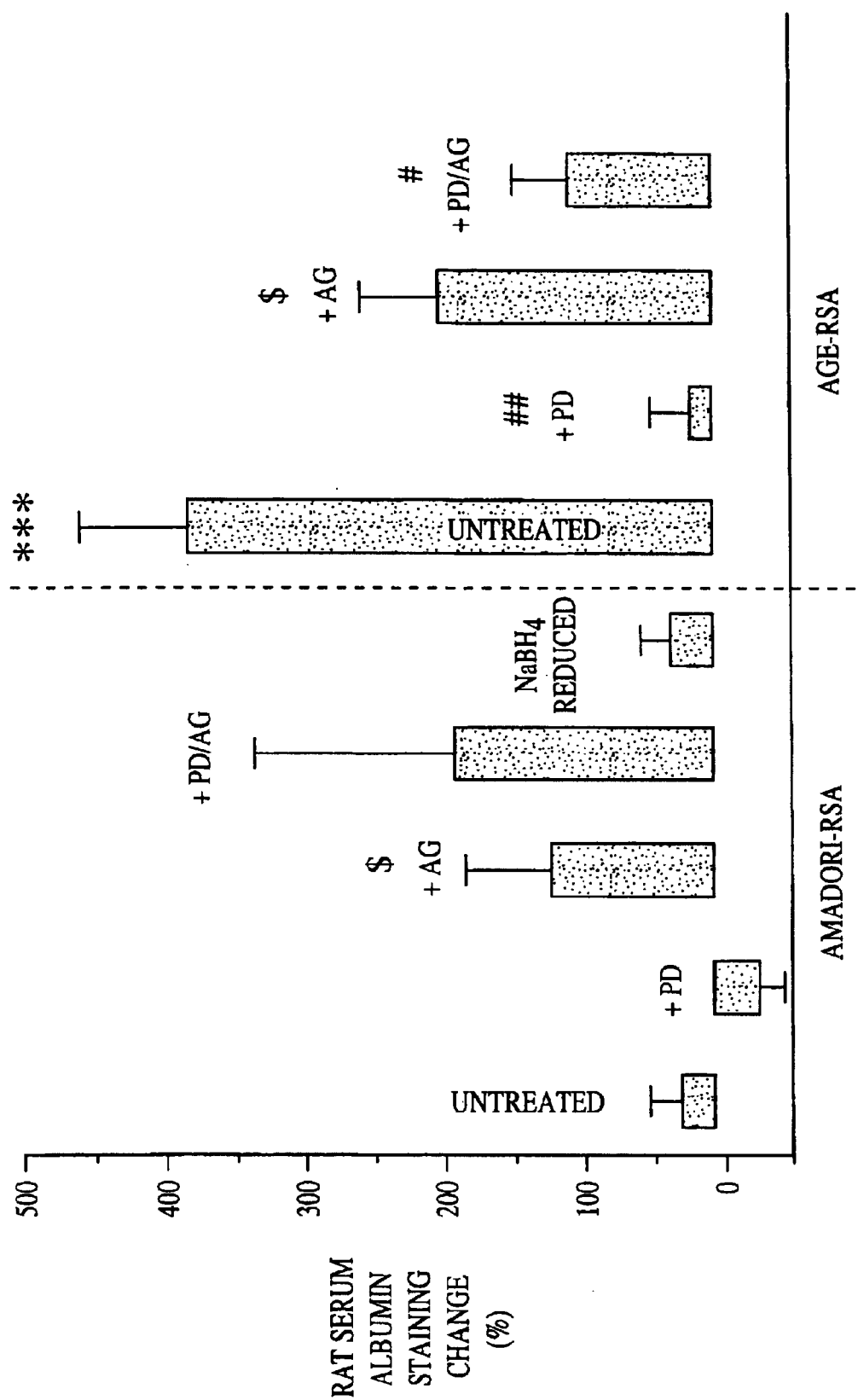
FIG. 41 Relative change in glomerular albumin immunofluorescent staining intensity (arbitrary scale) at 6 weeks. Rhodamine-conjugated anti-RSA was used. Values and standard errors for each group (n=4) are given as the percent change relative to controls. ANOVA analysis of statistical significance is reported for comparison with controls ($p<0.05$ *, $<0.01$ , $<0.001$ *), with untreated subgroups ($p<0.05$ #, $<0.01$ ##), and with pyridoxamine (PM) treated subgroups ($p<0.05$ $, $<0.01$ $$).

We also examined the question of whether glycated albumin was deposited in the glomerulus, presumably by glycation-induced cross-linking. Little albumin was detected in controls, including animals injected with unmodified RSA. Animals injected with AGE-RSA showed a striking deposition that was prevented when pyridoxamine was present in drinking water. Quantitative scoring of these staining intensities was obtained in a blinded fashion and the results are summarized in FIG. 41 which gives the changes relative to the controls at 6 weeks. Rhodamine-conjugated anti-RSA was used. Values and standard errors for each group (n=4) are given as the percent change relative to controls. ANOVA analysis of statistical significance is reported for comparison with controls (p<0.05 *, <0.01 , <0.001 *), with untreated subgroups (p<0.05 #, <0.01 ##), and with pyridoxamine (PM) treated subgroups (p<0.05 $, <0.01 $$).

It can be seen that AGE-RSA, with its four-fold increase (p<0.001), is particularly effective in leading to cross-linking of presumably glycated albumin to the glomerulus. This cross-linking is completely blocked in the presence of pyridoxamine (p<0.01) and partially by the combination of pyridoxamine plus aminoguanidine (p<0.05). Aminoguanidine at 25 mg/kg/day gave intermediate results but did not lead to statistically significant differences from either the controls or from the untreated subgroup. However, it was less effective (p<0.05) when compared to the pyridoxamine treated subgroup.

The Amadori-RSA injection in the presence or absence of pyridoxamine or aminoguanidine appeared to produced less albumin cross-linking and was not different from the controls (p=0.05). However, it is interesting that administration of pyridoxamine gave significantly lower cross-linking than Aminoguanidine (p<0.05). Borohydride reduction of Amadori-RSA also prevented cross-linking.

Influence of Pyridoxamine Administration on Vitamin B6 Status

Since pyridoxamine is endogenously present in small concentrations and is convertible to other members of the $B_6$ vitamers via transaminations and other modifications, we measured by HPLC the serum levels of the vitamers after administration of 25 mg/kg/day pyridoxamine in drinking water. The results (FIG. 42) are given as ratios of steady state to endogenous levels based on sampling at different times after a 48 hours pre-equilibration. The average of several subsequent samplings was determined by HPLC, as described in Methods. Values and standard errors for each vitamer are given as the percent change relative to its endogenous levels determined in control animals. The insets give the numerical ratios determined. Endogenous levels for these animals were on separate control animals It can be seen that only pyridoxamine is greatly elevated by approximately 300-fold. There is less than 10 fold perturbation in pyridoxal and pyridoxal phosphate, the two vitamers that are accepted measures of vitamin $B_6$ status.

DISCUSSION

Damage by nonenzymatically glycated proteins may be a significant contributor to diabetic complications, but the mechanisms by which this may occur are not well understood. This study shed light on this question by comparing the in vivo effects on the kidney by differently glycated albumins and by comparing two effective AGE inhibitors, one (pyridoxamine) being also specific for inhibiting conversion of Amadori intermediates to AGE products. Noting that similar AGE products are formed on proteins from ribose as from glucose, such as CML and pentosidine, we utilized ribose-modified rather than glucose-modified albumin for two major reasons. First, it was hypothesized that ribose-modified protein would undergo more rapid reaction, thus making laboratory studies practical for this otherwise protracted biological process. The second is that the same Amadori-albumin preparation could be converted to "AGE-albumin" under well-defined conditions that rapidly produce defined and maximal levels of certain AGEs such as CML and pentosidine. It is important to emphasize that this "AGE-albumin" can still undergo further glycoxidative degradation, as reflected by a continued formation of typical Ex335/Em385 AGE fluorescence (data not shown). The paired use of these Amadori-albumin and "AGE-albumin" should lead to a more meaningful in vivo comparison: both have the same number of lysines modified, and the "AGE-albumin," being derived from Amadori precursors, may be more representative of AGE-proteins formed under in vivo conditions. This follows because in vitro incubations with excess glucose lead to formation of different distributions AGEs products on albumin due to contributions from reactive products of autoxidation of glucose, such as glyoxal. These non-Amadori pathways may be attenuated or eliminated in vivo by competing reactions.

Despite the short-term duration of the study and the small number of animals involved, significant changes were observed in the kidney that could have an important impact on the integrity of glomerular function. Comparison of the differently glycated proteins reveals that both Amadori-RSA and "early" AGE-RSA are capable of inducing such changes. For example, up to 50% increases in glomerular volume (FIG. 39) and decreases in heparan sulfate (FIG. 40) were observed at 6 weeks. More importantly perhaps, most of the significant changes appear to be preventable. In this regard, pyridoxamine consistently showed inhibitory potency, whereas at the same concentration, aminoguanidine showed modest, if any, inhibition. Our results raise important issues, discussed below, that must be addressed: first, whether the effects seen are specifically due to damage by the glycated proteins; second, what are the mechanisms leading to the observed changes; and third, whether the damage seen is relevant to mechanisms contributing to diabetic complications.

The association of the changes seen with glycated protein attachment to the glomerulus can be made most strongly in the case of AGE-RSA. As quantitated in FIG. 41, administration of a small amount (<2% of total plasma albumin) of this glycated albumin results in several fold increase in RSA deposition in the glomerulus. Although the resolution is not sufficient to pin-point more precisely the site of localization, such an attachment is almost certainly due to chemical cross-linking of the AGE-RSA to the matrix. This is evidenced by the extremely effective blocking by pyridoxamine, a much more efficacious in vitro AGE inhibitor than aminoguanidine. Pyridoxamine also appeared consistently effective in completely preventing the associated glomerular volume increase and the loss of heparan sulfate that accompany the administration of AGE-RSA. Although the effects of Amadori-RSA did not achieve similar statistical significance for all the subgroups, the trends in inhibition were similar to those seen with AGE-RSA. In all cases, pyridoxamine appears to prevent the changes seen in these parameters, whereas aminoguanidine at a similar dose or the combination of pyridoxamine+aminoguanidine at lower doses were less effective.

Figure 40:
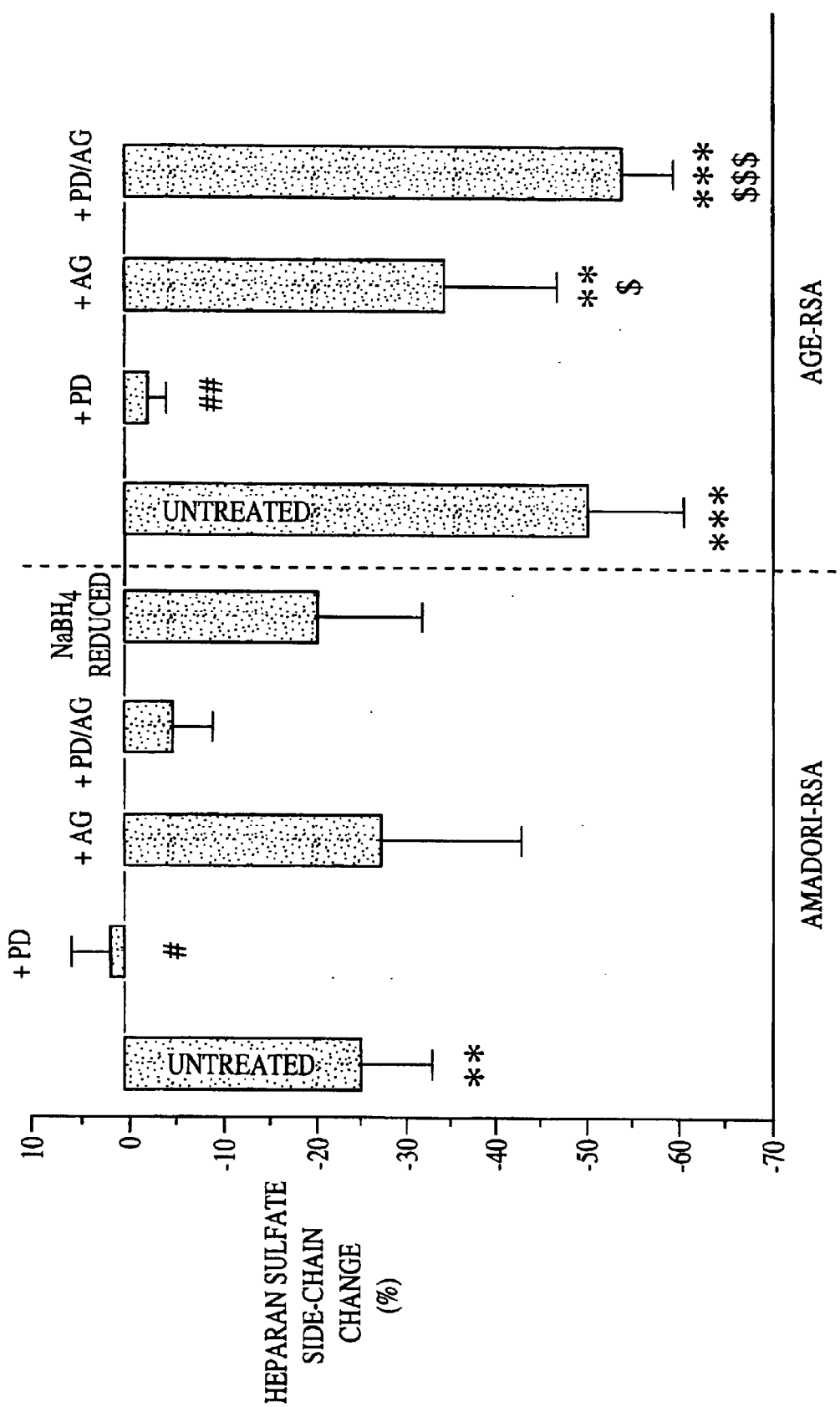
FIG. 40 Relative change in glomerular heparan sulfate side-chain immunofluorescent staining intensity (arbitrary scale) at 6 weeks. Fluorescein-conjugated JM-403 mAb was used. Values and standard errors for each group (n=4) are given as the percent change relative to controls. ANOVA analysis of statistical significance is reported for comparison with controls ($p<0.05$ *, $<0.01$ , $<0.001$ *), with untreated subgroups ($p<0.05$ #, $<0.01$ ##), and w pyridoxamine (PM) treated subgroups ($p<0.05$ $, $<0.01$ $$).

Insights into the mechanisms leading to glomerular changes may be provided by the novel observation of loss of heparan sulfate that accompanies administration of glycated albumins (FIGS. 40). Heparan sulfate is believed to be a central component in the glomerular anionic charge barrier to albumin excretion, and there have been several reports that loss of heparan sulfate leads to proteinuria, either in vivo or in diseases such as diabetes (Vernier et al. Kidney Int 41:1070–80, (1992); Tamsma et al. Diabetologia 37:313–20, (1994); van den Born and Berden Nephrol Dial Transplant 10:1277–9, (1995); van den Born et al., Diabetologia 38:161–72, (1995); van den Born et al., Diabetologia 38:1169–75, (1995)). We examined whether the changes seen, across all the samples and treatments, linearly correlate with loss of heparan sulfate. Significant trends were found when heparan sulfate loss is compared with glomerular RSA deposition (R=−0.45, p=0.001), with glomerular volume increase (R=−0.54, p=0.0001), and with urinary albumin excretion (R=−0.46, p=0.001). Furthermore, the glomerular volume increase linearly correlates with urinary albumin excretion (R=0.43, p=0.003). Recent studies (Kashihara et al., Proc Natl Acad Sci U.S.A. 89:6309–13, (1992); Raats et al., J. Biol Chem 272:26734–41, (1997)) have demonstrated the sensitivity of glomerular heparan sulfate to damage by reactive oxygen species, and furthermore, as observed here (Table 3), this is not accompanied by loss of heparan sulfate core protein. Since AGE-modified proteins undergo glycoxidative degradation leading to increased reactive oxygen species (Fu et al. Diabetes 41 Suppl 2:42–8, (1992) Thorpe and Baynes, Drugs Aging 9:69–77, (1996)), it is reasonable to hypothesize that the glycated albumin that deposits within the glomerulus causes damage through this mechanism of triggering depolymerization of heparan sulfate. These observations all lend further support to attributing the glomerular changes to deposited glycated albumin.

It is important to consider the degree to which the glomerular changes observed in this study are consistent with changes seen in diabetic nephropathy. The absence of consistent microalbuminuria as well as mesangial expansion, basement membrane thickening and glomerular sclerosis (data not shown) appear at variance with typical overt diabetic nephropathy. This is not unexpected, considering the limited 6 week duration of this study, as such manifestations are usually observed after 6 months in streptozotocin (STZ) diabetic rat models. However, the changes we see are surprisingly consistent with manifestations often reported for early stages of diabetic nephropathy. This may even include the small transient hyperfiltration (Table 2), which was not affected by pyridoxamine or aminoguanidine. Glomerular volume increases, alterations in the anionic charge barrier for filtration, and heparan sulfate side chain loss have all been previously reported in STZ diabetic rodent models. Thus our results and the significant linear correlations observed suggest that the glomerular changes seen are consistent with early diabetic stages leading to microalbuminuria. In general, our observations on glomerular changes, particularly the novel finding of significant heparan sulfate loss, extend and complement the findings of Cohen, Ziyadeh, Vlassara, Striker and others (Cohen and Ziyadeh, J Am Soc Nephrol 7:183–90, (1996); Vlassara et al., Proc Natl Acad Sci U.S.A. 91:11704–8, (1994)) of changes produced by glycated albumin both in vivo and in cell culture.

Figure 42:
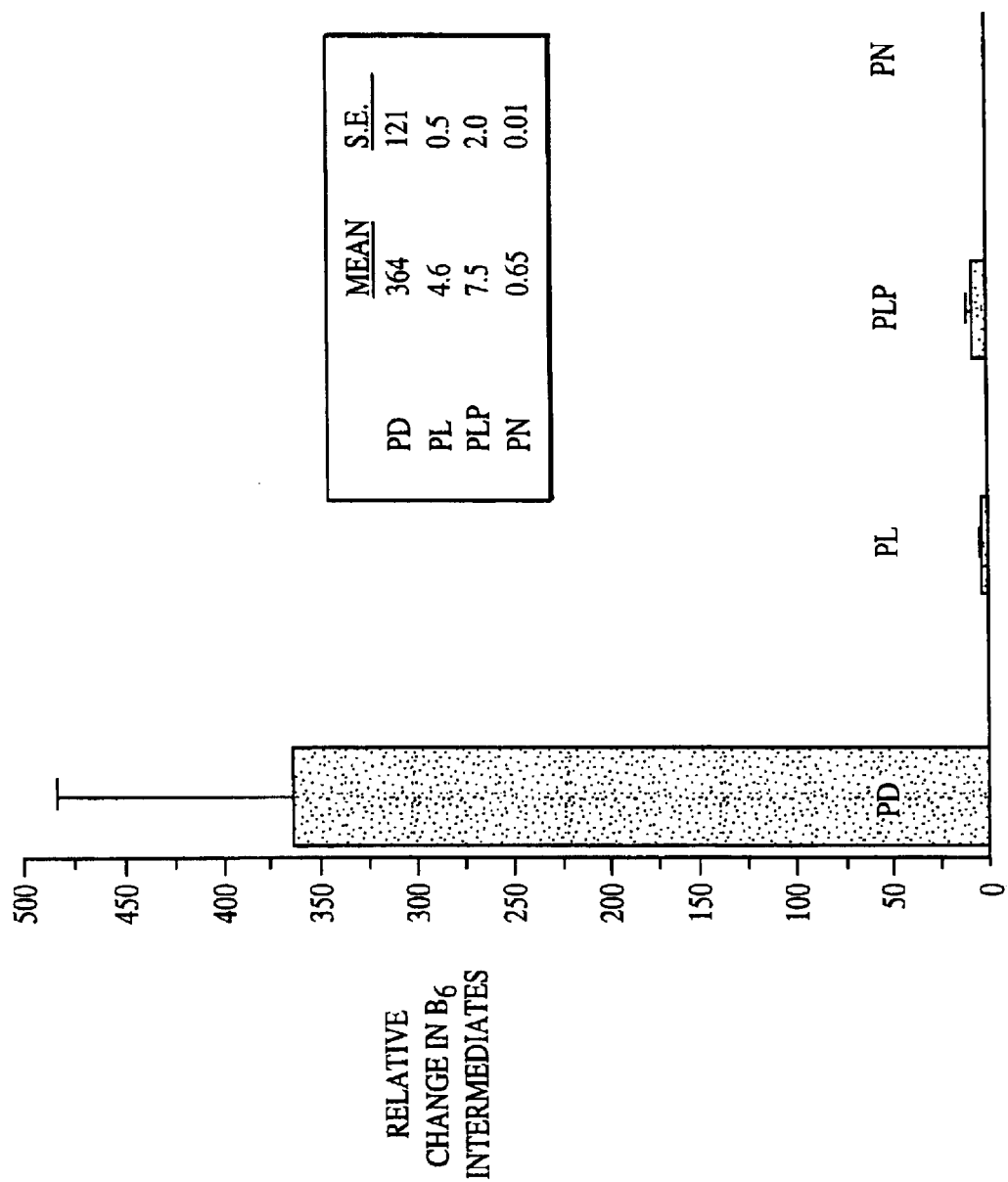
FIG. 42 Relative change in plasma concentrations of vitamin B6 intermediates. Animals (n=4) were pre-dosed for 48 h with 25 mg/kg/day of pyridoxamine (pyridoxamine). The average of several subsequent samplings was determined by HPLC, as described in Methods. Values and standard errors for each vitamer are given as the percent change relative to its endogenous levels determined in control animals. The insets give the numerical ratios determined. Endogenous levels for these animals were on separate control animals.

Finally, it is very encouraging that all the major changes are consistently and effectively preventable by pyridoxamine. We note that this inhibitor is not only a unique post-Amadori AGE inhibitor, as demonstrated herein, but it is also extremely effective in inhibiting overall AGE formation in the presence of excess glucose. Its present in vivo effects are highly unlikely to be due to metabolic perturbations of vitamin $B_6$ status, as pyridoxal phosphate appears to be well-regulated in the presence of excess pyridoxamine (pyridoxamine) (FIG. 42). The potent activity of pyridoxamine in preventing loss of heparan sulfate arising from glycoxidation (FIG. 40) also suggests that pyridoxamine may have therapeutic potential in other conditions and diseases where oxidative stress may be involved, where oxidative stress is defined as specific increases in reactive oxygen species and derived free radicals. Such conditions and diseases include, but are not limited to atherosclerosis, ischemia-reperfusion injury, inflammatory diseases such as arthritis, cancer, exposure to ionizing radiation and/or chemotherapeutic agents, pulmonary adult respiratory distress syndrome (ARDS), myocardial infarction and strokes, pancreatitis, or intestinal ulceration, and aging. (See, for example, U.S. Pat. Nos. 5,700,654 and 5,462,946).

EXAMPLE 7

Pyridoxamine Inhibits AGE Formation and Protein Cross-linking in a STZ Diabetic Rat Model In this example, we show that pyridoxamine inhibits the formation of AGEs and crosslinking of skin collagen in the streptozotocin-induced diabetic rat. Pyridoxamine was compared to aminoguanidine and AGEs were measured by chemical methods. Levels of three AGEs, $N^\epsilon$-(carboxymethyl)lysine, $N^\epsilon$-(carboxyethyl)lysine and pentosidine, increased ~2-fold in skin collagen of diabetic, compared to control, rats after 7 months of diabetes, along with a 2-fold increase in Maillard-type fluorescence and a 4-fold increase in the half-time for solubilization of skin collagen by pepsin. Neither drug affected the increase in blood glucose or glycated hemoglobin. Both pyridoxamine and aminoguanidine decreased the $N^\epsilon$-(carboxymethyl) lysine, $N^\epsilon$-(carboxyethyl)lysine and fluorescence, but not pentosidine, content of skin collagen of diabetic rats by ~50% toward non-diabetic levels, and reduced the half-time for digestion of collagen by ~25% toward normal. We conclude that pyridoxamine, like aminoguanidine, inhibits the chemical modification and crosslinking of collagen in the diabetic rat.

Abbreviations: AG, aminoguanidine; AGE, advanced glycation end-product; CEL, $N^\epsilon$-(carboxyethyl)lysine; CML, $N^\epsilon$-(carboxymethyl)lysine; FL, fructoselysine; Glcffb, glycated hemoglobin; Hyp, hydoxyproline; PBS, phosphate buffered saline; PM, pyridoxamine; RBC, red blood cell, erythrocyte; RBM, renal basement membrane; RP-HPLC, reverse phase high performance liquid chromatography; SIM-GC/MS, selected ion monitoring gas chromatography—mass spectrometry; STZ, streptozotocin.

Materials and Methods

Materials. Female Sprague-Dawley rats (8 weeks old, ~150 g) were obtained from Harlan Corp., Indianapolis, Ind. PM•(HCl)$_2$, AG hemisulfate and STZ were obtained from Sigma Chemicals Inc., St Louis, Mo.

Animal studies. Diabetes was induced by a single tail vein injection of 45 mg/kg of STZ in 0.1 M sodium citrate buffer, pH 4.5. Control animals were sham injected with buffer only. Diabetes was confirmed by measuring blood glucose levels at 2 and 3 days after the STZ-injection. Animals with plasma glucose higher than 16 mM were classified as diabetic. The diabetic rats were divided randomly into an untreated diabetic group (n=12) and two diabetic treatment groups, receiving either PM (n=13) or AG (n=12) at 1 g/L in drinking water. Two non-diabetic control groups were included, one receiving no treatment (n=13), the other receiving PM(HCl)$_2$ at 2 g/L in drinking water (n=12); the higher dose of PM in the PM-treated control group was designed to compensate, in part, for the lower water intake of non-diabetic, compared to diabetic animals. All animals were housed individually with a light dark cycle of 12 hours each, and had free access to food and water. To maintain body weight and to limit hyperglycemia, diabetic animals received 3 IU of ultralente insulin (Humulin U, Eli Lilly) three times per week; this was increased to 5 IU after week 15 to adjust for the increase in body weight.

Glycemic control. Glycemia was monitored by measurement of plasma glucose and glycated hemoglobin every four weeks, using a Sigma Trinder assay Kit (Sigma # 315). Blood (non-fasting) was obtained from the tail vein, using heparinized microhematocrit tubes, followed by sedimentation of red blood cells (RBC) in a bench-top microhematocrit centrifuge. A sample of plasma (5 µL) or glucose standard was mixed with 300 µL of reagent in a 96-well microtiter plate. The plate was shaken for 18 min and the absorbance at 490 nm was measured in a Wallac Victor 1420 multilabel counter (Wallac Inc. Gaithersburg, Md.). Glycated hemoglobin (GlcHb) was measured on whole blood by boronate affinity chromatography using a Sigma kit for total glycated hemoglobin (Sigma # 442-B).

Measurement of drug levels in plasma and urine. PM and AG concentrations in plasma were measured by reverse phase high performance liquid chromatography (RP-HPLC). PM and its B$_6$ vitamers were assayed as described by Sampson and O'Connor (*Nutrition Res.* 9:259–272 (1989)) and Sakurai et al. (*J. Nutr. Sci. Vitaminol.* 37:341–348 (1991)), using 293/393 nm excitation and emission wavelengths. AG was quantified at 380 nm as the 4-nitrobenzaldehyde conjugate (Beaven et al. 1969. *J. Pharmacol. Exp. Therapeutics* 165:14–22).

Necropsy and tissue sampling. Rats were treated according to the guidelines of the Institutional Animal Care and Use Committee of the University of South Carolina. Blood was drawn from anaesthetized (halothane) rats by heart puncture and transferred into heparinized vacutainer tubes on ice; an aliquot was removed for analysis of glycated hemoglobin. Rats were then killed by over-anesthetization, and liver and kidneys were removed, the kidney decapsulated, and both organs rinsed in PBS buffer, and weighed. The right kidney was cut in half transversely, and one half was removed for fixation for electron and light microscopy. The remainder of the right kidney and the whole left kidney were frozen at −70° C. until processed for isolation of collagen. Abdominal skin (2 cm$^2$) was also removed, rinsed in phosphate buffered saline (PBS) and stored at −70° C. Blood was separated into plasma and RBC within 30 minutes by centrifugation in a refrigerated bench-top centrifuge. RBCs were lysed in an equal volume of deionized water, and plasma and RBC lysates were stored at −70° C.

Isolation and analysis of collagen. The insoluble fraction of skin collagen was prepared by scraping the skin with a single-edged razor blade to remove hair and adventitious tissue, followed by a series of extractions with 0.5 M NaCl, 0.5 M acetic acid and chloroform/methanol (2:1 v/v), as described previously (Dyer, et al. 1993. *J. Clin. Invest.* 91:2463–2469). Total renal collagen was prepared from ~1.5 kidneys by an adaptation of the procedure of Fox et al. (*J. Biol. Chem.* 256:9313–9315 (1981)). Briefly, kidneys were minced and homogenized with a hand-held glass homogenizer in 10 mL of ice-cold water, containing 1 mM EDTA and 0.05% sodium azide. Remaining intact cells and subcellular organelles were then lysed by addition of another 15 mL of water, followed by incubation for 1 hour at 4° C., then centrifugation of the lysate for 30 minutes at 10,000 rpm at 4° C. in a Beckman (Palo Alto, Calif.) J-21 centrifuge. The pellet was resuspended in 10 mL of 3% Triton X-100 containing 0.05% sodium azide and stirred periodically for 2 hours at room temperature. Following centrifugation as above, the pellet was resuspended in 10 mL of 1 M sodium chloride containing 500 Kunitz units of DNase for 1 hour at room temperature. After centrifugation, the pellet was treated with a second detergent, 10 mL of a 4% solution of sodium deoxycholate/0.05% sodium azide for 3 hours at room temperature, centrifuged and then washed by centrifugation three times with water. The collagen was lyophilized and stored at −20° C. until analyzed. Hydroxyproline was measured in acid hydrolysates of collagen by the method of Stegemann and Stalder (*Clin. Chim. Acta* 18:267–273 (1967)). Analyses of the Hyp content of hydrolyzed protein from intermediate fractions indicated >95% recovery of collagen from the kidney homogenate. Based on amino acid analysis, the protein was relatively pure collagen, i.e. 30, 7.3 and 2.2 mol % glycine, Hyp and hydroxylysine (SD≦10%), compared to reported values of 25.6, 8.2 and 2.7 mol % for tubular and 20.4, 5.9 and 1.9 mol % for glomerular basement membrane collagens, respectively (Krisko et al. 1977. *Kidney Internat.* 12:238–243). There was no difference in collagen yield per mg kidney weight among the groups of animals.

Assays of glycation, AGEs, crosslintking and fluorescence in collagen. Fructoselysine (FL), a measure of the extent of glycation of collagen, and the AGEs, $N^\epsilon$-(carboxymethyl)lysine (CML) and $N^\epsilon$-(carboxyethyl)lysine (CEL) were assayed by isotope dilution, selected ion monitoring gas chromatography—mass spectrometry (SIM-GC/MS), and pentosidine by RP-HPLC, as described previously (Dyer, et al. 1993. *J. Clin. Invest.* 91:2463–2469). Levels of AGEs were normalized to the lysine content of the collagen since lysine is a common component of all three AGEs. The relative extent of crosslinking of collagen was estimated from the kinetics of digestion of the collagen by pepsin. For these analyses, 3 mg of collagen was hydrated for 2 hours in 7.5 ml of 0.5 M acetic acid at room temperature in a 20 ml capped polystyrene vial. Digestion was started by addition of pepsin (3 μL of 1% (w/v) solution; 20 μg pepsin/ml final concentration or 50 μg pepsin/mg collagen), and samples were incubated at 37° C. in a water bath with gentle mixing. At various times, an aliquot (250 μL) of the supernatant was removed and mixed with an equal volume of concentrated HCl and hydrolyzed for 24 hours at 110° C. Percent digestion of collagen at each time point was calculated as percent Hyp release into supernatant, compared to Hyp in the supernatant at 24 hours when complete digestion of all samples was achieved, i.e. no residual collagen pellet was present. The final hydrolysate was analyzed directly for total Maillard-type fluorescence (Ex=370 nm, Em=440 nm), which was also normalized to the Hyp content of the solution.

Statistical analysis. Statistical analyses were performed using Sigma Stat for Windows V1.00 (SPSS, Inc., Chicago, Ill.). P-values were calculated by non-parametric Mann-Whitney Rank Sum analysis.

Results

Figure 43:
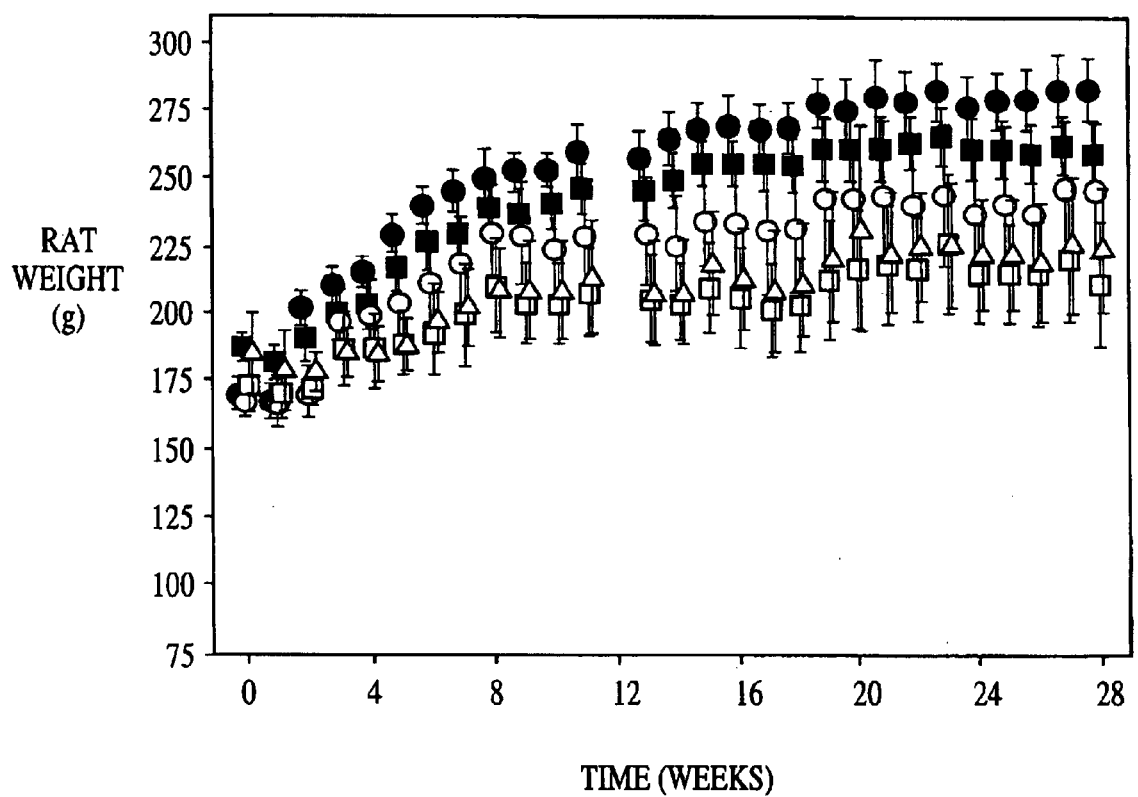
FIG. 43 Weight gain profile of various rat groups. Data are mean±SD for non-diabetic control (n=13, ●), non-diabetic control+PM (n=12, ■), untreated diabetic (n=12, ○), diabetic+AG group (n=12, □), and diabetic+PM (n=13, △) groups.

Animal model. The weights of the various groups of rats over the 28 weeks of the experiment are shown in FIG. 43. The mean weight of diabetic animals was significantly lower than that of non-diabetic animals, however the insulin regimen was sufficient both to permit weight gain in the diabetic animals during the early stages and to maintain their weight at the later stages of the study. Diabetic animals consuming PM or AG weighed slightly less than the untreated diabetic group; weights of the D+PM vs. D+AG groups were statistically identical.

Figure 44A:
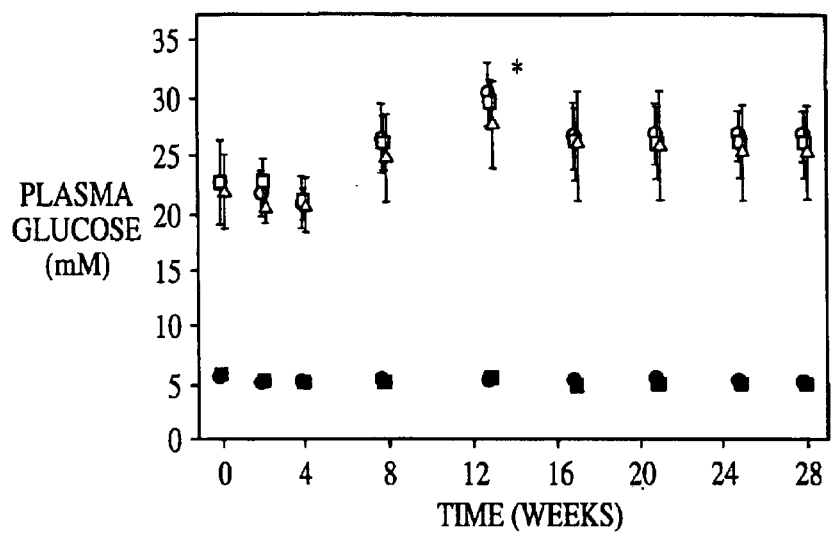
FIG. 44: Indices of glycemic control. Blood was drawn from the tail vein at 4-week intervals and analyzed for plasma glucose concentration (A) and glycated hemoglobin (B); * indicates time at which insulin dose was increased from 3 to 5 IU. Skin collagen glycation (C) was measured as FL at the end of the experiment (week 28). Data are mean±SD for non-diabetic control (●, C), non-diabetic control+PM (■, C-PM), untreated diabetic group (○, D), diabetic+PM group (□, D-PM), and diabetic+AG group (△, D-AG). D vs. C: $P<0.0001$ at all time points. Both PM and AG caused a statistically significant (12%, $p<0.05$) decrease in glycation of skin collagen.

Metabolic control. Acute, intermediate and long term measures of glycemic control were obtained by monthly measurements of plasma glucose (FIG. 44A) and glycated hemoglobin (FIG. 44B), and by measurement of glycated skin collagen (FIG. 44C) at the end of the experiment. Mean plasma glucose levels in both groups of control animals were ~5 mM for the duration of the study. In the diabetic groups, mean plasma glucose levels increased rapidly to ~21 mM and stayed at that level during the first 8 weeks of the study. During the next several weeks, mean plasma glucose levels rose gradually to nearly 30 mM in the diabetic groups. At week 15, the insulin dose was adjusted from 3 to 5 IU every other day in all diabetic groups, such that plasma glucose levels were ~26 mM or 5-fold higher than the non-diabetic animals throughout the remainder of the study. There was no statistical difference in mean plasma glucose or urinary glucose (not shown) among any of the diabetic groups.

Figure 44B:
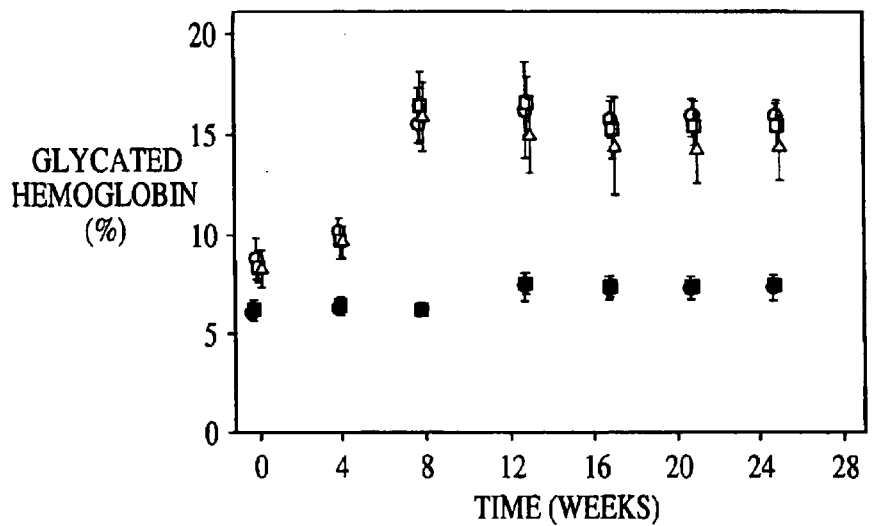
Figure 44C:
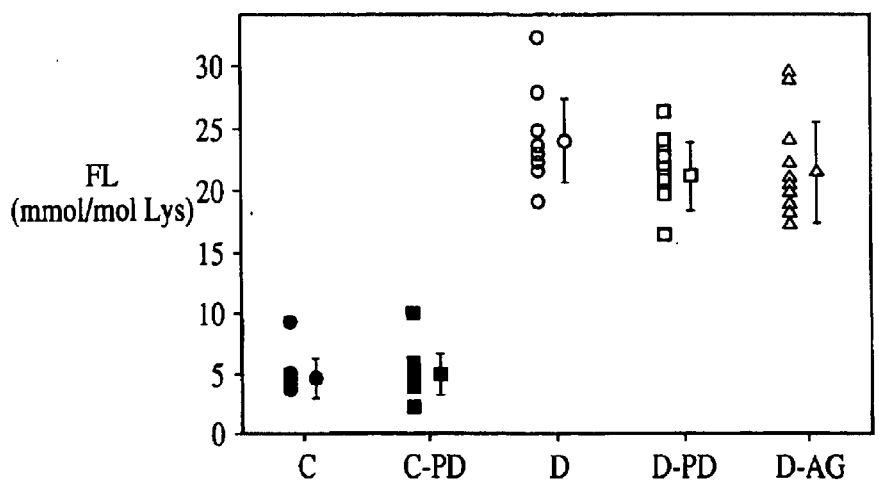

The increase in plasma glucose levels in the diabetic animals was accompanied by an increase in GlcHb (FIG. 44B). By 8 weeks, GlcHb reached a mean value of ~16% in all groups, compared to 6.2% in the non-diabetic animals. Neither PM nor AG had an effect on glycemic control in diabetic animals, as measured by either mean plasma glucose or GlcHb. Assuming minimal turnover of insoluble skin collagen, glycation of this collagen should reflect very long term, steady- state glycemic control. As shown in FIG. 44C, the mean concentration of FL in diabetic animals (23.8±3.4 mmol/mol lysine) was 4.8-fold higher than FL values in either non-diabetic group (5.0±1.6 mmol/mol lysine), compared to a 5-fold increase in mean plasma glucose and 2.5-fold increase in GlcHb in the diabetic animals, as measured by boronate affinity chromatography. Thus, measurement of FL in collagen provided a more sensitive and accurate index of the long-term increase in glycemia, than did GlcHb.

We have demonstrated that PM is a post-Amadori inhibitor in vitro (see above), i.e. PM prevents further conversion of Amadori adducts to AGEs. It seemed possible, therefore, that the concentration of the Amadori product, FL, might even be increased in diabetic animals treated with PM. However, as shown in FIG. 44C, despite essentially unchanged glycemic control (FIGS. 44A and 44B) diabetic animals consuming PM and AG had slightly, but statistically significantly lower levels of FL in skin collagen, ~12% below that of untreated diabetic animals (p<0.05). These data suggest that increased crosslinking of collagen in diabetic animals may have decreased its rate of turnover, leading to a further increase in glycation than would be predicted by changes in glycemia alone. Inhibition of crosslinking by PM, leading to an increase in collagen turnover, might therefore lead to slightly lower levels of FL in collagen of PM-treated diabetic rats.

Drug and metabolite concentrations in plasma and urine. Plasma concentrations of PM, vitamin $B_6$ metabolites and AG were measured at selected time points during the study. In non-diabetic animals, plasma PM concentration rose to ~6 μM during the first week of the study and remained at that level thereafter. For diabetic animals, which were polydypsic throughout the study, mean plasma PM and AG concentrations, measured at 28 weeks were 106±17 μM and 87±10 μM, respectively (p<0.01), compared to approximately 5 mM concentrations in drinking water (as prepared) and urine of diabetic animals (not shown). Although the molar concentration of PM was approximately 60% that of AG in the drinking water (both were administered at 1 g of the salt form/L), the mean concentration of PM in plasma was approximately 20% greater than that of AG.

In addition to PM, there are a number of other vitamin $B_6$ isoforms and metabolites that might be formed from PM in plasma. Table 4 summarizes plasma levels of several of these compounds after 21 weeks treatment with PM. Both pyridoxal, the precursor of pyridoxal-phosphate, and pyridoxic acid, a metabolite vitamin $B_6$, were increased in plasma of PM-treated animals. The concentrations of pyridoxal and pyridoxic acid were similar in the diabetic and control animals, despite significantly greater PM intake and nearly 20-fold higher plasma concentration of PM in the diabetic animals. Pyridoxine, the $B_6$ vitamin in the rat chow, was present in similar concentration in plasma in all groups. Urinary PM, measured at 23 weeks, was 824±44 μmol/day, while PM intake, estimated from water consumption, was 801±22 μmol/day, indicating that the majority of PM was recovered unchanged in the urine.

TABLE 4

Isoforms and metabolites of vitamin $B_6$ in plasma at week 21[A]

| Group | Pyridoxamine (μmol/L) | Pyridoxal (μmol/L) | Pyridoxine (μmol/L) | Pyridoxic acid (μmol/L) |
|---|---|---|---|---|
| Control + PM (2 g/L) | 6.3 ± 2.1 | 12.5 ± 2.7 | 2.4 ± 0.1 | 4.2 ± 2.1 |
| Diabetic | 0.8 ± 0.4 | ND | 2.2 ± 0.1 | ND |
| Diabetic + PM (1 g/L) | 76 ± 18 | 10.5 ± 2.9 | 2.5 ± 0.2 | 4.4 ± 2.9 |

[A]Analytes were measured in plasma of 4 animals in each group, by RP-HPLC, as described in Materials and Methods. Vitamers were not detectable (below 1 μmol/L limit of detection) in untreated control animals. Pyridoxal phosphate was also below 1 μmol/L in both control and PM-treated animals.

AGE levels in skin collagen. The effects of various drug treatments on AGE concentrations in skin collagen at the end of the study are shown in FIGS. 45 A–C. AGEs in PM-treated non-diabetic animals were statistically identical to those in the untreated non-diabetic group (data not shown). CML concentrations (FIG. 45A) increased by approximately 100%, from 0.057±0.01 to 0.124±0.01 mmol/mol lysine in non-diabetic controls vs. untreated diabetic animals. When PM or AG was administered in drinking water, mean values decreased to 0.092±0.02 and 0.10±0.02 mmol/mol lysine, respectively, a 35–45% reduction toward the level in non-diabetic animals. CEL increased, from 0.018±0.004 mmol/mol lysine in control to 0.028±0.004 mmol/mol lysine in diabetic rats (FIG. 45B). As with CML, both drugs decreased CEL up to 50% toward levels in non-diabetic control animals (FIG. 45B). The decreases in both CML and CEL were statistically significant in drug treated animals compared to untreated diabetic rats (FIG. 45, legend). The fluorescent AGE cross-link, pentosidine also increased approximately 2-fold, from 0.58±0.10 μmol/mol Lys in control to 1.1±0.16 μmol/mol Lys in diabetic rats (FIG. 45C). However, in contrast to CML and CEL, pentosidine concentrations were similar in all diabetic groups, i.e. neither drug had a statistically significant effect on the pentosidine content of skin collagen.

Figure 46A:
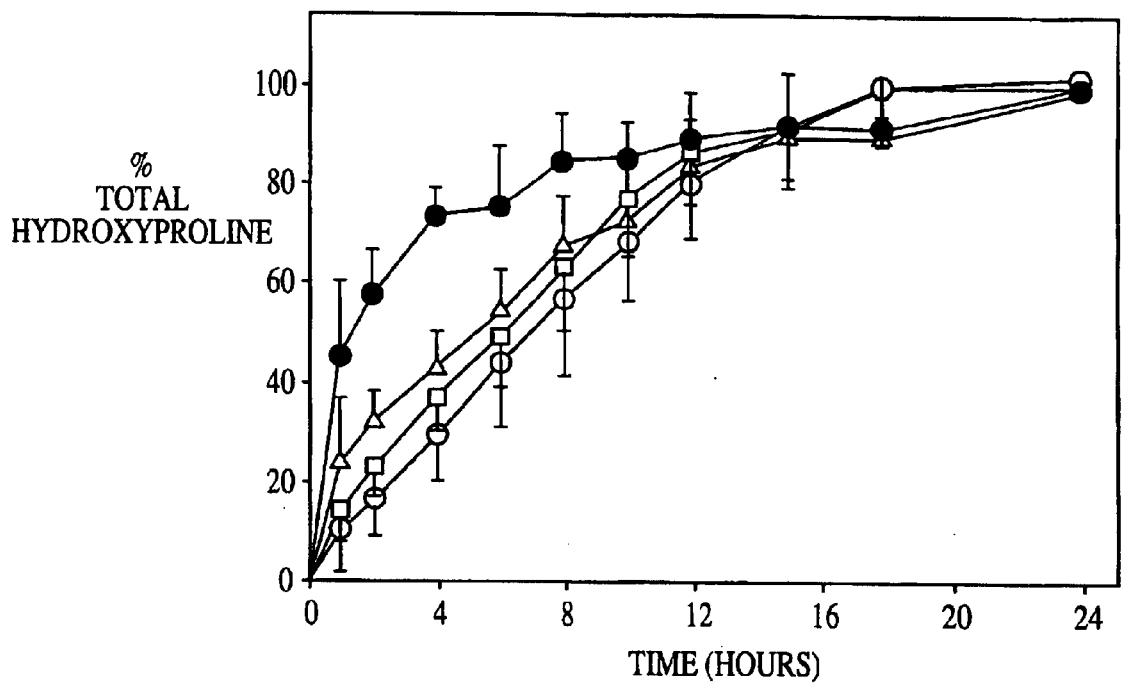
FIG. 46: Influence of diabetes and drug-treatment on crosslinking (proteolytic digestibility) of rat skin collagen. Collagen was digested with pepsin and Hyp release in the supernatant was measured as a function of time of digestion (A). The time for 50% digestion is shown in B; D vs. C: $p<0.0001$, D-PD vs. D: $p=0.03$, D-AG vs. D: $p=0.005$.
Figure 46B:
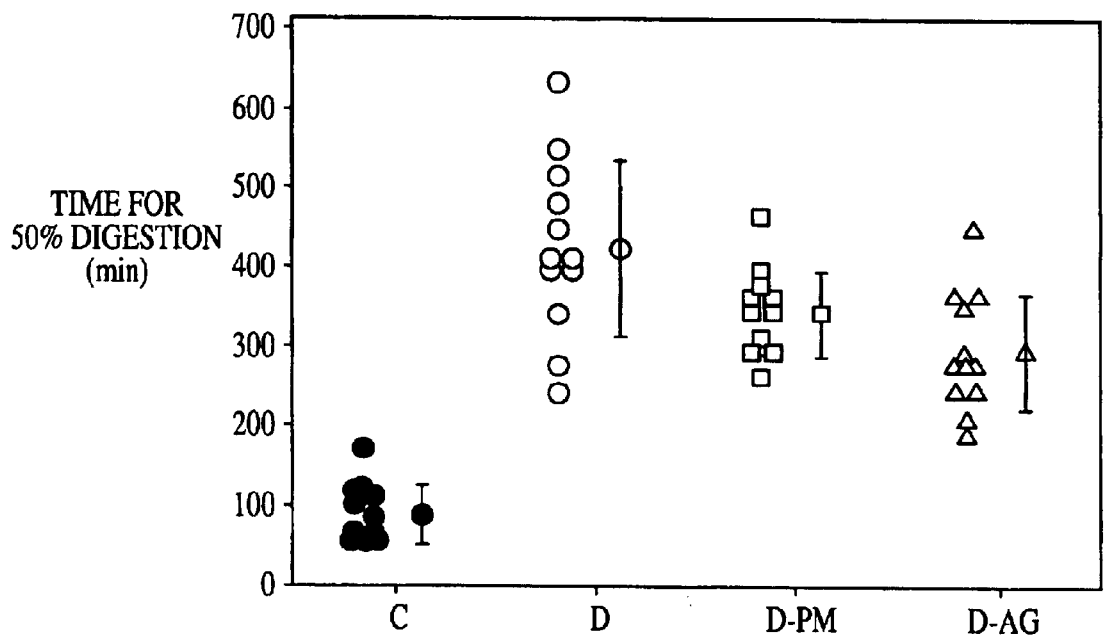

Pepsin digestibility and fluorescence of skin collagen. In addition to increased AGE content, collagen from diabetic animals typically shows a decrease in susceptibility to enzymatic digestion (Hamlin, et al. 1975. *Diabetes* 24:902–924). The kinetics of pepsin digestion of skin collagen from the various experimental groups are shown in FIG. 46A. In non-diabetic animals these kinetics were complex, with a burst of Hyp-containing peptides released during the first hour, followed by somewhat slower rates of digestion thereafter. In contrast, collagen from diabetic animals was digested in a more linear fashion, and at a slower rate throughout the 24-hour experiment. The half-time for digestion of skin collagen increased from 90 minutes in control animals to 450 minutes in diabetic animals (FIG. 46B). PM and AG reduced the half-time to mean values of 350 and 300 minutes, respectively, although differences between digestion of control and diabetic collagen were more impressive at shorter times. The 30–40% decrease in half-time for digestion of collagen suggests that both PM and AG inhibited crosslinking of the collagen. As shown in FIG. 45D, both PM and AG also caused about a 40% decrease in collagen-linked fluorescence toward values observed in non-diabetic rats. Thus, in contrast to their lack of effect on formation of the AGE crosslink, pentosidine, both PM and AG decreased the mean half-time for pepsin digestion and Maillard-type fluorescence of skin collagen in diabetic rats.

AGEs in kidney collagen. AGEs were also measured in kidney collagen (Table 5). The amounts of collagen required for these analyses (3 mg for CML and CEL by GC/MS, and 3 mg for pentosidine by RP-HPLC) required pooling of the total collagen extract from ~1.5 kidneys from each rat. As summarized in Table 5, the absolute concentrations of AGEs in non-diabetic RBM collagen were 2–3-fold higher than in skin collagen (FIG. 45). Levels of CML and pentosidine also increased by approximately 2-fold in diabetic vs. control animals. As observed in skin collagen (FIG. 45B), the increase in CEL was less impressive, ~11% in diabetic, compared to control, kidney collagen. In contrast to effects on skin collagen, however, there was not a significant decrease in the CML, CEL or pentosidine content of kidney collagen in animals treated with either PM or AG.

TABLE 5

AGE levels in renal basement membrane collagen[A]

| Group | CML (mmol/mol Lys) | CEL (mmol/mol Lys) | Pentosidine (μmol/mol Lys) |
|---|---|---|---|
| Non-diabetic (n = 12) | 0.15 ± 0.001[B] | 0.07 ± 0.007[C] | 1.69 ± 0.37[C] |
| Diabetic (n = 13) | 0.25 ± 0.04 | 0.08 ±0.01 | 3.17 ± 1.10 |
| Diabetic + PM (n = 13) | 0.23 ±0.03 | 0.08 ± 0.008 | 3.00 ± 0.90 |
| Diabetic + AG (n = 11) | 0.24 ± 0.05 | 0.07 ± 0.008[C] | 2.47 ± 0.64[D] |

[A]CML and CEL were determined by GC/MS and pentosidine by RP-HPLC, as described in Materials and Methods.
[B]$p < 0.001$ vs. untreated diabetic group.
[C]$p < 0.05$ vs. untreated diabetic group.
[D]$p = 0.07$ vs. untreated diabetic group.

Figures 47A, 47B:
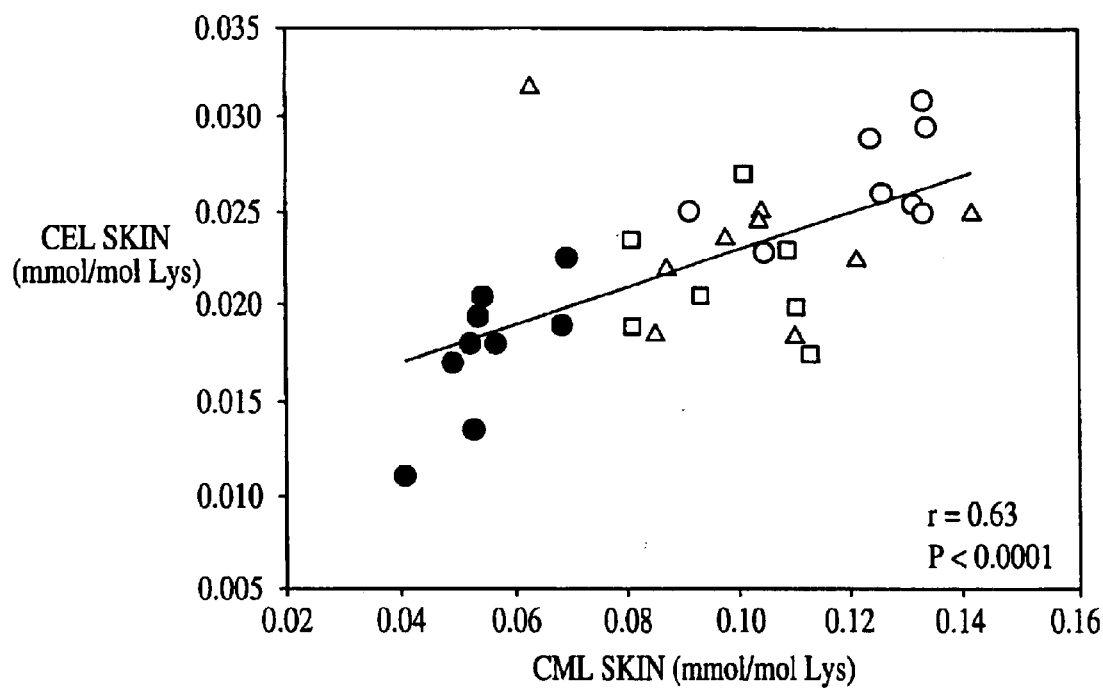
FIG. 47: Relationship between CML and CEL in skin and kidney collagen. Correlation between CML and CEL levels in skin collagen (A), and CML concentration in skin and kidney collagen (B). Statistical analyses were performed by a Pearson Product Moment calculation. Symbols as in legend to FIG. 45.

The concentrations of CML and CEL in skin collagen, and of CML in skin and RBM collagen, were strongly correlated with one another (FIGS. 47A and 47B). The correlation between CML and CEL in skin collagen in all groups and the effect of diabetes and drug treatment on AGE concentration is evident in FIG. 47 by the clustering of symbols for each experimental group, i.e. control animals grouped toward the lower left, untreated diabetic animals toward the upper right, and drug-treated animals in the intermediate range. Other relationships among the various AGEs in skin and kidney collagen are summarized in Table 6. In general, the correlations among the AGEs in skin were higher than among those in kidney.

TABLE 6

Relationships among AGEs in skin and kidney collagen.[A]

|  | $CML_{Skin}$ (n = 48) | $CEL_{Skin}$ (n = 48) | $Pent._{Skin}$ (n = 49) | $CML_{Kidney}$ (n = 49) | $CEL_{Kidney}$ (n = 48 |
|---|---|---|---|---|---|
| $CML_{Skin}$ | — | | | | |
| $CEL_{Skin}$ | $P < 0.0001$ $r = 0.63$ | — | | | |
| $Pent._{Skin}$ | $P < 0.0001$ $r = 0.69$ | $P < 0.0001$ $r = 0.65$ | — | | |
| $CML_{Kidney}$ | $P < 0.0001$ $r = 0.79$ | | | — | |
| $CEL_{Kidney}$ | | $P = 0.23$ $r = 0.21$ | | $P < 0.005$ $r = 0.40$ | — |
| $Pent._{Kidney}$ | | | $P < 0.0001$ $r = 0.54$ | $P < 0.0001$ $r = 0.64$ | $P = 0.016$ $r = 0.35$ |

[A]Statistics derived from Pearson Product Moment calculation

Discussion

AGEs in skin collagen. PM had no effect on glycemia or glycated hemoglobin in diabetic rats. Further, in the present studies, all diabetic animals developed sugar cataracts and were essentially blind after 8 weeks of diabetes. Thus, PM, like AG (Cameron, et al. 1992. *Diabetologia* 35:946–950), does not appear to affect polyol pathway activity in diabetic rats. The present studies are the first in which the AGEs, CML, CEL and pentosidine have been measured by specific chromatographic and spectrometric methods in control, untreated diabetic and AGE-inhibitor-treated diabetic animals. We demonstrate that the AGEs, CML, pentosidine, and the newly described CEL (Ahmed, et al. *Biochem. J.* 324:565–570,1997), as well as Maillard-type fluorescence, are increased by approximately 2-fold in skin and kidney collagen of diabetic animals, compared to controls, after 7 months of diabetes. We also observed an approximately 50% decrease toward non-diabetic values of CML, CEL and fluorescence in skin collagen of diabetic animals treated with PM or AG, establishing the activity of AG and PM as AGE inhibitors in vivo. The observations regarding effects on fluorescence of skin collagen are in agreement with previous reports that AG reduces fluorescence in aorta (Brownlee, et al. 1986. *Science* 232:1629–1632, Soulis-Liparota,et al. 1991 *Diabetes* 40:1328–1334; Soulis-Liparota, et al. 1995 *Diabetologia* 38:387–394) and skin collagen (Odetti, et al. 1990. *Diabetes* 39:796–801) of diabetic rats. These partial corrections in AGEs and fluorescence were achieved at relatively high plasma concentrations of the drugs, ~100 μM PM and AG, consistent with the hypothesis that AGE inhibitors compete in a stoichiometric manner with functional groups on proteins to trap reactive precursors of AGE formation. However, the competition appears to be fairly efficient, considering the overall concentration of reactive functional groups in tissue proteins. The total concentration of protein sulfhydryl, amino and guanidino groups in plasma and fixed tissues, for example, probably exceeds 100 mM. Albumin alone, which is present at ~0.5 mM concentration in plasma, accounts for ~25 mM lysine amino groups in plasma.

We reported recently that AG did not affect the increase in CML or pentosidine in skin collagen of STZ-induced diabetic Lewis rats (Degenhardt, et al. 1999. *Diab. Res. Clin. Pract.* 43:81–89). We confirm the previous observations regarding a lack of effect of AG on pentosidine, however AG significantly inhibited CML, as well as CEL, formation in the present study. Differences in drug transport, or severity of diabetes or hyperlipidemia between the Lewis and Sprague-Dawley diabetic rats may be significant. As noted above, however, we were surprised again by the failure of AG (or PM) to suppress the increase in pentosidine in skin collagen of diabetic rats, despite effects on collagen-linked fluorescence. Since pentosidine is derived exclusively from carbohydrates, the increase in pentosidine establishes that carbohydrates contribute to the increase in chemical modification of proteins in the diabetic rat. In in vitro studies using chelators and anaerobic conditions, we have noted that it is more difficult to inhibit the formation of pentosidine, compared to CML, from glucose (Dyer, et al. 1991. *J. Biol. Chem.* 266:11654–11660) and pentoses (Litchfield, et al. 1999. *Int. J. Biochem. & Cell Biol.* In press). Thus, it is possible that pentosidine formation might be inhibited only at higher doses of AGE inhibitors.

Digestibility of skin collagen. Several previous studies have noted that AG inhibits the increase in crosslinking of collagen in diabetic rats, as measured by changes in tail tendon stability (Oxlund and Andreasen 1992. *Diabetologia* 35:19–25) or protease digestibility of aortic (Brownlee, et al. 1986. *Science* 232:1629–1632), renal (Nyengaard et al. 1997. *Diabetes* 46:94–106), or tail tendon (Kochakian et al. 1996. *Diabetes* 45:1694–1700) collagen. In the present studies, we observed that the half-time for solubilization of skin collagen by pepsin was increased about 4-fold in diabetic, compared to control rats, and was decreased by 25–30% toward normal in diabetic rats treated with either PM or AG. Notably, however, CML appeared to be a good surrogate marker for protein crosslinking, since there was a significant correlation between the CML content and the half-time for solubilization of skin collagen ($p<0.0001$, $r=0.68$) and both the CML content and crosslinking of collagen were decreased by treatment with PM or AG.

AGEs in kidney collagen. Based on comparison of data in FIG. 45 and Table 5, basal levels of CML, CEL and pentosidine were about 2-fold higher in renal collagen, compared to skin collagen. These biomarkers increased in concert with the increase in AGEs in skin collagen of diabetic vs. control animals, confirming an assumption in previous studies that changes in skin collagen reflect systemic changes in collagen in other tissues (Dyer, et al. 1993. *J. Clin. Invest.* 91:2463–2469; McCance et al. 1993. *J. Clin. Invest.* 91:2460–2478). As shown in FIG. 47 and Table 6, levels of these biomarkers in skin and renal collagen also correlated well with one another. Although trends were apparent, neither PM nor AG significantly affected the increase in AGEs in kidney collagen in diabetic animals. These observations contrast with immunohistochemical data that indicate significant decreases in CML or other AGEs in the kidney (Soulis et al. 1997. *Kidney. Int.* 50:627–634) and mesenteric vasculature (Rumble et al. 1997. *J. Clin. Invest.* 99:1016–1027) of AG-treated vs. untreated STZ-induced diabetic rats. In the latter studies, however, the authors also noted a decrease in collagen synthesis in response to AG, so that there may have been, in fact, no change in the ratio of AGEs to vascular collagen in AG-treated vs. untreated diabetic rats.

The difference in results obtained by chemical and immunohistochemical analysis of AGEs may be attributed to limitations of both methods. Immunohistochemistry has limitations as a quantitative method, particularly when tissues in control and diabetic animals may differ in their content of collagen, proteoglycan and other proteins—in some cases, treatment with proteases or chemical agents is required to enhance staining and contrast. On the other hand, our chemical assays for AGEs require 1–3 mg protein and are not sufficiently sensitive for analysis of the AGE content of isolated glomerular or tubular basement membranes from individual rats. Thus, changes in AGEs in specific structures in the kidney may be obscured by less significant or contrasting changes in chemical modification of total renal collagen. Soulis et al. (*Diabetes* 40:1328–1334 (1991)) have noted, for example, that treatment of diabetic rats with AG caused a decrease in fluorescence in isolated renal glomerular and tubular collagen, but not in total kidney collagen. Interpretation of these observations is also complicated by the fact that the diabetic kidney undergoes hypertrophy, while both PM and AG partially inhibit the gain in kidney weight (see below). Thus, the average age of collagen in the untreated diabetic kidney may be less than that in drug-treated animals, which would decrease the difference in AGE content of collagen from untreated and drug-treated diabetic animals. Improvements in the sensitivity of AGE assays will eventually allow us to analyze isolated renal glomerular and tubular collagen and to gain a better understanding of the role of AGEs in pathological changes at specific sites in the kidney.

EXAMPLE 8

Compounds for Inhibiting Oxidative Protein Modification

The present invention encompasses compounds, and pharmaceutical compositions containing compounds having the general formula:

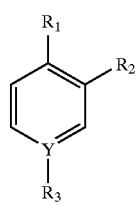

Formula I wherein $R_1$ is $CH_2NH_2$, $CH_2SH$, $COOH$, $CH_2CH_2NH_2$, $CH_2CH_2SH$, or $CH_2COOH$;

$R_2$ is OH, SH or $NH_2$;

Y is N or C, such that when Y is N $R_3$ is nothing, and when Y is C, $R_3$ is $NO_2$ or another electron withdrawing group;

and salts thereof.

The present invention also encompasses compounds of the general formula

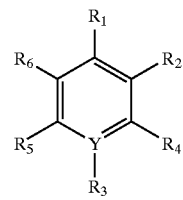

Formula II wherein $R_1$ is $CH_2NH_2$, $CH_2SH$, $COOH$, $CH_2CH_2NH_2$, $CH_2CH_2SH$, or $CH_2COOH$;

$R_2$ is OH, SH or $NH_2$;

Y is N or C, such that when Y is N $R_3$ is nothing, and when Y is C, $R_3$ is $NO_2$ or another electron withdrawing group;

$R_4$ is H, or C 1–18 alkyl;

$R_5$ and $R_6$ are H, C 1–18 alkyl, alkoxy or alkane; and salts thereof.

In addition, the instant invention also envisions compounds of the formulas

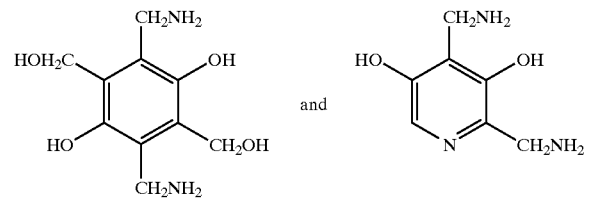

The compounds of the present invention can embody one or more electron withdrawing groups, such as and not limited to $-NH_2$, $-NHR$, $-NR_2$, $-OH$, $-OCH_3$, $-OCR$, and $-NH-COCH_3$ where R is C 1–18 alkyl.

By "alkyl" and "lower alkyl" in the present invention is meant straight or branched chain 15 alkyl groups having from 1–18 carbon atoms, such as, for example, methyl, ethyl, propyl, isopropyl, n-butyl, sec-butyl, tert-butyl, pentyl, 2-pentyl, isopentyl, neopentyl, hexyl, 2-hexyl, 3-hexyl, and 3-methylpentyl. Unless indicated otherwise, the alkyl group substituents herein are optionally substituted with at least one group independently selected from hydroxy, mono- or dialkyl amino, phenyl or pyridyl.

By "alkoxy" and "lower alkoxy" in the present invention is meant straight or branched chain alkoxy groups having 1–18 carbon atoms, such as, for example, methoxy, ethoxy, propoxy, isopropoxy, n-butoxy, sec-butoxy, tert-butoxy, pentoxy, 2-pentoxy, isopentoxy, neopentoxy, hexoxy, 2-hexoxy, 3-hexoxy, and 3-methylpentoxy.

By "alkene" and "lower alkene" in the present invention is meant straight and branched chain alkene groups having 1–18 carbon atoms, such as, for example, ethlene, propylene, 1-butene, 1-pentene, 1-hexene, cis and trans 2-butene or 2-pentene, isobutylene, 3-methyl-1-butene, 2-methyl-2-butene, and 2,3-dimethyl-2-butene.

By "salts thereof" in the present invention is meant compounds of the present invention as salts and metal complexes with said compounds, such as with, and not limited to, Al, Zn, Mg, Cu, and Fe.

One of ordinary skill in the art will be able to make compounds of the present invention using standard methods and techniques.

The instant invention encompasses pharmaceutical compositions which comprise one or more of the compounds of the present invention, or salts thereof, in a suitable carrier.

The instant invention encompasses methods for administering pharmaceuticals of the present invention for therapeutic intervention of pathologies which are related to AGE formation in vivo. In one preferred embodiment of the present invention the AGE related pathology to be treated is related to diabetic nephropathy.

The instant invention may be embodied in other forms or carried out in other ways without departing from the spirit or essential characteristics thereof. The present disclosure and enumerated examples are therefore to be considered as in all respects illustrative and not restrictive, the scope of the invention being indicated by the appended claims, and all equivalency are intended to be embraced therein. One of ordinary skill in the art would be able to recognize equivalent embodiments of the instant invention, and be able to practice such embodiments using the teaching of the instant disclosure and only routine experimentation.

We claim:

1. A method for treating a condition or disorder associated with oxidative stress, comprising administering to a hyperglycemic mammal an effective amount to treat the condition or disorder associated with oxidative stress of a compound of the general formula:

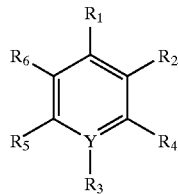

wherein $R_1$ is $CH_2NH_2$, $CH_2SH$, $COOH$, $CH_2CH_2NH_2$, $CH_2CH_2SH$, or $CH_2COOH$;

$R_2$ and $R_6$ is H, OH, SH, $NH_2$, C 1–18 alkyl, alkoxy or alkene;

$R_4$ and $R_5$ are H, C 1–18 alkyl, alkoxy or alkene;

Y is N or C, such that when Y is N $R_3$ is nothing, and when Y is C, $R_3$ is $NO_2$ or another electron withdrawing group, or salts thereof, and wherein the condition or disorder associated with oxidative stress is selected from the group consisting of arthritis, cancer, exposure to ionizing radiation, exposure to chemotherapeutic agents, pulmonary adult respiratory distress syndrome, strokes, pancreatitis, and intestinal ulcerations.

2. A method for treating a condition or disorder associated with oxidative stress, comprising administering to a hyperglycemic mammal an effective amount of pyridoxamine to treat the condition or disorder associated with oxidative stress, wherein the condition or disorder associated with oxidative stress is selected from the group consisting of arthritis, cancer, exposure to ionizing radiation, exposure to chemotherapeutic agents, pulmonary adult respiratory distress syndrome, strokes, pancreatitis, and intestinal ulcerations.

3. The method of claim 1 wherein the condition or disorder associated with oxidative stress is arthritis.

4. The method of claim 1 wherein the condition or disorder associated with oxidative stress is cancer.

5. The method of claim 1 wherein the condition or disorder associated with oxidative stress is exposure to ionizing radiation.

6. The method of claim 1 wherein the condition or disorder associated with oxidative stress is exposure to chemotherapeutic agents.

7. The method of claim 1 wherein the condition or disorder associated with oxidative stress is pulmonary adult respiratory distress syndrome.

8. The method of claim 1 wherein the condition or disorder associated with oxidative stress is strokes.

9. The method of claim 1 wherein the condition or disorder associated with oxidative stress is pancreatitis.

10. The method of claim 1 wherein the condition or disorder associated with oxidative stress is intestinal ulcerations.

11. The method of claim 2 wherein the condition or disorder associated with oxidative stress is arthritis.

12. The method of claim 2 wherein the condition or disorder associated with oxidative stress is cancer.

13. The method of claim 2 wherein the condition or disorder associated with oxidative stress is exposure to ionizing radiation.

14. The method of claim 2 wherein the condition or disorder associated with oxidative stress is exposure to chemotherapeutic agents.

15. The method of claim 2 wherein the condition or disorder associated with oxidative stress is pulmonary adult respiratory distress syndrome.

16. The method of claim 2 wherein the condition or disorder associated with oxidative stress is strokes.

17. The method of claim 2 wherein the condition or disorder associated with oxidative stress is pancreatitis.

18. The method of claim 2 wherein the condition or disorder associated with oxidative stress is intestinal ulcerations.

* * * * *